US009371541B2

(12) United States Patent
Mitchum et al.

(10) Patent No.: US 9,371,541 B2
(45) Date of Patent: Jun. 21, 2016

(54) GENES IMPLICATED IN RESISTANCE TO SOYBEAN CYST NEMATODE INFECTION AND METHODS OF THEIR USE

(75) Inventors: Melissa Goellner Mitchum, Columbia, MO (US); Pramod Kaitheri Kandoth, Columbia, MO (US); Greg Yeckel, St. Louis, MO (US); Nagabhushana Ithal, Bangalore (IN)

(73) Assignee: The Curators of the University of Missouri, Columbia, MO (US)

( * ) Notice: Subject to any disclaimer, the term of this patent is extended or adjusted under 35 U.S.C. 154(b) by 858 days.

(21) Appl. No.: 13/344,556

(22) Filed: Jan. 5, 2012

(65) Prior Publication Data

US 2012/0260368 A1 Oct. 11, 2012

Related U.S. Application Data

(60) Provisional application No. 61/430,120, filed on Jan. 5, 2011.

(51) Int. Cl.
*C12N 15/82* (2006.01)
*C07K 14/415* (2006.01)

(52) U.S. Cl.
CPC .......... *C12N 15/8285* (2013.01); *C07K 14/415* (2013.01)

(58) Field of Classification Search
None
See application file for complete search history.

(56) References Cited

FOREIGN PATENT DOCUMENTS

| | | | |
|---|---|---|---|
| WO | WO 2008/095972 | * | 8/2008 |
| WO | WO 2010/023186 | | 3/2010 |
| WO | WO 2010/027804 | | 3/2010 |
| WO | WO 2010/027809 | | 3/2010 |
| WO | WO 2012/018489 | | 2/2012 |

OTHER PUBLICATIONS

Lin et al, 2001, GenBank Accesion No. D84900.*
Yeckel, 2012, "Characterization of a Soybean BAG gene and Its Potential Role in Nematode Resistance", University of Missouri-Columbia, Master's Thesis.*
Guo et al (2004, Proc. Natl. Acad. Sci. USA 101: 9205-9210).*
Kang et al (2006, Cell Death and Diff. 13:84-95).*
Glyma19g04410 Soybease, http://www.soybase.org/sbt/search/search_results.php?category=FeatureName&search_term=Glyma19g04410, accessed Oct. 9, 2015.*
AT5G15780, https://www.arabidopsis.org /servlets/TairObject?type=locus&name=AT5G15780, accessed Oct. 9, 2015.*
Glyma19g04410 Phytozome (http://phytozome.jgi.doe.gov/pz/portal.html#!gene?search=1&detail=1&method=0&searchText=transcriptid:30511421), accessed Oct. 9, 2015.*
Acedo Jr, et al. (1984) Nematode population attrition and histopathology of *Heterodera glycines*-soybean associations. J Nematol 16: 48-56.
Alkharouf NW, et al. (2006) Time course microarray analyses reveal global changes in gene expression of susceptible *Glycine max* (soybean) roots during infection by *Heterodera glycines* (soybean cyst nematode). Planta 224: 838-852.
Balague C, Li et al. (2003) HLM1, an essential signaling component in the hypersensitive response, is a member of the cyclic nucleotide-gated channel ion channel family. Plant Cell 15: 365-379.
Bari R, Jones JD (2009) Role of plant hormones in plant defence responses. Plant Mol Biol 69: 473-488.
Branch C, et al. (2004) Salicylic acid is part of the Mi-1-mediated defense response to root-knot nematode in tomato. Mol Plant Microbe Interact 17: 351-356.
Century KS, et al (1995) NDR1, a locus of Arabidopsis thaliana that is required for disease resistance to both a bacterial and a fungal pathogen. Proc Natl Acad Sci U S A 92: 6597-6601.
Chao, Q., et al. (1997) Activation of the ethylene gas response pathway in arabidopsis by the nuclear protein Ethylene-INSENSITIVE3 and related proteins Cell, 89 (7), pp. 1133-1144.
Chiang GC, et al (2009) Major flowering time gene, flowering locus C, regulates seed germination in Arabidopsis thaliana. Proc Natl Acad Sci U S A 106: 11661-11666.
Clough SJ, et al. (2000) The Arabidopsis dnd1 "defense, no death" gene encodes a mutated cyclic nucleotide-gated ion channel. Proc Natl Acad Sci U S A 97: 9323-9328.
Colgrove AL, Niblack TL (2008) Correlation of female indices from virulence assays on inbred lines and field populations of Heterodera glycines. J Nematol 40: 39-45.
Coppinger P, et al. (2004) Overexpression of the plasma membrane-localized NDR1 protein results in enhanced bacterial disease resistance in Arabidopsis thaliana. Plant J 40: 225-237.
Eulgem T, Somssich IE (2007) Networks of WRKY transcription factors in defense signaling. Curr Opin Plant Biol 10: 366-371.
Gao X, et al. (2008) Maize 9-lipoxygenase ZmLOX3 controls development, root-specific expression of defense genes, and resistance to root-knot nematodes. Mol Plant Microbe Interact 21: 98-109.
Gechev, T.S., Minkov, I.N., Hille, J.(2005) Hydrogen peroxide-induced cell death in arabidopsis: Transcriptional and mutant analysis reveals a role of an oxoglutarate-dependent dioxygenase gene in the cell death process IUBMB Life 57 (3), pp. 181-188.
Grunewald W, et al. (2008) A role for AtWRKY23 in feeding site establishment of plant-parasitic nematodes. Plant Physiol 148: 358-368.
Hubert DA, Tornero P, Belkhadir Y, Krishna P, Takahashi A, Shirasu K, Dangl JL (2003) Cytosolic HSP90 associates with and modulates the Arabidopsis RPM1 disease resistance protein. EMBO J 22: 5679-5689.

(Continued)

*Primary Examiner* — Anne Kubelik
(74) *Attorney, Agent, or Firm* — Thompson Coburn LLP; J. Wendy Davis; Steven M. Ritchey

(57) ABSTRACT

Genes whose expressions are up-regulated or down-regulated in plant roots in response to nematode infection are disclosed. These genes may play an important role in plant defense against SCN infection. Several nematode-inducible promoters have also been identified in plants, which may be used in nematode inducible gene expression construct. Expression of these SCN responsive genes may be manipulated to obtain SCN resistant lines.

7 Claims, 21 Drawing Sheets

(56) References Cited

OTHER PUBLICATIONS

Hwang IS, Hwang BK (2010) The pepper 9-lipoxygenase gene CaLOX1 functions in defense and cell death responses to microbial pathogens. Plant Physiol 152: 948-967.
Ithal N, et al. (2007a) Parallel genome-wide expression profiling of host and pathogen during soybean cyst nematode infection of soybean. Mol Plant Microbe Interact 20: 293-305.
Ithal N, et al. (2007b) Developmental transcript profiling of cyst nematode feeding cells in soybean roots. Mol Plant Microbe Interact 20: 510-525.
Ji, J., et al. WOX4 Promotes Procambial Development, Plant Physiology, Mar. 2010, vol. 152, pp. 1346-1356.
Journot-Catalino N, et al. (2006) The transcription factors WRKY11 and WRKY17 act as negative regulators of basal resistance in Arabidopsis thaliana. Plant Cell 18: 3289-3302.
Kandoth, P.K. et al., The Soybean Rhg1 Locus for Resistance to the Soybean Cyst Nematode *Heterodera glycines* Regulates the Expression of a Large Number of Stress- and Defense-Related Genes in Degenerating Feeding Cells, Plant Physiology; vol. 155, No. 4, Apr. 2011, pp. 1960-1975.
Kang CH, et al. (2006) AtBAG6, a novel calmodulin-binding protein, induces programmed cell death in yeast and plants. Cell Death Differ 13: 84-95.
Khan R, Alkharouf N, Beard H, Macdonald M, Chouikha I, Meyer S, Grefenstette J, Knap H, Matthews B (2004) Microarray analysis of gene expression in soybean roots susceptible to the soybean cyst nematode two days post invasion. J Nematol 36: 241-248.
Klink VP, et al. (2005) Laser capture microdissection (LCM) and expression analyses of *Glycine max* (soybean) syncytium containing root regions formed by the plant pathogen *Heterodera glycines* (soybean cyst nematode). Plant Mol Biol 59: 965-979.
Klink VP, et al. (2007b) Laser capture microdissection (LCM) and comparative microarray expression analysis of syncytial cells isolated from incompatible and compatible soybean (*Glycine max*) roots infected by the soybean cyst nematode (*Heterodera glycines*). Planta 226: 1389-1409.
Klink, V.P. et al; Syncytium gene expression in Glycine max [Pl 88788] roots undergoing a resistant reaction to the parasitic nematode Heterodera glycines, Plant Physiology and Biochemistry, vol. 48, No. 2-3; Feb. 1, 2010; pp. 176-193.
Klink, VP et al. A time-course comparative microarray analysis of an incompatible and compatible response by *Glycine max* (soybean) to *Heterodera glycines* (soybean cyst nematode) infection; Jun. 25, 2007.
Lee M.W., et al. (2008) Arabidopsis proteins important for modulating defense responses to Pseudomonas syringae that secrete HopW1-1. Plant J 54: 452-465.
Lee MW, et al. (2007) A key role for the Arabidopsis WIN3 protein in disease resistance triggered by Pseudomonas syringae that secrete AvrRpt2. Mol Plant Microbe Interact 20: 1192-1200.
Li, Y. et al, Effect of the rhg1 gene on population development of Heterodera glycines, Journal of Nematology; vol. 37, No. 2, Jun. 2005; pp. 168-177.
Mahalingam R, Skorupska HT (1996) Cytological expression of early response to infection by Heterodera glycines Ichinohe in resistant Pl 437654 soybean. Genome 39: 986-998.
Manickavelu A, Kawaura K, Oishi K, Shin IT, Kohara Y, Yahiaoui N, Keller B, Suzuki A, Yano K, Ogihara Y (2010) Comparative gene expression analysis of susceptible and resistant near-isogenic lines in common wheat infected by Puccinia triticina. DNA Res 17: 211-222.
Meier S, Bastian R, Donaldson L, Murray S, Bajic V, Gehring C (2008) Co-expression and promoter content analyses assign a role in biotic and abiotic stress responses to plant natriuretic peptides. BMC Plant Biol 8: 24.
Melito S, Heuberger AL, Cook D, Diers BW, MacGuidwin AE, Bent AF (2010) A nematode demographics assay in transgenic roots reveals no significant impacts of the Rhg1 locus LRR-Kinase on soybean cyst nematode resistance. BMC Plant Biol 10: 104.
Morel JB, Dangl JL(1997) The hypersensitive response and the induction of cell death in plants. Cell Death Differ 4: 671-683.
Morse M, Pironcheva G, Gehring C (2004) AtPNP-A is a systemically mobile natriuretic peptide immunoanalogue with a role in Arabidopsis thaliana cell volume regulation. FEBS Lett 556: 99-103.
Nagpal, P., et al. (2005) Auxin response factors ARF6 and ARF8 promote jasmonic acid production and flower maturation Development 132 (18), pp. 4107-4118.
Nishizawa A, Yabuta Y, Yoshida E, Maruta T, Yoshimura K, Shigeoka S (2006) Arabidopsis heat shock transcription factor A2 as a key regulator in response to several types of environmental stress. Plant J 48: 535-547.
Nobuta K, Okrent RA, Stoutemyer M, Rodibaugh N, Kempema L, Wildermuth MC, Innes RW (2007) The GH3 acyl adenylase family member PBS3 regulates salicylic acid-dependent defense responses in Arabidopsis. Plant Physiol 144: 1144-1156.
Onishi M, et al. (2006) Molecular cloning and characterization of a novel salt-inducible gene encoding an acidic isoform of PR-5 protein in soybean (*Glycine max* [L.] Merr.). Plant Physiol Biochem 44: 574-580.
O'Rourke JA, et al (2009) Integrating microarray analysis and the soybean genome to understand the soybeans iron deficiency response. BMC Genomics 10: 376.
Potter S, et al. (1993) Regulation of a hevein-like gene in Arabidopsis. Mol Plant-Microbe Interact 6: 680-685.
Riggs RD, et al. (1973) Ultrastructural changes in Peking soybeans infected with Heterodera glycines. Phytopathology 63: 76-84.
Schlueter JA, Dixon P, Granger C, Grant D, Clark L, Doyle JJ, Shoemaker RC (2004) Mining EST databases to resolve evolutionary events in major crop species. Genome 47: 868-876.
Schlueter JA, Lin JY, Schlueter SD, Vasylenko-Sanders IF, Deshpande S, Yi J, O'Bleness M, Roe BA, Nelson RT, Scheffler BE, Jackson SA, Shoemaker RC (2007) Gene duplication and paleopolyploidy in soybean and the implications for whole genome sequencing. BMC Genomics 8: 330.
Shapiro AD, Zhang C (2001) The role of NDR1 in avirulence gene-directed signaling and control of programmed cell death in Arabidopsis. Plant Physiol 127:1089-1101.
Storey JD, Tibshirani R (2003) Statistical significance for genomewide studies. Proc Natl Acad Sci U S A 100: 9440-9445.
Szakasits, D. et al.; The transcriptome of syncytia induced by the cyst nematode Heterodera schachtii in Arabidopsis roots, Plant Journal; vol. 57 No. 5, Mar. 2008; pp. 771-784.
Takahashi A, Casais C, Ichimura K, Shirasu K (2003) HSP90 interacts with RAR1 and SGT1 and is essential for RPS2-mediated disease resistance in Arabidopsis. Proc Natl Acad Sci U S A 100: 11777-11782.
Vailleau F, Daniel X, Tronchet M, Montillet JL, Triantaphylides C, Roby D (2002) A R2R3-MYB gene, AtMYB30, acts as a positive regulator of the hypersensitive cell death program in plants in response to pathogen attack. Proc Natl Acad Sci U S A 99: 10179-10184.
Varet A, Hause B, Hause G, Scheel D, Lee J (2003) The Arabidopsis NHL3 gene encodes a plasma membrane protein and its overexpression correlates with increased resistance to Pseudomonas syringae pv. tomato DC3000. Plant Physiol 132: 2023-2033.
Varet A, Parker J, Tornero P, Nass N, Nurnberger T, Dangl JL, Scheel D, Lee J (2002) NHL25 and NHL3, two NDR1/HIN1-1ike genes in Arabidopsis thaliana with potential role(s) in plant defense. Mol Plant Microbe Interact 15: 608-616.
Wang W, et al. (2004) Role of plant heat-shock proteins and molecular chaperones in the abiotic stress response. Trends Plant Sci 9: 244-252.
Wang, X., et al.(2009) The Arabidopsis ATAF1, a NAC transcription factor, is a negative regulator of defense responses against neurotrophic fungal and bacterial pathogens Molecular Plant-Microbe Interactions 22 (10), pp. 1227-1238.
Wilsker, D.,et al.(2002) ARID proteins: A diverse family of DNA binding proteins implicated in the control of cell growth, differentiation, and development Cell Growth and Differentiation 13 (3), pp. 95-106.
Xiao YL, et al. (2005) Analysis of the cDNAs of hypothetical genes on Arabidopsis chromosome 2 reveals numerous transcript variants. Plant Physiol 139: 1323-1337.

(56) References Cited

OTHER PUBLICATIONS

Zhang C, et al. (2009) Development and use of an efficient DNA-based viral gene silencing vector for soybean. Mol Plant Microbe Interact 22: 123-131.
Zhang C, et al.(2010) The development of an efficient multipurpose bean pod mottle virus viral vector set for foreign gene expression and RNA silencing. Plant Physiol 153: 52-65.
Zheng MS, et al. (2004) Up-regulation of Arabidopsis thaliana NHL10 in the hypersensitive response to Cucumber mosaic virus infection and in senescing leaves is controlled by signalling pathways that differ in salicylate involvement. Planta 218: 740-750.
Zheng Z, et al. (2006) Arabidopsis WRKY33 transcription factor is required for resistance to necrotrophic fungal pathogens. Plant J 48: 592-605.
Zhong, R., Lee, C., Zhou, J., McCarthy, R.L., Ye, Z.-H. (2008) A battery of transcription factors involved in the regulation of secondary cell wall biosynthesis in Arabidopsis Plant Cell 20 (10), pp. 2763-2782.
PCTUS2012020375 Invitation to Pay additional fees and partial search report mailed Jun. 22, 2012, 11 pages.
Concibido VC , Diers BW, Arelli PR (2004) A decade of QTL mapping for cyst nematode resistance in soybean. Crop Sci 44: 1121-1131.
Cregan PB, Mudge J, Fickus EW, Danesh D, Denny R, Young ND (1999) Two simple sequence repeat markers to select for soybean cyst nematode resistance conditioned by the rhg1 locus. Theorl Appl Genet 99: 811-818.
Duan, Y, et al. (2010) An endoplasmic reticulum response pathway mediates programmed cell death of root tip induced by water stress in Arabidopsis. New Phytol 186: 681-695.
Jefferson RA (1987) Assaying chimeric genes in plants: The GUS gene fusion system. Plant Mol Biol Rep 5: 387-405.
Lamb C, Dixon RA (1997) The oxidative burst in plant disease resistance. Annu Rev Plant Physiol Plant Mol Biol 48: 251-275.
Raffaele S, Rivas S, Roby D (2006) An essential role for salicylic acid in AtMYB30-mediated control of the hypersensitive cell death program in Arabidopsis. FEBS Lett 580: 3498-3504.
Ross JP (1958) Host-parasite relationship of the soybean cyst nematode in resistant soybean roots. Phytopathology 48: 578-579.
Schmutz J, et al. (2010) Genome sequence of the palaeopolyploid soybean. Nature 463: 178-183.
Urade R (2009) The endoplasmic reticulum stress signaling pathways in plants. Biofactors 35: 326-331.
Vanderbeld B, Snedden WA (2007) Developmental and stimulus-induced expression patterns of Arabidopsis calmodulin-like genes CML37, CML38 and CML39. Plant Mol Biol 64: 683-697.
Wang X, et al. (2007) The tobacco Cel7 gene promoter is auxin-responsive and locally induced in nematode feeding sites of heterologous plants. Mol Plant Pathol 8: 423-436.
Century KS, et al. (1997) NDR1, A Pathogen-Induced Component Required for Arabidopsis Disease Resistance. Science 278: 1963-1965.
Endo B.Y. (1965) Histological responses of resistant and susceptible soybean varieties, and backcross progeny to entry development of Heterodera glycines. Phytopathology 55: 375-381.
Glazebrook J (2005) Contrasting mechanisms of defense against biotrophic and necrotrophic pathogens. Annu Rev Phytopathol 43: 205-227.
Jia, Y, Martin, GB (1999) Rapid transcript accumulation of pathogenesis-related genes during an incompatible interaction in bacterial speck disease-resistant tomato plants. Plant Mol Biol 40: 455-465.
Passardi F, et al (2004) Performing the paradoxical: how plant peroxidases modify the cell wall. Trends Plant Sci 9: 534-540.
Brucker E, et al. (2005) Rhg1 alleles from soybean Pl 437654 and Pl 88788 respond differentially to isolates of Heterodera glycines in the greenhouse. Theor Appl Genet 111: 44-49.
Cook et al., "Copy Number Variation of Multiple Genes at Rhg1 Mediates Nematode Resistance in Soybean", Science, 2012, pp. 1206-1209, vol. 338.
International Preliminary Report on Patentability in related application PCT/US2012/020375 mailed Jul. 18, 2013, 14 pages.
International Search Report and Written Opinion in related PCT Application No. PCT/US2012/020375 mailed Sep. 19, 2012, 22 pages.

* cited by examiner

| Affychip ID | Gene Model # | Fold-Upregulation (Microarray) | Description |
|---|---|---|---|
| AtWRKY23 | At2g47260 | N/A | WRKY transcription factor, induced in syncytia by *H. schachtii* in Arabidopsis |
| Gma.986.1.S1_at | Glyma15g04570.1 | 11.1 | Zinc finger (C2H2) transcription factor |
| Gma.15997.1.S1_at | Glyma15g06130.1 | 9.9 | Arabinogalactan protein |
| Gma.9553.1.A1_at | Glyma14g06080.1 | 8.08 | AP2 transcription factor, DREB family A2 |
| Gma.487.1.S1_at | Glyma18g43750.1 | 6.86 | AP2 transcription factor, DREB2B |
| GmaAffx.2469.1.S1_at | Glyma01g42500.2 | 6.92 | AP2 transcription factor, DDF1 |
| Gma.10412.1.A1_at | Glyma01g42440.1 | 5.92 | Nucleotide rhamonose synthase NRS/ER |
| GmaAffx.80271.1.S1_at | Glyma13g35100.1 | 3.77 | Extensin-like protein involved in seed germination |
| Gma.7147.1.A1_at | Glyma09g34110.1 | 2.98 | Acyltransferase 1, ATS1 |
| GmaAffx.7387.1.S1_at | Glyma18g18060.1 | 2.36 | Xanthine/uracil permease family protein |
| GmaAffx.45036.1.S1_at | Glyma19g04410.1 | 2.35 | Pollen protein, Ole e I family protein |

FIG. 4A (b)

| Gene Model Number | Promoter | GUS |
|---|---|---|
| Glyma15g04570.1 | -2164 → | -1 |
| Glyma15g06130.1 | -1781 → | -1 |
| Glyma14g06080.1 | -2586 → | -1 |
| Glyma18g43750.1 | -2496 → | -412 |
| Glyma01g42500.2 | -2130 → | -1 |
| Glyma01g42440.1 | -2361 → | +90 |
| Glyma13g35100.1 | -2068 → | -140 |
| Glyma09g34110.1 | -2167 → | -1 |
| Glyma18g18060.1 | -2499 → | -1 |
| Glyma19g04410.1 | -2510 → | -1 |
| Glyma03g35930.1(88182p) | -950 → | -1 |
| Glyma03g35920.1 (11004p) | -1980 → | -1 |

Table 1. Summary of *BAG6* Overexpression Phenotypes in Arabidopsis

| | $T_1$ Shoot Phenotypes[a] | | | | |
|---|---|---|---|---|---|
| Construct | WT-like (%) | Intermediate (%) | Severe (%) | $T_1$ lines (no.) | Total $T_1$ (no.) |
| *35S:AtBag6* | 43.9 | 40.9 | 15.2 | 6 | 66 |
| *35S:GmBag6A* | 42 | 52 | 6 | 12 | 100 |

| | $T_1$ Shoot Phenotypes[a] | | | | |
|---|---|---|---|---|---|
| Construct | WT-like (%) | Intermediate (%) | Severe (%) | $T_1$ lines (no.) | Total $T_1$ (no.) |
| *35S:AtBag6* | 42 | 46 | 12 | 8 | 50 |
| *35S:GmBag6A* | 38 | 50 | 12 | 8 | 66 |

[a]2-week-old seedlings; WT-like = indistinguishable from wildtype; intermediate = smaller rosettes, leaf lesions, malformed leaves; severe = dwarf, anthocyanin accumulation

FIG. 11

BPMV Control Plants

BPMV IQ-BAG domain overexpression plants

GmBag6A and 6B Gene Information

GmBag6A sequence from 7923R cDNA (3387 NT)(SEQ ID No. 162)

ATGAAGCTTGATCCATCCAAACCACCCTTTTCTTATGACCAACATTGGCCCTATGCCGGCAATTTTGGGCACCCTA
CTTCCCCACATTTCTGCTGTGGCCACAACAACTTCCCTTGTCATTATAGCTACATGCCTTCATATCCTCATGCCCC
TTCTCCAATGTACTATTCTGGAACTTGTCCTTCATATAGTGAACCATATTTTGTTCGTTATTCCCCACAACCACAT
TATACCATGGAGCTGCCTAGGTATGAAAATGACAAATGCATGCCCCGAGAGCTTCATTGTTCTGGTTCTGCTAATC
ATCCATGCAACCAAAAGGAAGGTAGAAGTGTGAAGATTGAAGAGCATGAACTGGATGGTGGAAAGAAAGAGAATGA
TGCTTTGGTCCCAATTCAGCTCAAGAATTATCCATATCCCTTAGTTTGGATTCCACAGGAGTACACAAGTAACAAA
CAGCTGAAAAATCCTAGTACAATGGAAGTTCGTGAACAAAACAAGCCTTCTAGTCTTGAGAATTCTAATGTTGATG
CACAGCCAACACAGGAGCCTATAGTATGGAATGGATGGCTTCCCTTCAATATAAAGGGTGCCCGGAACATGATTCA
CGATGGATATGGAACAAGAAACCAGAAACAGGAGTCTGGCAATAATAGAGGGGAATCTGAAAATGGAAAAATAGAC
CAGAAACATCAAAGTGAACAGAAGAGGTCAGAATTCCCATTCCCTATCTTCTGGTTGCCTTATTACAATAAGCAGG
AGGAGAGTGGAGAGACTAAGAACCAGGAGAAAAACATTTCTTCACCAAAAATTGTTGAGGAGGTACCCCATACATT
CAAATTTGTTCCAGTGAAGTCTCATGTTGATGAAGGTGGTAGGAACGGAACCGGATCAAATCAAGCTGATCAATCC
ACAAATACAAATGCTTCTTCGGATGCTGTAGAGAAAGTGAATAATGCCAGAAGCATACCTGTGAAGCAGATAGAAT
CCCACGAAGGAAAAAATGTTTCTCTCGATCAAATGGAAGAGAATGTGACACAAAAGGACTCTTGCACTGGGGACAA
AAAGAGACAATCTACATCTTCACCTAAAGGATCCAAGTTACCTCCGGTTTGTCTGAGAGTTGATCCACTACCAAGG
AAGAAAAATGGCCTCGGGAGTTCGAGTTCGAGGTCCCCAAGTCCACCTTCATCAAAAGGGAATTCCCAAGCTACAA
CTGGTGAAACATTCAAGACTCCTGTGAGTGGCACACGTGACAAGGCTCAGCCAAATTTGAATCATCAGAATGCTCC
AAACACCAGTGAGAAAGTTAAACCAAAGGAGAACACCATTCCGGTGTCAGAATGCATGACTAATGAAAACAAGGGT
GTTGACTGTAGGGATGGATGTCAGAGCCAGATGAAAGTAAACATACCCAGTAAAGGTCTGAAAGGGGCAAGGGAAA
CATGTCCAGATGATGATGACTATAAGACTGAAGATAAAAAGGCAGAGAAAGGAGCAGAAAATATGATGGAGGAAAC
TACTGAATCAAGGGAAGAGAAGGATTCAAGCACACGAACTGATGCAGGTCGAAAAGATGGAAGAGTTTTGTCAGAT
GCAGATGCTGCTGTTTTGATACAAGCTGCATATCGCAGTTATCTAGTTAGAAAATGGGAACCGTTGAAGACGTTGA
AGCAGATAGATGAAGTCAGGAAGGAGGTGACTCGTGTTCAAGGCCGTGTTCAAGCTTTTGAGAGATCTCCCGAACT
TCAAAATGATGACAAACAAAAAATTGCAATTGGAGAGACCATAATGAGACTCCTGCTGAAGTTGGATACTATACTG
GGTTTGCATCCAAGTTTCAGGGAGATCAGAAAATCCTTGGCTAGGGAGCTCATAATCTTGCAAGAAAGGCTTGATT
CTATAATGGCCAAGAAACCTCAGCAGCAGATGCCGGATGTTCAGGAACACGTTGAAATCACTCCAATGAACATGCA
GAGTGAAGAACATGTGCAAAAGCAGCAAGAAGAAAAGGTTGCTGTACCAGAGGATTCAGCTGAAGGCACTAGGGAT
GATGTAAAAGGTCCTTGTGCTAATGATGGTGGAAGTGAATCTCAGTCACCAGTTGATCCTCCATCAATTGAGGGAG
CAGAGTCTGTTGCACTTCCAAATGGCTCAGATAATGAGGACACCAGCCAAGTGGTTACATCTGATGCATTGAATTC
TTCAAGTGATCTGTCTGAGAGTGACAAAATGGCTGTGGAATCCGAAGCTAAATCAGAAGCGAAAGACAATCCGATT
GCGGAAGACATTCCCATTGAGGTTGATAAATTGGACAAGACTGTTTGGGAAGAATTGCCTGTGGGAGTTATTGATG
AAGATATCAATGATGTTAGTATTGAGAAGGAAGAACATGATGATGTTAGATCGGGAAGTCTCCCAGCCATGGTGAA
TGATTCGGCACAAGAAGGATTAAATTCAGAGAGCTATGCAATGATGGAACTGCCATTGGGATTACATGAGGAGCAT
GAAAGGGACAATGAAATGAATATTTCTAATGGAGAAACACGGTCTGAGAATGAGATATTTATTGAGGAGCTTCCTG
TGGGACTGCACGATGAAGATACAACAATATCTAAAGATAAGAGGGATGGTCAAGCTAAGCCTAAAACATATAAAGA
GGTTCGACTAGCTCAAGAAGGGGAATGCAATGCAGATGAGGAAACAAGTTCTTCCACAGATGACACTGCCAACGAA
ACTCAACTAGAGCAACAGCAGAAGCTGAAAGAGCAAGAAGAGGTGCATTCTTCTAGGGAATCAGATGGCTGGGTAA
AAATTGAGTACCCGGAAGAAGGTGAACTCAATGGTGATGCACCAATGGATATAAGAGTTGAGTGCAAGTCAGGTGA
GGAAGCTGGAACTGATACTAAGTTGCTTCCTTTAACAACACAAGTCAGTGATAATGAACCAGAAAATGAAGATGTA
TTCTCAGAAGCAAATTATGTAAATAACAAATTAACCGAGCCAATGGAGTTTGTACCTTCCAATGACACACAGAAGG
AGGAGACACCAGAGATGGTTGCTGAAGAGGCAATTATCCCTGATGATAAAGACACAGAAAATTTGGCCAAAGAGAA
AACTGAAGTATCTGCAGAACCACCACCTGCACTGCAAGACCGAGGGTTAAACGGTGACTCGAAGTTATTAGAAGAG
AATGAGAAGTTAAGGGAGATGATGAAGAAGTTGCTTGAAGCCGGGAATGAACAGTTAAGCGTGATATCAGATTTGA
CTGTCAGAGTGAAGGACTTGGAGAAGAAATTAGCCAGGAGAAGGAGTAAGAGAGTGAAGACAAAACAGTATAGACC
CGCAGCTTCCAAAATGTCTACCCATGAAATGAAATCCTCCTAA

FIG. 15A

Protein (1129 AA) (SEQ ID No. 163)

MKLDPSKPPFSYDQHWPYAGNFGHPTSPHFCCGHNNFPCHYSYMPSYPHAPSPMYYSGTCPSYSEPYFVRYSPQPH
YTMELPRYENDKCMPRELHCSGSANHPCNQKEGRSVKIEEHELDGGKKENDALVPIQLKNYPYPLVWIPQEYTSNK
QLKNPSTMEVREQNKPSSLENSNVDAQPTQEPIVWNGWLPFNIKGARNMIHDGYGTRNQKQESGNNRGESENGKID
QKHQSEQKRSEFPFPIFWLPYYNKQEESGETKNQEKNISSPKIVEEVPHTFKFVPVKSHVDEGGRNGTGSNQADQS
TNTNASSDAVEKVNNARSIPVKQIESHEGKNVSLDQMEENVTQKDSCTGDKKRQSTSSPKGSKLPPVCLRVDPLPR
KKNGLGSSSSRSPSPPSSKGNSQATTGETFKTPVSGTRDKAQPNLNHQNAPNTSEKVKPKENTIPVSECMTNENKG
VDCRDGCQSQMKVNIPSKGLKGARETCPDDDDYKTEDKKAEKGAENMMEETTESREEKDSSTRTDAGRKDGRVLSD
ADAAVLIQAAYRSYLVRKWEPLKTLKQIDEVRKEVTRVQGRVQAFERSPELQNDDKQKIAIGETIMRLLLKLDTIL
GLHPSFREIRKSLARELIILQERLDSIMAKKPQQQMPDVQEHVEITPMNMQSEEHVQKQQEEKVAVPEDSAEGTRD
DVKGPCANDGGSESQSPVDPPSIEGAESVALPNGSDNEDTSQVVTSDALNSSSDLSESDKMAVESEAKSEAKDNPI
AEDIPIEVDKLDKTVWEELPVGVIDEDINDVSIEKEEHDDVRSGSLPAMVNDSAQEGLNSESYAMMELPLGLHEEH
ERDNEMNISNGETRSENEIFIEELPVGLHDEDTTISKDKRDGQAKPKTYKEVRLAQEGECNADEETSSSTDDTANE
TQLEQQQKLKEQEEVHSSRESDGWVKIEYPEEGELNGDAPMDIRVECKSGEEAGTDTKLLPLTTQVSDNEPENEDV
FSEANYVNNKLTEPMEFVPSNDTQKEETPEMVAEEAIIPDDKDTENLAKEKTEVSAEPPPALQDRGLNGDSKLLEE
NEKLREMMKKLLEAGNEQLSVISDLTVRVKDLEKKLARRRSKRVKTKQYRPAASKMSTHEMKSS*

Based on W82 and Phytozome

GmBag6A: Glyma07g06750 (Based on W82 and Phytozome)

gDNA (3858 NT)(SEQ ID No. 164)

ATGAAGCTTGATCCATCCAAACCACCCTTTTCTTATGACCAACATTGGCCCTATGCCGGCAATTTTGGGCACCCTA
CTTCCCCACATTTCTGCTGTGGCCACAACAACTTCCCTTGTCATTATAGCTACATGCCTTCATATCCTCATGCCCC
TTCTCCAATGTACTATTCTGGAACTTGTCCTTCATATAGTGAACCATATTTTGTTCCTTATTCCCCACAACCACAT
TATACCATGGAGCTGCCTAGGTATGAAAATGACAAATGCATGCCCCGAGAGCTTCATTGTTCTGGTTCTGCTAATC
ATCCATGCAACCAAAAGGAAGGTAGAAGTGTGAAGATTGAAGAGCATGAACTGGATGGTGGAAAGAAAGAGAATGA
TGCTTTGGTCCCAATTCAGCTCAAGAATTATCCATATCCCTTAGTTTGGATTCCACAGGAGTACACAAGTAACAAA
CAGCTGAAAAATCCTAGTACAATGGAAGTTCGTGAACAAAACAAGCCTTCTAGTCTTGAGAATTCTAATGTTGATG
CGCAGCCAACACAGGAGCCTATAGTATGGAATGGATGGCTTCCCTTCAATATAAAGGGTGCCCGGAACATGATTCA
CGATGGATATGGAACAAGAAACCAGAAACAGGAGTCTGGCAATAATAGAGGGGAATCTGAAAATGGAAAAATAGAC
CAGAAACATCAAAGTGAACAGAAGAGGTCAGAATTCCCATTCCCTATCTTCTGGTTGCCTTATTACAATAAGCAGG
AGGAGAGTGGAGAGACTAAGAACCAGGAGAAAAACATTTCTTCACCAAAAATTGTTGAGGAGGTACCCCATACATT
CAAATTTGTTCCAGTGAAGTCTCATGTTGATGAAGGTGGTAGGAACAGAACCGGATCAAATCAAGCTGATCAATCC
ACAAATACAAATGCTTCTTCGGATGCTGTAGAGAAAGTGAATAATGCCAGAAGCATACCTGTGAAGCAGATAGAAT
CCCACGAAGGAAAAAATGTTTCTCTCGATCAAATGGAAGAGAATGTGACACAAAAGGACTCTTGCACTGGGGACAA
AAAGAGACAATCTACATCTTCACCTAAAGGATCCAAGTTACCTCCGGTTTGTCTGAGAGTTGATCCACTACCAAGG
AAGAAAAATGGCCACGGGAGTTCGAGTTCGAGGTCCCCAAGTCCACCTTCATCAAAAGGGAATTCCCAAGCTACAA
CTGGTGAAACATTCAAGACTCCTGTGAGTGGCACACATGACAAGGCTCAGCCAAATTTGAATCATCAGAATGCTCC
AAACACCAGTGAGAAAGTTAAACCAAAGGAGAACACCATTCCGGTGTCAGAATGCATGACTAATGAAAACAAGGGT
GTTGACTGTAGGGATGGATGTCAGAGCCAGATGAAAGTAAACATACCCAGTAAAGGTCTGAAAGGGGCAAGGGAAA
CATGTCCAGATGATGATGACTATAAGACTGAAGATAAAAAGGCAGAGAAAGGAGCAGAAAATATGATGGAGGAAAC
TACTGAATCAAGGGAAGAGAAGGATTCAAGCACACGAACTGATGCGGGTCGAAAAGATGGAAGAGTTTTGTCAGAT
GCAGATGCTGCTGTTTTGATACAAGCTGCATATCGCAGTTATCTAGTTAGAAAATGGGAACCGTTGAAGAAGTTGA
AGCAGATAGATGAAGTCAGGAAGGAGGTGACTCGTGTTCAAGGCCGTGTTCAAGCTTTTGAGAGATCTCCCGAACT
TCAAAATGATGACAAACAAAAAATTGCAATTGAAGAGACCATAATGAAACTCCTGCTGAAGTTGGATACTATACTG
GTACTTGTCAGATTACCCTATTTACTTATGATGAAATCTGTAGTCCACTTTTTGATATTCTTTGATTCATTGACAA
TAAACATTACACAGAATATTAAAGTGTTTTGATTTTGTATTTTACGGTCAAAATTCTCCTACGTATTTATTAGCTA
ATCTTAATTAATTGAGATTCATGACATCTGTGATAGAGTTTTGATATTATCTTATGATCTTATCTTGGGATATCAT
GGCATCAGTGACATAGTTTTGATATTTCTTCATTTTATGGATATGGAAAATGAATTTTTTTAAGCTATTAAAAAGC
ACTCTGCTTAACCGCATTTGAACTAAGATGAGCATTTTGATCTACACAGATAAGTGTTGTTTGTGGTTTGTCTGAG
CTATTAGTCATTGATCATCTTAATTATGATGGTTAATATAGTTCTCCTTTTTTGTTCAATGTTATGCTTACATTCG
TTCAATCTATATCAGGGTTTGCATCCAAGTTTCAGGGAGATCAGAAAATCCTTGGCTAGGGAGCTCATAATCTTGC
AAGAAAGGCTTGATTCTATAATGGCCAAGAAACCTCAGCAGCAGATGCCGGATGTTCAGGAACACGTTGAAATCAC
TCCAATGAACATGCAGAGTGAAGAACATGTGCAAAAGCAGCAAGAAGAAAAGGTTGCTGTACCAGAGGATTCAGCT
GAAGGCACTAGGGATGATGTAAAAGGTCCTTGTGCTAATGATGGTGGAAGTGAATCTCAGTCACCAGTTGATCCTC
CATCAAATGAGGGAGCAGAGTCTGTTGCACTTCCAAATGGCTCAGATAATGAGGACACCAGCCAAGTGGTTACATC

FIG. 15B

TGATGCATTGAATTCTTCAAGTGATCTGTCTGAGAGTGACAAAATGGCTGTGGAATCCGAAGCTAAATCAGAAGTG
AAAGACAATCCGATTGCGGAAGACATTCCCATTGAGGTTGATAAATTGGACAAGACTGTTTGGGAAGAATTGCCTG
TGGGAGTTATTGATGAAGATATCAATGATGTTAGTATTGAGAAGGAAGAACATGATGATATTAGATCGGGAAGTCT
CCCAGCCATGGTGAATGATTCGGCACAAGAAGGATTAAATTCAGAGAGCTATGCAATGATGGAACTGCCATTGGGA
TTACATGAGGAGCATGAAAGGGACAATGAAATGAATATTTCTAATGGAGAAACACGGTCTGAGAATGAGATATTTA
TTGAGGAGCTTCCTGTGGGACTGCACGATGAAGATACAACAATATCTAAAGATAAGAGGGATGGTCAAGCTAAGCC
TAAAACATATAAAGAGGTTCGACTAGCTCAAGAAGGGGAATGCAATGCAGATGAGGAAACAAGTTCTTCCACAGAT
GACACTGCCAACGAAACTCAACTAGAGCAACAGCAGAAGCTGAAAGAGCAAGAAGAGGTGCATTATTCTAGGGAAT
CAGATGGCTGGGTAAAAATTGAGTACCCGGAAGAAGGTGAACTCAATGGTGATGCACCAATGGATATAAGAGTTGA
GTGCAAGTCAGGTGAGGAAGCTGGAACTGATACTAAGTTGCTTCCTTTAACAACACAAGTCAGTGATAATGAACCA
GAAAATGAAGATGTATTCTCAGAAGCAAATTATGTAAATAACAAATTAACCGAGCCAATGGAGTTTGTACCTTCCA
ATGACACACAGAAGGAGGAGACACCAGAGATGGTTGCTGAAGAGGCAATTATCCCTGATGATAAAGACACAGAAAA
TTTGGCCAAAGAGAAAACTGAAGTATCTGCAGAACCACCACCTGCATTGCAAGACCGAGGGTTAAACGGTGACTCG
AAGTTATTAGAAGAGAATGAGAAGTTAAGGGAGATGATGAAGAAGTTGCTTGAAGCCGGGAATGAACAGTTAAGCG
TGATATCAGATTTGACTGTCAGAGTGAAGGACTTGGAGAAGAAATTAGCCAGGAGAAGGAGTAAGAGAGTGAAGAC
AAAACAGTATAGACCCGCAGCTTCCAAAATGTCTACCCATGAAATGAAATCCTCCTAA cDNA (2991 NT)(SEQ ID No. 165)

ATGAAGCTTGATCCATCCAAACCACCCTTTTCTTATGACCAACATTGGCCCTATGCCGGCAATTTTGGGCACCCTA
CTTCCCCACATTTCTGCTGTGGCCACAACAACTTCCCTTGTCATTATAGCTACATGCCTTCATATCCTCATGCCCC
TTCTCCAATGTATGAAAATGACAAATGCATGCCCCGAGAGCTTCATTGTTCTGGTTCTGCTAATCATCCATGCAAC
CAAAAGGAAGGTAGAAGTGTGAAGATTGAAGAGCATGAACTGGATGGTGGAAAGAAAGAGAATGATGCTTTGGTCC
CAATTCAGCTCAAGAATTATCCATATCCCTTAGTTTGGATTCCACAGGAGTACACAAGTAACAAACAGCTGAAAAA
TCCTAGTACAATGGAAGTTCGTGAACAAAACAAGCCTTCTAGTCTTGAGAATTCTAATGTTGATGCGCAGCCAACA
CAGGAGCCTATAGTATGGAATGGATGGCTTCCCTTCAATATAAAGGGTGCCCGGAACATGATTCACGATGGATATG
GAACAAGAAACCAGAAACAGGAGTCTGGCAATAATAGAGGGGAATCTGAAAATGGAAAAATAGACCAGAAACATCA
AAGTGAACAGAAGAGGTCAGAATTCCCATTCCCTATCTTCTGGTTGCCTTATTACAATAAGCAGGAGGAGAGTGGA
GAGACTAAGAACCAGGAGAAAAACATTTCTTCACCAAAAATTGTTGAGGAGGTACCCCATACATTCAAATTTGTTC
CAGTGAAGTCTCATGTTGATGAAGGTGAGAAAGTGAATAATGCCAGAAGCATACCTGTGAAGCAGATAGAATCCCA
CGAAGGAAAAAATGTTTCTCTCGATCAAATGGAAGAGAATGTGACACAAAAGGACTCTTGCACTGGGGACAAAAAG
AGACAATCTACATCTTCACCTAAAGGATCCAAGTTACCTCCGGTTTGTCTGAGAGTTGATCCACTACCAAGGAAGA
AAAATGGCCACGGGAGTTCGAGTTCGAGGTCCCCAAGTCCACCTTCATCAAAAGGGAATTCCCAAGCTACAACTGG
TGAAACATTCAAGACTCCTAGCCAGATGAAAGTAAACATACCCAGTAAAGGTCTGAAAGGGGCAAGGGAAACATGT
CCAGATGATGATGACTATAAGACTGAAGATAAAAAGGCAGAGAAAGGAGCAGAAAATATGATGGAGGAAACTACTG
AATCAAGGGAAGAGAAGGATTCAAGCACACGAACTGATGCGGGTCGAAAAGATGGAAGAGTTTTGTCAGATGCAGA
TGCTGCTGTTTTGATACAAGCTGCATATCGCAGTTATCTAGTTAGAAAATGGGAACCGTTGAAGAAGTTGAAGCAG
ATAGATGAAGTCAGGAAGGAGGTGACTCGTGTTCAAGGCCGTGTTCAAGCTTTTGAGAGATCTCCCGAACTTCAAA
ATGATGACAAACAAAAAATTGCAATTGAAGAGACCATAATGAAACTCCTGCTGAAGTTGGATACTATACTGGGTTT
GCATCCAAGTTTCAGGGAGATCAGAAAATCCTTGGCTAGGGAGCTCATAATCTTGCAAGAAAGGCTTGATTCTATA
ATGGCCAAGAAACCTCAGCAGCAGATGCCGGATAGTGAAGAACATGTGCAAAAGCAGCAAGAAGAAAAGGTTGCTG
TACCAGAGGATTCAGCTGAAGGCACTAGGGATGATGTAAAAGGTCCTTGTGCTAATGATGGTGGAAGTGAATCTCA
GTCACCAGTTGATCCTCCATCAAATGAGGGAGCAGAGTCTGTTGCACTTCCAAATGGCTCAGATAATGAGGACACC
AGCCAAGTGGTTACATCTGATGCATTGAATTCTTCAAGTGATCTGTCTGAGAGTGACAAAATGGCTGTGGAATCCG
AAGCTAAATCAGAAGTGAAAGACAATCCGATTGCGGAAGACATTCCCATTGAGGTTGATAAATTGGACAAGACTGT
TTGGGAAGAATTGCCTGTGGGAGTTATTGATGAAGATATCAATGATGTTACCATGGTGAATGATTCGGCACAAGAA
GGATTAAATTCAGAGAGCTATGCAATGATGGAACTGCCATTGGGATTACATGAGGAGCATGAAAGGGACAATGAAA
TGAATATTTCTAATGGAGAAACACGGTCTGAGAATGAGATATTTATTGAGGAGCTTCCTGTGGGACTGCACGATGA
AGATACAACAATATCTAAAGATAAGAGGGATGGTCAAGCTAAGCCTAAAACATATAAAGAGGTTCGACTAGCTCAA
GAAGGGGAATGCAATGCAGATGAGGAAACAAGTTCTTCCACAGATGACACTGCCAACGAAACTCAACTAGAGCAAC
AGCAGAAGCTGAAAGAGCAAGAAGAGGTGCATTATTCTAGGGAATCAGATGGCTGGGTAAAAATTGAGTACCCGGA
AGAAGGTGAACTCAATGGTGATGCACCAATGGATATAAGAGTTGAGTGCAAGTCAGGTGAGGAAGCTGGAACTGAT
ACTAAGTTGCTTCCTTTAACAACACAAGTCAGTGATAATGAACCAGAAAATGAAGATGTATTCTCAGAAGCAAATT
ATGTAAATAACAAATTAACCGAGCCAATGGAGTTTGTACCTTCCAATGACACACAGAAGGAGGAGACACCAGAGAT
GGTTGCTGAAGAGGCAATTATCCCTGATGATAAAGACACAGAAAATTTGGCCAAAGAGAAAACTGAAGTATCTGCA
GAACCACCACCTGCATTGCAAGACCGAGGGTTAAACGGTGACTCGAAGTTATTAGAAGAGAATGAGAAGTTAAGGG
AGATGATGAAGAAGTTGCTTGAAGCCGGGAATGAACAGTTAAGCGTGATATCAGATTTGACTGTCAGAGTGAAGGA
CTTGGAGAAGAAATTAGCCAGGAGAAGGAGTAAGAGAGTGAAGACAAAACAGTATAGACCCGCAGCTTCCAAAATG
TCTACCCATGAAATGAAATCCTCCTAA

FIG. 15C

Protein (996 AA)(SEQ ID No. 166)

MKLDPSKPPFSYDQHWPYAGNFGHPTSPHFCCGHNNFPCHYSYMPSYPHAPSPMYENDKC
MPRELHCSGSANHPCNQKEGRSVKIEEHELDGGKKENDALVPIQLKNYPYPLVWIPQEYT
SNKQLKNPSTMEVREQNKPSSLENSNVDAQPTQEPIVWNGWLPFNIKGARNMIHDGYGTR
NQKQESGNNRGESENGKIDQKHQSEQKRSEFPFPIFWLPYYNKQEESGETKNQEKNISSP
KIVEEVPHTFKFVPVKSHVDEGEKVNNARSIPVKQIESHEGKNVSLDQMEENVTQKDSCT
GDKKRQSTSSPKGSKLPPVCLRVDPLPRKKNGHGSSSSRSPSPPSSKGNSQATTGETFKT
PSQMKVNIPSKGLKGARETCPDDDDYKTEDKKAEKGAENMMEETTESREEKDSSTRTDAG
RKDGRVLSDADAAVLIQAAYRSYLVRKWEPLKKLKQIDEVRKEVTRVQGRVQAFERSPEL
QNDDKQKIAIEETIMKLLLKLDTILGLHPSFREIRKSLARELIILQERLDSIMAKKPQQQ
MPDSEEHVQKQQEEKVAVPEDSAEGTRDDVKGPCANDGGSESQSPVDPPSNEGAESVALP
NGSDNEDTSQVVTSDALNSSSDLSESDKMAVESEAKSEVKDNPIAEDIPIEVDKLDKTVW
EELPVGVIDEDINDVTMVNDSAQEGLNSESYAMMELPLGLHEEHERDNEMNISNGETRSE
NEIFIEELPVGLHDEDTTISKDKRDGQAKPKTYKEVRLAQEGECNADEETSSSTDDTANE
TQLEQQQKLKEQEEVHYSRESDGWVKIEYPEEGELNGDAPMDIRVECKSGEEAGTDTKLL
PLTTQVSDNEPENEDVFSEANYVNNKLTEPMEFVPSNDTQKEETPEMVAEEAIIPDDKDT
ENLAKEKTEVSAEPPPALQDRGLNGDSKLLEENEKLREMMKKLLEAGNEQLSVISDLTVR
VKDLEKKLARRRSKRVKTKQYRPAASKMSTHEMKSS*

GmBag6B:Glyma16g03320 gDNA (3850 NT) (SEQ ID No. 167)

ATGAAGCTTGATCCATCCAAACCACCCTTTTCTTATGACCAACATTGGCCATATGCTGGCAACTTAGGGCACCCTA
TTCCCCCACATTTCTGCTGTGGCCACAACAACTTCCCTTGTCATTATAGCTACATGCCTTCAAATCCTCATGCTCC
TTCTCCAATGTACTATTCTGGAACTTGTCCTTCATATAGTGAACCATATTTTGTTCCTTATTCACTACAACCACAT
TATACTATGGATCTGCCCAGGTATGAATATGACAAATTTATGCCCCGAGAGCATCATTGTTGTGGCTGTCCTAATC
ATCCATGCAGCCAAAAGGAAGGTAGAAGTGTGAAGATTGAAGAACATGAACCTGATGGTGGAAAGAAAGTGAATGA
TGCTTTGGCTCCAATCCAGCTCAAGAATTACCCATATCCCTTAGTTTGGATTCCACAGGAGTACACAAGTAACAAA
CAGCTGAAGAATCCTAATACAATGGAAGTTGGGGAACAAGACAAGTCTCCTCGTTTTGAGAATTCTAATGCTGATG
CACAGCCAGCACAGGATCCTAGAGTATGGAATGGATGGCTTCCCTTCAATATAAAGGGTGCCCCGAACGTGATTCA
CGATGGATATGGAACAAGAAACCAGAAACAGGAGTCTGGCAATAATAGAGGGGAATCTGAAGATGGAAAAGTGGAC
CAGAAACATCAAAGTGAACAGAATAGGTCAGAATTTCCATTCCCTATCTTCTGGTTGCCTTATTACAATAAGCCGG
AGGAGGGTGGTGAGACTAAAAACCAGGAGAAGAATACTTTTTCACCAAAAGTTATTGAGGAGGTACCCCATACATT
AAAATCTGTTCCAGCAAAGTCTCATGTTGATGAAGGTGGTAGGAATAGGAACGGAACCGGATCAAATCAAGCTGAA
TACACAAATACAAATGCTGCGGATGTTGTAGAGAAAGTGACTAATGCCAGAAGCATACCTGTGAAGCAAATGGAAG
AGAATGTGACAA
AAAAGGACTCCTGCACTGGTGACAAAAAGAGGCAATCTGCATCTTCACCAAAAGGATCCAAGTTACCTCCGGTTTG
TCTGAGAGTTGATCCACTACCAAGGAAGAAAAATGGCAACGGGAGTTTGAGTTTGAGTTCAAGGTCGAGGTCCCCA
AGTCCACCTTCATCAAAAGGGCAATCCCAAGCTACAACTGGTGAAACATTCAAGACTCCTGTGAGTGGAACACATG
ATAAAGGTCAGCCAAATTCGGATCATCAGAATGGGCCAACAAACACCAGTGAGAGAGTTAAACCAAAGGAGAAGAC
CATTCCGGTGTCAGAAATATGCAAGACTAATGAAAACCAGGGTGTTGAGTGTAGGGATGGATGTCAAAGCCAGATA
AATGTAAACATACCTAGTGAAGATCCGAAAGGGACAAGGGGAACATGTCCAGATGGTGATGACTTCAAGACTGAAG
ATAAAAAGGCAGATAAAGGGGCAGATAAAATGAGGGAGAAAACTGCAGAACTAAAAGATGTGAAGGATTCAAGCGC
ACAAACTGACGCAGGTCAAAAGGAGGTAAGAGTTCTGTCAGATGCAGATGCTTCTGTTTTGATACAAGCTGCATAT
CGCGGACATCAAGTTAGAAAATGGGAAGCATTGAAGAAGTTGAAGCAGATAGATGAAGTCAGGAAGGAGGTGACTG
ATGTTCGAGACCGTGTTCAAGCCTTTGAGAGATCTTCTGATCTTCAAAATGATGACAAGCAAAAAATTGCAATTGG
AGAGACCATTATGAGACTCCTGCTGAAGTTGGATACTATACAGGTACATGTCAGATAACCGTTACTTAAAATGAAA
TCAGTAATGCATTTTTTATATTTTTGATTCATTGACAATAAACATTACATGGAATATGAAATTGTTTTGCTTTTGT
ACTTCAGTAAAAAGATTCCATTTTTATTTATTAGGTAATCTTAATTGAGATATCATGACATCAGAGTATAGTTTTG
ATATTAGCTAATCTTAGTTAGATATCATGACATCTGTAATATAGTTTTGATATTTCTTCATTCATGGATATGGGTA
GTGACTTTTACATGCCTAATTACCTGTTACAACTTACAAGCACTCCGCATTTGAACAAAGATTAGCATTTTGATCT
GCACAGATATGAATGTTGGTTGTGGTTTGTCTGAGCTATTAATCGTTGTTCATCTTATTTATGATTTTTTTTAATT
TAGTTATACTTCCTTGTTCAATGTTATGCTTACATATCGCTCAACATTTATATCAGGGTTTGCATCCAAGTATCAG
GGAGATCAGAAAATCCTTGGCTAGAGAGCTGACAATTTTGCAAGAAAGGCTTGATTATATAATGGCCAAGAAACCT
CAGCAGCAGGTGCAGGATTTCAATGTTCAGGAACATGTTGAAGTCACTCCAATGAATATGCAGAATGAAGAACAAG
TTGCTGTACCAGCAGACTCAGCTGAAGGCATTAGTGATGATGCAAAAGGTCCTTGTGCTAATGTTGGTGGAAGTGA

FIG. 15D

ATCCCAGTCACCAGTTGATCCTACATCAGATAAGGGAGCAGAGTCTGTTGTGCTTCCGAATGGCTCGCATAATGAT
GATACTAGCCAAGTGGTTACAGATGACACATTGAATTCTACAAGTGATCTGTCTGAGACGGACAAAATGGCTGTGG
AACCCGAAGCTAAATCAGAAGCGAAAGACATTCCCACTGCGGAAGACATTCTAAACGAGGTTGATAAATTGTATAA
GACTGTTTTGGAAGAATTTCCTGTGGGAGTTGTTGATGAAGATATCGATGATGTTATTATTGAGAAGGAAGAACAA
GATGATGTTAGTTCTGGAAGTCTCCAAGCCATGGTGGATGATTCGGCACGAGATGGATTAGAGAACCATGCAATGA
TGGAAATGCCAGTGGGATTATTTGATGAGGATGAAAGGAACAATGAAATGAATATTTCTAAAGAGGGAACACAAAC
TGAGAATGACATATTTATTGAGCTTCCTATGGGACTACTTGATGAGGATACAGCAATATCTGAAGTTAAGAAGCAC
GATCGAGCTAAGCCTAAAACATATAAAGAGGTTCTACTAGCTCAAGAAGGGGAATGCAATGCAGATGAGAAAACAA
GTTCTTCAACAGATAACACTGCGAACGAAACTCAACTAGGGCAACAGCAGAAGCTGGAAGAGCAAAAAGAGGTGCA
TTCTTCTGGGGAATGCTGGGTGAAAATCAAGTACCAGGAAGAAGGTGAACTCAATGGTGATGCACCAATAGATATA
AGAACTGAGTGTAAGTCAGGTGAGGAAGTTGAAAATGATACTAAGTTACCTCCTTTGACAACACAAGTCAATGATC
ATGGACCAGGAAATGAAGATGTATGCTCAAAAGCAAATGATGTAAATAACATATCGCCCGAGGCCAAGCCAATGGA
GTTAGTACCTTCCAATGAAACACAGAAGGAGGAGGAACCAGAAGAGAAGATTGCACTTAGGGAGACACAAGAGATG
GTTACTGAGCAGGCAATTGGTGCTGATGATAAAGACCCAGAAGCTTTGTTTAAAGAGAAAACCGAACTATCTTCGC
CTCCACCTGCATTACAAGAACCTGAGCTGCCTGCGGCCATGCGCGATGGAGAGTTCAACGGTGACACGAAGTTACT
GGAAGAGAATGAGAATTTAAGGGAGATGATGAAGAAGTTGCTTGAAGCCGGGAATGAACAGTTAAGCGTGATAACA
AATTTGACTGGCAGAGTGAAGGACTTGGAGAAGAAACTAGCCAGGAGCAGGAGTAAGAGAGTGAAGACAAAACGGT
ATAGACCAGCAACTTCCAAAATGTCTTGCATGAAATGA cDNA (2715 NT) (SEQ ID No. 168)

ATGAAGCTTGATCCATCCAAACCACCCTTTTCTTATGACCAACATTGGCCATATGCTGGCAACTTAGGGCACCCTA
TTCCCCCACATTTCTGCTGTGGCCACAACAACTTCCCTTGTCATTATAGCTACATGCCTTCAAATCCTCATGCTCC
TTCTCCAATGTATGAATATGACAAATTTATGCCCCGAGAGCATCATTGTTGTGGCTGTCCTAATCATCCATGCAGC
CAAAAGGAAGGTAGAAGTGTGAAGATTGAAGAACATGAACCTGATGGTGGAAAGAAAGTGAATGATGCTTTGGCTC
CAATCCAGCTCAAGAATTACCCATATCCCTTAGTTTGGATTCCACAGGAGTACACAAGTAACAAACAGCTGAAGAA
TCCTAATACAATGGAAGTTGGGGAACAAGACAAGTCTCCTCGTTTTGAGAATTCTAATGCTGATGCACAGCCAGCA
CAGGATCCTAGAGTATGGAATGGATGGCTTCCCTTCAATATAAAGGGTGCCCCGAACGTGATTCACGATGGATATG
GAACAAGAAACCAGAAACAGGAGTCTGGCAATAATAGAGGGGAATCTGAAGATGGAAAAGTGGACCAGAAACATCA
AAGTGAACAGAATAGGTCAGAATTTCCATTCCCTATCTTCTGGTTGCCTTATTACAATAAGCCGGAGGAGGGTGGT
GAGACTAAAAACCAGGAGAAGAATACTTTTTCACCAAAAGTTATTGAGGAGGTACCCCATACATTAAAATCTGTTC
CAGCAAAGTCTCATGTTGATGAAGGTGGTAGGAATAGGAACGGAACCGGATCAAATCAAGCTGAATACACAAATAC
AAATGCTGCGGATGTTGTAGAGAAAGTGACTAATGCCAGAAGCATACCTGTGAAGCAAATGGAAGAGAATGTGACA
AAAAAGGACTCCTGCACTGGTGACAAAAAGAGGCAATCTGCATCTTCACCAAAAGGATCCAAGTTACCTCCGGTTT
GTCTGAGAGTTGATCCACTACCAAGGAAGAAAAATGGCAACGGGAGTTTGAGTTTGAGTTCAAGGTCGAGGTCCCC
AAGTCCACCTTCATCAAAAGGGCAATCCCAAGCTACAACTGGTGAAACATTCAAGACTCCTGTGAGTGGAACACAT
GATAAAGATCCGAAAGGGACAAGGGGAACATGTCCAGATGGTGATGACTTCAAGACTGAAGATAAAAAGGCAGATA
AAGGGGCAGATAAAATGAGGGAGAAAACTGCAGAACTAAAAGATGTGAAGGATTCAAGCGCACAAACTGACGCAGG
TCAAAAGGAGGTAAGAGTTCTGTCAGATGCAGATGCTTCTGTTTTGATACAAGCTGCATATCGCGGACATCAAGTT
AGAAAATGGGAAGCATTGAAGAAGTTGAAGCAGATAGATGAAGTCAGGAAGGAGGTGACTGATGTTCGAGACCGTG
TTCAAGCCTTTGAGAGATCTTCTGATCTTCAAAATGATGACAAGCAAAAAATTGCAATTGGAGAGACCATTATGAG
ACTCCTGCTGAAGTTGGATACTATACAGGGTTTGCATCCAAGTATCAGGGAGATCAGAAAATCCTTGGCTAGAGAG
CTGACAATTTTGCAAGAAAGGCTTGATTATATAATGGCCAAGAAACCTCAGCAGCAGGTGCAGGATTTCAATGTTC
AGGAACATGTTGAAGTCACTCCAATGAATATGCAGAATGAAGAACAAGTTGCTGTACCAGCAGACTCAGCTGAAGG
CATTAGTGATGATGCAAAAGGTCCTTGTGCTAATGTTGGTGGAAGTGAATCCCAGTCACCAGTTGATCCTACATCA
GATAAGGGAGCAGAGTCTGTTGTGCTTCCGAATGGCTCGCATAATGATGATACTAGCCAAGTGGTTACAGATGACA
CATTGAATTCTACAAGTGATCTGTCTGAGACGGACAAAATGGCTGTGGAACCCGAAGCTAAATCAGAAGCGAAAGA
CATTCCCACTGCGGAAGACATTCTAAACGAGGTTGATAAATTGTATAAGACTGTTTTGGAAGAATTTCCTGTGGGA
GTTGTTGATGAAGATATCGATGATGTTATTATTGAGAAGGAAGAACAAGATGATGTTAGTTCTGGAACAATATCTG
AAGTTAAGAAGCACGATCGAGCTAAGCCTAAAACATATAAAGAGGTTCTACTAGCTCAAGAAGGGGAATGCAATGC
AGATGAGAAAACAAGTTCTTCAACAGATAACACTGCGAACGAAACTCAACTAGGGCAACAGCAGAAGCTGGAAGAG
CAAAAAGAGGTGCATTCTTCTGGGGAATGCTGGGTGAAAATCAAGTACCAGGAAGAAGGTGAGGAAGTTGAAAATG
ATACTAAGTTACCTCCTTTGACAACACAAGCAATTGGTGCTGATGATAAAGACCCAGAAGCTTTGTTTAAAGAGAA
AACCGAACTATCTTCGCCTCCACCTGCATTACAAGAACCTGAGCTGCCTGCGGCCATGCGCGATGGAGAGTTCAAC
GGTGACACGAAGTTACTGGAAGAGAATGAGAATTTAAGGGAGATGATGAAGAAGTTGCTTGAAGCCGGGAATGAAC
AGTTAAGCGTGATAACAAATTTGACTGGCAGAGTGAAGGACTTGGAGAAGAAACTAGCCAGGAGCAGGAGTAAGAG
AGTGAAGACAAAACGGTATAGACCAGCAACTTCCAAAATGTCTTGCATGAAATGA

FIG. 15E

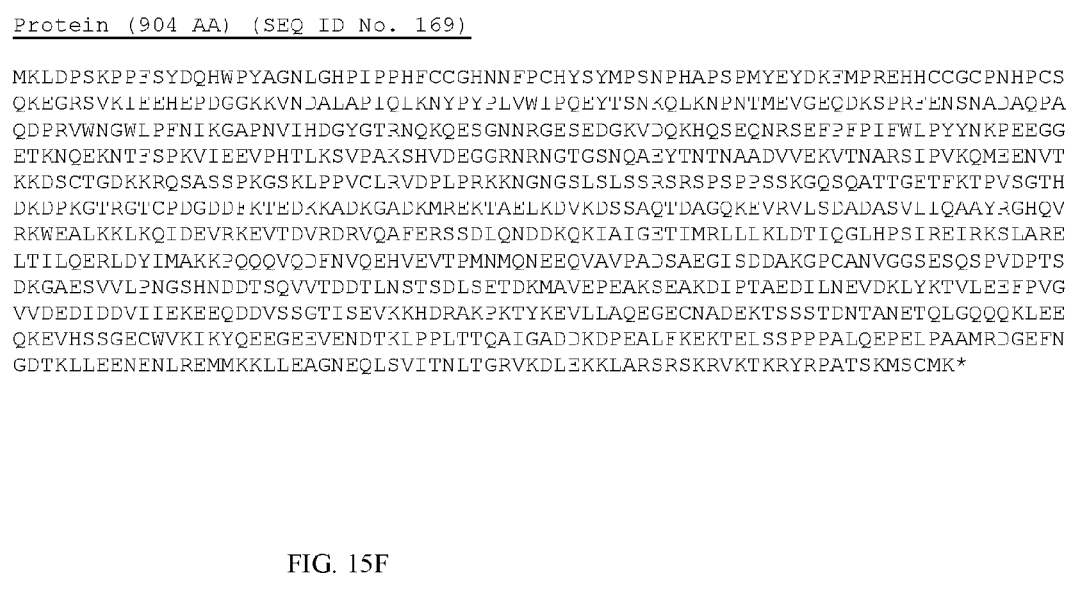

Protein (904 AA) (SEQ ID No. 169)

MKLDPSKPPFSYDQHWPYAGNLGHPIPPHFCCGHNNFPCHYSYMPSNPHAPSPMYEYDKFMPREHHCCGCPNHPCS
QKEGRSVKIEEHEPDGGKKVNDALAPIQLKNYPYPLVWIPQEYTSNKQLKNPNTMEVGEQDKSPRFENSNADAQPA
QDPRVWNGWLPFNIKGAPNVIHDGYGTRNQKQESGNNRGESEDGKVDQKHQSEQNRSEFPFPIFWLPYYNKPEEGG
ETKNQEKNTFSPKVIEEVPHTLKSVPAKSHVDEGGRNRNGTGSNQAEYTNTNAADVVEKVTNARSIPVKQMEENVT
KKDSCTGDKKRQSASSPKGSKLPPVCLRVDPLPRKKNGNGSLSLSSRSRSPSPPSSKGQSQATTGETFKTPVSGTH
DKDPKGTRGTCPDGDDFKTEDKKADKGADKMREKTAELKDVKDSSAQTDAGQKEVRVLSDADASVLIQAAYRGHQV
RKWEALKKLKQIDEVRKEVTDVRDRVQAFERSSDLQNDDKQKIAIGETIMRLLLKLDTIQGLHPSIREIRKSLARE
LTILQERLDYIMAKKPQQQVQDFNVQEHVEVTPMNMQNEEQVAVPADSAEGISDDAKGPCANVGGSESQSPVDPTS
DKGAESVVLPNGSHNDDTSQVVTDDTLNSTSDLSETDKMAVEPEAKSEAKDIPTAEDILNEVDKLYKTVLEEFPVG
VVDEDIDDVIIEKEEQDDVSSGTISEVKKHDRAKPKTYKEVLLAQEGECNADEKTSSSTDNTANETQLGQQQKLEE
QKEVHSSGECWVKIKYQEEGEEVENDTKLPPLTTQAIGADDKDPEALFKEKTELSSPPPALQEPELPAAMRDGEFN
GDTKLLEENENLREMMKKLLEAGNEQLSVITNLTGRVKDLEKKLARSRSKRVKTKRYRPATSKMSCMK*

FIG. 15F

SEQUENCE LISTING

```
<160> NUMBER OF SEQ ID NOS: 285

<210> SEQ ID NO 1
<211> LENGTH: 519
<212> TYPE: DNA
<213> ORGANISM: Glycine max

<400> SEQUENCE: 1

gagttttttt tttttttttt taaaagaatg cagccagata ttgatgcctc gggtgctaaa      60

gctaaaaaac tctcagccaa aatgttatgc acctttcaaa cttcccacag ctttttgcta     120

gaactatgcg aaagatacaa ctcaatcatg tatttccgtg agaacctgag atttttcaag     180

tacaaatatg atcataaatg tcatcataat taaactatat cgagtggtat aaacatatgt     240

aacgtatcca aactattatc ctatgcactc ttgatcatct aggagcagca gaaaactgac     300
```

acatttagga attcaagggc ctcgcactat tactaattaa gattcttcct tctgtagcat 360
ccatacatat aagactataa acataatcgt taagaaaccc aaaacaaaag agttgtgctc 420
aatatgtatc aacacatatg gcagaaactt gcacagtttg aatgaaacaa gaaactacaa 480
aaccaacaaa taattatgtg aggcaaagtg aactcatta 519

<210> SEQ ID NO 2
<211> LENGTH: 1329
<212> TYPE: DNA
<213> ORGANISM: Glycine max

<400> SEQUENCE: 2
atgctgccag tcttaggatc caacatgtct caaacactaa gctgcagaag actacaccca 60
atggactcaa ctttgatgaa gtcaatgtcc cacaatccaa aaaagtccta ttctaccgca 120
ttcacaaggc actttgccaa aaaatctggt tttttgatca agatcatggc ttctgctaca 180
cctacagcag ctgctatcac ctttggattc aagaatttgt tggaaacatt cactgttgat 240
gtgcatagag cagagaacag gccactgaat gtgcccctaa tagcaccttt taccattgct 300
acctctagat tggacaaggt ggagaacgtg gccataaggg ttgagttgag caacggtgcg 360
gtggggtggg gtgaggcacc aattttgcct tttgttactg cagaggacca aaccactgcc 420
atggtcaagg cttctgaggc atgtgccttc ttgaggaaat gtccagcact cactttgggt 480
tccatgttgg gggagattgc tggtattctt ccagggcatc aatttgcttc agctagggcc 540
gggattgaga tggcaataat tgatgctgtt gcaaatagta ttcgtgtgcc actgtggagg 600
ctttttggtg gggcttcaaa taccataacc actgatatta caatcccaat tgtttctcca 660
gctgaagcag ctgaattggc ttctaagtac tataaagaag gatttaagac tttaaagctg 720
aaagtgggca agaatctgaa tgcagatata gaagtgcttc aagctatacg tgttgcacac 780
cctaagtgtc agtttattct tgatgctaat gaggggtata actctgagga agcagtggat 840
gttcttgaga aactacatga tatggggttg actcctgttc tatttgagca accagttcat 900
agagatgatt gggatggtct tcggtatgtc ggtaatatag caagagagag atatggagta 960
tctgttgcag ctgatgagag ttgcagaagt ataattgatg tttacaaaat tgtggaaggg 1020
aatgttttag atgtcattaa cattaagctt gccaaagttg ggttatgggg tgcccttgaa 1080
attattgaaa aggcaaaagc agcaggatta gatttgatga ttggtggtat ggttgagact 1140
agacttgcta tgggttttgc tggccaactt gctgctggcc ttggctgttt taagttcatt 1200
gacttagaca caccacttct gctgtcagat gatccagttc ttgaaggcta tgaagtttca 1260
ggtgccactt ataagttcac aaacgctagg ggacatggtg gatttcttca ctgggacaac 1320
cttgcttat 1329

<210> SEQ ID NO 3
<211> LENGTH: 3222
<212> TYPE: DNA
<213> ORGANISM: Glycine max

<400> SEQUENCE: 3
atgacggagt cagaagaagc tggggcaaag ccaatgaaca cattgggtgg ccaagtctgc 60
cagatctgtg gtgataatat tgggaacaat gtgaatggcg atcctttcat tgcttgcgat 120
gtttgtgctt tccctgtctg cagggcgtgc tatgaatatg aaaggaagga tggaaatcag 180
tcttgccctc agtgcaagac ccggtacaag aggcacaaag gaagtcctgc aattcttgga 240
gaccaggaag aggatggggg tgctgatgag ggtgctagtg acttaaatta caattcagaa 300

-continued

```
aatcagaatg aaaaacagaa gattgagcgc atgttgggct ggcaaatggc acatgggcga    360
gcagaggagg ctgttgctcc aaattatgat aaggaagttt ctcacaatca cattcctctg    420
ctctctggtg gacaagaggt ttctggagaa ttatctgcag cctcacctga gaggctgtca    480
atggcatctc caggtggccg agggaagcgt gtccataatc ttcaatattc ctctgacctt    540
aatcaatcac caaatattag ggttggggat cctggattgg gtaatgtggc atggaaagaa    600
agagttgatg gctggaaaat gaagcaagat aagaatgttg ctccaatgag cacaggccaa    660
gctacttctg aaagaggagc tggagatatt gatgctagta ctgatgtgct tgtggacgat    720
tccttgttga atgatgaagc tcggcaaccc ctctctagga aggtttctat tccatcatct    780
aggatcaatc catatcgtat ggtcattgct ctgcggctgg ttatcctatg catttttctg    840
cattatcgaa taacaaatcc tgtgcccaat gcatatgcat tgtggttgat atcagtcata    900
tgtgagattt ggtttgccat atcgtggata tttgatcaat tccccaagtg gctccctgtg    960
aaccgtgaaa cctatcttga cagacttgca ctaagatatg atcaggaagg ggaaccatca   1020
cagctagcag ctgttgacat ttttgtcagt actgttgatc cattaaaaga acccccactt   1080
gtgactgcga acactgtcct atctattctt tctgttgact acccagtgga taaggtctca   1140
tgttatgtct ctgatgatgg tgctgctatg ttgacatttg aagctctggc tgagacatca   1200
gagtttgcta ggaaatgggt tcctttcagc aagaaatata acattgaacc tcgggcacct   1260
gagtggtatt ttgcacagaa gattgactac ttgaaggata aggttcaacc atcatttgtc   1320
aaagatcgta gagcaatgaa gagagaatat gaagaattta aaattcgcgt caatggactt   1380
gttgcgaagg cacaaaaggt tcctgaagaa ggatgggtga tgcaagatgg tacgccatgg   1440
cctggaaaca acactagaga ccatccagga atgattcagg ttttcttggg ccaaagtgga   1500
ggacttgaca ccgagggtaa tgaacttcca cgtttagtct atgtttctcg tgaaaaacgt   1560
ccagggttcc aacatcacaa gaaggctggt gccatgaatg cacttgttcg agtctcagca   1620
gtccttacta atggaccttt cttattgaat cttgattgtg atcactacat aaacaacagt   1680
aaagccttga gggaagctat gtgctttatg atggatccca accttgggaa aaatgtttgc   1740
tatgtccagt ttccacagag gtttgatggt attgatagga atgatcgata tgccaatcgc   1800
aatactgttt tctttgatat aaacttgaga ggtttggatg gcattcaagg tcctgtttat   1860
gtgggtactg gatgtgtctt taatagaaca gctttgtatg gctacgagcc tcctattaaa   1920
cctaagcata aaaagcctgg gttgctttct tcactctgtg gtggtaaccg aaagaagaga   1980
tcaaaatcta gcaagaaagg ctcagacaag aaaaaatcta gcaagaatgt tgacccaact   2040
gtgcccatct ttagtcttga ggatatagaa gagggggtgg aaggtgctgg atttgatgat   2100
gagaaatcac tacttatgtc acaaatgagc cttgagaaaa ggtttggtca gtctgctgtc   2160
tttgttgcct ctacactcat ggagaatggt ggtgttcctc agtctgcaac tccagaaact   2220
cttcttaagg aggctattca tgttatcagt tgtggttatg aggataaaac agaatgggga   2280
agtgagattg gatggattta tggttctgtc acagaagata ttcttactgg attcaagatg   2340
catgcccgtg gttggaggtc tatatactgc atgcccaagc tcccagcgtt taaaggttct   2400
gctcctatca atctttcaga ccgtctgaac caagtgcttc gatgggcttt aggttcggtg   2460
gaaattcttt ttagtcgaca ctgtcccatc tggtatggtt atagtggaag gctaaagtgg   2520
ctcgagaggt tcgcatatgt gaacaccaca atctatccag tcacttccat tccccttctc   2580
atgtattgta ccttacctgc tgtctgtctc ctgactaaca agttcattat tccacagatt   2640
```

```
agtaacattg caagtatatg gtttatctct ctctttcttt ccatctttgc aaccggtatc   2700

cttgagatga ggtggagtgg tgttggaatt gatgagtggt ggagaaatga acaattttgg   2760

gttattggtg gtgtttcggc ccatcttttt gccgtgttcc aaggtttact caaagtgctt   2820

gctggaattg acactaactt caccgttacc tcaaaggcat cagatgagga tggagacttc   2880

gcagaactct acttgttcaa atggacaacc cttctcatcc cacccacgac acttctcatc   2940

ataaacctgg tgggggttgt tgcaggcatc tcctatgcca tcaacagtgg ttaccaatca   3000

tggggtcccc tctttggtaa gcttttcttt gcattttggg tgatcatcca tctctacccc   3060

ttcctcaaag gtctcatggg tcgccagaac agaacaccaa ccattgttgt agtctggtcc   3120

attcttcttg catccatttt ctctctgctg tgggtccgaa tcgacccgtt tacgacaaga   3180

gtcactggtc ctgatgttga gcagtgtgga atcaactgct ag                       3222


<210> SEQ ID NO 4
<211> LENGTH: 666
<212> TYPE: DNA
<213> ORGANISM: Glycine max

<400> SEQUENCE: 4

atgtcccagt tgaacggagc ctactacggc ccctccatcc cgccgccgaa aacttcctac     60

caccgtcctg ggcgcggcgg aggcctcggc tgctgctgcg ggtgcctctt cagcctcatc    120

ttcaagctca tcctaaccgt gatcatcatc attggcatcg ccgtgttcct tttctggctc    180

atagtccgtc ccaacgtggt gaaattccac gtcaccgagg ccaccctgac gcagttcaac    240

tacaccccca acaacacgct ccactacgac ctcgccctca acatcacggt ccgaaacccc    300

aacaagaggc tcggaatcta ctacgaccgc atcgaggcgc gtgcaatgtt ccacgacgcg    360

aggtttgatt cccagttccc ggaaccattc taccagggcc acaagagcac caacgtgctg    420

aacccggtgt ttaagggtca gcaattggtg ccactcaacg ctgaccaatc cgcggaactg    480

aagaaggaga acgccactgg ggtgtacgag atcgatgtga agatgtacct tagggtcagg    540

ttcaagttgg gtgtcttcaa gaccaagacg cttaagccca aagtatcatg cgacttacgt    600

gttcctttga aaggaagcgc cggtgctggt gtctttcaga ccaccaagtg cgactgggat    660

cgctga                                                               666


<210> SEQ ID NO 5
<211> LENGTH: 744
<212> TYPE: DNA
<213> ORGANISM: Glycine max

<400> SEQUENCE: 5

atggcagaac aaaaccaaaa ccaaacaact gaagctggaa ggcaccaaga ggttggtcac     60

aagagccttc tccagagtga tgctctttac cagtatattc tggagacaag tgtctaccca    120

agagaacctg aatccatgaa agaactgaga gagttgacag caaaacaccc atggaacatc    180

atgacaacct ctgcagacga agggcagttc ttgaacatgc tccttaagct catcaatgcc    240

aagaacacca tggaaattgg tgtctacact gggtattcac ttcttgccac cgctctcgct    300

cttcctgaag atggaaagat cttggccatg gacattaaca gggagaatta tgaattgggt    360

ttgcctgtaa ttaaaaaagc tggtgttgac cacaaaattg aattcagaga aggtcctgct    420

ctaccagttc ttgatgaaat gattaaagat gagaagaacc atggaagcta tgacttcatc    480

tttgttgatg cggacaagga caactacctc aactaccaca agaggttgat agagcttgta    540

aaagttgggg gcgtgatcgg gtacgacaac accctatgga acggatctgt ggtggcaccc    600
```

-continued

```
cctgatgctc ctcttaggaa gtatgttagg tactacaggg acttcgtgct ggagctcaac    660

aaagccctcg ctgtggaccc caggatcgag atttgcatgc tcccggttgg tgatggaatc    720

actatctgcc gtcggatcaa gtga                                           744


<210> SEQ ID NO 6
<211> LENGTH: 927
<212> TYPE: DNA
<213> ORGANISM: Glycine max

<400> SEQUENCE: 6

atgaccggcg gcggatccac ggggaggttg ccgacgtgga aggagagaga gaacaacaag     60

aggagagaga gaagacgaag agcgattgca gctaagatct acactggcct tcgagcccag    120

gggaactaca agcttccaaa gcactgcgac aacaacgagg tcctgaaagc tctctgcgcc    180

gaagctggct ggatcgtgga agaagatggc acaacttatc gaaagggatg taagagaccc    240

acgagtgaga ttggaggaac accactgaac ttaagcgcgt gttcttccat tcaggcaagt    300

ccacaatcct cgtcataccc gagtcctgta ccatcctacc atgctagccc aacctcttcc    360

tcgttcccaa gccccacgcg cattgacgga aaccaccctt cttcctttct catcccattc    420

atccgcaaca taacttccat ccccgccaac ctccctcctc tcaggatatc caacagcgcc    480

cccgtcaccc cacctctttc ttctccccga agctcaaagc gcaaggcgga tttcgactcc    540

ctccgccacc ctctttttgc cacctccgcc ccgtccagcc ccacgcgccg ccaccacgtt    600

gccacctcca ccatcccgga gtgcgacgag tccgacgcct ccaccgtgga ctccgcctcg    660

ggccgctggg ttagtttcca ggttcagacg acgatggtgg ctgcggcggc ggctgctcct    720

ccttcgccta cctttaacct catgaagccc gcgatgcagc agatcgctgc ccaggaaggc    780

atgcagtggg gttctgttgc cgagagaggc agaggaggct ccgattttga cttcgagaat    840

ggcagagtga aaccctggga gggtgagaga atacacgagg ttggaatgga tgatttggag    900

cttactctag gagttggaaa ggcttga                                        927


<210> SEQ ID NO 7
<211> LENGTH: 174
<212> TYPE: DNA
<213> ORGANISM: Glycine max

<400> SEQUENCE: 7

atggccggtg acggtgcagc tacatgcata gacatccttc ttgccattat tctccctcct     60

cttggtgtct ttctcaaata tggttgccag gtggagttct ggatttgttt ggtgctgacc    120

ctttttggtt atatacctgg aattatctat gctgtctatt ctatcaccaa gtga          174


<210> SEQ ID NO 8
<211> LENGTH: 1017
<212> TYPE: DNA
<213> ORGANISM: Glycine max

<400> SEQUENCE: 8

atgccttctt cagaatcatc aacaggcttc tccgaaacca tttgtgtgac cggcgctggt     60

ggcttcatcg cctcttggat ggtcaaactc ctcttggaga aaggctacac tgtccgagga    120

accctcagaa acccagatga tcccaagaac gggcacttaa aagagtttga aggagcttcc    180

cagagactaa ctctgcataa ggttgacctc cttcatcttg actccgttag atctgttatt    240

aacggctgtc atggtgtctt tcacactgct tctcccgtca ccgataaccc cgaagaaatg    300
```

```
gtggagcctg cggtgaatgg agctaagaat gtgatcatag cagctgcaga ggctaaagtt    360

agacgcgtgg tgttcacctc atccattggt gccgtttaca tggaccccaa aaggagcatc    420

gatttggtgg ttgacgagtc ctgttggagt gatttagaat tttgcaagaa caccaagaat    480

tggtattgct atgggaaggc tgtggctgaa gaagcggcat gggacacagc aaaagagaaa    540

ggggtggaca tggttgtagt gaacccagtt ttggtacttg gaccattact gcaacccagc    600

ataaatgcta gtacaattca catcctcaag tacctcactg gctctgctaa gacctatgca    660

aatgccacac aggcgtatgt tcatgttagg gacgtggcat tggcccacat acttgtttat    720

gagaagcctt ctgcctctgg tagatacata tgtgccgaaa gctctctcca ccgtggagaa    780

ttagttgaaa ttctcgccaa gtatttcccc gactacccag ttcccaccaa gtgttcagat    840

gaaaagaatc cgagagcaaa accctacact tttcaaatc aaaaactgaa agatttggga    900

ttggaattca ccccagtgag tcagtgttta tatgaagccg tcaagaacct gcaggagaaa    960

gggcaccttc ctgttcctgc aaggcagcag gaagattcaa ctactgtgaa accttaa      1017
```

```
<210> SEQ ID NO 9
<211> LENGTH: 426
<212> TYPE: DNA
<213> ORGANISM: Glycine max

<400> SEQUENCE: 9

atgagagtga gcgcagagtt tgagcgtgtt ctcaagtatt tcgatgaaga tggggatggt     60

aagatttccc catctgagct taggaaccgg ctatgcatga tgggtggtga gttattgttc    120

aaagacgctg aaaagttgat tgaggaattg gattctgacg gtgatgggtt tttgagtttg    180

gaagattttg tgaagataat ggaggcagca ggggaagatg agaagttgaa ggatttggcg    240

gaagcttttg agatgtacca tgacactgaa atgcttgggt ttattacacc caaaagcttg    300

caaaggatgc tgaataggtt gggagaatca aaatccatgg agcaatgcag agcaatgatt    360

ggccattttg atttgaatgg agatggcgtg cttagctttg atgaatttgg agtgatgatg    420

cagtga                                                               426
```

```
<210> SEQ ID NO 10
<211> LENGTH: 774
<212> TYPE: DNA
<213> ORGANISM: Glycine max

<400> SEQUENCE: 10

atggctttgg aggctttgaa ttcaccaaca gcagccacca ctcccttccg tggttaccaa     60

gaagaggagg aggaggttga ccttcaccta cgcgagcctt gggccaagag aaaacgctcc    120

aaacgacctc gttttgagtc ggaggaagag tacttggctc tttgcctcat catgcttgca    180

caaagcggta acaacaacaa cacccaatta ccgtcttcgt cacagtcaca caaagaagcg    240

tcaccgccgc tgaaactatc acacaggtgc accgtttgca acaaggcttt tccttcttac    300

caagcactcg gtggacacaa ggccagccac cgcaaggcct cgtcggaatc caacaccacc    360

gcctccgccg tcgccgtctc tgccacagcc aacgacagcg tttccgcttc gaccgtcggc    420

ggcggaagga tgcacgagtg ttccatctgt cacaagagtt tccctaccgg tcaggccctg    480

ggtggccaca agcgctgtca ctacgacggc ggaaacaacc acagtaacag caacgccaac    540

ggcaacaaca gcagcggcgt cactacctcc gacggcggcg ctgcctcctc ctcctcccac    600

gcgttccgtg ggtttgacct gaaccttccg gctccgctga cggagttctg gtcgccggcg    660

gggtttgatt tcggaaagaa gaaggttggc gttgaacaag aggtggaaag cccgttgccg    720
```

gtaaccgcca agaggccgcg tttgttttcg ggggaagata atgaagaggc gtag 774

<210> SEQ ID NO 11
<211> LENGTH: 879
<212> TYPE: DNA
<213> ORGANISM: Glycine max

<400> SEQUENCE: 11
atgaagattc agtgcaacgt gtgcgaggcc gcggaggcca aggttctgtg ctgcgcggac 60
gaggcagcac tgtgctggga atgcgacgag aaggttcacg cagcaaacaa gctcgccagc 120
aagcaccaga gggtccctct ctctctctcc gcctctcaca tgcccaagtg tgacatatgc 180
caggaaatgg ttggttattt cttctgttta gaggatcgag ctttgctatg taggaattgt 240
gatgtatcta tacatacagc aaatgcctgt gtctctgatc atcaaaggtt tttgcttact 300
ggtgtgagag taggccttga agctactgag cgcggtgctt cctcgtcttc tgtgaagtca 360
cagtctgggg agaaaatgtc tgatgctaaa tcttcatcca tctccagaaa tgtttcctca 420
ctgccccagc catcaaatgc caatgaagtg ttacccctcc aaatgcaagg agttgaggag 480
tttccaccaa gcaatttctc aggttatact tctggaaacg tctcacaatg gcccattgaa 540
gaatttctcg gattaaatga actcagtcag tattataatt acatggatgg atcatctaag 600
gctgacagtg gtaaacttgg ggattctgat tcttctgttt tgaggtctgg tgaagaggat 660
atggatgatg acggcttctt gggacgtgtt ccagattcat cctggacagt tcctcagatc 720
ccttcccctc ctacagcttc gggtttatat tggccgaaag tccctcaata tacatctgac 780
agtgccatgt ctgttcctga catatgcttt tctcatgtgc gacagcccca ccatgcccag 840
cataattcta atgtttccaa aaggcgtagg caactataa 879

<210> SEQ ID NO 12
<211> LENGTH: 303
<212> TYPE: DNA
<213> ORGANISM: Glycine max

<400> SEQUENCE: 12
atggctctct caaagcttct agttgcatcc cttctggtat cctttgtcct cttccatctc 60
gttgatgctg atgatcaatc ggcatacgca cagactcagg gttctcttgt tcagcagata 120
gattgtaatg ctgcatgtgc tgcgaggtgc cgtttagcat ctcgtcagcg catgtgccac 180
agagcgtgtg gaacttgctg cagacgctgc aactgcgtgc caccgggaac ttccggtaac 240
caagaagtgt gtccctgtta tgccagtctc agaacccacg gggcagacg caagtgccct 300 taa 303

<210> SEQ ID NO 13
<211> LENGTH: 996
<212> TYPE: DNA
<213> ORGANISM: Glycine max

<400> SEQUENCE: 13
atggcgttga acaatggcgt ccccgccacc ggcaccggcc tcatcgtcag cttcggtgag 60
atgctcatcg acttcgtccc caccgtctct ggcgtgtccc tggccgaggc ccctggcttc 120
ctcaaggccc ccggcggcgc ccccgctaac gtcgccatcg ccgtgtcgcg cctcggcggc 180
aaagccgcct tcgtcggcaa gctcggcgac gacgagttcg gccacatgct cgccggaatc 240
ctcaaggaaa acggcgttcg cgccgacggc atcaactttg accagggcgc acgcaccgcc 300
ctggccttcg tgaccctacg cgccgacggg gagcgtgagt tcatgttcta cagaaacccc 360
agcgccgaca tgctcctcaa gcccgaagaa ctcaatctcg aactcatcag atctgcaaaa 420
gttttccatt acggatcaat cagtttgatc gtggagccat gcagatcagc acacttgaag 480
gcaatggaag tagccaagga atctgggtgc ttgctctcct atgaccccaa ccttcgtcta 540
cctttgtggc cttcggctga ggaagctcgt aagcaaatac tgagcatttg ggagaaggct 600
gatttgatca aggtcagtga tgcggagctt gagttcctca caggaagtga caagattgat 660
gatgaatctg ctttgtcatt gtggcacccc aatttgaagt tgctccttgt cactcttggg 720
gaacatggtt ccagatacta caccaagagt ttcaaaggat cggtagatgc tttccatgtc 780
aatacagttg atacaactgg tgccggtgat tcctttgttg gtgctttatt ggccaagatt 840
gtcgatgatc agtccatact tgaagatgaa ccaaggttaa gagaagtact aaagtttgca 900
aatgcatgtg gagctattac aactacccaa aagggagcaa ttccggccct tcccaaagag 960
gaggctgcac tgaaactgat caaagggggg tcatag 996

<210> SEQ ID NO 14
<211> LENGTH: 672
<212> TYPE: DNA
<213> ORGANISM: Glycine max

<400> SEQUENCE: 14
atggccgtca cgaaaagcct ctcaatcttc ctcttcatcg caatgagctg cgtcgccgca 60
gctcaggcag cgaacttcaa catcacaaat aactgcacct acacggtgtg ggccgctgcc 120
gtgcccggcg gcggcgcaag gcttaaccct ggcgaatcgt ggaacatcag cgtgacgaac 180
ggcacaacaa gaggacgcat ctggggtcga acaaactgca ccttcgacaa cgcgggacgc 240
gggaagtgcc tcaccggcga ctgcgagggt gttctggagt gcaacaaaac aggtacaccc 300
ccgaacacgg tcgttgattt cgcgttgaac cagtataaca acctcgactt ctacgacatc 360
tccctcgtcg acggtttcaa cgttccccta cagctgaccc cgacctacaa ctgcagttcc 420
gttaaatgcg ccgccgacat catcggagag tgccccactc agctccaggt tcctggcggc 480
tgcaacaacc cctgcacggt tttcaatacg actcagtact gttgtagcac cggagctgct 540
gggtgcggtc ccacagatta ttccaagttc ttcaaggaga ggtgccctga tgcctacagt 600
taccctatgg acgatgcaac cagcatgttc acttgcatgg gatccgatta tagggttgtg 660
ttttgccctt aa 672

<210> SEQ ID NO 15
<211> LENGTH: 975
<212> TYPE: DNA
<213> ORGANISM: Glycine max

<400> SEQUENCE: 15
atgacagtag atctggtagg tgctgccaag atggggatgg aggagaatat agcgatacaa 60
gaagctgctt ccgctgggtt gaagagtatg gagcatctga ttcgtgtgct ttcttctcaa 120
atcccttctt ctgcttcgtc ttcttctaac gcacaccacc accgtcttaa tctcaaccac 180
cttgactgca ccgaaatcac cgacttcact gtctccaagt tcaaacaagt catcaacttg 240
ttgaatcgca cgggacacgc tcgctttcgt agcgcacctt ctcatccttc tccttctact 300
tctcttcctt ctcaacctca acctcaacca caaccacaac catatgcact gactcttgat 360
ttcgcaaaac ctgttatgct taagtcaaat cccaacccta acccttcttc taccgatttg 420
tcggtttctc aatattctaa gaccaaggac accaccacct ctagtatatc tcctcccgtg 480
tccaccacca cctcctcatt catgtcctcc atcaccgccg acggaagtgt ctccgacgga 540
aagatcggcc ccgccatcat cgctgccggc aagcctcctc tctcctcatc ccaccggaaa 600
aggtgtcacg acgccaccct ctctgccgga aaagcctctt cctccgctca ctgccattgc 660
tccaagagaa gaaaatctcg tgtgaaacga atgatacgtg tgccggcgat aagttcgaag 720
attgccgata tcccagtgga cgagtactca tggcgaaagt atggtcaaaa accaatcaaa 780
ggttcacctt acccgcgagg gtattacaag tgcagtagcg tgagagggtg tccggcgagg 840
aagcacgttg agcgagccca ggatgacccc aacatgctca tcgttaccta cgagggagag 900
caccgtcatc cgcaaccgcg tctgccggaa actgctgccg gcgccggcgg gacttttgcc 960
gctcatcctg tttaa 975

<210> SEQ ID NO 16
<211> LENGTH: 3381
<212> TYPE: DNA
<213> ORGANISM: Glycine max

<400> SEQUENCE: 16
atggctgagg ccagactcta cgctcccccc tctcaattgg atattaagca aattatttta 60
gaagcacagc atcgatggct acgtccggct gaaatttgtg caattctcgg taattataag 120
aagtttcgaa ttgctccaga acctgcacat atgccaccaa gtggttcact tttcttattt 180
gatcggaagg tgctgagaca cttcagaaag gatggccata actggaggaa gaaaaaagat 240
ggaaaaacag tgagagaagc tcatgagaga ctaaaggctg gaagtgtgga tgtgttgcat 300
tgctactatg cccatggaga agaaaatgaa aattttcaaa gacgcacgta ttggttgctt 360
gaagataata tccagaaagg aatgaagaaa acctgggctc ttcttcttat gtgtttttc 420 ttgtttgagg atggtggaac tctctcacat tgttctcgtc cattatcgac aagtgaagta 480
tgcacaattc tccttccccc tttctcaaat tttgactctg gaaccaaggc gaattttaca 540
agtgctaaag aaaatgaaga atctcttcct tatgctcaac aaactgataa aattatgccc 600
caaacagaga tggacacttc tttatcatct actcttcatc cacatagtta ccaggttcct 660
tcaaaaactg tcgatacaag catgaacagt gcccaaacat cagaatatga agaagctgaa 720
tctgcattca ataaccatgc aagttctgag ttttattctt tcctcgattt aactttgatg 780
cattatgatc aagagaagtt acctattatt cctggggtga attatatctc actcactcaa 840
gacaataaaa acaaagacat tcttaatgct ggattgacat atgaatcccc aaaacccctt 900
ggcttttcct catgggaagg tatcttagaa aataatgctg gaagtcaaca tgtgcatttt 960
cagcctttat ttcctggaac acagcctgat aacatgggaa tcaatagcaa tttttctcaa 1020
ggagaagaga taatggtgcc atatttgacc accagcattg ctaagcagca tgagaatgga 1080
agtatcatta aagctgaagg aaattggcag tgttgttggt atgatgctgc aaatattttt 1140
gacatcttaa tgacttgttt cgtgtttctg caaacatata atcaagcaat ggattttgct 1200
ttatgcaact gtgagcagga agttaatgat gttgattttc agaaatcctt ggaacagtgt 1260
cttctacatt cacacaaaca aaacaaggtt ctcatgcaaa atgatcttca agaaaaactt 1320
ttgaatgaaa aagaaaagat aaaatcaaat ctagaggcct atggaataga agacacatat 1380
ttatctttta aaaggactct gttagatgga cctccagctg aagagggtct gaagaagctt 1440
gacagtttca accaatggat gagtaaagag cttggagatg tggaagaatc aaataaacca 1500
tccacttctg gtggttattg ggatacagtt gaaactgaaa atgaggttgg caacacaact 1560

-continued

```
attccttccc aagggcacct ggacacctat gtattggatc catctgtttc ccatgatcag   1620
ctttttagca ttattgacta ttccccaagc tgggcatttg aagggtcaga aattaaggtt   1680
atcatttctg gagaattcct aagaagtcaa catgaagcag aacaatgtaa gtggtcatgc   1740
atgtttggtg aggtagaagt gccagcagtg atcattgcaa aggtgttctt ttgttgtcat   1800
acacctccac acaaggctgg gagggtacct ttctatgtaa cttgttccaa taggttagca   1860
tgtagtgaag tgagagaatt tgatttccaa gtccactata ctccagaaga cactacaggt   1920
gagaatagag gaagcacttt tgatactttt agtatccgat ttggagaact tttgtccctg   1980
gggcatgcct ttcctcagaa ttcagattca attagtgtaa gtgagaaatc tcaactgaga   2040
agtaaaatca attctttatt gagggaggat gatgatgatt gggacaagct actaaaactt   2100
actcaagaga aagatttttc tccagaaaat ttacgggagc agctgcttca aaatcttctg   2160
aaagataagt tacatgcatg gctccttcag aaaataactg aagaagggaa aggccctaat   2220
gtattagatg agggtggcca aggtgtgctt cattttgcag ctgctcttgg ctatgattgg   2280
gccctagaac ccacaatagt tgctggtgtg aatgtgaact ttcgtgatgt aaatggatgg   2340
acttctcttc attgggcagc attttgtggc agggagcgca cagttgcttt cctcatctct   2400
ctcggcgcag cacccggagc actgactgat ccatgtccag aacatccttc tggtagaaca   2460
ccagctgacc tagcttctgc aaatggacac aaaggaattg cagggtatct tgctgagtct   2520
tcactaagtg cacacctcac aactctcgat ttgaacaggg acgcgggaga aaattccgga   2580
gcaaaagtag tccaaagact ccaaaacatt gctcaagtta atgatcttga tggtttatca   2640
tatgaactgt cattgaaaga ttcactggct gcagtgtgta acgccaccca agccgcagct   2700
cgtattcatc aagttttcag aatgcaatca tttcagagaa aacaactgaa ggaatatgat   2760
gatgacaaac ttggattatc tgatgagcgt gctctttcac tcataaaaat gaatgtaaaa   2820
tcacacaagt ctggaccacg tgacgagcct gtccatgctg ctgcaatacg aatccaaaac   2880
aaattccgca gttggaaggg aagaagagaa tttttaatga ttcgacaacg catagtaaaa   2940
attcaggctc acgtgagagg tcaccaggtc aggaaaagct gtgggaagat aatttggtcc   3000
gttggaatct tggagaaggt tattttacgt tggcgtcgaa aaggtagtgg cttgcgtgga   3060
tttaaaccgg aggccaattc tgagggaact atgatacaag atgtatcttc aacagatgat   3120
gactatgatg tcttaaaaga aggcaggaag caaacagagc aaaggttgca gaaagcccta   3180
gctagggtga agtcaatggt tcagtatcca gaggcaagag accaatacca taggctgttg   3240
aatgttgtaa ctgagatcca agaaaatcag gtaaagcatg agagcagttc taacaattca   3300
gaagaaccga gagaattcgg tgacctcaat gatcttgaag cattgttgga cgaagatatt   3360
ttcatgccta cagcaactta a                                              3381
```

<210> SEQ ID NO 17
<211> LENGTH: 333
<212> TYPE: DNA
<213> ORGANISM: Glycine max

<400> SEQUENCE: 17

```
atggcattac gcgagcttct tatgatgggg atattgctgc tggtttcatc tgatgttaac     60
atgcaaaagg aagaagatga agaacttcgc tttcctaatc accctcttat cgtgagagac    120
gggaacagaa ggctaatgca agacatagat tgcggaggat tgtgcaagac aaggtgcagt    180
gcccattcga ggccaaacgt gtgcaacagg gcttgtggca cgtgttgtgt gaggtgcaag    240
tgtgttcccc caggaacttc aggcaacagg gagctctgtg ggacctgcta tactgatatg    300
```

atcactcacg gcaacaagac caagtgtccg tag 333

<210> SEQ ID NO 18
<211> LENGTH: 708
<212> TYPE: DNA
<213> ORGANISM: Glycine max

<400> SEQUENCE: 18
atgggaaggt ccccttgctg tgagaaagca cacacaaaca aaggtgcatg gaccaaagaa 60
gaagatcatc gcctcatttc ttacattaga gctcacggtg aaggctgctg gcgctctctc 120
cccaaagccg ccggccttct ccgttgcggc aagagctgtc gtctccgctg gatcaactat 180
ctccgccctg acctcaagcg cggcaatttc tccctcgaag aagaccaact catcatcaaa 240
ctccacagcc tccttggcaa caagtggtct ctaattgctg gtagattgcc cggtagaact 300
gacaatgaga tcaagaatta ctggaatact cacatacgca ggaagcttct gagcagaggt 360
attgaccctg ccactcacag gcctctcaac gattcttctc atcaagaacc tgctgctgtc 420
tctgcccctc ctaaacatca agagtccttt caccatgaac gctgccctga cttgaacctt 480
gagctaacca ttagtcctcc ccatcatcct caacctgatc atccgcactt gaagaccctt 540
gtgacaaact caaacctttg ctttccctgc agtctgggtt tgcataatag caaagattgt 600
agctgtgccc tccacactag tactgccaac gctactgcta ctggctatga tttcttggcc 660
ttgaaaacca ccgtcgtttt ggattacaga accttgcaca tgaaatga 708

<210> SEQ ID NO 19
<211> LENGTH: 576
<212> TYPE: DNA
<213> ORGANISM: Glycine max

<400> SEQUENCE: 19
atggcttcta attccattct tcttctttgt atctttcttg tggttgccac taaggttttt 60
tcctatgatg aagatctcaa gacagtggtt cctgcacctg ctccaccagt gaaggcacca 120
actcttgccc ctccagtgaa atcaccatct taccctccag ggccagtgac cacaccaaca 180
gttccaacac ccactgttaa ggtacccccct cccccctcagt ctccagtagt taagccacca 240
acaccaacag ttccaccacc cactgttaag gtacccccctc cccctcagtc tccagtagta 300
aagccaccaa ctccaacacc aacttcccca gtggtgtacc ctcctcctgt tgctccatct 360
ccaccagctc ctgtagtgaa atcaaacaag gattgcattc cactatgtga ttataggtgc 420
tcattacact caaggaagaa attgtgcatg agagcatgca taacctgttg tgaccgatgc 480
aaatgtgtcc ctcctggaac ttatggtaac agggaaaagt gtggcaagtg ctacactgac 540
atgctgactc acggcaacaa attcaagtgc ccatag 576

<210> SEQ ID NO 20
<211> LENGTH: 324
<212> TYPE: DNA
<213> ORGANISM: Glycine max

<400> SEQUENCE: 20
atgcgcatgc tcaccggcga ctccgctgcc gacaactcct tccgcttcct tccgcagtcc 60
atcgccgcct tcggctccac cgtcatcgtc gagggctgcg acaccgcccg caacattgcc 120
tgggtccacg cctgcaccgt cacggatggg ataattactc agatcagaga gtacttcaac 180
accgccctca ccgtcacccg catccacgat tccggcgaga ttgttccggc tagctccggc 240
gccggccgtt tgccctgtgt ctgggaaagc agcgtctccg gtcgggtcgg gaaatccgta 300
cccggtttgg ttcttgcaat ataa 324

<210> SEQ ID NO 21
<211> LENGTH: 242
<212> TYPE: DNA
<213> ORGANISM: Glycine max

<400> SEQUENCE: 21
cctggaaatc tatttgttgc ggtgaatgaa gggttatggg ataacggggc agcgtgtgga 60
aggagataca gaataaggtg tgtgagtgga aacaataggc catgcaaagg tggtagcatc 120
gatgttaaag tggtagattc ctgttcaagg tcaccatgtc ccaacaccct cctcatgtca 180
aatgatgcat ttgcagctat tgcacgcttc cctcatgtta aaatcaatat tgaatatacc 240
ca 242

<210> SEQ ID NO 22
<211> LENGTH: 450
<212> TYPE: DNA
<213> ORGANISM: Glycine max

<400> SEQUENCE: 22
atgagttgca tgttaagcat atcagggatt acaggaacaa ggaaaggaga ctattaccgg 60
tatttggcag aatttaaagc tggcaatgaa aagaaagagg tggcagatca gtcacttaaa 120
gcatatcaga cagcttctac cactgctgag agtgaactac aacctacaca tcctattcgt 180
ttgggtctgg ctctaaattt ctcagtgttt tattatgaga tattaaattc acctgaaagg 240
gcctgccatc ttgcaaagca agcctttgat gatgctgtct cggagctgga taccctgaat 300
gaggattctt acaaggacag taccttgatt atgcagctgt tgagggataa ccttacttta 360
tggacttctg atatccccga agagggtgag gacctaaaaa tggaaagcgc agccagggtt 420
gatcaaggag aagatgagtt aggccgctaa 450

<210> SEQ ID NO 23
<211> LENGTH: 1848
<212> TYPE: DNA
<213> ORGANISM: Glycine max

<400> SEQUENCE: 23
atggcaggca tggcaagagg aagagcagat gtgaaatcta gaaaaaattt ggtcactaca 60
actgtgttgg ttttggtgac tgttggtggt tttttctact tctattctca gaatagtgat 120
tcatcatctt ctgttgagta tggtgctaaa tctttgagcc acactggttt gggaggggac 180
aaagatgatg gtgtatcttc ctccacactt gttggaggag aagtcattgc tgtaccaaag 240
agcattccag tctgtgatga tcgattatcc gagctgattc cttgtctgga cagaaacctc 300
atataccaaa caagattgaa gcttgattta tctttgatgg agcactatga gagacactgc 360
ccaacacctg ataggagatt caactgttta attcctcctc ctccagggta caaggttcca 420
gtcaagtggc ccaaaagcag agaccaggtg tggaaggcaa atatacctca tacccatctt 480
gcaactgaaa aatctgacca gaactggatg gttgtgaaag gcgaaacaat agtgtttcct 540
ggtggaggaa cccacttcca taatggtgct gataaataca ttgcttcaat tgctaatatg 600
cttaattttc caaacaacaa tataaacaat gggggaagag tcaggtctgt tcttgatgtt 660
ggctgtgggg ttgctagctt tggaggatac ctcctttcct ccaatgtgat agcaatgtca 720
ttggcaccaa atgatgttca tcaaaatcaa atccagtttg ccttagagag gggaattcca 780

-continued

```
gcatatcttg gtgtcttggg gacccaaaga ctcccttatc cgagtagatc atttgaactt    840
gctcattgtt cgcgctgtag aattgattgg ctccagagag atggtttact tctccttgag    900
ctggataggt tactgaggcc aggaggttat ttcgcgtact cgtctcccga agcctatgca    960
caggatgaag aggataggag gatatggaga gaaatgagtg ctcttgtgga gaggatgtgt   1020
tggaaaatag ctgctaagaa ggatcagact gttatttggg tcaagcctct cactaatagc   1080
tgctacttaa agagattgcc tggtactaag cctccactct gcagatctga tgatgatcct   1140
gatgctgttt tgggagttaa aatgaaagct tgcatttcac gttattcaga tcaaatgcac   1200
aaagcaaaag gaagtggttt ggctccttgg cctgctcgat tgactactcc acctcctcgt   1260
ctggcagaaa ttcactattc tactgaaatg tttgagaagg acatggaagt ttggaaacaa   1320
cgagttcata attactggag caagctagcc agtaagatta agcctgacac aattcgcaac   1380
gtgatggata tgaaggcgaa tttgggttca tttgcagcag ctttgaagga caaagatgtt   1440
tgggttatga atgtggtgcc agaaaatgaa caaaaaaatc tcaagataat atacgacaga   1500
ggactgatag gaacagttca caactggtgt gaagcatttt caacctaccc tcgaacgtac   1560
gatctactcc atgcatggac tgtgttttct gatattatta agaaagaatg cagtccagag   1620
gatttattaa ttgagattga cagaatccta aggccaaagg gtttcatcat catccatgat   1680
aagcgttcca tggtggagta cataaagaaa tacctgtcag cattacactg gaatgctgtg   1740
accatatatg atgtagatca aggtaaagat gatgatgatg atgaagtagt gcttataatt   1800
caaaagaaga tgtggctcac aagtgaaagc attaaggtct cagaatag                1848
```

<210> SEQ ID NO 24
<211> LENGTH: 1440
<212> TYPE: DNA
<213> ORGANISM: Glycine max

<400> SEQUENCE: 24

```
atgggtcgcg aaactatgtg cctttcaacc ccaccaccaa ccactgccac caccacagtg     60
aacccagtgc cgccaccgcc accagcacca cctacctctc ttgctccagg cttcaggttc    120
cacccaactg atgaggagct tgttatttat tacctcaagc gcaaggtttc tggcaaaagc    180
ttccgatttg atgccatatc tgaggttgac atatacagga gcgaaccctg ggacctagca    240
gacaagtcaa ggttgaagac tagggaccag gagtggtatt ttttcagtgc attggacaag    300
aaatatggga atggtgggag gatgaacagg gctaccagca aagggtactg gaaagccact    360
gggaatgatc gaccggtgag gcatgaccaa aggaccgtgg ggctgaagaa aacgttggtg    420
tttcatagtg gcagagctcc tgatgggaag aggactaact gggtcatgca tgagtacagg    480
cttgttgaag aggagcttga gagggctggg actggatcct gtcagcctca gaaggatgcg    540
tatgttttgt gtagagtgtt tcacaaaaat aacataggac ctccaaatgg gcaacggtat    600
gcgcccttca ttgaagaaga gtgggatgac gcatcaggaa tggttccagg ggcagaccat    660
gtggataacc gctcttttgc ccaccaacca cgtgttgaag gcaatggtga tgttgtcatc    720
gaagttctga tatgttgcca atcgcaagta gagctactgg tgcatgtaag ccacaagctg    780
ccatcttgtc ttttgttcat gatcgcgctg ccacaaaatc aacaacccat tgacactcaa    840
tctttcaaca aagctccatt tgatgtgaac aagcttccta tagaaactca aaatcttcta    900
gctgatgata ataattgtaa gcacatggat gactaccctt cacctcaaac agataatcca    960
aagcctttct ctcaaatata caaacgaagg cgtcataact tgaactccaa caactctaat   1020
```

-continued

```
gtttctggag attcagtccg aaccagccag gatccgtgct cctctacaat aactaccgct   1080

gcaactgcac tcccaaccgc aactgttgct ggcacagcca ccaacactgc accgaaaaaa   1140

cattttctgt ctgcactggt ggagttttcc ctgctagaat cccttgaatc aaaggacaac   1200

cttgcttcaa ttaaggcacc ggattttgac actgaaaatc tcgagtcatc catgcctcca   1260

agttgcgcaa agttcatcaa gcaaatgcag agtgagatgc agaagctttc agttgaaaag   1320

gagacgataa ggtttgagat gatgagcgca caagcgatga ttaacattct ccagtctcgc   1380

atcgacgttc tcagcaaaga aaatgaggat ttgaagagga tggtggccca aaatccatag   1440
```

<210> SEQ ID NO 25
<211> LENGTH: 1296
<212> TYPE: DNA
<213> ORGANISM: Glycine max

<400> SEQUENCE: 25

```
atgtttttc aacaaagttc attctaccca cgagtcgatt caacaaaccc agacgctaat     60

tctcccttct ctaaccccgc accatcttct tcttcttctt ccatttatcc ctcagtggaa    120

acaacagaga atctcatttg ggaagagcca aacacgacta cagaagaagc catggaaaac    180

gttctggtca cggtcccggg tgcgattctg catctgatag aaaaggattc cagcgtgcac    240

cttgcttcgg gcgacctcac catatcgacc ctcggagaag gcgacaaagt ggtggcggtt    300

ctggcatgcg tcggcgatca ggttcagtgg ccgttggcga aagacgtgtc ggcggtgaag    360

ctggatgagt cgcactactt cttcacggtc caggtcccac aggagcacgg ggaggagaag    420

ggattcgagg tgttgaatta cggtttaacg gtggcggcga agggacaaga gagggtgctg    480

agggaactgg acgaggttct ggacaagtac agctttctgt cgaaggagaa actgaagggg    540

gttggaggtt gggaagtttt ggatggttca gtttcgacgg agacatcgcc ggaggagtta    600

caaggatcgg aagagaggaa ggaagtggtg gaggagcgtt ctggggcata ctggacgacg    660

ttggcgccaa acgtggagga ttacagtggg agtttcgcga gatggattgc agcagggtcg    720

gggcaagtgg ttagggggat tctgtgggct ggggatgtga ctgtggacag gttgaagtgg    780

gggaatgatt tcttgaagaa gaggttggag cctggttcac actcccaggt tagtcctcag    840

gcactggaga gcatcaaaag ggttaagaag ttgaccaaga tgtctgagaa ggttgccact    900

ggtgtcctct ctggggttgt caaggtgtct ggattcttca caagttctgt agtcaactcc    960

aaagctggaa agaagttctt tagccttctt ccaggggaaa ttgtccttgc taccatggat   1020

ggattcaata aggttttgga tgctgcagaa gtagctggaa ggaatgtcat gtccacttca   1080

tcagttgtga ccaccggcct agtttcgcat aaatatggag aggaagcagc acatgttaca   1140

aatgaaggcc ttgacgcagc agggcatgcg attgggacag cttgggccgt gttcaaactt   1200

gggaaggcac tcaaccccaa gagcgcaatc aagccaacaa cactagctaa agctgctgct   1260

gaagcaagtt cagctagact gaaggctaag aaataa                             1296
```

<210> SEQ ID NO 26
<211> LENGTH: 1365
<212> TYPE: DNA
<213> ORGANISM: Glycine max

<400> SEQUENCE: 26

```
atgaagagga tcattcgagt agcagggcct atggtgtttg tgtatgcttc ccagaatctg     60

ttgcaggttg tgtccatcat gatgattggt catctcaatg acgagctttt tctttccggc    120

gccgccttag ccatctctct tgccaccgtc actggtttca gccttcttac gggaatggct    180
```

```
agtggacttg aaactatatg tggacaagct tacggagctc gacaatatca aaaaactgga    240
gtgcaaacat acactgctat attctctctc acatgtgttt gtcttcccct gactataatt    300
tggatcagct tggaaaatat actagttttc ataggccaag accctctcat tgcacacgaa    360
gcaggaaact ttataatttg gcttcttcca gcactttttg catatgcaat tctgcagccg    420
ttagttcgat attttcaaat gcaaagtctg cttcttccca tgcttgcaac ttcttgtgtc    480
actctttgtc tccacatacc cctttgttgg gctttggtgt tcaagactga actgagtaat    540
gttggtggag cattagcaat gagcatttca atatggttaa atgtgatttt tctcgtatta    600
tacatgagat actctcctgc atgtgaaaaa acccgtgcac cagtgtctat ggagctgttc    660
caaggaattt gggagttttt tcgctttgct atcccttctg cagtgatgat ttgccttgaa    720
tggtggtcat ttgagctgct tatcttactg tctgggttgt taccaaatcc acaacttgaa    780
acttcagttc tatccatttg tctcaacacc atttccacac tctatgcaat agcttttgga    840
attgctgctg cagcaagcac aaggatttca aatgaattag gtgcagggaa tccacattct    900
gcccgtgttg ctgtgttggc ttcaatgtct tttgcaatca tggaggcaac tataattagc    960
ggaatcctct ttgtctgtcg ccatgttttc ggttatactt tcagtaacaa gaaggaagtt   1020
gttgattatg tcactgttat ggctcctctg gtttgcatat ctgttatact ggacaatata   1080
caaggtgttc tcgcagggat tgctagaggt tgtggatggc aacacatagg ggtttatgtg   1140
aatctagggg cattctacct ctgcgggatt cctgttgctg catcattggc atttttggct   1200
aaaatgagtg gaaaaggact ttggattggt ttacaagtcg gtgcctttgt tcaatgtgct   1260
ctactttcta ccgtaacaag ttgcacaaac tgggaacaac aggcaatgaa ggcaagaaag   1320
cggttatttg atagtgaaat ttcagcagaa aatatactgg tatga                   1365
```

<210> SEQ ID NO 27
<211> LENGTH: 234
<212> TYPE: DNA
<213> ORGANISM: Glycine max

<400> SEQUENCE: 27

```
atgagctact acgatcatca gcaacagcct ccaattggtg ttcctccccc tcaagggtat     60
ccaggaaagg acgcttaccc tccaccaggg taccctgcac aaggttaccc tccaccaggg    120
taccctcccc aaagctatgc cccacagtat gctcaacaac ctcctcccag gcaagaagtt    180
ggttttcttg aaggatggta ttttggctgc actctgctgc tgttgcatgc ttga          234
```

<210> SEQ ID NO 28
<211> LENGTH: 1260
<212> TYPE: DNA
<213> ORGANISM: Glycine max

<400> SEQUENCE: 28

```
atggaagaag aagaagaaga agacacgtcg ccaccgttct ggacggaaag cggcggtcgc     60
cgccgtctcc gccgctcgta ctcgctgttc ctcagctcca gtgcacctct aatatgcctt    120
ctggtgattg cactcgcatt catgctggtc ataattccca cgctgcactc tttcaccacc    180
caaattttca aacccaattc ggtgaagaag agctgggact ccctcaactt tgtgcttatc    240
ctcttcgcca ttctctgtgg cttcctcagc aggaacaact ccaacaccaa cgaaagcttc    300
tccgacacgc cacttgagta cgacaaacca aaccctccat taccgcgacc gtggtacgag    360
gaatcagatc gaacgccgta caaatcgtat aacaggctga ggagtttcag ctcccacccg    420
```

-continued

```
gatctccggc aagagtcgca gtggctcgcc gccgatgaac ggtggcgatt ctatgacgat    480

acgcacgtta acggttaccg tggatttgac ttggaggaac accggcagca tagaacggag    540

gccggagaag aagagagcgt tgagaacata gaagtggttg cgaaggaggt tccaccaccg    600

ccagctccgg cggagaggag gagtggggga aataagaata agagaacaag tgcaactaaa    660

gagttgttga catcttcgaa gggaaagaag aagaaacaaa gacaaggaaa cgttgaaagt    720

gttaagagca ttccttcaca accttcctca gtttttcata atatgttttc ttctaaggaa    780

agcaagctca agaaagttaa ctctgcttca tcgtcgcatg tttcattttc caaaacccaa    840

ccggttcgtg ggatgtggt ggctacttcc agtagatcaa acaagagaga ggatttctat    900

gcttcagaag aaaatgtggt tgttactggc aacgactcac ctttgatctc gatacctcca    960

ccgccgccac caccgccgtt caaaatgccg gcatggaagt tccgggtgca gggtgacttt   1020

gttagaatag atggcattag tagctggagt agtgatttgg aagatgaaat tgtggaatca   1080

ccgagcagtg aagatggtgg agcacctgaa atcttattgt tctatcctag tcctgatgtt   1140

gataccaaag ctgatacttt tattgaaagg ttcagagctg gtttaaggga ggagaagaag   1200

ggaattcgta cgtccaatct acgcccttca ccaaagccag aagctggacg gaccaagtag   1260
```

```
<210> SEQ ID NO 29
<211> LENGTH: 1182
<212> TYPE: DNA
<213> ORGANISM: Glycine max

<400> SEQUENCE: 29

atgggtgctt atgatcaagt ttctcttaag ccattggatt cttctagaaa gaggaaaagt     60

aggagcagag ggtatgggac tggatccgtg gctgagacta ttgcaaagtg gaaggaatac    120

aacgaacatc tttattctgg caaagatgat agtagaacaa ctcgaaaggc accggctaaa    180

ggttcgaaga aagggtgcat gaaagggaag ggaggacctc aaaactctca gtgtaactac    240

agaggagtta ggcagaggac atgggggaaa tgggttggtg agattaggga gcccaataga    300

ggaagcaggc tttggttggg taccttctct tctgcccagg aagctgctct tgcctatgat    360

gaagctgcta gagctatgta tggtccttgt gcacgcctca attttcccgg catcacagat    420

tatgcttctt ttaaggaatc gttgaaggaa tctccgatgg ccgcatcgtc ctcttgttct    480

tcggcagaaa ctgcaacatc tgacactact actacatcca accaatcgga ggtttgtgca    540

gctgaggatg ttaaggagaa tcctcgactt gtcaatgtga atgataaggt taacgattgt    600

cataaggctt atgaagctgc ctcaccaact agcagaatga agcaagagcc taaggatgag    660

gctgtggatc acatggtccc cggggctggg aaaattctag atgtcagacc agaaggaaca    720

catgatgccg ggcaggttgc agaggatgta aacaaagatc agatggactt gccatggatt    780

gatggctttg attttagtga caattacttg aacaggtttt ccacggatga gttatttcag    840

gtggatgaac ttttggggct tatagataat aacccaattg atgagtctgc gttgatgcaa    900

agtttggatt ttggacaaat gggttttcct ggagatggta atcctcaggt ggatgatacg    960

ctttcaagct ttatttatca gttgcaaaat ccagatgcca agttgttggg aagtttgccc   1020

catatggagc agacaccttc aggttttgat tatggattag atttcttaaa aacagtggag   1080

tcaggggatt ataatggtgg aggggaagaa ccgcgatttc ttaatttgga tgatgatctg   1140

aaccctgatt caaagggcat gcaagcaagg aaggatgact ag                      1182

<210> SEQ ID NO 30
<211> LENGTH: 1761
```

<212> TYPE: DNA
<213> ORGANISM: Glycine max

<400> SEQUENCE: 30
atggatacaa tcaagtcctt caagggctac ggcaaagttg acgagttgga gcagcaagcc 60
tatcagaaga agacacgtaa gcgcctcata ataatcacag tctcttcaat cgttctaatt 120
gcggtgatca tcgccgctat cgcaggggtt gtcatacaca agcgcaacac ctcatcatct 180
ccctcatccg actcgccccc gcaaactgag ttaaccccgg ccgcgtcact caaagcggtt 240
tgcgacgtga ctcagtaccc taactcgtgc ttctccgcaa tctcctcgtt accggattcc 300
aacactactg atccggagct cctcttcaag ctctctctcc gcgtcgccat tgacgaatta 360
tccaagctct cgagctttcc ttcgaagctc cgcgctaatg cggaacacga cgcacgtctc 420
cagaaggcga tcgatgtctg cgggaacatt tttggcgacg cgctggaccg gctcaacgac 480
tccatctccg cgctcggaag cagcggcggc gccgggaaga ttatctcccc ggcgagtgtt 540
agcgacgtgg agacgtggat cagcgccgcg ctcacggacc aggacacgtg cctcgacgcg 600
ctcggagagc tgaactccac cgccgcgagc ggcgcgttgc gcgagatcga aaccgccatg 660
aggaactcca cggagttcgc gagcaacagt ttggcgattg tcacgaagat cctagggttg 720
ctgtcgcagt tcgcggcgcc gattcaccac cggcggctgc taggatttcc ggagtggctc 780
ggggcggcgg agcggaggtt gcttcaggtg aacagcagcg aaacaacgct ggacgctgtg 840
gtggcgcagg acggtagcgg acagttcagg acgatcggtg aggcgctgaa attagtgaag 900
aagaagagcg agaagaggtt cgtggtgcac gtgaaggaag ggcgttactt agagaacatt 960
gatttggata agaatacgtg gaatgtgttt atcttcggtg acggcaagga caaaaccgtc 1020
gtcgtcggta gccggaactt catggacggc acgccgactt tcgaaaccgc caccttcgct 1080
gtgaaaggca agggattcat tgccaaagac ataggttttg tgaacaatgc aggtgcatct 1140
aagcaccagg ctgtggcatt tagatctggt tcggaccgtt ctgtgttctt tagatgctca 1200
ttcaatggct tccaggatac cctctatgcc cattccaatc gccagttcta ccgtgactgt 1260
gacattacag gcaccataga cttcatattc ggaaatgcag ctgcagtgtt ccaaaactgc 1320
aaaataatgc ctagacagcc tctaccaaac cagttcaaca ccatcacagc tcagggcaag 1380
aaggaccgaa accagaacac tggaatcata atccagaaat caaaattcac tcccttggaa 1440
aacaatctca cagctcccac ataccttggt aggccatgga aagatttctc caccactgtg 1500
atcatgcaat ctgatattgg gtcattcttg aagcctgtgg ggtggatgag ttgggtcccc 1560
aatgtggaac ctgtaagtac catcttctat gctgaatacc agaatactgg gcctggagct 1620
gacgtgtcac agagggtcaa atgggctggg tataagccca ctctcacgga cggggaggca 1680
gggaagttca ctgtgcagtc ctttatccaa ggccctgagt ggttgcccaa tgctgctgtg 1740
cagtttgatt ccaccttgtg a 1761

<210> SEQ ID NO 31
<211> LENGTH: 879
<212> TYPE: DNA
<213> ORGANISM: Glycine max

<400> SEQUENCE: 31
atgggtatac tgaaatcaaa acaccacaag cacacgctcc tcttttttct tagtatttcg 60
tttcctctgt ttcttcttac acctattact acctcagaca acacaaactt gatctacaaa 120
ggttgcgccg accagaagat gcaaggccaa tactcccaga accttaaacc gctcttggat 180

```
tcactagtgt cggcgtcggc gcaaaagggc ttcgccgcga ctacacaaaa cgcgctcacg    240

ggcgcgtacc aatgcagagg ggacctctcc aactccgaat gctacaactg cgtcagcaag    300

attccaaaca tgctggggcg cctctgcggc ggtgatgacg tggcggcggc gcgggtgcag    360

ctgagcgggt gctacctgcg gtacgaggtg gtcgggttca aggtggtccc ggccacgcag    420

ctgctgtaca aggtgtgcgg ggcccgcaag gtggtcgacg gcggagggtt cgaggcgagg    480

agggacgcgg cgtttgggat ggcggagaac ggcgtgcaga acagcggaaa tttgttctac    540

acggggagtt accagagcct ctatgtgttg gggcagtgcg agggtagttt gggaaatgcg    600

gattgtgggg gttgtatcaa gagtgctgcg gaacaggctg ggatcagtg tgctgactcc    660

atctccgcgc aggtttatct ccagagttgt tttcttagtt atagctttta ccccaatggt    720

gttcccacct tgtcatcttc ctcaggagga ggagggggc atccacacac ggagaggaca    780

gtggcacttg cggtgggagg ggtggcggct ctgggattct tgattgtttg tttgttattt    840

ctcaagtcgg tgttgaagag aagaggtggg aagcgttga                           879
```

<210> SEQ ID NO 32
<211> LENGTH: 396
<212> TYPE: DNA
<213> ORGANISM: Glycine max

<400> SEQUENCE: 32

```
atggggatcc ttagcgatca tcataatcag aagcatcacc accaccacca tcatctcatg     60

agttttcatt tgcacattcc tcaccttcag tactttcacc atcaccaaca acaagagaag    120

aaggaggatc tgaaggacat tccaaaaggg tgtttggcca tcttggtagg gcaaggggag    180

gagcaacaga ggtttgtgat ccctgtgatg tacatgaacc acccattgtt catgcagttg    240

ctgaaaaaag ctgaagagga atacgggttc gaccagaaag gccccatcac cattccttgc    300

cacgtggagc acttccgctc tgttcaaggc ttgattgata aggacaaatc cctccaccat    360

ggccatcacc accatgcttg gtgcttcaaa gtttga                              396
```

<210> SEQ ID NO 33
<211> LENGTH: 624
<212> TYPE: DNA
<213> ORGANISM: Glycine max

<400> SEQUENCE: 33

```
atgttttcca tcaatcattt ctccgaccca gatgccacct cgccggggtc gggaggaagc     60

tcccgaccgg cgctgtcgga cgaggatttt tttctggcgg caagcaatcc caagaaacgc    120

gccgggagga agaagttccg ggagacgcgc cacccggtgt accgcggcgt gagaaggcgg    180

gactccggca agtgggtgtg cgaggtgcgc gagcccaaca agaagtccag gatttggctc    240

gggacctttc ccacggcgga gatggcggcg cgtgcgcatg acgtggcggc gatcgcgctg    300

aggggaaggt cagcctgcct caacttcgcc gactccgcgt ctcggctccc ggtgccggcg    360

acggcggagg ccagggacat tcagaaggct gcggcggagg ccgcagaggc gtttcgccct    420

gggaaggatg atgatgcggt ggcggagagg gtggcagcga cggcgacgga gcgtgaagaa    480

gaacaagaag aagggatggt gccggagtat ctgaggaaca tggtgctcat gtcgccgacg    540

cattgcttcg ggagtgatga gtatggaagt gctgacgtgg aatttgacga tgctgaagtt    600

tctctgtgga gttactccat ttaa                                           624
```

<210> SEQ ID NO 34
<211> LENGTH: 855

<212> TYPE: DNA
<213> ORGANISM: Glycine max

<400> SEQUENCE: 34
atggacgaat tagaagaaac cctactcacc caaatcgact gggaatcgtt cctcgacgac 60
atacctgaac ttaacgtcga tgattttttg caggacgaca acgccgttcc tgttgttacc 120
gacaatcatt cctccccgaa cgacgacccc gttttgtccg agatcgagaa catgctcatg 180
acgcaggccg aaaacgacgc tgtcgttttg cccgagacgc cgtcttcgga ggccgggtat 240
tacaagctct tcgaggagat tctggtggag gagcccaagg aaggacccgt gagcccgcct 300
tcaaaaatag agtccgagga aggctccgac aaagacaaga ccgatgatgc tgcttccgat 360
gaacccatgt cgaagaaatt aaagaggcag ttgaggaaca gggatgctgc tgtgaggtca 420
agggagagga agaagttgta tgtgaaaaac cttgagatga agagtaggta cctagaaggg 480
gaatgcagaa gactggggca tttgctccag tgctgctatg ctgagaacaa cgctttgcgg 540
ctttgcttgc aattgcgtgg tacatatggt gcttcaatga ccatgcagga gtctgctgtg 600
ctcttgttgg aacctctgct gttgggttcc ctgctgtggt gcatgggcat catatgccat 660
ctcagtctgc ctctaatgct gtgggttgca gcagtacttc caagagaaaa catcgagcag 720
aagggcctaa gaagggtaac tcaaaaagga tcagaaagta agatctctga gtgtttccag 780
atgcaatcat ttttaaagag tagaaaaagc cgagcttcaa gaacaaagat gaaattcaat 840
tttatagtgt tctaa 855

<210> SEQ ID NO 35
<211> LENGTH: 852
<212> TYPE: DNA
<213> ORGANISM: Glycine max

<400> SEQUENCE: 35
atgaatacca acaacgacac cgaaaaaaac caatcatttc cagaagcaca aggagcatca 60
tcatcatcat cttctccacc caatgttggg actgagaatt ggggaactca cataatgggc 120
acccctgctg ttccaagcag ccacccagat aacaaaaaag cagctttaca aagtggacaa 180
cctcaaccag ttcaatacta ccatgaccaa catcaacatc cctacgtgca acatagccca 240
gttgacaaac caagcaacag tcccatggag tcaatcctta acatgttcga ttcatggagc 300
aaaaaagctg aagccaccgc acacaacgtc tggcacaacc ttaaaactgg tccatcagtg 360
tcttcagctg cactggggaa gatgaatctg actgtgaaag caatatcaga gggtggattt 420
gagtcccttt acaagcaaac attcacaacc tatccaaacg agaagctcaa gaagagcttt 480
gcttgttacc tttcaacatc aacaggtcct gttgcaggaa ccctttacct gtccaatatt 540
catgtagcgt tttgcagcga tcgccctttg tgtttcactg caccctctgg ccaagaaact 600
tggacatact acaaggtaat ggtgcctttg ggaaaggttg gagtggtcaa cccagtgacc 660
atgagggaaa acccatcaga aaagtacatt caggttgtaa cggtggaagg gcatgatttt 720
tggttcatgg gttttgttaa ttttgacaaa gcagttaaga acatctcaga aggtatctca 780
cattttgtag cgccaggagt ggccgtgcca tccactagtg gttcggaagc taatcgaaag 840
aactttcagt ga 852

<210> SEQ ID NO 36
<211> LENGTH: 888
<212> TYPE: DNA
<213> ORGANISM: Glycine max

<400> SEQUENCE: 36
atgaaaaccc ttaacaaagc ctcacttatt ttattccctc tcttgttcct ttccctattc 60
aagcattccc atgctgcagg aatcgctatc tactggggcc aaaacggtgg agaaggcacc 120
ttagcagaag cttgcaacac tagaaactac caatatgtga acatagcctt cttgtccact 180
tttggcaacg gccaaactcc acaactcaac cttgcaggtc attgtgaccc caacaacaat 240
ggctgcactg ggttgagcag tgacatcaaa acttgccaag accttggcat caaagtgttg 300
ctctcccttg gtggtggtgc tggaagctac tccctcagct cagctgatga tgccactcaa 360
cttgcaaact acctctggca gaatttcctt ggaggtcaaa ccgggccatt aggtaatgtt 420
atattggatg gcattgactt tgacattgaa tctggtggga gtgaccatta tgatgaccta 480
gccagggcat taaatagctt cagctcacaa aggaaggtgt acttgtctgc agccccacag 540
tgcataatcc ctgatgctca cttggataga gccatccaaa ctgggctttt tgactatgtg 600
tgggttcaat tctacaacaa cccttcatgc caatactcca gtggaaacac caacaatttg 660
atcaattcat ggaaccaatg gatcacagtg ccagcttctc aaatcttcat ggggcttcct 720
gcatctgagg cagctgctcc aagtggtggc tttgtgcccg ctgatgtgtt gacttctcag 780
gttcttcctg tgattaaaca gtcttcaaag tatggtggag tcatgctctg gaacagattc 840
aatgatgtcc aaaatggtta tagtaatgct attattggaa gtgtttaa 888

<210> SEQ ID NO 37
<211> LENGTH: 1011
<212> TYPE: DNA
<213> ORGANISM: Glycine max

<400> SEQUENCE: 37
atgggaaggc aaccttgctg tgacaaagtg gggttgaaga aggggccatg gaccgcagag 60
gaggataaga aactcatcaa tttcatcctc actaatggcc aatgttgctg gagagctgtc 120
cctaaactag cagggctgtt aaggtgtggc aaaagttgca ggctcaggtg gacaaattat 180
ctgaggccag acttgaagag aggccttcta tcagaatatg aagagaaaat ggtcattgat 240
ctccatgctc aacttggcaa tagatggtct aagattgctt ctcatctccc aggaagaact 300
gataatgaga tcaagaatca ctggaacacc cacataaaga aaaagctcaa gaaaatggga 360
attgatcctg ttactcacaa gccactttcc aataaaactg agcaaactca agcccaacca 420
gatgaacaac aaacccacca accattgcaa gaacaacaag aagaacctat cccagttgag 480
aaagacacca aatttgaacc tgaaaaagag caaaacaagg agccagagaa gccagagagt 540
tcaattgaat cattaaccat cactgaagaa gccaaggagg aagaccaaat tatgacaccc 600
ttatttgact catgggaact aatgaatgag ttctgcactg atgaagttcc cataatagaa 660
tcaaatgaga ttctagttcc ttctgctcct tcttccactt caccaaccac tactactact 720
acatcatctt caacatcaac atcagcatct tcaaattcaa attcatccaa cttccttgaa 780
gaccttctgc tcccagattt tgagtggtct gatgattaca atgatactaa ttttgacaat 840
aataacaata gcagcatggc cttgtgggat gatgacttta ttagaagttg gaatttgctt 900
attaatgatg atgatggtga tggtgacaga aagcaagtgt ttgaggctcc tatcaatcag 960
tacccaagag tgatcatgga ttcagattct tgggcctatg gcttgttttg a 1011

<210> SEQ ID NO 38
<211> LENGTH: 654
<212> TYPE: DNA
<213> ORGANISM: Glycine max -continued

<400> SEQUENCE: 38

```
atggcggcgg agcacgacag ctgctgctcg cgctgtgtca ccttcctaat aaccataggc     60
ctcacagcgc tcttcctatg gctgagtctc cgcgttgacg aaccaaaatg ctacctcgac    120
tacatttacg ttcctgccct caacaaaacc ctaaattcca attccactca caacaaaaac    180
accacaatac tcttcgctct caagctcacc aacgggaaca aggacaaagg catccaatac    240
gacgacgttc tcctctcctt cagagtcttc gagagcgtca acctcacgcg cccactcggc    300
aacgccaccg tgcaaaggtt ctaccagggc caccagaaga aggccaccaa gcacggaaac    360
ttcagcggcg gcggcggaaa cctcaccgcg gcggtggctg ggagaatgtg gtaccgtgtg    420
gactatgcta ctgcggtgaa gtacaagatt ctcttctggt acacgaaacg gcaccgttta    480
tggggagggg caaatgtgga aattggcgat tcgggaatga aggtgtatcg taaagccgtt    540
aggcttggag ggaagaaccc cgtggtgatc gagtccggcg catctaagct cagtggacgc    600
tatcgtgcgc ttcttctttc ccttcttctc cctttttgtg gcttgtgggt ttag          654
```

<210> SEQ ID NO 39
<211> LENGTH: 1668
<212> TYPE: DNA
<213> ORGANISM: Glycine max

<400> SEQUENCE: 39

```
atgatggctt cttcctctct cttctacctt tctctctccc tcatcctaac cctcacctcc     60
gccgcgcgcc acaaacccca cccctcaccg gccaagccac cagccaagcc cgccgtgacc    120
accgccacct cgccggcaat tcaacaagcc tgcgccgcga cgcgcttccc gcagcaatgc    180
gaagcctctc tctcccaatc ccagaacctc cctccgaacc cgaacccgac ccctctccag    240
ctcctccagt ccgccatcgc gctctcctcc gacaacctcg ccaccgcaca gacgatggtc    300
aagtcactcc acgacgcctc cgccgacagc cgcaaccgca ccgtcgccgc cgccacctgc    360
atcgagatat tagccaactc ccattaccgc atttccctcg ccagcgacgc gctcccacga    420
ggcaggacca aggacgcgcg tgcttggctc ggcgccgccc tcgcctacca gtacgactgc    480
tggaacagcc tcaaatatgc caacgacacc gaaatggtcg gcaaaaccat gttgttcatc    540
gataacctcg aaactctctc cagcaacgca ctcagcatgg cgttttcctt cgacgccttc    600
ggaaacgaca ccgcttcgtg gaagccccca gtaacggagc gcgacgggtt ctgggaggct    660
gtgggctcgg gtggccccgc gtccgcggga ggggtaccgc cgaatttgac gcccgacgtt    720
acggtgtgta acaatggagg agacgggtgt tataagacgg tgcaggaggc cgtaaacgcc    780
gcgccagcga acggaacaaa gaggtttgtg atatacataa aagaaggggt ttacgaggag    840
accgttagga ttccattaga aaagaggaat gtggtgttct tgggcgacgg cattggcaaa    900
accgtcatca ccggtaacgg caacgtggga caacaaggga tgacaactta caactctgcc    960
actgtcgcgg ttcttggcga tggattcatg gcaaaggaac tgacggtcga aaacacagca   1020
ggtcctgatg ctcaccaagc agtggcattc agattagaca gtgatctttc tgtgattgag   1080
aattgcgaat tcttgggcaa tcaagacact ctctatgctc actcactgcg ccagttttac   1140
aagtcatgcc gcattgaggg cagcgtggac ttcatctttg gaaacgctgc agcagttttc   1200
caagactgcc aaatcctagt tcgtcccagg caagtgaagc cagagaaggg tgagaacaat   1260
gccatcacag cacacggcag aacagaccct gcagaaccca caggctttgt tttccaaaac   1320
tgtttgatta atggcactga ggaatatata gcattgtacc tcagcaagcc tcaagtgcac   1380
```

-continued

```
aagaactatt tgggtaggcc ttggaaggag tattctagaa cggttttcat taattcgatc   1440

ttggaggctc ttgtcacacc acagggttgg atgccatgga gcggtgactt tgctctcaag   1500

acactttact atggggagtt tgagaacaag ggtactggct ctgatttgtc tcagagggtg   1560

ccatggagta gcaagatccc tgctgaacac gtattgacgt attcggtgca gaatttcatt   1620

caaggaaatg attggattcc atcatctgtt ggtagcccat cctcgtaa               1668
```

<210> SEQ ID NO 40
<211> LENGTH: 3942
<212> TYPE: DNA
<213> ORGANISM: Glycine max

<400> SEQUENCE: 40

```
atggaagcag agactttgaa tgcaaatcac cctcccggtt ttcttcaccg gtcgctcccc     60

gctgttgtgc ctatcctttt gatttcaata ggatatgttg accctggaaa gtgggtggca    120

attgctgaag gaggtgcacg atttgggttc gatctgatgg ccttcatgct tatctttaat    180

tttgcagcca tcttctgtca gtacatatca gcaaaaattg gtgttatcac aggaaaggat    240

cttgctcaga tttgcagtga tgagtacgat aattggacat gcatgcttct tggagttcag    300

gcagaacttt cggtgattat gctagacctt aacatgatat tgggcatggc acatggatta    360

aatattcttt ttgggtggga cttgttcact tgtgtctttt taattgctac tggtgctgtt    420

ttccatctcc ttctttttgc cctcctggac attgagaagg tgaagatcct gggcctgttt    480

gtgtcaggtt ttgtatttct ttcgtttgta cttggaacac tcattaatca accagacatt    540

ccattatcca ttaatggaat actaacaaag ttgagtgggg agagtgcatt tgtgctgatg    600

agtctattag gagcaactct tgtgcctcac aacttctacc ttcattcctc tattgtacag    660

tggcatcagg gatcaactac catttctaag gatgctttat gtcataacca tttttggcc     720

atcatgtgtg tcttcagtgg cctttatttg gtaaataatg tgctgatgaa tgctgcagca    780

aatgagttct acagtatggg tcttgttttg actacttttc aggatgcatt atcaccaatg    840

gaacaggtgt tgcgtagtcc aatagccatg cttgcttttt tactcattct gttttttca     900

aatcaaacca cagcattaac ttggagtttt ggtggagaag tagttgtgca aagtttctta    960

aaattggata ttccgggttg gcttcattat gctacaatta gagtaattgc tgttctgcct   1020

gccctttatt gtgtttggag ttcaggagct gaagggatgt atcaactact tatattcact   1080

cagattgttg tagctctgca acttccatct tctgtgatcc cccttttttcg gatcgcctca  1140

tctagatcaa taatgggggt acacaagatc cctcaatttg tggaattttt ggcattgatc   1200

atattcattg ggatgcttgg cttgaatatt gtctttgttg tagaaatgat atttggcagt   1260

agtgattggg tgggcaattt gagatggaat gtggggactg gtgtgtctct ctcttatttg   1320

gttcttcttt gcactgcgtt tgcatcattc tgtctgatgc tttggttagc tgccacacct   1380

ttaaagtctg ctagtgttca attggatgat cagcaatgga actgggacat gccacaggcc   1440

gtaccaaaat cacggattga taacgaggaa acagatttaa aagaaacaag atatcaagga   1500

gatgcatcag ttcaggggaa ggaaccatca ccagctctag caaggaccct ggaatattca   1560

gatgtaccag ttgcaagttt tcatcttgat ctacctgaaa ctatcatgga gcctgatgtt   1620

cctgtgacta ctgtaaggga gactcatcca tttacatcat ttccttgctc cccaacatct   1680

gttaaggaat cagcttccac ttcagaatcg gaggcagtac cagctgtaag taatgagact   1740

tctgatatta tattgggaca ttccaaaact ttgaaaacag aaactactgc ccctgttgag   1800

aaaactgtag aaattgaggg agattcaaat gccgaaaggg atgatgatga tggagattca   1860
```

```
tgggaaactg aagaaataca aaaagtggtc tcactagccc catcttcagc atcagatggc   1920
ccagcatcat tcaggagcct tagtgggaaa agtgatgatg gagggaatag cattggtagt   1980
ctttcgagat tagcaggttt agggcgcggt gcaagacgtc aactagctgc tattcttgat   2040
gaattctggg gacaacttta tggtttccat ggtcaattta cccaggaagc taaggccaag   2100
aaacttgatg ttttactggg aatagattca agactcactg gttctttgca aagaatggat   2160
ccatgtggaa aggaatattc tgaatattta atatctgtag gaagtagagc tccagatact   2220
ttaatgaact ctgctccata tgaatctccc aggcagaata ggatccaaag taatttagat   2280
gcttcctatg ggcctcaaag gagttcttcc tcactgcggg caaatcctgt ccagtttatg   2340
gatgaatatg ttcagacctc cagccgcaat ctcctcgatg ctggtgaaag gcgctattcc   2400
agtgtgcgca atttacctac gtctgcagcc tgggattatc agccagctac tatacatggt   2460
tatcaggttt catcgtatat taatcaggtt ggtaaagaca caaattctga taacttaaat   2520
ggtctgaggg aatccccttc catgggtaat acgaaccact acaggaattc tatgggtaat   2580
acgaactaca ggaattctat tgcatttgct ttgggtaaaa agttgcaaaa tggttcaggt   2640
ttaagccaac ccccagggtt ccagaacatt gctgtctcta agaatagcca attgccatct   2700
gagaggtcct attatgattc tcgcccttcc ggacctgtgg atagtacagt cagttcagtc   2760
aatgctaaaa agtaccacag cttgccagat atttcaggat atgccattcc tcacagggat   2820
gtttacatgt ctgataagag tgctccatgg gatggttctg ttggtggata tagatcttct   2880
gcaagtagga ctcattatga accgtcatta tattcaaact ctggatcaag gacaggagct   2940
cctttagcct ttgatgtact ctctccatca aaagcctaca gtgatgaact ttcttctcag   3000
ttgagttctg gttttggcac tggatccctc tggtccagac agccttttga gcagtttggg   3060
gtggatgata aaattcataa tgctgcaaca gaagatgttg gaaataggcc tagtgcaact   3120
actcaagaaa ctacttcagt ggtggatata gatggcaaac ttcttcaatc ttttagacaa   3180
tgtattttga aactcttaaa attggaaggg tctgattggt tgtttaaaca gaatgatggg   3240
gctgatgaag atctgattga tcgtgttgct gcaagggaga aatttgttta tgaaattgaa   3300
accacagaga tgaaccgcaa tcatatggga gaaactcgat atctttcttc tgatgggaag   3360
tcttgttctt caatgaagaa taatgaggct aattggtcta gtttttccgt aacctcaatc   3420
cctaactgtg gagatggatg tgtatggaga gcagacataa taataagctt tggggtgtgg   3480
tgtatcaaac gtgttcttga cctctcatta atggagagcc ggccagagct gtgggggaag   3540
tacacttatg tactcaatcg cctccagggc atcattgatc tggctttctc caagcctcgt   3600
agtcccatga ccccatgctt ttgccttcaa gttcccatga cttaccagca gaagtcaggc   3660
tcacctcctt ccaatgggat gctgccccct gcatcaaaac caggccgtgg aaaatgcaca   3720
actgcgtcag tggtgtttga gatggtcaag gatgtggaga tagcaatctc tagccggaaa   3780
ggtcgcacag gaactgctgc tggtgatgta gctttcccaa agggaaagga gaatttggca   3840
tctgttctca aacggtataa gcgtagatta tccaataaac cagttggcac tactcaagaa   3900
gggattcgca agattcccac atcagcacca tacaacttgt ag                      3942
```

<210> SEQ ID NO 41
<211> LENGTH: 684
<212> TYPE: DNA
<213> ORGANISM: Glycine max

<400> SEQUENCE: 41

-continued

```
atggccgata agcaacccca cttgaatggt gcttattacg gtcccgccat tcccccggcg     60

gagcaaccac actaccgccc tagccgcgaa agaagctgct gttgctgcct cttcggaatc    120

ttgtggaaga ttctggttgc actcattgtc ctcgttggcc tcgcggtcct catcttctgg    180

ctggtggttc aaccccgttc cttcaagttc cacgtcacga aagccaacct aacacaattt    240

gattactata ccaacaacaa caccccttcac tacaacatgg tcctcaactt cactgcacgc    300

aaccccaaca aaaaactcag catatactac gacaaagtag aggcattagc attctacgag    360

gatgtcaggt tcgccaatta cagtgtgata acgcacatga actccttccg ccagtacaag    420

aagaccacca gccacatgag cgccgttttc tcggggcagc aagtgttgcc gctcgacaac    480

gacctagtct cagagttgaa ccaagacaag agtggtgggg tgtacgagat cgatgtgaag    540

ctctacttca ggattaggtt caggctcggg gatgtcaaaa cccgtcgctt caagcccgag    600

gtcaaatgtg atatcagggt tcccttgagg accaatggca gcgtaacttt gtttcagacc    660

accaagtgtg atgtcgatta ctag                                           684
```

<210> SEQ ID NO 42
<211> LENGTH: 1185
<212> TYPE: DNA
<213> ORGANISM: Glycine max

<400> SEQUENCE: 42

```
atggcacaag aaacctttct attcacatct gaatctgtaa acgagggtca ccccgacaag     60

ctgtgcgacc agatctctga tgcagtactt gatgcgtgcc ttgaacagga ccctgacagc    120

aaggttgcct gtgagacatg caccaagacc aacatggtca tggtcttcgg agagatcaca    180

accaaggcca acgtagacta tgaaaagatt gtccgcgaca catgccgcga aattggattc    240

atctctgatg atgttggtct tgatgctgac aaatgcaagg tgttggtcaa cattgagcaa    300

cagagcccgg atatcgccca gggtgtgcac ggccacttca ccaagcgccc agaggaggtt    360

ggtgctggtg accagggtca catgtttggg tatgccaccg atgaaacccc cgagtacatg    420

cccctcagcc atgtccttgc aaccaaactt ggtgctcgcc tcacagaggt taggaagaat    480

ggcacctgtg cttggttgag gccagatggt aagacacaag taaccgtcga gtactacaat    540

gacaatggtg ccatggttcc agttcgtgtc cacactgtcc taatttccac ccaacatgat    600

gagactgtga gcaatgatca aattgctgcg gaccttaaag agcatgttat caagcctgtc    660

attcctgaga agtaccttga tgagaagacc atcttccacc ttaacccttc tggccgtttt    720

gtcattggtg gccctcatgg tgatgctggt ctcactggaa gaaagatcat cattgatacc    780

tatggtggct ggggtgctca tggtggaggt gccttttcag ggaaggaccc taccaaggtt    840

gacagaagtg gtgcctatat tgtaaggcag gctgcaaaga gtgtcgtggc aaatggcctt    900

gctagaaggt gcattgtgca agtttcctat gccattggtg tccctgagcc cttgtcagtg    960

tttgtggaca cttatggaac tgggaagatt cctgacaagg agattctgca aattgtgaag   1020

gagaatttcg acttcagacc tggaatgatc accattaact tggaccttaa gaggggtggt   1080

cataggttcc tcaagacagc tgcttatgga cactttggaa gggatgatgc agacttcacc   1140

tgggaagttg tgaagccact caagtcagag aagcctcaag cttaa                   1185
```

<210> SEQ ID NO 43
<211> LENGTH: 2991
<212> TYPE: DNA
<213> ORGANISM: Glycine max

<400> SEQUENCE: 43

-continued

```
atgaagcttg atccatccaa accacccttt tcttatgacc aacattggcc ctatgccggc     60
aattttgggc accctacttc cccacatttc tgctgtggcc acaacaactt ccccttgtcat   120
tatagctaca tgccttcata tcctcatgcc ccttctccaa tgtatgaaaa tgacaaatgc    180
atgccccgag agcttcattg ttctggttct gctaatcatc catgcaacca aaaggaaggt    240
agaagtgtga agattgaaga gcatgaactg gatggtggaa agaaagagaa tgatgctttg    300
gtcccaattc agctcaagaa ttatccatat cccttagttt ggattccaca ggagtacaca    360
agtaacaaac agctgaaaaa tcctagtaca atggaagttc gtgaacaaaa caagccttct    420
agtcttgaga attctaatgt tgatgcgcag ccaacacagg agcctatagt atggaatgga    480
tggcttccct tcaatataaa gggtgcccgg aacatgattc acgatggata tggaacaaga    540
aaccagaaac aggagtctgg caataataga ggggaatctg aaaatggaaa aatagaccag    600
aaacatcaaa gtgaacagaa gaggtcagaa ttcccattcc ctatcttctg gttgccttat    660
tacaataagc aggaggagag tggagagact aagaaccagg agaaaaacat ttcttcacca    720
aaaattgttg aggaggtacc ccatacattc aaatttgttc cagtgaagtc tcatgttgat    780
gaaggtgaga aagtgaataa tgccagaagc atacctgtga agcagataga atcccacgaa    840
ggaaaaaatg tttctctcga tcaaatggaa gagaatgtga cacaaaagga ctcttgcact    900
ggggacaaaa agagacaatc tacatcttca cctaaaggat ccaagttacc tccggtttgt    960
ctgagagttg atccactacc aaggaagaaa aatggccacg ggagttcgag ttcgaggtcc   1020
ccaagtccac cttcatcaaa agggaattcc caagctacaa ctggtgaaac attcaagact   1080
cctagccaga tgaaagtaaa catacccagt aaaggtctga aggggcaag ggaaacatgt    1140
ccagatgatg atgactataa gactgaagat aaaaaggcag agaaaggagc agaaaatatg   1200
atggaggaaa ctactgaatc aagggaagag aaggattcaa gcacacgaac tgatgcgggt   1260
cgaaaagatg gaagagtttt gtcagatgca gatgctgctg ttttgataca agctgcatat   1320
cgcagttatc tagttagaaa atgggaaccg ttgaagaagt tgaagcagat agatgaagtc   1380
aggaaggagg tgactcgtgt tcaaggccgt gttcaagctt ttgagagatc tcccgaactt   1440
caaaatgatg acaaacaaaa aattgcaatt gaagagacca taatgaaact cctgctgaag   1500
ttggatacta tactgggttt gcatccaagt ttcagggaga tcagaaaatc cttggctagg   1560
gagctcataa tcttgcaaga aaggcttgat tctataatgg ccaagaaacc tcagcagcag   1620
atgccggata gtgaagaaca tgtgcaaaag cagcaagaag aaaaggttgc tgtaccagag   1680
gattcagctg aaggcactag ggatgatgta aaaggtcctt gtgctaatga tggtggaagt   1740
gaatctcagt caccagttga tcctccatca aatgagggag cagagtctgt tgcacttcca   1800
aatggctcag ataatgagga caccagccaa gtggttacat ctgatgcatt gaattcttca   1860
agtgatctgt ctgagagtga caaaatggct gtggaatccg aagctaaatc agaagtgaaa   1920
gacaatccga ttgcggaaga cattcccatt gaggttgata aattggacaa gactgtttgg   1980
gaagaattgc ctgtgggagt tattgatgaa gatatcaatg atgttaccat ggtgaatgat   2040
tcggcacaag aaggattaaa ttcagagagc tatgcaatga tggaactgcc attgggatta   2100
catgaggagc atgaaaggga caatgaaatg aatatttcta atggagaaac acggtctgag   2160
aatgagatat ttattgagga gcttcctgtg ggactgcacg atgaagatac aacaatatct   2220
aaagataaga gggatggtca agctaagcct aaaacatata aagaggttcg actagctcaa   2280
gaaggggaat gcaatgcaga tgaggaaaca agttcttcca cagatgacac tgccaacgaa   2340
```

-continued

```
actcaactag agcaacagca gaagctgaaa gagcaagaag aggtgcatta ttctagggaa   2400

tcagatggct gggtaaaaat tgagtacccg gaagaaggtg aactcaatgg tgatgcacca   2460

atggatataa gagttgagtg caagtcaggt gaggaagctg gaactgatac taagttgctt   2520

cctttaacaa cacaagtcag tgataatgaa ccagaaaatg aagatgtatt ctcagaagca   2580

aattatgtaa ataacaaatt aaccgagcca atggagtttg taccttccaa tgacacacag   2640

aaggaggaga caccagagat ggttgctgaa gaggcaatta tccctgatga taaagacaca   2700

gaaaatttgg ccaaagagaa aactgaagta tctgcagaac caccacctgc attgcaagac   2760

cgagggttaa acggtgactc gaagttatta gaagagaatg agaagttaag ggagatgatg   2820

aagaagttgc ttgaagccgg gaatgaacag ttaagcgtga tatcagattt gactgtcaga   2880

gtgaaggact tggagaagaa attagccagg agaaggagta agagagtgaa gacaaaacag   2940

tatagacccg cagcttccaa aatgtctacc catgaaatga aatcctccta a            2991
```

<210> SEQ ID NO 44
<211> LENGTH: 423
<212> TYPE: DNA
<213> ORGANISM: Glycine max

<400> SEQUENCE: 44

```
atgatgaggg gtgcggaata cgagcgtgtg ctaaggtact tcgatgaaga cggtgatgga     60

aagatttcac cctcagagct aaggaacaga atagcaatga tgggtggtga ggttatgttg    120

aaggaggctg agatggcgat cgaggcgttg gattcggacg gcgacgggtt gttgtgtttg    180

gacgatttga tgaatctgat ggaggctgct ggagaagaag agaagttgaa ggatttgaga    240

gaagcctttg atatgtatga tacggagagg tgtgggttta ttactccaaa ggccttgaag    300

aggatgctga agaagttagg ggaatctaag tcaatggtag agtgcaaagt gatgataagt    360

aggtttgatt tgaatgggga tggcatgctt agctttgaag agttcagaat tatgatgaag    420

tga                                                                  423
```

<210> SEQ ID NO 45
<211> LENGTH: 480
<212> TYPE: DNA
<213> ORGANISM: Glycine max

<400> SEQUENCE: 45

```
atgtcgttga ttccaagttt cttcggcacc gggcgaagaa ccaacgtctt cgacccccttc    60

tccctcgacg tgtgggaccc attccatggc ttccccggca ccaccgccct ctccgctccg    120

cgctccgaga cggcggcctt cgccaacacg cgtatcgact ggaaggagac ggcggaggcg    180

cacgtgttca aggcagacct gccggggctg aagaaggaag aggtgaaggt ggagatcgag    240

gaggagggaa gggtgctgca gataagcgga cagagaacaa aggagaagga ggacaagaac    300

gacacgtggc accgcctcga acgctccagc ggcagctttc tccgccgctt ccgcctgccg    360

gagaacgcga aactcgatca ggtgaaggcc ggcatggaga acggagtgct cactgtcact    420

gttcccaagg tggatgtcaa gaagcccgat gtcaagcccg ttcagatcac tgaaggctaa    480
```

<210> SEQ ID NO 46
<211> LENGTH: 588
<212> TYPE: DNA
<213> ORGANISM: Glycine max

<400> SEQUENCE: 46

```
atgaggctgc cacaactaaa cttgttctta gtgtcatttt tgttgctctt tgttgccaga     60
```

gcaaatggtt ctctgctccc attcatagat cctcccacca ctctcttggc tgatctctgg 120
tccgatcgct tcccggaccc gtttcgagtg ctggaacaga ttccatttgg tgttgacaaa 180
gatgaaccct ccatggctat gtcacctgct agagtggact ggaaggagac accagagggg 240
catgttataa tgctggacgt gccggggctg aagagagaag agataaagat agaggtggag 300
gagaataggg tgctgagagt gagtggtgag aggaagaagg aagaggagaa gaaaggggat 360
cactggcata gagtggagag gtcctatggc aagttctgga ggcagttcag gttgccacaa 420
aatgtggact tggattctgt taaggctaag atggagaatg gggtgctcac tttgacactt 480
gacaagttgt cacctgataa gatcaaaggt cccaggttgg tcagcattgc tggagaggat 540
cagcaacaag gtaacctcaa cagtgatggg gtcaagcagg agctttga 588

<210> SEQ ID NO 47
<211> LENGTH: 1059
<212> TYPE: DNA
<213> ORGANISM: Glycine max

<400> SEQUENCE: 47
atggcaatgc acaagagcag ttcaggttca gcattgggtc cgggaggctt ggacttaact 60
caagccttct tcaagtcgat catgaacgct gcagcttctt ctcccaccaa acgccacaac 120
aaaatctctg ttgttggggc aggcaacgtg ggaatggcca tagcccaaac catcctcact 180
caggatctca ccgacgagct tgtgctcgtg gatgcaattc ctgacaaact ccgcggcgag 240
atgcttgacc tccagcacgc cgctgccttc ctcccccgca ccagaattca ggcctccacc 300
gattactcgg tcacgctggg ctctgacctc tgcattgtca cagccggggc tcgtcaaatt 360
aatggcgagt cccggctcaa tctcctacag aggaatgtca cactctttca gaaaatcata 420
cctcctttgg ctcgttactc cccagacacc attcttctca tcgtttcaaa tcccgtggac 480
gtgctcactt acgtggcatg gaagctttca gggttccctt caaaccgcgt cattggctcc 540
ggcactaact tggactcttc ccgttttcgt ttcctcattg ctgatcatct tgatgtcaac 600
gctcaagatg tccaggcttt tatagtgggg gaacatggtg acagctcagt ggctctgtgg 660
tctagtatta gtgttggggg tgttccggtg ctgagttttt tggagaagca agaaattgcg 720
tatgagaagg aaatgttgga gaacatacac aaggaagtta tacagggtgc ttatgaagtt 780
atcaatctga aagggtacac ttcttgggca ataggatact cggtggcaaa cttggcacga 840
accattctca gggaccaaag gagggtccac cctgtctcgg ttcttgcaaa gggtttttat 900
ggcattgatg atggggaagt gtttctcagc ttgcctgcac aactaggaag aggaggggtt 960
ttgggtgtaa ccaatgtgca cttgactgaa gaagagacac agaggcttag ggactcagct 1020
aagacaatcc tccaagtgca gaatcagttg gttatttga 1059

<210> SEQ ID NO 48
<211> LENGTH: 462
<212> TYPE: DNA
<213> ORGANISM: Glycine max

<400> SEQUENCE: 48
atgtctttga ttccaagttt ctttggtggc agaaggagca atgttttgga tcctttctcc 60
ctcgatgtgt gggacccttt taaggatttt ccttttccca cttctctttc tgctgaaaat 120
tcagcgtttg tgagcacacg agtggattgg aaggagacac cagaagcaca cgtgttcaag 180
gctgatattc cagggctgaa gaaggaggaa gtgaagctgg agattcaaga tgacagaatt 240

-continued cttcagataa gtggagagag gaacgttgag aaggaagaca agaacgacac gtggcaccgc 300
gtggagcgaa gcagtggtaa gttcatgagg agtttcagat tgccagataa tgctaaagtg 360
gatcaagtta aggcttccat ggaaaatggg gttctcactg taactgttcc aaaggaagag 420
attaagaagc ctgatgttaa ggccatagaa atttctggtt aa 462

<210> SEQ ID NO 49
<211> LENGTH: 174
<212> TYPE: DNA
<213> ORGANISM: Glycine max

<400> SEQUENCE: 49
atggccggtg acggtgcagc tacatgcata gacatccttc ttgccattat tctccctcct 60
cttggtgtct ttctcaaata tggttgccag gtggagttct ggatttgttt ggtgctgacc 120
ctttttggtt atatacctgg aattatctat gctgtctatt ctatcaccaa gtga 174

<210> SEQ ID NO 50
<211> LENGTH: 477
<212> TYPE: DNA
<213> ORGANISM: Glycine max

<400> SEQUENCE: 50
atggatatca ggttgatgga tttggactct ccattgttca acactctgca ccgaatcatg 60
gatctgacag aggacgcaga gaagaacttg aacgctccga cgcggacata cgtgcgcgac 120
gcgaaggcaa tggctgcgac tcctgcggac gtgaaggagt accctaacta ctacgtgttc 180
gtgatcgaca tgccaggcct gaaatccggg gacattaagg tgcaggtgga ggatgataac 240
gtgcttctga taagcggcga gaggaagagg gaggaggata aagagaaaga aggggctaag 300
tatttgagga tggagagaag ggttggcaag ttcatgagga agttcacgct tcccgagaat 360
gccaacaccg atgctatctc tgccgtctgc caagacggtg tgctcactgt cactgtcaac 420
aagctgcctc ctcctcagcc caaaaagccc aagaccatag aggttaagat cgcctga 477

<210> SEQ ID NO 51
<211> LENGTH: 624
<212> TYPE: DNA
<213> ORGANISM: Glycine max

<400> SEQUENCE: 51
atgttttcca tcaatcattt ctccgaccca gatgccacct cgccggggtc gggaggaagc 60
tcccgaccgg cgctgtcgga cgaggatttt tttctggcgg caagcaatcc caagaaacgc 120
gccgggagga agaagttccg ggagacgcgc cacccggtgt accgcggcgt gagaaggcgg 180
gactccggca agtgggtgtg cgaggtgcgc gagcccaaca agaagtccag gatttggctc 240
gggacctttc ccacggcgga gatggcggcg cgtgcgcatg acgtggcggc gatcgcgctg 300
aggggaaggt cagcctgcct caacttcgcc gactccgcgt ctcggctccc ggtgccggcg 360
acggcggagg ccagggacat tcagaaggct gcggcggagg ccgcagaggc gtttcgccct 420
gggaaggatg atgatgcggt ggcggagagg gtggcagcga cggcgacgga gcgtgaagaa 480
gaacaagaag aagggatggt gccggagtat ctgaggaaca tggtgctcat gtcgccgacg 540
cattgcttcg ggagtgatga gtatggaagt gctgacgtgg aatttgacga tgctgaagtt 600
tctctgtgga gttactccat ttaa 624

<210> SEQ ID NO 52
<211> LENGTH: 681

<212> TYPE: DNA
<213> ORGANISM: Glycine max

<400> SEQUENCE: 52
atggcaagtt atcaaaagca ctacgatgat cagggtcgca aggttgacga gtatggcaac 60
gttgagaagc aaaccgacga atacggcaac cctgttcatg ctgctagtgt cacctatgta 120
gccaccagaa ctgctgctgg tggttacagt gatgacatta ataagcaaca tgataccacc 180
aatgcctacg gcgtagacac tggtagacag cattctagtg gtggctacga tggtgacact 240
aataaacatc atggaactac tggtggctat aatgatgaca ccaatagaca tcatggaact 300
accggtgtct atggtataga caccgatagg caacaacatg ggactactgg tggctatgcc 360
ggtgacactg gtaggcaaca tgggaacatc ggtggccctt actatggaac caacaccgca 420
gacaccggta ctggtcccag aagtggaacc acgggcggca ccggttatgg aggcactggt 480
ggcactgatt atggaacaac tggtggcact ggttatggaa gtggaactgg gtatggagtc 540
aacactgggg gtgcgcacac tgaagcagga tataggaagg aacatcgtca gcatgaccaa 600
tctcatggtg atcagaacga gaagaaaggg attatggaca agattaagga gaagcttcct 660
ggaggacaca gtgacaagta g 681

<210> SEQ ID NO 53
<211> LENGTH: 1617
<212> TYPE: DNA
<213> ORGANISM: Glycine max

<400> SEQUENCE: 53
atggattcaa gagtagttca aagtgtagtg catgagaacg atgaacatta cccccacatt 60
gttgccttag agcaagtgac acacggtgca gaagaagacc actttgatca tgagaagaag 120
tctgttctga ataaggtcaa ggcaaaggct aagaaaatta aggacacgat taagaagcat 180
ggccatcaag tgcttgatcg tggtcatgag tataacaatg aagatcagca tacccttgat 240
gatcatgact tagacgagga tgatgaaatg gctgaagacc cacaagttca taaaacacca 300
attcacgaaa gtgaagatgt taaaactgca acacctacat ctgagcaagt cgaaaatttg 360
gggaagtcag gaattgattc tggaggcaca agaggtacaa cagttatggg agaggaaccc 420
cgtcatgatg cactacttgg aggtgtttct tcaactactg aaattgatca aaacatagcc 480
actgactcgg ccaaaacatt ttctgtggaa gaaaaggcag ggccaccaaa ggacaatttg 540
gagaagtcaa taggcttgga cttggaggaa gagcctcacg ctccaggaag tagacctgag 600
gcatatcccc ctaccaatta tcaaaccaaa atcactgatc caagtgtgat aggaaaggat 660
gaaatagaag aaatcacacc agttgaggaa tcttttgcaa aaatgaatat gcatgatgag 720
ccaaaaccta ctccagaacc aaatatccaa gcaactgttg ttgattctga ataccctcct 780
gttggaaacc acgatcagtt tgtgccacac ctctctgctg caacacaaac tcagtatcct 840
tctgctgaaa gtcatgatca gttcaatcag gaaacaacat ccacaaatat caacagaaac 900
ctggtaaatc ccacagaaac tggacaaact ttcaacacca tcacaaccac aattgaagaa 960
aaaccactct atgaagcaaa gactgatgaa gttatctctc ctaaagatgt catagcttct 1020
gaggctggtt caggagagaa agatgccata aaggacaagg tggtaacaaa taaagagcaa 1080
caaaaaattg gggatgcttc taacatgtct ggctcaactg cacaacatgg aaagaacatt 1140
gctcactctc tgactgagaa attagctcca gtttatgata aggttgcagt ggtaggaagt 1200
gcagtgaagt ccaaagtgac tggaactagc actggtggtg ttggaactga gacaaagaat 1260
gaggtttctg tgaaggacta tttggctgag aagctaaagc ctggtgaaga agacaaggca 1320
ctttctgagt taatttcaga agctttacat aagaaaaagg aagagccagt gaaaaatgag 1380
gatggaaact tggatgacgg caatgataaa atgtgtgaag agatcagtgt gaagagtcca 1440
gggaaaggtg tggttggcaa gcttaagggt gttgttggct cttggtttgg caaagccgag 1500
gaaaaaggag gtgaagattt atccaagaat acaaattctg gtgcagaagt ggaacaggtt 1560
caccaggttg taggtgaaat caagagtggt ccaattgaag aacaagggac tggctga 1617

<210> SEQ ID NO 54
<211> LENGTH: 684
<212> TYPE: DNA
<213> ORGANISM: Glycine max

<400> SEQUENCE: 54
atggccgata agcaacccca cttgaatggt gcttattacg gtcccgccat tcccccggcg 60
gagcaaccac actaccgccc tagccgcgaa agaagctgct gttgctgcct cttcggaatc 120
ttgtggaaga ttctggttgc actcattgtc ctcgttggcc tcgcggtcct catcttctgg 180
ctggtggttc aaccccgttc cttcaagttc cacgtcacga aagccaacct aacacaattt 240
gattactata ccaacaacaa caccccttcac tacaacatgg tcctcaactt cactgcacgc 300
aaccccaaca aaaaactcag catatactac gacaaagtag aggcattagc attctacgag 360
gatgtcaggt tcgccaatta cagtgtgata acgcacatga actccttccg ccagtacaag 420
aagaccacca gccacatgag cgccgttttc tcggggcagc aagtgttgcc gctcgacaac 480
gacctagtct cagagttgaa ccaagacaag agtggtgggg tgtacgagat cgatgtgaag 540
ctctacttca ggattaggtt caggctcggg gatgtcaaaa cccgtcgctt caagcccgag 600
gtcaaatgtg atatcagggt tcccttgagg accaatggca gcgtaacttt gtttcagacc 660
accaagtgtg atgtcgatta ctag 684

<210> SEQ ID NO 55
<211> LENGTH: 666
<212> TYPE: DNA
<213> ORGANISM: Glycine max

<400> SEQUENCE: 55
atgtcccagt tgaacggagc ctactacggc ccctccatcc cgccgccgaa aacttcctac 60
caccgtcctg ggcgcggcgg aggcctcggc tgctgctgcg ggtgcctctt cagcctcatc 120
ttcaagctca tcctaaccgt gatcatcatc attggcatcg ccgtgttcct tttctggctc 180
atagtccgtc ccaacgtggt gaaattccac gtcaccgagg ccaccctgac gcagttcaac 240 tacacccccca acaacacgct ccactacgac ctcgccctca acatcacggt ccgaaacccc 300
aacaagaggc tcggaatcta ctacgaccgc atcgaggcgc gtgcaatgtt ccacgacgcg 360
aggtttgatt cccagttccc ggaaccattc taccagggcc acaagagcac caacgtgctg 420
aacccggtgt ttaagggtca gcaattggtg ccactcaacg ctgaccaatc cgcggaactg 480
aagaaggaga acgccactgg ggtgtacgag atcgatgtga agatgtacct tagggtcagg 540
ttcaagttgg gtgtcttcaa gaccaagacg cttaagccca aagtatcatg cgacttacgt 600
gttcctttga aaggaagcgc cggtgctggt gtctttcaga ccaccaagtg cgactgggat 660
cgctga 666

<210> SEQ ID NO 56
<211> LENGTH: 1182

<212> TYPE: DNA
<213> ORGANISM: Glycine max

<400> SEQUENCE: 56
atgggtgctt atgatcaagt ttctcttaag ccattggatt cttctagaaa gaggaaaagt 60
aggagcagag ggtatgggac tggatccgtg gctgagacta ttgcaaagtg gaaggaatac 120
aacgaacatc tttattctgg caaagatgat agtagaacaa ctcgaaaggc accggctaaa 180
ggttcgaaga aagggtgcat gaaagggaag ggaggacctc aaaactctca gtgtaactac 240
agaggagtta ggcagaggac atgggggaaa tgggttggtg agattaggga gcccaataga 300
ggaagcaggc tttggttggg taccttctct tctgcccagg aagctgctct tgcctatgat 360
gaagctgcta gagctatgta tggtccttgt gcacgcctca attttcccgg catcacagat 420
tatgcttctt ttaaggaatc gttgaaggaa tctccgatgg ccgcatcgtc ctcttgttct 480
tcggcagaaa ctgcaacatc tgacactact actacatcca accaatcgga ggtttgtgca 540
gctgaggatg ttaaggagaa tcctcgactt gtcaatgtga atgataaggt taacgattgt 600
cataaggctt atgaagctgc ctcaccaact agcagaatga agcaagagcc taaggatgag 660
gctgtggatc acatggtccc cggggctggg aaaattctag atgtcagacc agaaggaaca 720
catgatgccg ggcaggttgc agaggatgta aacaaagatc agatggactt gccatggatt 780
gatggctttg attttagtga caattacttg aacaggtttt ccacggatga gttatttcag 840
gtggatgaac ttttggggct tatagataat aacccaattg atgagtctgc gttgatgcaa 900
agtttggatt ttggacaaat gggttttcct ggagatggta atcctcaggt ggatgatacg 960
ctttcaagct ttatttatca gttgcaaaat ccagatgcca agttgttggg aagtttgccc 1020
catatggagc agacaccttc aggttttgat tatggattag atttcttaaa aacagtggag 1080
tcaggggatt ataatggtgg aggggaagaa ccgcgatttc ttaatttgga tgatgatctg 1140
aaccctgatt caaagggcat gcaagcaagg aaggatgact ag 1182

<210> SEQ ID NO 57
<211> LENGTH: 987
<212> TYPE: DNA
<213> ORGANISM: Glycine max

<400> SEQUENCE: 57
atggctccta atatcaccac tgtcaaaacc accatcaccg acgctcaagc caaggtcgcc 60
accgatcatg gtcgtgccta cgtcaccttc ctcgccggaa acggtgacta tgtgaaaggt 120
gtcgttggct tggcaaaagg tctgagaaaa gtgaagagca tgtaccctct ggtggttgca 180
gtgctacccg atgttcccca agatcaccgc aacattctca cctcccaagg ttgcattgtt 240
agagagattg agcccgtgta ccccccagag aatcaaaccc agtttgccat ggcatattac 300
gtcatcaact attccaagct acgtatttgg gagtttgtgg agtacagcaa gatgatatac 360
ctagacggtg atatccaagt ttttgacaac attgaccact tgtttgactt gcctgataac 420
tacttctatg cggtgatgga ctgtttctgt gagccaactt ggggccacac taaacaatat 480
cagatcggtt actgccagca gtgcccccat aaggttcagt ggcccactca ctttgggccc 540
aaacctcctc tctatttcaa tgctggcatg tttgtgtatg agcccaattt ggctacttac 600
cgtgacctcc ttcaaacagt ccaagtcacc cagcccactt cctttgctga acaggatttt 660
ttgaacatgt acttcaagga caaatatagg ccaattccta atgtctacaa tcttgtgctg 720
gccatgctgt ggcgtcaccc tgagaacgtt gagcttgaca aagttaaagt ggttcactac 780
tgtgctgctg ggtctaagcc ttggaggtac actgggaagg aggagaatat ggagagagaa 840
gatatcaaga tgttagtgaa aaagtggtgg gatatatatg aggatgagac tttggactac 900
aacaatccac tcaatgtgga taagttcact gcggcactta tggaggttgg tgaagtcaag 960
ttcgtccgtg ccccatctgc tgcttaa 987

<210> SEQ ID NO 58
<211> LENGTH: 1296
<212> TYPE: DNA
<213> ORGANISM: Glycine max

<400> SEQUENCE: 58
atgttttttc aacaaagttc attctaccca cgagtcgatt caacaaaccc agacgctaat 60
tctcccttct ctaaccccgc accatcttct tcttcttctt ccatttatcc ctcagtggaa 120
acaacagaga atctcatttg ggaagagcca aacacgacta cagaagaagc catggaaaac 180
gttctggtca cggtcccggg tgcgattctg catctgatag aaaaggattc cagcgtgcac 240
cttgcttcgg gcgacctcac catatcgacc ctcggagaag gcgacaaagt ggtggcggtt 300
ctggcatgcg tcggcgatca ggttcagtgg ccgttggcga aagacgtgtc ggcggtgaag 360
ctggatgagt cgcactactt cttcacggtc caggtcccac aggagcacgg ggaggagaag 420
ggattcgagg tgttgaatta cggtttaacg gtggcggcga agggacaaga gagggtgctg 480
agggaactgg acgaggttct ggacaagtac agctttctgt cgaaggagaa actgaagggg 540
gttggaggtt gggaagtttt ggatggttca gtttcgacgg agacatcgcc ggaggagtta 600
caaggatcgg aagagaggaa ggaagtggtg gaggagcgtt ctggggcata ctggacgacg 660
ttggcgccaa acgtggagga ttacagtggg agtttcgcga gatggattgc agcagggtcg 720
gggcaagtgg ttagggggat tctgtgggct ggggatgtga ctgtggacag gttgaagtgg 780
gggaatgatt tcttgaagaa gaggttggag cctggttcac actcccaggt tagtcctcag 840
gcactggaga gcatcaaaag ggttaagaag ttgaccaaga tgtctgagaa ggttgccact 900
ggtgtcctct ctggggttgt caaggtgtct ggattcttca caagttctgt agtcaactcc 960
aaagctggaa agaagttctt tagccttctt ccaggggaaa ttgtccttgc taccatggat 1020
ggattcaata aggttttgga tgctgcagaa gtagctggaa ggaatgtcat gtccacttca 1080
tcagttgtga ccaccggcct agtttcgcat aaatatggag aggaagcagc acatgttaca 1140
aatgaaggcc ttgacgcagc agggcatgcg attgggacag cttgggccgt gttcaaactt 1200
gggaaggcac tcaaccccaa gagcgcaatc aagccaacaa cactagctaa agctgctgct 1260
gaagcaagtt cagctagact gaaggctaag aaataa 1296

<210> SEQ ID NO 59
<211> LENGTH: 936
<212> TYPE: DNA
<213> ORGANISM: Glycine max

<400> SEQUENCE: 59
atgaatctag aaggccaatt gagttcaacc ttctattcta gcacatgctc caatgtgtct 60
tctatagtga ggagtgctgt tcagcaggct cttcaatctg attcacgaat tggtgcaagc 120
ctctctcgcc tccactttca tgattgcttt gtcaatgggt gtgatgcgtc catttttgtta 180 gaccaaggtg gtaacatcac acaaagtgag aaaaatgctg ctcccaacgt caattccatt 240
cgaggctttg atgttgttga taacatcaag agctccctcg aaagttcatg ccctggagtt 300
gtatcttgtg ctgatattct tgctcttgca gcagaatctt ctgtgtcctt gtcaggagga 360

```
ccttcatgga acgtactact tggaagaagg gacggtttaa ctgcaaacca agctggtgcc    420

aatagttcca ttccctctcc atttgagagc cttgccaatg tcacttccaa attctctgct    480

gttggcttag acacaaccga tcttgttgca ttatctggtg cacacacttt tggtcgtgcc    540

caatgccaat tttctcccca aaggttattc aacttcagtg gcacaggaag ccctgatcca    600

accttgaact caacctattt ggccactctt cagcaaaatt gtccccaaag tgggagtgga    660

tctacattga acaaccttga cccttctacc cctgacactt ttgacaacaa ctatttcacc    720

aatcttctca tcaaccaagg tcttctccaa acagatcaag aactcttctc ctctaatggc    780

tcttccacaa tctccatcgt taacaacttt gccaacaacc aatcagcctt cttcgaagct    840

tttgtgcagt caatgatcaa catgggtaac atcagccctt tgactggatc ccaaggagaa    900

attagaactg attgtaagaa attgaatgga agttga                             936
```

<210> SEQ ID NO 60
<211> LENGTH: 672
<212> TYPE: DNA
<213> ORGANISM: Glycine max

<400> SEQUENCE: 60

```
atggccgtca cgaaaagcct ctcaatcttc ctcttcatcg caatgagctg cgtcgccgca     60

gctcaggcag cgaacttcaa catcacaaat aactgcacct acacggtgtg ggccgctgcc    120

gtgcccggcg gcggcgcaag gcttaaccct ggcgaatcgt ggaacatcag cgtgacgaac    180

ggcacaacaa gaggacgcat ctggggtcga acaaactgca ccttcgacaa cgcgggacgc    240

gggaagtgcc tcaccggcga ctgcgagggt gttctggagt gcaacaaaac aggtacaccc    300

ccgaacacgg tcgttgattt cgcgttgaac cagtataaca acctcgactt ctacgacatc    360

tccctcgtcg acggtttcaa cgttccccta cagctgaccc cgacctacaa ctgcagttcc    420

gttaaatgcg ccgccgacat catcggagag tgccccactc agctccaggt tcctggcggc    480

tgcaacaacc cctgcacggt tttcaatacg actcagtact gttgtagcac cggagctgct    540

gggtgcggtc ccacagatta ttccaagttc ttcaaggaga ggtgccctga tgcctacagt    600

taccctatgg acgatgcaac cagcatgttc acttgcatgg gatccgatta tagggttgtg    660

ttttgccctt aa                                                        672
```

<210> SEQ ID NO 61
<211> LENGTH: 1938
<212> TYPE: DNA
<213> ORGANISM: Glycine max

<400> SEQUENCE: 61

```
atggcgacaa aggaaggcaa agccataggc atcgatctcg gcacgaccta cagctgcgtg     60

ggcgtgtggc aaaacgaccg cgtcgagatc atccccaacg accaaggcaa ccgaaccact    120

ccctcttatg tagccttcac cgacaccgag aggctcatcg gagacgcggc gaagaaccaa    180

gtcgccatga acccgcagaa caccgtcttc gacgccaagc gtttaatcgg tcgcagattc    240

tcagactctt cagttcaaaa cgacatgaag ctgtggccgt ttaaggtcgt ggctggccct    300

ggcgacaagc ccatgatcgt ggtcaattac aaaggcgagg agaagaaatt ctccgccgaa    360

gagatatctt ccatggtgtt ggtcaagatg agggaagtgg cagaggcgtt tctcggacac    420

gccgtgaaga acgctgttgt cactgtccct gcgtacttca acgactcgca gaggcaggct    480

acgaaggacg caggggcaat ttcgggtttg aatgtgttga ggattatcaa tgaacccacc    540
```

gctgctgcca ttgcgtatgg gttggataaa aaagcttcga gaaaaggtga acagaacgtg 600
cttatctttg accttggtgg tggtactttt gatgtttcga tattgaccat cgaggaaggg 660
attttcgaag tgaaggccac tgctggtgat actcatctcg gaggtgaaga ttttgataac 720
agaatggtga atcactttgt ttctgaattc aaaaggaaga acaagaagga tattagtggg 780
aatgccagag cgttgaggag gttgaggaca gcgtgtgaga gagccaagag aacgctctct 840
tccacagcgc agacaactat tgaaatcgat tcactatacg aagggattga tttctatgct 900
acaattacga gagctaggtt tgaggagatg aacatggatt tgttcaggaa gtgcatggag 960
ccggtggaga agtgtttgcg tgacgccaag atagacaaga gtcaggttca tgaggttgtg 1020
cttgttggag gttccactag gatccccaag gttcagcaac tcttgcagga tttcttcaac 1080
gggaaagagc tttgcaagag tattaacccc gatgaagctg tggcgtacgg tgctgctgtt 1140
caggccgcga tcttgagcgg cgaaggagac gagaaggttc aggatttatt gctgctggat 1200
gttacaccac tcagtctcgg tcttgaaact gctggtggtg tcatgactgt gctgattccg 1260
cggaacacaa ctattcccac gaagaaggag cagattttct caacctattc tgataaccag 1320
cccggggtgt tgatccaagt gtttgaagga gaacgggcta gaacaaagga caacaatctt 1380
ctcgggaagt tcgagcttac agggatccct ccagcaccaa gaggagtgcc tcagatcaat 1440
gtctgcttcg acatcgacgc taacgggatt ctgaatgtct ctgcagagga taagactgct 1500
ggtgtgaaga acaagatcac gatcacaaac gacaagggta ggttgagcaa ggaggagatt 1560
gagaagatgg tgaaggatgc agagaggtac aaggcagagg atgaagaggt gaagaaaaaa 1620
gtggaggcta aaaattcgct tgagaattac gcgtataaca tgaggaacac gataaaggat 1680
gagaagatag gagggaagct gagcccggat gagaagcaga agattgagaa ggctgtggag 1740
gatgcgatac agtggttgga gggaaaccag atggcggaag tggacgagtt tgaggacaag 1800
cagaaggagt tggaagggat ctgcaacccc atcattgcta agatgtacca gggtgctgct 1860
ggacctggtg gagatgttcc tatgggtgct gacatgcctg ctgctggtgc tggacctaaa 1920
attgaagaag ttgactaa 1938

<210> SEQ ID NO 62
<211> LENGTH: 423
<212> TYPE: DNA
<213> ORGANISM: Glycine max

<400> SEQUENCE: 62
atggggaagc aagttggttt tgaggatgtt cttagatatt tcgacgaaga tggtgatgga 60
aaggtttcac cttcagagct gaagcacggg ctgcgaatga tgggtgggga gcttttgatg 120
aaggaagctg agatggcaat tgcggcattg gattctgatg gagatgggtt gctgagtttg 180
gaggatttga ttgctcttat ggaagctggg ggagaggagc agaagttgaa tgacttgaag 240
gtggcttttg agatgtatga cactgaaggg tgtgggttta taacccccaa gagcttgaag 300
aggatgctta agaagatggg cgagtccaag tccattgatg agtgcaaagc catgatcaaa 360
cagtttgatt tgaatgggga tggtgtgcta agcattgaag aattcagaat tatgatgcag 420
tga 423

<210> SEQ ID NO 63
<211> LENGTH: 1647
<212> TYPE: DNA
<213> ORGANISM: Glycine max

<400> SEQUENCE: 63
atgaccactt ctttctctga ccttctttct tctcccacct ccaatcacca caatctcgga 60
ggcttcgaaa gacctcatca tgagtcctac tcgtcggatc aaacaggttc ttcaggcggt 120
gtgccaaaat tcaagtccac accccctcct tctctccctc ttagccataa tcatcctcaa 180
acaccaatat tttctccttc ttcttacttt aacatccctc atgggttaag cctcgctgaa 240
cttcttgact cccccgttct ccttaactct tccaacgttc tgccatctcc aacagctgga 300
tcatttggtg gtcaaggctt caattggaag agcagttatg gggaaagcca gcagcatatc 360
aaagaagaag acaaaagctt ctctagtttc tccttcccaa cacaaacaca ccctcctctt 420
ccatcttcaa ctggatttca atcttcaacc ggcatagttc aaaccggatg gagttttcca 480
gaaactgcta aacaggatgg ttttgcttca agaataagta tgagcatggt gaaaactgaa 540
accacttctg ccatgcagag tttgacccct gagaataata accacaggaa tggttttcaa 600
tcagatcata aaaactacca accacaacaa gttcagacct tgagcagaag atcagatgat 660
gggtacaatt ggaggaaata tggcaaaaag caagtgaaag gaagtgaaaa tccaagaagc 720
tactacaagt gcacataccc caattgtcca acaaagaaaa aagttgagaa atccttagat 780
ggacaaatta ccgagatagt ttacaaaggc actcataacc atcccaagcc tcaagctgcc 840
aagaggaact cattgtctgc ctcatcatca cttgcaattc ctcattcaaa tcatggcagc 900
aatgaactac cacatcatca aatggattcg gttgccactc ctgaaaattc atcaatttca 960
atggatgatg atgattttga tcatactaaa tcaggaggag atgagtttga taatgatgaa 1020
cctgatgcca aaagatggag aatagaaggt gaaaatgagg gtatatcagc tgtaggaagt 1080
agaacagtga gagaacccag agttgtggtt cagacaacca gtgacatcga tattctagat 1140
gatggataca ggtggaggaa atatggacag aaagtggtca agggaaatcc aaatccaagg 1200
agttactaca agtgcacatt cccaggatgt ccagtgagga agcacgtaga gagagcctca 1260
caagacctaa gggcagtgat cacaacctat gagggaaaac acaaccatga cgtgcctgca 1320
gcacgtggca gtggcaacaa ctctatcagt agatcattgc caataataac caatacaaca 1380
aacaacacca ctagtgtagc aacttctatc agcactaata acaattctct tcagagtctt 1440
agaccaccag ctccaccaga aaggccatca ttatcacact tcaaccctaa tatgcagcac 1500
agttcaggaa gctttggatt ctcagggttt ggaaatccat taatggggtc ttacatgaat 1560
caacaatctt acaataatgt tttcaccacc actagagaca aggaggagcc tggagatgac 1620
tcgtttcttg actctttgct atgttaa 1647

<210> SEQ ID NO 64
<211> LENGTH: 1569
<212> TYPE: DNA
<213> ORGANISM: Glycine max

<400> SEQUENCE: 64
atggctacta cgaagatagg actcggagtt ggtcccgtcc caacaaccac tcaccgagtc 60
accgccgtcg ccgcccccttc ctccgccgta ttctccccgc cgccgcaccg cctcttcctc 120
atcaactcgc gccggccgcc cctccgacct cgcccctccc ccctccccct ccgcgtcgcc 180
tcctcctcct cctcttcctc ctccgtcgcc gcgccaggaa aaggagttga aaatgtggta 240
attataggtt caggccctgc aggatacacg gcagcaatat atgctgcacg tgccaatttg 300
aaacctgtgg tgtttgaggg gtaccaagct ggtggtgtcc ctggggggca gttgatgact 360
acaactgaag tggagaattt tcctggattt ccagatggca taagtggacc tgatctgatg 420

-continued gacaggatgc gacggcaagc tgaacgttgg ggtgcagaat tgtatcagga agatgttgaa 480
gctattgatg tgaaaagtag tccttttact gtccaaagta gtgaacgtaa ggttaagagc 540
catactgtca tttatgctac tggagctact gcaaaacgac ttaggctacc ccgagaagat 600
gaattttgga gccgaggaat tagtgcttgt gcaatttgtg atggagcatc acctctattc 660
aagggtcaag ttcttgctgt tgttggaggg ggggatacag ctacagaaga agcattatac 720
ttaacaaaat atgctcgcca tgtacatttg cttgtacgtc gggaccatct gagggcttcc 780
aaagctatgc aagatagagt gtttgacaat cccaatgtcg ctgtgcactt caatacagag 840
gcagtggacc ttgtaagcaa caccaaagga cagatgtctg gcattttagt aagaaagatt 900
gatactgggg aggaatatgt gcttgaggca aaagggctgt tttatggcat aggccattcg 960
ccaaataccg aactgttgaa aggccaagtc gaattagacc actctggcta tgtacaagtt 1020
caggagggta ctgcaaaaac ttcagttgaa ggtgtatttg ctgctggaga tgtgcaggac 1080
catgaatgga ggcaagctat aactgctgct ggatctggat gcgttgcagc tttatcagtt 1140
gagagatatc ttgtgagcaa tgatcttctt atagagttcc atcagcccaa aactgaagag 1200
gttaagaagg aactaacaga cagggatgta cacgagggct ttgacattac acttacaaag 1260
cataaggggc agtatgctct tcgaaaattg tatcatgaca gtccaaggct tatatgcgta 1320
ttatatacat caccaacatg tggtccctgt aggactctga agccaatcct tagtaaggtg 1380
attgatgaat ttgatcagaa tgtacatttt gttgaaattg atatagagga agatccagaa 1440
atagcagaag cagctggaat aatgggtact ccatgtgtgc agtattttaa aaacaaggag 1500
atgctcaaga ctgtctcagg agtcaaaatg aagagagaat acagagaatt tattgaagca 1560
aacaaatag 1569

<210> SEQ ID NO 65
<211> LENGTH: 1212
<212> TYPE: DNA
<213> ORGANISM: Glycine max

<400> SEQUENCE: 65
atgggtaaga agcttgatgc tctccttggt agaaccttca aggtatcaaa gttcaaggct 60
attgttaacc ttgccatctc acgcctagct gttctcaaga accagcgcca ggctcgcctt 120
agacatgccc gttctgatgt ccttgaactc ctccaacttg gccaccaaga acgtgcttca 180
cttcgagttg agcatgtgat caaggatcag aacatgttgg atgtgtatgg caggattgaa 240
ggatacttca acctcttgat cgaaagggtc cacctcattg agcaagagag agaatgtccc 300
gaggaactga aggaggcagc atcgggattg ctctatgcag cttcaaggtg tggagatttt 360
cctgagattc aacagattcg tgtaattttg acatcacggt ttggcaagga gtttgctgct 420
cgatctattg agttgaggaa caactgtgga gtccatcctc agatgataca gaaattgtca 480
acaaagatgc caagcctgga aagcagaatg aaggtactca aagacattgc ttctgagaat 540
ggtattgttc tgcagctcga agaaacttct gtttcggttg aggaacaatc cagtgtagaa 600
aagcaaaacc aacatgaacc tgagaagaag gaagagaatg taagcatttt gcctagcagg 660
gggaaagatg aaaagttaat tgattcctat aagggaagaa aaacgtacaa ggacgtagct 720
gatgcagcac aagcagcttt tgagtcagca gaatatgctg cagctgctgc aagagcagca 780
ctggaactct cccgatctga atcacatgat cccgatgatc atgatagcac aagactccaa 840
ccaagaaaag tggaggaagg acatgatgtg agacctcaaa tggaagaaaa ggaaatcctc 900
agtgaaactc aaagagaaga tgagttaaaa aagtcgaaag acattataag ttgcaattca 960
actgatgagg ttttgaaggg ggctactgcc ttggtggatg gtgaaattga ggctgatcct 1020
ttggaaaagg aagtgatttt cgatgatagt gatgatgaga atgataataa acagaatata 1080
aatcaatctt ctaagcagac atcttcaggg tatggtgctg gtatagtagt aaatacagtg 1140
ccaggatcca agatgcagaa tgcgcctcag ttggatttgc agaagaggcc tatttcagtg 1200
aggactagat ga 1212

<210> SEQ ID NO 66
<211> LENGTH: 1191
<212> TYPE: DNA
<213> ORGANISM: Glycine max

<400> SEQUENCE: 66
atgggtaaga agcttgatgc tctccttggt agaaccttca aggctgcaaa gttcaaggct 60
attgttaacc ttgccatctc gcgccttgcc gttctcaaga accagcgcca ggctcgcctt 120
agacaggccc gttctgatat ccttgaactc ctccaaattg gtcaccttga acgtgcttcg 180
cttcgagttg agcatgtgat gaaggatcag aacatgttgg atgtgtatgt caggattgaa 240
ggatactgca acctcttgat tgagagggtc catctcatcg agcaagagag agaatgtcct 300
gaggaactga aggaggcagc atcgggatta ctctatgcag cttcaaggtg tggagatttt 360
cccgagattc aagagattcg tgcaattttg acatcacggt ttggcaagga gtttgctgct 420
cgatctattg agttaaggaa caactgtgga gtccatcctc agatgacaca gaaattgtca 480
acaaggatgc caagcctgga aagcagaatg aaggtactca aagacattgc ttctgagaat 540
ggtattgttc tgcagcttga agaaacttct gtttcggttg aggaacaatc cagtgtagaa 600
aagcaaaacc agcatgaatc tgagaagaaa gaagagaatg taagcatgtt gcctaataga 660
gggaaagatg agaagttaac tgattcctac aagggaagga aaaagtacaa ggacgtagct 720
gatgcagcac aagcagcttt tgagtcagca gaatatgctg cagctgctgc aagagcagca 780
ttggaactct cccgatctga atcacatgat cctgatgatc attatagtcc aagactccaa 840
ccaagaaaag tggaggatgg acatgatgat gtgagacctc aactggaaga aaaggaaatc 900
ctcagtgaaa ctcaaaggga agatgagtta gaaaagtcag aagacattat aagttgcaat 960
tcaactgatg aggctttgaa gggggctact gccttggtag atggtgaaat tgaggctgat 1020
cctttggaag aggaagtggt tttcgacaat agtgatgatg agactgataa taaacagaat 1080
agaaatcaat ctcctaagtg gacatcttca gggtatggtg ctggtatagt agtaaataca 1140
acgcctcagt tggatttgca gaagaggcct atttcagtga ggactagatg a 1191

<210> SEQ ID NO 67
<211> LENGTH: 2100
<212> TYPE: DNA
<213> ORGANISM: Glycine max

<400> SEQUENCE: 67
atggaagaca ccgcacaaca aatcaagcgt ccttttggtg ttcctgaagg accagaattc 60
actgttgggt tggatgtacc tttgagcgag ttgaaggtgg agcttcttaa agaaggtgtg 120
tccatcatta tgctgactgg tttaggtgga tcaggaaaaa ccactttggc tacaaagctt 180
tgttgggatg aacaagtcat agagaatcat tttctcttga tcatgagcat aataagttac 240
tttcatttcc gttcatgttc ctttttttata atgttaaatg tgcctaagtt gaagattatt 300
gtagaaagac tatttgaaca ttgtggatat caagtgcctg agtttcaaag cgatgaagat 360

-continued

```
gcagtcaatc aattgggact tttgctgagg aaaattgatg caagtcctat gttgctggtc    420

ctggatgatg tctggcctgg ctcagaagcc ttagttgaga aatttaaagt tcagatatca    480

gattataaaa ttttggtgac ttcaagaata gcattccata gatttggcac tccattcatc    540

ttaaaacctc ttgttcacaa tgatgcaata acccttttcc gtcaccacgc tctcttagaa    600

aaaaacagtt caaacattcc cgacgaagat cttgtccaaa aggttgtgag acattgcaag    660

ggtttaccgc ttgccattaa agtgattggt agatcactaa gtaatcgatc ttatgagatg    720

tggcaaaaga tggtggagga attttcacat ggtcatacta tacttgattc taacattgaa    780

ttaattactt ccctccaaaa gatcttagat gtcttggaag ataatcacat catcaaagag    840

tgcttcatgg acttagcttt atttcctgaa ggccaaagaa ttcctgttgc tgctcttgtt    900

gatatgtggg tagagttgta tggactagat aatgatggca tagcaacggc cattgtcaaa    960

aaattagctt ccatgaatct ggctaatgtc ttagtgacaa ggaaaaatac aagtgataca   1020

gacagttact attacaataa ccatttcatc attctccatg atattttaag agacttcgca   1080

atttatcaaa gcaaccagga acaagttgaa cagagaaaaa gactgatgat tgacataaca   1140

gaaaataaac ctaaatggtg gcccagagaa aaacagcaag gcttgatgat ccgcgtactg   1200

tcaaatattt ttggatggcg tgttgaacaa aaaccccaac agatccctgc acgggcattg   1260

tctatatcga ccgatgaaac ttgcacatca tattggtccc acctgcaacc agttcaagct   1320

gaggttctga ttttaaactt tcaaactaat cagtacacct ttccaaagtt cctgaaagaa   1380

atgagtaaac taaaagttct gacagtcata catcatggtt tccatccttc taaaatgaac   1440

aattttgagt tacttggctc attatccaac ctaaaacgaa tcagattaga gaggattttg   1500

gttcctccct ttgtcacatt gaagaatcta aaaaagttat ccctcttctt gtgtaataca   1560

agacaggctt ttgaaaatgg aaacatgcta atttcagatg cttttccaaa tctagaagat   1620

ttgaatattg actattgcaa agatctgata gaattgccta agggggtctg tgatatcacc   1680

tccctgaaga tgctcagcat tactaattgc cataagcttt ctgcattgcc tcaacaattt   1740

ggaaacttgg agaatttgaa acttctaagg ctaagttcct gtactgattt gcaagagata   1800

ccaaattcta ttggaagact ttcgaatcta agacatatgg acatctcaaa ctgcattaac   1860

cttccaaatt taccagagga ctttggtaat ctttgtaatc taagaaatct gtacatgaca   1920

agttgtccaa ggtgtgaatt gccaccctta atcatcaatc ttgagaattt aaaagaggtg   1980

gtatgtgatg aagagacggc tgcttcatgg gaagctttta aacctatgct tcccaatcta   2040

aagatagatg ttcctcaact tgatgttaac ttaaattggc ttcatgaaat tcgctcctaa   2100
```

<210> SEQ ID NO 68
<211> LENGTH: 210
<212> TYPE: DNA
<213> ORGANISM: Glycine max

<400> SEQUENCE: 68

```
atgggatcca acggaacatc ttgggctgac cagtgggata acgggcctga cccagtgact     60

gtctccaatg aatcaaagaa aaagaacaag aaggccttcg gcaagaccaa ggcagttgct    120

tccaccggcg tgaagaagtt gaaggagggt acctctgttg gcctccattg gatcaagacc    180

aagtatcaca acaccaccca gaagcattaa                                      210
```

<210> SEQ ID NO 69
<211> LENGTH: 528
<212> TYPE: DNA
<213> ORGANISM: Glycine max

<400> SEQUENCE: 69
atgatgctag aaacagtggc tgcagtccct gggatggtag caggcatgct acttcactgc 60
aaatccctaa gaagatttga gcacagtggt ggttggatca aagcactgct ggaagaagca 120
gagaacgagc gtatgcacct aatgaccttc atggaagtgg caaagccaaa gtggtatgag 180
cgtgcactag tgataactgt gcaaggtgtt ttcttcaatg catacttctt ggggtatttg 240
ttgtcaccta aattcgcaca ccgcatggtt ggttacctgg aggaggaagc aattcactcc 300
tacacagagt tccttaagga gctggacaag ggcaatatcg aaaatgtgcc ggctccagcc 360
attgccattg actactggca gctcccacca ggctccactt taagggatgt tgtcatggtt 420
gtaagagctg atgaggcaca ccatcgtgat gtcaaccact ttgcatcgga cattcactat 480
caagggcgag agttacgaga ggctgctgct ccaattggtt atcactaa 528

<210> SEQ ID NO 70
<211> LENGTH: 1119
<212> TYPE: DNA
<213> ORGANISM: Glycine max

<400> SEQUENCE: 70
atgaagggag ttacagtgaa agttgaagaa acaatggcgt atgctaatgc tgcttcaact 60
agcccaacaa catcttcaaa cctctccccg caacccatgg aagggttgca cgaggtgggt 120
ccccctccgt ttctcaccaa aaccttcgac gtggtggaag acccatccac caacgacatc 180
gtttcgtgga gcagatcccg caacagtttc gtcgtttggg actctcacaa gttctctacc 240
accatcctgc ctcgctactt caagcacaac aatttctcca gcttcgtacg acaactcaac 300
acctacggtt ttagaaaaat tgatcctgac aagtgggagt ttgcgaacga agggtttttg 360
gcggggcaga ggcaattgtt gaagacgata aagaggagga ggcacgtgac agtgacacag 420
acacagtcac acgagggagg aagtggggct tgtgttgaat tgggggagtt tgggttggaa 480
ggtgagatgg agaggttgag gagagacagg acagtgttga tggctgaaat tgtgaggttg 540
agacaacaac agcacaactc gagggagcaa ttgttgtcca tggagactag gttgcaagcc 600
actgagaaga aacatcaaca gatgatgaat ttctggcta aagcactcaa caaccaggct 660
tttattcagc agtttcttca aaggaatgct cagaacaaag agttgcaagg tgcgagaaga 720
aagaggagac taactgctac cccaagtgtg gagaatttgc agcaagatca tttcgctttg 780
tcaattgaag aaggatcggc tactattgag tcacagatgg agtctttttt ctcagctgcg 840
tgtaatgatc cgttagaatc aaacagtgaa ctcaaagacc caatattgag ttcagttcca 900
gttgcaagtg ggagtaattt gggggaggtg agtgattctg tttgggagga cttgctgaac 960
caagacttgg ttgctgggga ccctgaagag gaagttgtga ttggtgattt ttcacaagtt 1020
gatgttcctg tggaggattt gattgcggat gctgatgagt ggagtgagga tttgcagaac 1080
cttgtggatc acatgggtta tcttgggtcc aaaccgtag 1119

<210> SEQ ID NO 71
<211> LENGTH: 651
<212> TYPE: DNA
<213> ORGANISM: Glycine max

<400> SEQUENCE: 71
atggcagatg aggtggttct gctagatttc tggccaagtc catttgggat gagggtcagg 60
attgcacttg ctgaaaaggg tatcaaatat gagtccaaag aagaggactt gcagaacaag 120

```
agccctttgc tcctcaaaat gaacccggtt cacaagaaaa tcccggttct catccacaat    180
ggcaaaccca tttgtgaatc tctcgttgct gttcagtaca ttgaggaggt ctggaatgac    240
agaaatccct tgttgccttc tgacccttac cagagagctc aggctagatt ctgggctgac    300
tttgttgaca ataagatatt tgatcttgga agaaagattt ggacatcaaa gggagaagaa    360
aaagaagctg ccaaaaagga gttcatagag gcccttaaat tattggagga acagctggga    420
gacaagactt attttggagg agacgatcta ggttttgtgg atatagcact tattccattc    480
gacacttggt tcaagacttt tggcagcctc aacatagaga gtgagtgccc caagtttgtt    540
gcttgggcca agaggtgcct gcagaaagac agtgttgcca agtctcttcc tgatcaacac    600
aaggtctatg agttcattat ggacataaga aagaagttcg acattgagta g             651
```

<210> SEQ ID NO 72
<211> LENGTH: 654
<212> TYPE: DNA
<213> ORGANISM: Glycine max

<400> SEQUENCE: 72

```
atggcggcgg agcacgacag ctgctgctcg cgctgtgtca ccttcctaat aaccataggc     60
ctcacagcgc tcttcctatg gctgagtctc cgcgttgacg aaccaaaatg ctacctcgac    120
tacatttacg ttcctgccct caacaaaacc ctaaattcca attccactca caacaaaaac    180
accacaatac tcttcgctct caagctcacc aacgggaaca aggacaaagg catccaatac    240
gacgacgttc tcctctcctt cagagtcttc gagagcgtca acctcacgcg cccactcggc    300
aacgccaccg tgcaaaggtt ctaccagggc caccagaaga aggccaccaa gcacggaaac    360
ttcagcggcg gcggcggaaa cctcaccgcg gcggtggctg ggagaatgtg gtaccgtgtg    420
gactatgcta ctgcggtgaa gtacaagatt ctcttctggt acacgaaacg gcaccgttta    480
tggggagggg caaatgtgga aattggcgat tcgggaatga aggtgtatcg taaagccgtt    540
aggcttggag ggaagaaccc cgtggtgatc gagtccggcg catctaagct cagtggacgc    600
tatcgtgcgc ttcttctttc ccttcttctc cctttttgtg gcttgtgggt ttag          654
```

<210> SEQ ID NO 73
<211> LENGTH: 639
<212> TYPE: DNA
<213> ORGANISM: Glycine max

<400> SEQUENCE: 73

```
atggcgtcct ctctcattgc gaagcgcttc ctctcctctt ccctcctctc caggtccctc     60
cttcgccccg ccgcttccgc ttcccaccgc tctttcaaca ccaacgccat gcgccagtat    120
gacaaccgcg ccgacgacca cagcaccgac atcgatcgtc actccgaacg ctctttccct    180
agcactgcgc gccgcgacga tatcttctca ggtaatgtgt tggatccatt ttttccgact    240
cggagtttga gccaggttct gaacatgatg gaccaggtca tggacaatcc gttcctctcc    300
gcgtcgcgcg ggatcggagc tggcgctgga gtgcgtcgcg gatgggacgc gagggagaca    360
gaggatgctc tgcatctgcg cgtggacatg cctgggctcg gcaaggaaga cgtgaagatc    420
tccgtggagc agaacactct cattatcaaa ggtgaaggtg ctaaagaagg cgatgaagaa    480
gagagcgctc gtcgctacac tagcaggatt gacttgccgg acaagctcta caagattgac    540
cagatcagag ctgagatgaa gaacggtgtg ctcaaggtcg ttgtgccgaa aatgaaggag    600
gaagagagga aagacgtgat cagtgttaag gttgagtag                            639
```

<210> SEQ ID NO 74
<211> LENGTH: 225
<212> TYPE: DNA
<213> ORGANISM: Glycine max

<400> SEQUENCE: 74
atggagagga aaacatttgg gtttttgttc ttgctcctcc ttgtcttagc ttctgatgtg 60
acggtgaaga gagcagaggc gaaagattgc ttgacaagga ggcacgggtt ccagggtaga 120
tgcttattcg acaggcaatg tgcacatgtg tgcaggagcg atggtttcat cggtggtcag 180
tgccgaggcc ctcttcgcaa atgcttttgc agcaggccat gttga 225

<210> SEQ ID NO 75
<211> LENGTH: 528
<212> TYPE: DNA
<213> ORGANISM: Glycine max

<400> SEQUENCE: 75
atgatgctag aaacagtggc tgcagtccct gggatggtag caggcatgct acttcactgc 60
aaatccctaa gaagatttga gcacagtggt ggttggatca aagcactgct ggaagaagca 120
gagaacgagc gtatgcacct aatgaccttc atggaagtgg caaagccaaa gtggtatgag 180
cgtgcactag tgataactgt gcaaggtgtt ttcttcaatg catacttctt ggggtatttg 240
ttgtcaccta aattcgcaca ccgcatggtt ggttacctgg aggaggaagc aattcactcc 300
tacacagagt tccttaagga gctggacaag ggcaatatcg aaaatgtgcc ggctccagcc 360
attgccattg actactggca gctcccacca ggctccactt taagggatgt tgtcatggtt 420
gtaagagctg atgaggcaca ccatcgtgat gtcaaccact ttgcatcgga cattcactat 480
caagggcgag agttacgaga ggctgctgct ccaattggtt atcactaa 528

<210> SEQ ID NO 76
<211> LENGTH: 2583
<212> TYPE: DNA
<213> ORGANISM: Glycine max

<400> SEQUENCE: 76
atgtattcag gggtgaaagg gttgttcaac agaagccaga aggtgaaggg aacggtggtg 60
ttgatgcgta agaatgtgct tgacatcaac agcataacga gtgtgagagg gcttattggc 120
accggcatca acataattgg ctcaacaatt gatggtctta cttccttctt gggtcgttct 180
gtgtgtcttc agttgattag tgctaccaag gctgatggaa atggaaatgg ggtagttgga 240
aagaagacct atttggaagg tattattacg tcgataccaa cattgggagc aggccaatct 300
gcgttcacta ttcattttga atgggacgca gacatgggaa ttcctggagc atttttaata 360
aaaaattata tgcaagttga gctcttccta gtgagtttga ctcttgaaga cattcctaat 420
caaggaagca tgcactttgt ttgcaactca tgggtttaca attctaaagt ttacgaaaag 480
gatcggattt tctttgccag tgagacatat gttccaagtg aaacaccagg tccattagtg 540
acatatagag aagcagaatt gcaggctcta agaggaaatg gaacagggaa gcgcaaggaa 600
tgggacagag tttatgatta tgatgtttac aatgatttgg gcaatcctga cagtggtgaa 660
aactttgctc gtccagttct tggaggatct ctcactcatc cctaccctcg taggggaaga 720
accggtagaa aaccaacaaa gaaagatccc aacagtgaga aacctggcga ggcttatata 780
ccaagagatg aaaatttcgg tcacttgaaa tcatctgatt tccttactta tgggctaaaa 840
tctttaactc gaagcttctt gcctgcactc aaaactgttt ttgatataaa tttcacaccg 900

-continued

```
aacgagtttg atagcttcga agaagtgcgt gcactctgtg aaggtggaat taaactgcct    960

acagatatac ttagcaaaat tagcccctta cctgtgctca aggaaatctt ccgcactgat   1020

ggtgaaagtg tcctaaagtt ttcagtacct gatttaatta aagttagtaa atctgcatgg   1080

atgactgatg aagaatttgc aagagagatg attgctggtg taaacccttg tgtgattcgt   1140

cgtctacaag agttcccacc acaaagcaag cttgatccct cagtctatgg tgatcaaaca   1200

agtaaaatga ctatagatca cttggagatt aaccttgaag ggctcacagt agataaggcg   1260

attaaggatc agagattatt catattagat caccatgaca catttatgcc atttttgaga   1320

aggatagatg aatctaaatc atcaaaggct tatgccacta gaacaatcct tttcttgaaa   1380

gatgatggga ccttaaagcc attggccatc gaattaagtt tgccacatcc aggtcaacaa   1440

cagcttggtg cctatagtaa agtcatcttg cctgcaaacc aaggtgtaga aagtacaatt   1500

tggctgttgg caaaggctca tgttattgtg aatgactcgt gttatcatca actcataagc   1560

cactggttga atactcatgc cgtgattgag ccatttgtca tagcaacaaa caggaatctc   1620

agtattcttc accctattta taaacttcta tttcctcact atcgtgacac aatgaatatc   1680

aatgcacttg ctcgacaatc acttattaat gctgatggct ttatagagaa aaccttttttg   1740

ggtggaaagt atgctgtgga gatatcttcg tcaggttaca aaaattgggt tttcctcgac   1800

caagcattac ctgctgatct catcaagaga ggaatggcta ttgaggattc atcttgtccc   1860

aacggccttc gtcttgtgat agaggactac ccttatgctg ttgatggact agaaatatgg   1920

gatgctatta agacatgggt acaagagtat gtctccttgt actatgcaac aaatgatgca   1980

attaaaaaag accatgaact ccaagcatgg tggaaagaag ttgttgagaa gggacatggt   2040

gacttgaaag acaagccttg gtggcctaaa atgcagactc ttcaagagct tattcaatca   2100

tgttctacta tcatatggat tgcttcagct ctccatgcag ctgttaattt tggacaatac   2160

ccttatggtg gttttatcct aaaccgtcca actcttagca ggagatggat tccagaagaa   2220

ggaactccag aatatgacga gatgacaaag aatcctcaaa aggcttattt gagaacaatc   2280

acgccaaagt ttcaggctct tgttgatctt tcagtgatag agatattgtc aagacatgct   2340

tctgatgagg tctaccttgg acagagggac aatccaaatt ggacctctaa tccaaaggca   2400

atagaagcct ttaaaaagtt tggaaaaaag ctagcagaga ttgagacaaa aatctcagaa   2460

agaaaccatg atccaaatct tagaaatcga accgggccgg ctcaattgcc ctacactgtg   2520

cttcttccta ccagtgaaac agggttgact tttagaggaa ttcccaacag catctctatc   2580

taa                                                                 2583
```

<210> SEQ ID NO 77
<211> LENGTH: 855
<212> TYPE: DNA
<213> ORGANISM: Glycine max

<400> SEQUENCE: 77

```
atggacgaat tagaagaaac cctactcacc caaatcgact gggaatcgtt cctcgacgac     60

atacctgaac ttaacgtcga tgattttttg caggacgaca acgccgttcc tgttgttacc    120

gacaatcatt cctccccgaa cgacgacccc gttttgtccg agatcgagaa catgctcatg    180

acgcaggccg aaaacgacgc tgtcgttttg cccgagacgc cgtcttcgga ggccgggtat    240

tacaagctct tcgaggagat tctggtggag gagcccaagg aaggacccgt gagcccgcct    300

tcaaaaatag agtccgagga aggctccgac aaagacaaga ccgatgatgc tgcttccgat    360

gaacccatgt cgaagaaatt aaagaggcag ttgaggaaca gggatgctgc tgtgaggtca    420
```

agggagagga agaagttgta tgtgaaaaac cttgagatga agagtaggta cctagaaggg 480
gaatgcagaa gactggggca tttgctccag tgctgctatg ctgagaacaa cgctttgcgg 540
ctttgcttgc aattgcgtgg tacatatggt gcttcaatga ccatgcagga gtctgctgtg 600
ctcttgttgg aacctctgct gttgggttcc ctgctgtggt gcatgggcat catatgccat 660
ctcagtctgc ctctaatgct gtgggttgca gcagtacttc caagagaaaa catcgagcag 720
aagggcctaa gaagggtaac tcaaaaagga tcagaaagta agatctctga gtgtttccag 780
atgcaatcat ttttaaagag tagaaaaagc cgagcttcaa gaacaaagat gaaattcaat 840
tttatagtgt tctaa 855

<210> SEQ ID NO 78
<211> LENGTH: 636
<212> TYPE: DNA
<213> ORGANISM: Glycine max

<400> SEQUENCE: 78
atgggaaaag cttgggtagg cctggtggta ttgctgtgtt tgattgtcac ggccatcgcc 60
gaacaatgcg gtcgtcaagc tggcgggcag acatgtccca acaacctatg ctgcagccag 120
tacggttggt gtggaaacac cgaagaatac tgttcccctt ctaagaactg ccagagcaac 180
tgctggggag gcggcggcgg tggcggtggc ggcggcggcg gtgaaagtgc ttctaatgtc 240
cgcgccacat atcattacta tgagccagag caacacgggt gggacttgaa cgccgtgagt 300
gcttattgct caacttggga cgctagcaaa ccttactcat ggcgcagtaa atatggctgg 360
accgctttct gtggtcccgt tggtcctcgt ggccgtgatt cttgtggaaa gtgcttgcgg 420
gtgacaaata caggaacagg agcaaacaca attgtgagaa tcgtagatca gtgcagcaac 480
ggagggttgg atttggacgt gggagtgttc aatcggatag acacagatgg aagaggatat 540
caacaggggc atctcattgt taactatcag tttgtggatt gtgggaatga gctcgacctc 600
accaaacctt tactctccat cctcgatgct ccctaa 636

<210> SEQ ID NO 79
<211> LENGTH: 2100
<212> TYPE: DNA
<213> ORGANISM: Glycine max

<400> SEQUENCE: 79
atggcggacg ctgaaacctt cgctttccag gctgagatca accagcttct cagcctcatc 60
atcaacacct tctacagcaa caaggagatt ttcttgcgtg aactcatcag caacgcttct 120
gatgctttgg ataagattcg atttgagagt ttaaccgaca agagcaagct cgatgctcag 180
ccagagctct tcattcgtct tgtgcccgac aaggccaaca agactctttc cgttattgac 240
agcggcattg gaatgaccaa agcagatttg gtgaacaact tgggtaccat tgcgaggtcc 300
gggaccaagg agttcatgga ggcattgcag gctggtgctg atgtaagcat gattgggcag 360
ttcggtgtgg ggttctactc tgcttacctc gttgcagaga aggtcattgt taccaccaag 420
cacaatgatg atgaacagta catttgggag tctcaggccg gtggctcttt cactgttact 480
agggacaccg atggcgagca actcggaagg ggaaccaaga tgaccctctt cctcaaggaa 540
gatcagttgg agtacttgga ggagagaagg atcaaagatc tggtgaagaa gcactctgaa 600
ttcattagct atcctattta cctatggact gagaagacca ccgagaaaga aatcagcgat 660
gatgaagatg atgagccaaa gaaggaggaa gaaggggacg ttgaggatgt tgacgaggac 720

```
aaggagaagg attccaagaa aaagaagaag atcaaggagg tgtctcatga gtggcaactc    780
atcaacaagc agaaaccaat ttggctgcga aagccagaag agatcaccaa ggatgaatac    840
gcttctttct acaagagcct caccaatgac tgggaagaac acttggctgt gaaacatttc    900
tctgttgagg gccagcttga gttcaaggcc attctctttg tgccaaagag ggcacccttt    960
gatttgtttg acaccaggaa gaagatgaac aacatcaaac tttatgtcag gagggtgttc   1020
atcatggaca actgtgagga gctcattccc gagtacctcg gatttgtgaa gggtgttgtc   1080
gactccgatg acttgcccct caacatttct cgtgagctgc tgcagcagaa caagatcctg   1140
aaggtgatca ggaagaatct tgtgaagaag tgcattgaga tgttcaatga aattgcggag   1200
aacaaggaag actacaacaa gttctatgat gctttttcga agaatttgaa gttgggtatc   1260
cacgaggata gccagaacag gtccaagttg gctgatttgc tcagatacca ctcaacaaag   1320
agtggagacg aattgacaag cttgaaggac tatgttacac gaatgaagga gggccagaag   1380
gacatttact acattacagg agagagcaag aaggcagtgg agaactctcc tttcttggag   1440
agactcaaga agaagggcta tgaagttctc ttcatggtgg atgcaattga tgagtatgca   1500
gttgggcaac tcaaggaata cgatggcaag aaattggttt cagccacaaa ggaagggttg   1560
aagctggatg atgagactga ggaggagaaa aagaagaaag aggataagaa gaagtcattt   1620
gatgagctct gcaaggtcat caaggaaatt ctgggagaca aagtggagaa ggttgttgtc   1680
tctgacagaa ttgttgactc tccttgctgt ttggtgactg gtgaatacgg atggagtgca   1740
aacatggaga ggatcatgaa ggctcaggct ctgagagaca gcagcatgag tggctacatg   1800
tctagcaaga agacaatgga gatcaaccct gacaatggta tcatggagga gttgaggaag   1860
agggctgaag ctgacaagaa tgataagtct gtgaaggatc ttgtgttgct tctctttgag   1920
actgcccttt tgacttcagg tttcagcctt gatgatccca acacatttgc ttcgaggatt   1980
cacaggatgt tgaagttggg tcttagcatt gatgaggatg acaatggtgg agacgatgtt   2040
gatatgcccc cattggaaga ggacggtgct gaggagagca agatggagga agtggactaa   2100
```

<210> SEQ ID NO 80
<211> LENGTH: 1005
<212> TYPE: DNA
<213> ORGANISM: Glycine max

<400> SEQUENCE: 80

```
atgggaagac caccttgttg tgacaaagaa ggggtcaaga aagggccttg gactcctgaa     60
gaagacatca tattggtgtc ttatattcag gaacatggtc ctggaaattg gagggcagtt    120
cctgccaaaa cagggttgtc aagatgcagc aagagttgca gacttagatg gactaattac    180
ctgaggccag gaatcaaacg gggcaacttc acagaacaag aggagaagat gataatccat    240
cttcaagatc ttttaggaaa cagatgggct gcaatagctt catacctttcc acagagaaca    300
gacaatgaca taaagaacta ttggaacacc catttgagaa agaagctgaa gaagatgcaa    360
gtaggttgtg aaggtggtag ctttggagaa gggttttcag cctcaaggca aatccctaga    420
ggccagtggg aaagaaggct ccaaactgat atccaaatgg caaagagagc cctcagtgaa    480
gctctttcac cagagaagcc atcttgtaat ttatctgcct caaactcaaa cccttcagat    540
agtagcagct ccttctcttc cacaaaacca acaacaacac aaactgtgtg ctatgcctca    600
agtgctgaca acatagctag aatgctaaag ggttggatga aaaacccacc aaagtcctca    660
agaacaaact catcatctgt gactcagaac tccttcaaca actttgctgc agcaggtgct    720
gatactgctt ctagtattgg agcaaaggga ccaccaagca gtgctgaatt gtctgaaaac    780
```

aattttgaat cattgtttga ttttgatcag tctttggagt cttcaaactc tgatgaattc 840
tctcggtcat tgtctcctga ggccactgtt ttgcaagatg aaagcaagcc tgatgttatt 900
ggtgcagaaa ttatgccatt ctctttgctt gagaaatggc ttcttgatga ggctggttgc 960
caagagaaat tagttggttg tggtgatgat gccaagtttt tctaa 1005

<210> SEQ ID NO 81
<211> LENGTH: 987
<212> TYPE: DNA
<213> ORGANISM: Glycine max

<400> SEQUENCE: 81
atggatccat tggggaaacg ccctgctgcc gaggacgatt ccctaatttc cgattgcgag 60
agcggggttt ccgctggaga cacgccgccg ccgttcgtcg aaaacgccga cctcgtccgg 120
accagattcg ttcgtggcct cgtcgcgcac tgcttcaaac ccgaggttct ggcagttcgc 180
agaaacgtgt gttcctccgt catggccctg gcgcgtcaac attcctttca cgtcttcgcg 240
cgtgccgtgg ccgaattgcg cggcggcaat gccaacgtga agttcgcctg gtacggtgcg 300
tccagtaagg aagagataaa tgacatcatt cagcacggtt tcggtcacgc tcacagtaac 360
ggcctgcgtc tctctccaca agattctcca cttgaaaggc acgcgcaatt tcattatttt 420
aattttatga atgttgcgca cttgttgctg tgccgcgtta tcttggggaa gacggaggtg 480
gttccacgtg gctcctacca atgccgttcg agttctcaag agtttgattc tggggtggat 540
gatctttcca atcccaagga gtatgttatt tggtgtaacc agatcaacac tcatgttttg 600
cccgaatatg ttttgagttt cagacttcct tcaccattga aagggattgt gaagattggg 660
gaacctttga ggccttcttc gccgtggatg gcattcccag ctttgatttc gatgctttcg 720
aagattttgc ctccgtccga ggttgcctcc attgccaagt ttcacaagga ttatagagaa 780
aagaggattt ctcgacatga gctgatacag aaagtgagag taatagcagg cgacaaattg 840
ctactttccg tcatcaaatc tttcagagcc aagaaaatac ctgcaaactt taaagatgac 900
aaggcgaaag aatggcaagc ggacagccag cagcttgaac ggaatgattg ttcatatggg 960
agttctatta gctattacag gaagtga 987

<210> SEQ ID NO 82
<211> LENGTH: 744
<212> TYPE: DNA
<213> ORGANISM: Glycine max

<400> SEQUENCE: 82
atggacacct tcttcaattc tcaatcttct tcttcttcga gaagccgctg gagttacgat 60
actctcaaga atttccgtga gatctctccg ctggttcaga atcacatcaa acgggtttat 120
tttacgttat gttgcgctgt ggtggctgct gctgttggag ccttccttca tgttctgtgg 180
aacattggcg gttttctcac cacggtggct tccattggga gcatgttttg gttgctatct 240
acaccccctg ttgaagagca aaagaggttg tctctgttga tggcttcggc cttgtttcag 300
ggcgcttcca ttggacctct gattgatttg gctattgcca ttgatcctag ccttattgtt 360
agtgcatttg tggcaacttc tttggctttt gcttgcttct ctgcggcagc tttagttgca 420
aggcgtaggg agtacctcta ccttggtggt ttgctttctt ctgggctgtc cattcttatg 480
tggttgcact ttgcttcctc tctctttggg ggctcaattg cactcttcaa gtttgagctg 540
tactttgggc ttttggtgtt tgtgggctac gttatagtag acactcaaga aattattgaa 600

```
agggctcact ttggtgacct ggattatgtg aagcatgcat tgacattgtt cactgatttg    660

gctgcaatct ttgtgcgaat tcttattata atgttgaaga attcatctga gagaaatgag    720

aagaagaaga aaaggagaga ttag                                           744


<210> SEQ ID NO 83
<211> LENGTH: 1197
<212> TYPE: DNA
<213> ORGANISM: Glycine max

<400> SEQUENCE: 83

atggaggaga agagagagaa agagaaaaac tcaaagtcat catcatctac catggcaaat     60

tctgtggcat tttccgacga gattcctaac atgagcatga gcttcccttt ctcccctgct    120

ttctctagta gcatctttga catgatgcca ccaccaccac cttcctcatc tcacgatcct    180

aaagctccca actttgctaa tagcttcatg gacttgctcg ctgtccctgc tgattattat    240

accccttctt tattcgactg gtcccaaaac accgccccca cgtcagcacc accaccttcc    300

accacccaaa tcaaccaccc tcttccgtcg ccagccagct ccaatgtccc cgacggctcc    360

gaggttctca acactccggc gtctcccaat tcttcgtcta tttcatcatc gtccaacgaa    420

gcagcagccg ccaccaccgc caacaaaaca acgggaaatg ataatgaaga ggaggaagat    480

gaaacagcaa tagatgcaac agcaggcaga gaagaagaag atcatcaaga ccaagacaag    540

actaagaaac agctcaagcc aaaaaagaag aaccaaaaaa agcaaagaga gccgagattt    600

gcgttcatga caaagagtga agtggatcac ctcgacgatg gctatagatg gcgcaagtac    660

ggtcaaaaag ccgtcaaaaa cagccctcat ccaaggagct attatcgttg caccaccgcg    720

acatgcggcg tgaagaagcg cgtggagcgt tcctcggagg atcctacggt ggtggtgaca    780

acctacgagg ggcaacacac tcacccgtgt cctgccacgt cacgggctag cttcgggttc    840

atgcactccg aagcaagtgg gttcggaccc accagtggac taggttcggc acactttatg    900

ctgcaacaac aacaacagtt tcgggaccaa gcacaagcac aagcagcaat gttgtataac    960

tccacctcat cgtcattgtc attgccactg aatgttgtta actcagcttc ttgtgttaat   1020

aatagctatg ccaatacgtc atcgttgagt ggctttcttc agggccaaga gaatcatcag   1080

cgaggttttg tgccgtctag ggtggtggct cctcatattt tcttgaggga caatgggctt   1140

cttcaggaca ttgttccaac gcagatgggg aatgaggaga atgaagatcg tgtgtag      1197


<210> SEQ ID NO 84
<211> LENGTH: 744
<212> TYPE: DNA
<213> ORGANISM: Glycine max

<400> SEQUENCE: 84

atggacacct tcttcaattc tcaatcttct tcttcttcga gaagccgctg gagttacgat     60

actctcaaga atttccgtga gatctctccg ctggttcaga atcacatcaa acgggtttat    120

tttacgttat gttgcgctgt ggtggctgct gctgttggag ccttccttca tgttctgtgg    180

aacattggcg gttttctcac cacggtggct tccattggga gcatgttttg gttgctatct    240

acaccccctg ttgaagagca aaagaggttg tctctgttga tggcttcggc cttgtttcag    300

ggcgcttcca ttggacctct gattgatttg gctattgcca ttgatcctag ccttattgtt    360

agtgcatttg tggcaacttc tttggctttt gcttgcttct ctgcggcagc tttagttgca    420

aggcgtaggg agtacctcta ccttggtggt ttgctttctt ctgggctgtc cattcttatg    480

tggttgcact ttgcttcctc tctctttggg ggctcaattg cactcttcaa gtttgagctg    540
```

tactttgggc ttttggtgtt tgtgggctac gttatagtag acactcaaga aattattgaa 600
agggctcact ttggtgacct ggattatgtg aagcatgcat tgacattgtt cactgatttg 660
gctgcaatct ttgtgcgaat tcttattata atgttgaaga attcatctga gagaaatgag 720
aagaagaaga aaaggagaga ttag 744

<210> SEQ ID NO 85
<211> LENGTH: 918
<212> TYPE: DNA
<213> ORGANISM: Glycine max

<400> SEQUENCE: 85
atgttgatgg aagaggttgt tgatttgaaa caagagcagc gaagaatggc tcaccgcgca 60
ggagaagtga atcaaaggct ccaatccaca gaacaaaggc agaaacaaat ggtttctttc 120
ctggtcaagt taatccagaa ccccgccttt ttagcccgcc ttaggcatga ggagcaaaaa 180
gaaatagatt ctccaagagt ggtaaggaag tttgtcaagc agcaccaaca tgaaactgga 240
acagcagaaa ctctccaaga agggcagata gtgaggtacc aacatgattg gagaaatata 300
ggcatgtctt ccgaaactcc aaaactaagt ccagtttcca ttgaacagtc tcctcactac 360
ctttcacagg gtttggcagg agaagtgagt gtaggcgcag aagatcttac tgctcaaata 420
gagaatattg tatcaaatga cttggctgca gtgcacggga tcacagtgtc tcaggaaatt 480
atgattggag aaggattatc tagctttgga gctgaagacc ccctttttcaa agggaaaagt 540 gtcatgagtc caattctaga agttcctcca gagtattttg cttccttccc agagggtttg 600
accaagggga aagactttca agatttttct gctcttggaa ctgaaggcat gataaagcta 660
gaagatatat gggactctgg ccttaatgtt agtggtgctg cttcaggtag tgggaatgag 720
ctgtggagca atcatgtcaa ctatgaagag tttccagaat ttggagtcac aagtggtatg 780
tctgactcag acatctggga tattggctta ggaagtttgg gaattgataa gtggccaact 840
gatgaacctt ctcttggtga aacaaatggt caagctggtc aaccaaaaga agataggcct 900
aagaattttg gtccatag 918

<210> SEQ ID NO 86
<211> LENGTH: 918
<212> TYPE: DNA
<213> ORGANISM: Glycine max

<400> SEQUENCE: 86
atgaacgact tgttctccgg ctccttctcc cgcaccaatg accaagtctc gccggaccac 60
caccatgtga tcgagatggc ggccaccgca tcgccaacgg ccgagggaag cgtgaatctc 120
gaaaagttct ttcaagaagt tgagcaggta aaagaggagc tgaaggagct agagcgtctc 180
catgaaaatc tgcgtgggtc ccacgagaaa agcaagatcc ttcacagcgc caaagctgtg 240
aaggaacttc gcttacgcat ggacagtgac gtgacacttg ctctaaagaa tgcaaagctc 300
gttaaggttc ggcttgaggc actggaccgg tccaaccaga ccagtcaaag cttgcctggt 360
tcgggacctg gttcgtcctc agaccggacc agaacgtccg ttgtgagcgg actgaggaag 420
aagctgaagg actcgatgga cagcttcaac agcctcagac aaaagatatc gtcagagtat 480
agggaaaccg tgcagcgtag atattatact gtcaccggag agaaccctga tgacaaaacc 540
attgatctcc ttatttctac gggtgagagt gaaacattct tgcagaaggc gatccagcag 600
caaggtagag ccagtgtgat ggacacgatc caagagattc aagagaggca cgacacagtc 660
aaggaaatag agagaaacct aaacgagctc caccaagtgt tcttggacat ggccgtgctg 720
gtgcagtccc agggcgaaca actggacgac atcgagagcc acgtggcgcg cgccaattcg 780
tacgtgcggg gtggggtcca gcagttgcac gtggcaagga agcaccagaa gaacacccga 840
aagtggacat gcatagccat catactgctc attattatca tcttgattat agtcctccct 900
atagttctaa gaaattga 918

<210> SEQ ID NO 87
<211> LENGTH: 873
<212> TYPE: DNA
<213> ORGANISM: Glycine max

<400> SEQUENCE: 87
atggagaata ataagatgat gggtgtgaag aaagaggact atgctgccaa tataggatct 60
tcatccctcc cttcttgtaa taattatcca ttctttgatt tctctgaaga taagggctct 120
ttagggttta tggagctatt gggtgtgcaa gactacaatc atctccttga tttccctcta 180
tcgtcacacg tgtcagtgcc tcaaacctct gcggttaagg aaccacctga gactaagaaa 240
gagtgttccg aggtaaccaa caaccagcaa ccgacgactc cgaactcttc atccatttcc 300
tccgcgtcca gtgaggttct ctatgatgaa cagaataaaa ctgtagacct agcacctgaa 360
caccaaaaga caaaggaaca gttgaaggca aagaagacaa atcagaagag acagagagaa 420
ccgagattcg cgttcatgac gaaaagcgag gtggatcatc tggaagatgg gtacagatgg 480
agaaagtacg gtcaaaaagc tgtgaaaaac agcccctttc ccaggagcta ctatcgttgc 540
accagtgttt catgtaatgt gaagaaacgc gtggagcgat ctttcagcga cccaagcatt 600
gtggtgacaa cctacgaagg ccaacacacg catccaagcc cagttatggg tcgctccaac 660
aactttggta cggtaatgtc tggatctgct ggaaactaca tgtcccaata ttatcatcag 720
caacaagtcc acgtcaatgc attgtcttct ttgggtttcc tctcttcttc ttcgtcttca 780
aggaatgcca ctttttctca agagactgcc ttgttaagtg actatgggct tcttcaagat 840
gttgttcctt cacatatgtt gaaagaagac tag 873

<210> SEQ ID NO 88
<211> LENGTH: 669
<212> TYPE: DNA
<213> ORGANISM: Glycine max

<400> SEQUENCE: 88
atggcgccga agcacgacaa ctgctgctcg cgctgcatcg gcttcctaat agccataggc 60
ctcactgcgc tcttcctctg gctgagtctc cgcgtggacg aacctaaatg ctacctcgac 120
tacatttacg ttcctgccct caacaaaacc ctaaattcca gttcaaattc cactcacaac 180
aaaaacgcca caatagtctt cgctctcaag ctcgccaatg agaacaagga caagggcatc 240
caatacgacg acgttctcct ctccttcaga gtcttcgaga gcgtgaacac cacgcgcccc 300
ctcggcaacg ccaccgtgga aaggttctac cagggccaca agaagaaggc caccaagcgc 360
ggaaacttca ccgtcggagg tggcggcgga aacctcacgg cggcgctgga tgggaaagtg 420
tggtaccgtg tggactatgc tactgcggtg aagtacaaga ttattttctg gtacacgaaa 480
cggcaccgtt tgtggggagg ggcaaatgtg gaaattggtg aattgggaac gaaggtgaat 540
cgtaaagccg ttagacttgg agggaagaac cccgtggtga tcgagtccgg cgcatcgaag 600
ctcagtggac gctatcgtgc gcctcttctt ctccctttttg cttatctcct ggcttgtggg 660
cttagttga 669

<210> SEQ ID NO 89
<211> LENGTH: 2271
<212> TYPE: DNA
<213> ORGANISM: Glycine max

<400> SEQUENCE: 89

```
atggaaggat ttggaaatgc gtaccccagt tatgtcccat ccgaactggt gagttgttca     60
tcaaaaggta gaaatgtaac ataccattgc tatttgatgg agttggagca gcactacgag    120
tatcaggtgt cggttaatga cattgtactt gcaattagga gtgaacttga ctcagaaatt    180
gtagacacat tatcaggcac atcatttgat gtgaaaaggg gaaaattgtt agtgaacctc    240
agacatttgg aacccattca acttagccca gaaaaggttc aaagttgtag aagatttcag    300
actaccctct ttaggatcct cctaaatcgg gacgttacta agttaacaag tgtttcagat    360
gatttcagtt tgggagataa tcctgaaatt gattttcttc tgctcccagc cactgttaaa    420
caccagagac cttcaaattc gattattgat tggaagcctg ttttatcggt tcctttttca    480
tctgaaagta cctgtgattg taaggatcat gcatgtaatg tgaggattcg aaatgattca    540
gtttgctctt gcaaacttga aaattgtgta gtctacactc ctcataatgg tagtatttat    600
atcatttata ccactgatgg tacaaagaaa ttgaatggaa attcaactct aaaccaagga    660
cttaagggaa ttactactta caaggagcac ttcaaaaaac gccacgggat tgaattgggt    720
tttgaacatc aatccctact tcatggaagg aatcttttca aagtggagaa ttaccttctg    780
aagaccagac aaaagacgga gaaaggaaaa aatatgagct ctgttgactt gccgccagaa    840
gtttgttctg taatcatgtc accaatatca atcggtacca tatattcatt ttcttttatt    900
ccatcaatca tgcattggct tgagggcttg ctcgttgctt tcaacttaaa aaggatgctc    960
ttggatcatt tcacgccaaa tgatatccca atcagcaagg tattgcaagc aataactgca   1020
aagggatgtg aagaggccta cgattatgat tacttagaga cacttggaga ttcttatctg   1080
aaatacattg ttagtcaaca gcttttcaag accaatcaaa atgatcggga gggcgccctt   1140
tcagacaaga ggaagaacat catttccaat gatgtcttgt ttaagtatgg gtgtacccgc   1200
ccacttccgg gtttcatacg gaaagataaa tttgatccaa agcagtggga tgtacccggt   1260
gataagtcaa acagtattct cttgctaaaa cagaagttgg actccagtag aacaagagta   1320
tatgttcgaa agacgagaga aatagacttg ggaatcattg ctgatgttgt tgaggcacta   1380
attggtgcct ttattagcac agaagatgaa aaggctgctt tatcgtttat taattggatt   1440
ggtatcaatg ttgacaccaa cattatgccg tatgagaatg agaggcacat tagcattatt   1500
gccccagagg agcttgtaaa agccaaactt ttaaaatccc ggctgaacta ctcgtttaaa   1560
gacccttatc ttttagtaga ggctctcacc catagttctg gcaaacggcc agaaattcgg   1620
acatgttatg agcgactaga gtttcttggg gacgcagtgt tggactatgt catcactatg   1680
catttctaca aggaatattc taatgacaaa ttctcagcag aatttttcac taacatgagg   1740
tctatttctg tgaacaatga gtgttacgca ctgtcagcca ttaaagccaa gctggatgaa   1800
cacatactct gtgactcggt agtaaaaaat aacattgccc agacaatgga aggtgttaag   1860
aacttatctt tggaatcaac ttttggatgg gagctagaaa catatttctg tcaggtgctg   1920
gcagatgtta tagaatctat agcaggagcg atttttgttg attcagggta caagaaggag   1980
gttgttttcc aaagcataaa gccccttttg gaaccccttg ttacacctga aacagcaagg   2040
agacatccta ttagtgagtt gcacgaacta tgccaaaaaa aaggctacaa aatgaaagta   2100
```

```
tatccccccg tccgcgtcaa cggtgaaact tcagttacaa ttgaggtgaa aaccaacggg   2160

atcacttaca agaataatcc tcctgctaaa gcatctaata acgatacagc tcgtaaactg   2220

gctgccaagg atgttttaaa acaaattaag atttgcaagt ctcttggcta a            2271


<210> SEQ ID NO 90
<211> LENGTH: 1950
<212> TYPE: DNA
<213> ORGANISM: Glycine max

<400> SEQUENCE: 90

atggctggaa aaggcgaggg tcctgctatc ggaatcgatt tgggaacgac gtactcttgc     60

gtcggcgtgt ggcaacacga tcgtgttgaa atcatagcca acgatcaggg taacagaact    120

accccatcct acgtggcttt caccgacaca gaacggttga tcggcgatgc ggcgaagaac    180

caggtcgcta tgaacccaac caacaccgtt tttgatgcta agcgtttgat tggaaggcgt    240

ttttccgatg catcagtaca aggtgacatg aaattgtggc cgttcaaggt gattcctggc    300

cctgctgaga aacctatgat tgtggtgaac tacaaggggg aggagaaaca gttttccgcg    360

gaagagatat cctccatggt tcttatgaag atgaaggaga ttgcggaggc gtatctaggt    420

tccaccataa agaatgcggt tgtcactgtg cctgcttact tcaacgactc acaacgtcaa    480

gccaccaagg acgctggtgt catttctggg ctcaacgtga tgcgaattat caacgagcct    540

accgcggctg ccattgctta tggctcgac aaaaaggcca ctagctctgg ggagaagaat    600

gttctcattt ttgatctcgg tggtgggact tttgatgtct ctcttctcac catcgaggag    660

ggtattttcg aggtgaaggc cactgctggt gatactcact tgggaggtga agattttgat    720

aacagaatgg tgaaccattt tgttcaggaa ttcaagagga agaacaagaa ggatattagt    780

ggaaatgcca gagctctgag gaggttgaga acagcatgtg agcgggcaaa gaggactctc    840

tcttccactg ctcaaaccac catagagatt gattccttgt acgagggtat tgacttctac    900

acaaccatta cccgtgcccg ttttgaagag ctaaacatgg atttattcag gaagtgcatg    960

gagcccgtgg agaagtgttt gcgggatgcc aagatggata agagtaccgt ccatgatgtt   1020

gttcttgttg gtggttctac taggattccc aaggttcaac agttgttgca ggacttcttc   1080

aacggaaagg aactttgcaa gagtattaac ccagatgaag ctgttgctta tggtgctgca   1140

gtgcaggctg cgattctcag tggcgagggt aatgagaaag tgcaggatct tcttttgttg   1200

gatgttactc ctctatccac tggtttggag actgcaggag gagtcatgac tgtgttgatt   1260

cccagaaaca caaccattcc caccaagaag gagcaggtgt tctcaaccta ctctgacaac   1320

cagcccggtg tgttgattca ggtctatgaa ggtgaacgaa cgaggactcg tgacaacaat   1380

ttgcttggca aatttgagtt atctggaatt cctcctgctc ccagaggtgt tcctcagatc   1440

actgtttgct tcgacattga tgccaacggt atattgaacg tgtctgcgga ggacaaaacc   1500

actggacaga agaacaagat tacaattacc aacgacaagg gcaggctttc taaggaggag   1560

attgagaaga tggtgcagga agctgagaaa tacaagtctg aggacgagga gcataagaag   1620

aaagtggagg ccaaaaatgc attggaaaat tatgcctata acatgaggaa cacaatcaag   1680

gatgacaaga ttgcttccaa actgtcttct gatgataaga agaaaattga agatgcgatt   1740

gagcaggcta tccaatggct agatggaaac caacttgctg aggctgacga atttgaggat   1800

aagatgaagg agttggagag catttgtaat cccatcatag caaagatgta ccagggtgct   1860

ggtggtgatg cgggtggagc catggatgag gatggtcctg cagctggcag tggaagcggt   1920

gctggaccca aaattgagga agtcgattaa                                    1950
```

<210> SEQ ID NO 91
<211> LENGTH: 735
<212> TYPE: DNA
<213> ORGANISM: Glycine max

<400> SEQUENCE: 91
atgtcccatc taaacggcgc gtactacggc ccctccgttc cgccgccgaa atcctaccac 60
cgcccctccc gcggcggccg cgacggctgc tgctgcggct gcctgagctg cttctgcggc 120
tgcatcttcg actgcatcct gggcctcatc tgcaagatcc tcaccacaat cctcatcatc 180
gtagcaatac tcggctttct cttctggttc atcgtgcgcc ccaacgtgct caaattccac 240
gttaccgacg cgtccctcac gcgcttcgac tacaccacca acaacactct ccactacgac 300
ctcgccctca acgtctcgat ccgcaacccg aaccgcaggg tcggcgtcta ctacgaccac 360
atcgaagcgc acgcgctgta ccaggatgtt ttgttcggga accagacatt agggccgttc 420
ttccagcacc acaagaacac caccttcgtg aatccccttt tcaagggcca gcgcgtgacg 480
ccactcgccg ggaaccaggt cgaggtgttt gacaaggaga agggttcggg tgtttacacc 540
atcgatttga agctctttat ggtggttcgg ttcaagttct tgctgttcaa gagtgcgagc 600
gtgaagccca agattcggtg tgcgttgcac gtgccgctga aatcgcgtaa cgcaacaaca 660
actatctccc ccgatgctgc gtttcaaccc acagagtgcg gttgggatta cgggaaaaaa 720
tggtggatcc attag 735

<210> SEQ ID NO 92
<211> LENGTH: 1512
<212> TYPE: DNA
<213> ORGANISM: Glycine max

<400> SEQUENCE: 92
atggcgggta cggtttcgac ttgtttcttc ttcgtgtttc ttctttctct ccttcttcct 60
tttcagatct ccgctgagga atcctcggag aaggagttcg tactcacatt ggatcactct 120
aactttcacg acactgtcag caagcacgat ttcatcgtcg tcgagttcta cgccccatgg 180
tgtggtcact gtaagaagct tgctccggag tatgagaaag ctgcttctat cttgagtagt 240
catgatcctc ctattgtttt ggctaaagta gatgccaatg aggagaagaa caaagacctt 300
gcatcacaat atgatgttaa gggattccca acaattaata ttctgagaaa tgggggaaag 360
aatgttcagg aatacaaagg tccccgtgaa gcagatggca tcgttgacta tttgaagaaa 420
caaagtggtc ctgcttcaac tgaaattaaa tctgctgatg aagctactgc ttttattggt 480
gaaaataaag ttgctattgt tggagttttc ccgaaatttt ctggagagga gtttgacaac 540
ttttctgcct tagcagagaa gttgcgttct gattatgact ttggtcacac tctgaatgcc 600
aaactccttc caagaggaga gtcatcagtt tctgggcccg tagttaggct gttcaagcca 660
ttcgatgaac tttttgttga cttccaggat ttcaatgtgg aagctctaga gaagtttgtt 720
gaggaatcta gtacccctgt tgttactgtc tttaacaatg aaccgagcaa tcaccctttc 780
gttgtcaaat tcttcaacag tcccaacgca aaggcaatgt tgttcatcaa cttcactgcc 840
gaaggtgctg aagctatcaa atcaaaatac cgtgaagctg ctgagcaata taaacaacag 900
ggtgtcagct tttggtggg agatgttgag tctagtcaag gtgctttcca gtattttgga 960
ctgaaagaag agcaagtacc tctaattatc attcaacata atgatgggaa aaagtttttt 1020
aaacccaatt tggaagctga tcacattcca acctggttga aggcatacaa ggatggtcat 1080

-continued

```
gttgcaccat ttgttaagtc tgaacccatt cccgagacta acgatgaacc tgttaaagtg   1140

gtagttgggg ccagtcttga ggacattgtt ttcaaatctg ggaagaatgt tctgctggag   1200

ttttatgctc cctggtgtgg tcattgcaaa cagttggctc caatattgga tgaagttgct   1260

atctcatatc aaaatgaagc tgatgttgtt attgcaaaac tggatgcaac tgccaacgat   1320

atcccaagtg aaacctttga tgtccaaggt tatcctaccg tgtacttcag gtcagcaagt   1380

ggaaagttat cacaatacga cggcggtagg accaaggaag acatcataga attcatcgaa   1440

aagaaccggg ataaacctgc tcagcaagaa caaggaaaag atgagcaaga acaaggaaaa   1500

gatgagcttt ga                                                       1512
```

<210> SEQ ID NO 93
<211> LENGTH: 1008
<212> TYPE: DNA
<213> ORGANISM: Glycine max

<400> SEQUENCE: 93

```
atgaacgact tgttctccgg ttccttctcc cgcttccgca gcgaccagtc ctccccggac     60

cgccaccacg acatcgagat gggcgccacc gcctccagcg gcggtcgcgg cggcgaggtg    120

aaccttgaca agttcttcga ggacgtggaa ggcgtgaagg aggaactaaa ggagttggaa    180

ggtttggctc agagtctaag gagcagccac gagcagagca agacgctgca caacgcgaag    240

gcggtgaggg acctgcgcgc gcgcatggac ggcgacgtct cggcggcgct gaagaaggcg    300

aagctgatca agctcaagct cgaggcgctg gagcggtcca acgccgcgaa ccggaacatg    360

cctgggtgtg gaccgggttc gtcctcggac cggacccgga cctccgtggt caacgggctc    420

aagaagaagc tgaaggatgc tatggagagt tttaacgaga ttcgccagct tgtgtcctcg    480

gagtaccgcg agaccgtgca gcggcggtac ttcaccgtca ccggcgagaa tcccgatgac    540

aagactctcg atctcttgat ctccactggt gagagtgaga ctttccttca gaaggccatt    600

caagagcaag gaaggggtag aattctggac accatcacgg agattcaaga gaggcatgat    660

gctgtcaaag agatagaaaa gaatctcaag gagttgcacc aagtgttcct tgacatgaca    720

gtgttggtgc aacatcaagg tgagcaattg gatgatattg agagccatgt ggcaagagct    780

cattcgtttg tgcgcactgg agctgagcag ttgcagactg cgcggaagca ccagaagaac    840

accaggaaat ggacctgcta ttgtatcata cttcttctgg tgatcatctt gtttgtggtg    900

ctcttcactg tgaagccgtg ggaaaatagc agtagtggcg gcaatggggg tggtcagcct    960

gcaccagctc aaacacctcc atcaccttca cctcctgtta atgcttaa                1008
```

<210> SEQ ID NO 94
<211> LENGTH: 702
<212> TYPE: DNA
<213> ORGANISM: Glycine max

<400> SEQUENCE: 94

```
atggcatcat ccgagaacgt agccagcatt gagccatgta tgcttcgtcc ccctgtcacc     60

gattcatggc tcgcagagtt cttcgctcgt gacgccgatg ccttaaccaa ggctcttcag    120

aagtctctct ccggtactgt cttgccggac gaggaaaact acttttctcc ctttctgccc    180

aagtcagacc ccgccgtcgc cacccccacc gtctccagcc tctccggctc cgatcaggac    240

tcggcgccgc gccgccgcgc gccgcttccg ccgtccggga agatctccaa gaggaagtcc    300

cgcgcctcga agcgctcgca gacgacgttc atcacggcgg accccgccaa cttccgacag    360

atggtgcagc aggtcaccgg cgtgcggttc ggcggcgccg gccagccaat tgcgccggcg    420
```

```
gcgggggttg tgaagcccga gccgcagcgt gcctcgggcc ttgccaggtt ccccgccggc    480

gcggggtgcc tgccgacgct cgacacgtcg gccttcctgc tggaccatca ccagcaggtg    540

gtggggccct cctctgttaa ctctgggcct gccaccgggc tttctgggcc cggcccgctc    600

cccttcgccc aacccctcct tgacgcttcc ttcgcctccg cagggttaga ttttgacacc    660

ttctccagct tccccactct cgagtcgtgg aaagtcatgt ga                       702
```

<210> SEQ ID NO 95
<211> LENGTH: 627
<212> TYPE: DNA
<213> ORGANISM: Glycine max

<400> SEQUENCE: 95

```
atgacagagg ggaacggtga caaaactctg cgaaagatcg cagacgcatt caatgacctt     60

gcaaacgttt tcaccgattc tcagagcgca gaagcagagg tcaaggttgc tcccttctct    120

catgcctgct ctctcgtctc ccctctcttc ggttgcttgg gcgtcgcctt caagttcgcc    180

gaaatggatt acgtcgccaa ggttcatgat ctggcagagg cgtccaagtc tattcagaat    240

ctgcagtctc tgattgagct ggatgtgcaa gctaacactg ttaggaaagg aggtagccat    300

acgcggaatc tgctcagagt gaagcgcgga cttgacatgg tcagagtgct ctttgagcag    360

attctagtta cagagggtaa ttcccttagg gatccagctt ccaaagctta cgaacaggtg    420

tttgcacctc accatggctg ggcgatcagg aaggctgttt ctgcgggaat gtatgccctt    480

cctacaaagg aacagcttct gaagaaactc aatgaggatg aggcatcggc aaaagaccac    540

atgcaaagtt atgtcactgc ttccgcacct ctaatccaat acattgacaa actctttgtt    600

tctagagact tgggaataga ttggtga                                         627
```

<210> SEQ ID NO 96
<211> LENGTH: 735
<212> TYPE: DNA
<213> ORGANISM: Glycine max

<400> SEQUENCE: 96

```
atggacgcct tcaattcctt cttcgattca agaaaccgat ggaattacga tactctcaaa     60

aacttccgtc agatttctcc ggtcgtgcag aatcacctga agcaggttta ttttactctg    120

tgttttgccg tggttgctgc ggctgtcggg gcttaccttc atgtcctctt gaacattggg    180

ggttttctta ctacagtggc atgcatggga agcagctttt ggttactctc cacacctcct    240

tttgaagaga ggaagagggt gactttgttg atggccgcat cactgtttca gggttcctct    300

attggaccct tgattgattt ggctattcat atcgatccaa gccttatctt tagtgcattt    360

gtgggaacag ctttggcctt tgcatgcttc tcaggagcag ctttggttgc aaggcgtagg    420

gagtacctgt accttggtgg cttggtttct tctggattgt ccatccttct ctggttgcac    480

tttgcttctt ccatctttgg aggctcaaca gctctcttta agtttgagtt gtactttggg    540

ctattggtgt ttgtaggtta cattgtagta gacacccaag aaatagttga gagggcacac    600

ttgggcgatc tggactatgt aaagcatgcc ttgaccttgt ttaccgattt ggtcgcagtt    660

tttgtccgga ttcttgttat tatgttgaag aattcgactg agaggaatga gaagaaaaag    720

aagagaagag attga                                                      735
```

<210> SEQ ID NO 97
<211> LENGTH: 5040
<212> TYPE: DNA

<213> ORGANISM: Glycine max

<400> SEQUENCE: 97
atggaaccct ccttaagcgt ctccaatcaa ctgcagtccc tgagtctttc ccaagacaaa 60
aaccatgatg actcagtcaa gaaagatccc cggaaaattg caagaaagta tcagttggag 120
ttatgcaaaa aagctatgga ggaaaatata attgtgtatt tagggacagg gtgtgggaag 180
acccacattg ctgtgcttct tatgtatggg atgggtcatt tgattcggaa accgcagaag 240
aacatatgtg tctttcttgc ccctactgtg gctttagtcc atcagcaagc aaaggttata 300
gcagactcta ctaattttaa ggttgggaca tactgtggaa gttccaagcg cttgaaacgt 360
catcaagact gggagcagga gattggacaa tatgaggttc ttgttatgac cccacaaata 420
ttacttcata acttatctca ttgcttcatc acaatggaga tgattgcact tttgatattt 480
gatgaatgcc atcatgctca agtcaaaagc aaccatgctt atgcagttat catgaaagtc 540
ttctacaaaa gtaattcctc aaaggttccc cgtatatttg gcatgactgc ttcccctgtt 600
gtaggaaaag gtgcttctag tgaagcaaat ctagcaaaaa gcatcaatag tcttgaacat 660
atacttgatg ctaaggtagg gttacttcga gacagattgc ctactaaagc aaacttaaat 720
aggcggcagg tggaaataca ggaccaaact tgcccattct gcagaagcac agtggaggat 780
acaccacacc tatttttcca atgcagcaaa atcatacctc tttggtggga aaccacgtcc 840
tgggtgaaca tctccactgt ttttccactg caccaaaggc aacattttgc ccaacatatg 900
attgatgggg tcaaaggaat ttgtgttagt aggtggaggg tctggtgggt ggcacttaca 960
tggtctgtgt ggcagatgag aaataacatt atattctcaa atgggatctt caatggaaac 1020
aaactgatgg aggatgctat atttttgttt ttgacatggc taagaaacta tgagaaggat 1080
tttgtaacta attataatca atggtcatct aaccttatag aggcttttgc ttgcatagca 1140
aaccttggta ggagtataga agatcaccag aaaaggatga atgcaaagaa acttctgaac 1200
cggatgcatg ataatgtgat tttcggtctg cagaatcttg gcatttgggg agcattgcaa 1260
gctagtcata ttcttctgag tggtgatcgt tctgagaggc atgagttagt ggaggctgaa 1320
ggaaattcaa gtgatgactc tctgtgtgat aaatatcttg ctcaggctgc tgaactgttt 1380
acttcacaat gcatgatagg cgacagggta actgatttat cttctgtgga aatattaaaa 1440
gagccatttt tctcagcaaa gcttttacga ctcattggga tattatccaa ctttaggttg 1500
caaaagaaca tgaaatgtat aatttttgtg aatagaattg tgacagcaag atccctgtca 1560
tacattctac agaagctcaa gcttctaaga caatggagga gtgatttcct agtaggagtc 1620
catgctggac tgaagagtat gtcacgaaag accatgaaca tcattgttga taagtttcgc 1680
tctggagagt tgaatctact ggttgcaacc aaagtgggtg aagaaggact tgacattcag 1740
acgtgttgcc tcgtcatacg atttgatctt ccagaaactg ttgccagctt tatacagtca 1800
agaggtcgtg cacgtatgcc tcagtcagaa tatgcatttt tggtggacag tggcaataag 1860
aaggaacttg acataattga tggctttgag aaagatgaat accgaatgaa tatggaaatt 1920
acttttcgaa catccaagga gacatacata atccctgagg aaagaatatt cagagttgat 1980
tcgtctggtg cttctgttag ttctggatat agtatctcat tgcttcacca gtattgttca 2040
aagcttccac atgatgagta ctttgacccc aagccatgtt tttattactt agatgattca 2100
ggggggattt cctgccatat aacattgcct tccaatgcac caataaacca aattttaggt 2160
acaccacagt tgtctatgga ggcttccaaa agagatgctt gcctgaaagc aatagaagaa 2220
ctgtataatt taggcacttt aagtgattgt ctcttgccaa aacaagatga tgcagagcca 2280

-continued

```
gaggcgcagg tttcaggctc ttctgatgaa gatgaatgtg aagatgccat atcaagagga   2340
gaattacatg agatgctagt tccttctgcc tttggacagt catggataaa tgaggataac   2400
atcgtccgtc tcaactctta ctacataaaa ttttgtccct atccagagga tagggtctac   2460
aaagagtttg gtcttttcat catggttcgg cttccaatgg aggctgagaa attggaactt   2520
gatctccatc ttgctcatgg tcgatctgtg atgacaaaat ttgtcccatt tggagttgta   2580
gaatttgaca aagatgagat taagatggca gagaattttc aagaaatgtt cctcaaaatt   2640
attcttgata gattagaatt cgtttctgag tttgtagact tgggtatggg tgctgaatct   2700
cacacaggca catcaacctt ctacctttg  cttccagttg tattgcaaga atatggaaat   2760
gccatgaaag tagactggaa gactgtgaag agatgccttt gttcaccaat tttcaggcat   2820
ccagctgata ctatggataa aaaagttttc cctttagata ttcacctgca acttgccaat   2880
ggttacagaa gtgtaagaga tgtcgagaat agtttagtgt atgccccaca taagaagaac   2940
ttttatttg  tcacgaatgt taactaccaa aagaatggat atagtcctca taatgattca   3000
ggcacttcaa gctatgtgga ttacttcatt gaaaagtttt ccattcacct caaatgtcca   3060
gaacaaccac ttctacatgt taaaccagtc tccaatttgc acaacctgct acacaaccga   3120
aagcatgagg atgcagaacc acaggagctg gacgaatact taatttattt gcctcctgag   3180
ctttgtgaac taaaaataat aggtttttcg aaggatattg gcagttccat atctttgcta   3240
ccttcaatta tgcaccgtct tggaaacttg ctggtggcta ttgaactaaa gcacaggcta   3300
tcttcttcct ttccagaggc agctgaaatt agtgccctta gagttttaga agctctcact   3360
actgagaagt gtcaggagcg cttttccctt gaaagacttg aagtgcttgg tgatgctttt   3420
cttaaatttg ctgttgcacg tcattttttt ctcatgcatg acagccttca tgaaggagac   3480
cttacaaaaa ggcgctccaa cgctgtgaat aattccaatc tgtttaagtt ggctatcaag   3540
cgcaatttgc aggtctatat atgcgatcag acatttgatc ccactcagtt ttatgcatta   3600
ggccgtcctt gcccaagact ttgtagcaat gaaaccaaag aaagcataca cttctgttta   3660
aattctgtta aggaacaagg aaaagtaact gaaacccaat gtaacaaaaa tcatcattgg   3720
ttacatagga aaacaattgc tgatgtggtt gaagctctgg ttggagcatt tctagttgac   3780
agtggcttta aagctgcaat tgcttttctt tcatggattg gcattcaagt tgattttgaa   3840
gcttcacaag tggttgatat ttgcatagca agtgctagtt atttacctct ttcttctgaa   3900
gtagacattc cttctcttga aggtaagcta ggacatcact tttttcataa gggcctgctt   3960
ctccaggcat ttgtacatcc ttcttacaat aagcttggag gaggctgtta tcaggcaagt   4020
cgattggagt ttcttggaga tgctgtcttg gattatttga ttacttcata tgtattctca   4080
gcttatccca aactaaagcc tggtcaattg acagatttga gatcattgtc tgttaacaac   4140
aaggcatttg cttgtctagc ggtagatcgc agttttgata aatttctttt atgtgattca   4200
agtggcctgt ctgaggcaat aaaaaagtat gttgactaca ttagaagacc tgtatcagat   4260
aacagcatta aagaagggcc aaaatgtccc aaggcactgg gtgacttagt ggaatcttgt   4320
gttggtgcca tccttcttga ttcagggttc aatttgaaca aagtttggaa gattatgact   4380
tcgttcttgg actcaatcat gaaattctca tcaagcttgc agctcagtcc tgttagggat   4440
ttgcgagaac tttgccaatc tcataaatatg gagttggagt ttctgccagt gccctcaaaa   4500
ttgactaaaa ggttttcagt tgaagctaaa gtgagtggga atggtgtatg tgaaacagct   4560
tcagcaactg gtcaaaataa aaaagaggct tgcagaattg cttcactgct actttttca    4620
```

-continued

```
aagttcaagg taaagcaatt atgtttagtt ttattttttc catccttatt ttctcaactc   4680

aacaccttag aattagcatt tctttattgt acagtgacac cacagaataa tgcaagagtt   4740

gttggagcta ttgatagtag gaactcacac acaatggaac aatttataaa gaggaagaga   4800

gaagatttag gctttgcaca aaagatgccc acacatgcac actatttggt aaatctgttg   4860

gacaatgcac tgcttcgatc aacttgttgt ctattaggag cttcaactct gatttctttc   4920

agcagtgagt taagccaaat aactaggcat gcaacatatg ccccagctat atattctgct   4980

tcacaagagg acaatactac cactgactgt ttcttgacac cagaaaactt aaagatataa   5040
```

<210> SEQ ID NO 98
<211> LENGTH: 1731
<212> TYPE: DNA
<213> ORGANISM: Glycine max

<400> SEQUENCE: 98

```
atgatgacag acgaggaatt gttgcagaaa cttgaagact taaccaaaaa cgcccaacac     60

caccacttgg agactctccg ctcgatcctt cttcacaatg gaatcgtgca ctatcttcaa    120

tccttcaaga agggttctct tcttcatctt gatccatcaa ctttcgcacg tgtcgtgccc    180

ttgtccacgt atgaggacta cgttgactac attaaccaga tggcagaagg gaaagatgac    240

ccttttctct ccgttgaccc tctccgctgc ttcttttaca gctcgggaac aagttcaagc    300

accatgaaac cgaaattgat cccttacttt gattcaagcc tttccaaagc tgcctccttt    360

attggtcacc gaggcagtgt tgctgttcgt caaaggctat ttcctccaag gccagaagtg    420

aacaagatcc tatggtttct ctatgctgac aacattacta ccactaaatg tggcttgaaa    480

gtcatggctg catctacata ccctttgcaa agtggtaatg ctacccctca acaacttgct    540

gccttttcca gtcccctaga agtgattctt gccactaatg ttgagaatca aatgtactgc    600

caccttctat gtggccttag gaatcttgac cttatagatg gaattgcaac cccttatgct    660

ataggcttga ttaaagcatt tggttttttg gagtccaagt gggagcagct atgtgatgat    720

cttgaccatg gatttccatg taatgaaatt tctgaggggg caatgaggga agctgtgacc    780

aacacacttg gtggacctca gccagaattg gcaaatagaa taaggttaat ctgtgaaggt    840

aataactggg gcggaattgt gtatagattg tggccaaaca ttcgttatat taggtgtgtt    900

accactggaa gcatgaagca gtactaccaa aagctcaagt attatgcagg agaggtacct    960

attttaggag gagattattt tgcttcagag tgctgtgttg gtctaaattt agacataatg   1020

caacccccctg agacaacacg gtttgtgatg cttccaactt ttgcctactt tgagtttctt   1080

ccatttaaca taaatgagga caatgatgct agcaaggaag ctgtggacta tagcagtgta   1140

gaggttggca agatgtatga agtggttgtt actacttaca gaggatatta ccgataccgt   1200

ttgggcgata tagtgagagt tgttggtttc tataattcat ctccactagt agagtatgtg   1260

atgagagcac ctaaaactcc tgctgagatt gtgactgaga aggacttgat ttcagcagtt   1320

gaaaattttc aacttgcact tagaggtgct atgagaattg agattgttga gtttgcaagt   1380

ttcttggacc aggagtcaat gccgaagcag ttgaaggtat ttgtggaagt ccaagaggaa   1440

tctgattttc tggaggataa gctagaggaa tcagttagag ttttgagaag ttgtatctcc   1500

tctcttgaga gtgggttggg agctatatac aaggtgcaga aggataaagg tcaactaagg   1560

agcttacgga tattcatcat aaggcctgga gcttttgatc agttatcaga attagccatt   1620

aaaaatggaa catcagctag tcaatataaa ccacccaaga tcataaggaa tcatgaagtt   1680

gtcaaactct tggaaaaatt agcctttgtg gcagtatcat tcgatggcta a            1731
```

<210> SEQ ID NO 99
<211> LENGTH: 363
<212> TYPE: DNA
<213> ORGANISM: Glycine max

<400> SEQUENCE: 99
atgccatcac agatttttat gtgtaaaatt aatttacttg gtcccattac tcaatcaata 60
gcattactaa ctgagtatgt gagggacaga tatcagtgga gaaaatatgg taaaaaagtc 120
accagagata acccttctcc tagggcttac ttcaagtgtt catatgcccc aagctgccca 180
gtgaacaagt ttgatttata tgaccttttt ccgcggatca tgttaatcac tgactctgta 240
atgagtcatt taagtcaagt gcagtcgcag attgagcaac ctatttttatc acctctaata 300 ataaatatgg gtaagatcgc ttgttgggga ggaggatgtt tcatattagg aaccaaaatt 360
tga 363

<210> SEQ ID NO 100
<211> LENGTH: 1785
<212> TYPE: DNA
<213> ORGANISM: Glycine max

<400> SEQUENCE: 100
atgatgaacc acctacctcg aatattcggc catagaaaga agcaagcctc cgacaacatg 60
gacccgacga caaagaacaa gaagaagagt aagaagaagc agcagcccaa actcgagcgc 120
cgcaacgcct ccaatcactt cgaatacgac gccggatcgt cgtgctcctg gcgcggcggc 180
gacgagaagg acgcttccgt ctcgacgtcg tcgtcgtcgt cgtcgtcgtt gcattgcaca 240
cgctcgatgg acctctacga ccgcacgagc ttccgaattg agggcgtgga gggcgagttc 300
gaccggattt gccgcagcct cggcctctcc ggccccgagg acttctccat tccggccgcc 360
gcttgggagg ccatgaagct ccgctgctcc tcggacctgc ttcctcgccg ccccaagcac 420
ggcggcgatg aattcgacga agaggcgaag gagaaagagg aaattgaagt tgtcgagagc 480
gaggatcgag ctagggtttt ggatgaatgt gttgtttctg ctgagagcag tggttgctgt 540
ggtggaatca agggttttcg gcctccgatg ctgaagccgc cgccgggagt tagggtttcg 600
gtggtggacg acgccacgtg ttccacgtgg gatttgatgc gggattttgc gccgaatggg 660
gaaggagaag ggaaggatag ttacgtggag ttaaattctt ttgatgatga agatgatcat 720
gagcgagtag agaaggaaga agaggaagat gaagaagatg aagaagaaga agaaggggaa 780
gttggtggag tgagggagaa gagtgtagaa gaggaaaatg cggcgaggat tgcggaaatt 840
gtggatgatt tttcagggtt ttctactccg aacgaagatg attcttcaag cactaccacg 900
ggtcctaggt ctaacagtat atctcccaat gggagaatca agcgtgttat taccgcgggt 960
aattggcaga agggtgacct gttggggcgg ggttcgtttg gttctgttta tgaagggatt 1020
tctgaagatg gattcttttt tgctgtcaaa gaagtgtcac tacttgatca agggaatcat 1080
ggaaggcaaa gtgtatatca actggaacag gaaattgcac ttttgagtca atttgaacat 1140
gaaaatatag ttcaatacat tggcactgaa atggatgcat caaatctgta tatctttatt 1200
gagcttgtaa ccaaaggttc ccttcgaaac ctttaccaga gatataatct tcgagattct 1260
caagtatctg cctatacaag acagattttg catggcttaa agtatcttca tgagcgaaat 1320
attgttcaca gggatattaa atgtgcaaat atattggtgg atgcaaacgg atctgttaag 1380
cttgcagatt ttggattggc aaaggcaacc aaattgaatg atgttaagtc atgcaaggga 1440

```
acagcattct ggatggcccc agaggttgta aaagggaaaa gcagaggtta tgggcttcca   1500

gctgatatat ggagtctggg atgtactgtg ttggagatgt taacgggcga atttccatac   1560

tctcacttag aatgtatgca ggctttgctt agaatcggaa gaggtgagcc acctcctgtg   1620

cctgattctc tttcaagaga tgcacaggat tttatcatgc agtgtctaaa agttaatcca   1680

gatgaacgtc ccggtgctgc tcaactctta aaccatacct ttgtccaaag gccactacat   1740

tcccagtcct ctggttccac atctccttat attagaaggg gttaa                    1785
```

<210> SEQ ID NO 101
<211> LENGTH: 242
<212> TYPE: DNA
<213> ORGANISM: Glycine max

<400> SEQUENCE: 101

```
cctggaaatc tatttgttgc ggtgaatgaa gggttatggg ataacggggc agcgtgtgga     60

aggagataca gaataaggtg tgtgagtgga aacaataggc catgcaaagg tggtagcatc    120

gatgttaaag tggtagattc ctgttcaagg tcaccatgtc ccaacaccct cctcatgtca    180

aatgatgcat ttgcagctat tgcacgcttc cctcatgtta aaatcaatat tgaatatacc    240

ca                                                                   242
```

<210> SEQ ID NO 102
<211> LENGTH: 978
<212> TYPE: DNA
<213> ORGANISM: Glycine max

<400> SEQUENCE: 102

```
atggaggaac gtagtttgta ctcactagtg tttcttgtgc ttgctttggc tattgtgaac     60

aaagtgcatg ggcaagggac gcgtgtaggg ttctattcga gtacatgccc acgcgctgag    120

tccattgtta agtccacagt tacaacccat gttaattctg atagtacttt ggctgctggg    180

ttgcttcgga tgcacttcca tgattgcttt gtgcaaggtt gtgacgcttc tgttctcatt    240

gccggttctg gcactgagag aacagcattt gcaaaccttg gtttacgagg atttgaggtt    300

attgatgatg caaagaaaca gctcgaggct gcatgccccg gtgttgtgtc ttgcgctgat    360

atccttgctc ttgctgctcg tgattccgtt gttctgagtg gtggactgag ttatcaagtg    420

cttactggac gcagagatgg acgcatatca caggcttccg acgtgagtaa cttgcctgct    480

ccttttgact ctgttgatgt tcagaaacaa aagttcacag caaagggcct caacactcaa    540

gacctcgtca cccttgttgg tgcacatacc attggtacta cagcttgcca gttcttcagt    600

aacagattgt acaacttcac cgcgaatggt cctgaccctt ccatcgaccc ttcatttctt    660

tcccaactac aatcactatg ccctcaaaac ggtgacggtt caaaacgagt agcgctagat    720

acgggtagtc aaaccaaatt tgatttatct tactatagta atttgaggaa ttctcgtgga    780

attctgcaat ctgatcaagc actatggagt gatgcttcca caaagacaac tgttcagagg    840

tacttgggct taataagagg gttacttgga ttaacattca acgtggaatt tgggaagtct    900

atggtgaaaa tgggcaacat tgagttgaaa accggtaccg atggtgaaat tcgcaagata    960

tgttctgcca tcaactag                                                  978
```

<210> SEQ ID NO 103
<211> LENGTH: 2097
<212> TYPE: DNA
<213> ORGANISM: Glycine max

<400> SEQUENCE: 103

-continued

```
atggctatag aacaacactt ctcagagagt cagaataata agcaagaagc ctcatcacgt     60
gccccgcacg tgctcgacta cgccaccact acatccgacg acgacacgga aaaggaggag    120
gaggagctgg tacacgagca aaacgaatcc tccggcggag ggcggtggtt tccggcggcg    180
tgcggtggcg gcacgcggcg gagcggggga ggcgcgttag ggcgagttct tgacccaagg    240
gcgaagtggg tccaggaatg gaacagggtg ttcctgctag tgtgcgccgc ggggttgttc    300
gttgaccctc tcttcttcta cgcgctctcc gtcagcgact cgtgcatgtg cgtcttcgtt    360
gacgggtggc tcgccgtcac cgtcacggtg ctgcggtgca tgaccgacgc actgcacgtg    420
tggaacatgg ttataaggtg caagatggcg aaacgcacct tcggactcgg cgcctccacc    480
acttcttccg gcagaggaac atcctcgtcc tctgtcggac tcagagatac ccgaccgcgt    540
tccgtcgcga tgggatatct catgtcacgg accggattct tttttgatct gttcgttatt    600
cttcctctac cacagattgt actatgggtg gcaatcccct ccttgttgga gaaaggttca    660
gtgacattgg tgatgacagt gttcttaatt atctttctct tccaatacct tcccaaaatt    720
tttcattcgg tttgccattt gcgacgcacg caaaacctct ctggctacat ttttggaaca    780
gtttggtggg gaatcgccct taacatgatc gcgtattttg ttgcttccca tgcagcaggg    840
gcatgttggt acttgctagg gatacaaagg gcagccaagt gtctcaaagt gcagtgtgag    900
aaaacaagtg gttgtggcat gaaaatcttg tcttgtcaaa cacccatata ttacggaagc    960
aacagttttc tagttaggga tagggcaagg ttggcttggg cagagaacag ggaagtgaga   1020
cacacatgcc taaatggtcc tgacaactac aactatggag cttatagatg gtctgttcag   1080
cttgtcacaa acgataatcg attggagaag atacttttcc ctatcttctg ggcctaatg    1140
actctcagca cttttggaaa cctagagagt acaaccgaat ggctggaagt agttttcaac   1200
atcattgtgc tgaccagtgg ccttcttctt gtcactatgt tgattggaaa catcaaggta   1260
tttttgcatg caacaacgtc aaaaaagcaa gcaatgcaat tgaagatgag gaatattgaa   1320
tggtggatga ggaaacgacg cttgccgcta gggtttaggc agcgcgtgcg taactatgag   1380
aggcaacgtt gggctgccat gcgtggggtt gatgaatttg agatgactaa aaatcttcct   1440
gagggattaa gaagagacat taaataccat ctttgtctag acttggtgag acaggtgcct   1500
ctatttcaac acatggacga tctggttcta gagaacatct gtgaccgtgt gaagtctctg   1560
atattcacaa agggagaaac aatagctaga gaaggagacc cagttcagag aatgctattt   1620
gtagtaaggg gtcaccttca aagcagccaa gtcctaaggg atggtgtgaa gagttgttgc   1680
atgttaggtc caggaaactt cagtggggac gaactcctct catggtgttt aaggagaccc   1740
ttcatagaac gccttccacc atcttcatcc acactcatca cgttggaaac caccgaggct   1800
tttggccttg aagccgagga tgtgaagtat gtgacacaac atttaggta cacatttgtt    1860
aaggagaagg tgaagagaag tgcaaggtat tactcaccag ggtggagaac ttgggctgct   1920
gtggccattc aattggcatg gaggaggtac aagcataggt tgactttgac ttcattgtcc   1980
tttataaggc ctaggaggcc tttgtcaagg tcctcttcca tgggagagga caggcttcgc   2040
ctctacacgg ctttgttaac ctccccaaag cctaatcagg atgattttga cttttga      2097
```

<210> SEQ ID NO 104
<211> LENGTH: 978
<212> TYPE: DNA
<213> ORGANISM: Glycine max

<400> SEQUENCE: 104

```
atggaggaac gtagtttgta ctcactagtg tttcttgtgc ttgctttggc tattgtgaac     60
aaagtgcatg ggcaagggac gcgtgtaggg ttctattcga gtacatgccc acgcgctgag    120
tccattgtta agtccacagt tacaacccat gttaattctg atagtacttt ggctgctggg    180
ttgcttcgga tgcacttcca tgattgcttt gtgcaaggtt gtgacgcttc tgttctcatt    240
gccggttctg gcactgagag aacagcattt gcaaaccttg gtttacgagg atttgaggtt    300
attgatgatg caaagaaaca gctcgaggct gcatgccccg gtgttgtgtc ttgcgctgat    360
atccttgctc ttgctgctcg tgattccgtt gttctgagtg gtggactgag ttatcaagtg    420
cttactggac gcagagatgg acgcatatca caggcttccg acgtgagtaa cttgcctgct    480
ccttttgact ctgttgatgt tcagaaacaa aagttcacag caaagggcct caacactcaa    540
gacctcgtca cccttgttgg tgcacatacc attggtacta cagcttgcca gttcttcagt    600
aacagattgt acaacttcac cgcgaatggt cctgaccctt ccatcgaccc ttcatttctt    660
tcccaactac aatcactatg ccctcaaaac ggtgacggtt caaaacgagt agcgctagat    720
acgggtagtc aaaccaaatt tgatttatct tactatagta atttgaggaa ttctcgtgga    780
attctgcaat ctgatcaagc actatggagt gatgcttcca caaagacaac tgttcagagg    840
tacttgggct taataagagg gttacttgga ttaacattca acgtggaatt tgggaagtct    900
atggtgaaaa tgggcaacat tgagttgaaa accggtaccg atggtgaaat tcgcaagata    960
tgttctgcca tcaactag                                                  978
```

```
<210> SEQ ID NO 105
<211> LENGTH: 996
<212> TYPE: DNA
<213> ORGANISM: Glycine max

<400> SEQUENCE: 105

atggtgaagt ctataaactt tctcctgctt ctgtctctac tagcctttgt tccctcctgt     60
cactgcaaaa agaaaatagg aggttacctc taccctcaat tttacgacgg ttcatgcccc    120
agagctcaag agattgtcca atccatcgtt gccaaggctg tggcaaaaga accccgcatg    180
gctgcttcgt tgctcagact acatttccat gattgttttg tcaagggctg tgatgcatcg    240
gtgttgctag atagcagtgg aactattatc agtgagaaga ggtcaaatcc gaaccgtgat    300
tcagctcgag gatttgaagt cattgatgaa attaaatctg cactagagaa ggaatgtcca    360
catacagtgt catgtgctga cattttggct ctagctgcta gagattccac tgttcttacc    420
ggtggaccaa gctggggagt acccttgggc agaagggact ctcttggtgc gagtattagt    480
ggctccaata acaacattcc tgctcccaac aacacatttc agaccatctt aactaagttc    540
aagcttaagg ggcttgacat tgttgatcta gttgctctat ctgggagcca cactatagga    600
aattcccgat gcaccagctt caggcaaaga ctatacaacc aaacaggaaa tggaaaagca    660
gacttcactc ttgatcaagt gtatgctgct gaattgcgca ctaggtgtcc aagatctggt    720
ggggaccaga atctctttgt cctagacttt gttaccccaa ttaaatttga caacttctat    780
tacaagaact tgttggccaa caagggtctc ttaagttctg acgaaattct cttgacaaag    840
aatcaagtat cagcggattt agtgaagcag tatgcagaaa acaacgatct tttctttgaa    900
caatttgcca agtccatggt taagatggga aacattactc ctttaacagg gtcaagggga    960
gagatcagaa agaactgcag aggaattaac aagtga                              996

<210> SEQ ID NO 106
<211> LENGTH: 990
```

-continued

<212> TYPE: DNA
<213> ORGANISM: Arabidopsis thaliana

<400> SEQUENCE: 106
atggcgcggt tcagtctggt tgtagtcgtg actcttagtc ttgccatctc tatgttccct 60
gacacaacca ctgctcaact caaaaccaat ttctacggaa actcatgtcc gaatgttgaa 120
caaatcgtga aaaaagtcgt ccaagaaaaa atcaaacaga ccttcgtcac catcccagct 180
actctccgcc tcttcttcca cgattgcttc gtcaatggat gtgatgcgtc ggtcatgatt 240
caatcaacgc ctaccaacaa agccgagaag gatcatccag acaatatttc tttggccgga 300
gatggatttg acgttgtgat caaagccaag aaagctcttg acgctatccc aagttgcaaa 360
aacaaagtct cttgtgctga tattcttgct ttagccaccc gtgatgttgt tgtcgccgcc 420
aaaggtccgt cgtacgcagt ggaactcgga aggtttgatg gtttggtgtc gactgcggct 480
agcgttaacg gaaacttgcc cggaccaaat aacaaagtta cagaacttaa caagcttttt 540
gccaaaaaca aacttaccca agaggacatg atcgctcttt cagcggctca cacacttgga 600
ttcgcccatt gtggcaaagt gttcaacaga atctacaact tcaacctcac acacgccgtt 660
gacccaactc taaacaaagc ctacgctaaa gaacttcagt tggcttgtcc caagacagtt 720
gacccaagaa tcgccatcaa catggaccca accactccaa gacaattcga caacatttac 780
ttcaagaatc tgcaacaagg caaaggactc ttcacttccg accaagttct cttcaccgat 840
ggtcgctcaa agcccaccgt taacgattgg gccaagaatt ctgttgcttt caacaaggct 900
ttcgtaaccg ctatgaccaa actcggccgc gttggcgtta agactagacg caacggtaac 960
attcgtcgtg actgtggtgc ctttaactga 990

<210> SEQ ID NO 107
<211> LENGTH: 627
<212> TYPE: DNA
<213> ORGANISM: Glycine max

<400> SEQUENCE: 107
atggctcagc ttaacctcat acttatctgg ttattttat tgagtctgtg cctttattca 60
tgtcctactt cggcccagtt aagtagacac cactatgcaa aaacatgccc caatgttgaa 120
aacattgtca gagaagcagt caaaaagaag tttcatcaaa catttgttac ggttcctgct 180
accattcgtc tcttcttcca tgattgcttc gtgcagggtt gtgatgcctc ggttttggtt 240
gcatccacaa aaaacaacaa agcagagaag gatcacccag ataatgtttc actagctgga 300
gatggatttg acacagtgat taaagcaaaa gaagcagttg atgcagttcc attgtgcagg 360
aacaaagttt catgtgctga tattttagcc ttggcaaccc gtgatgttat tgaactggcc 420
ggtgggcctt tctacgaggt tgaattggga agatttgatg ggctaagatc taaagattca 480
gatgtaaacg ggaggctgcc tcatccagag ttcaacttga accagctcaa ttcactgttt 540
gcggccaacg gtctcaccca aacggaaatg atagctctat cagagtatac aatttcaaga 600
gcaaaagtcg agtggaccct acactga 627

<210> SEQ ID NO 108
<211> LENGTH: 3378
<212> TYPE: DNA
<213> ORGANISM: Glycine max

<400> SEQUENCE: 108
atgggaaaaa caattgagtt gtatggattc cctacatctg tgaatgtgtc tgatgtaaag 60

-continued

```
acatttgtag agcagtatac tggtgaagga actgtgttcg ccattaaatt aagacatgga    120
aaaggtcggg ttccaagagc atttgcaatt attcaattca ccaccgcaaa ttctgctaca    180
tctatgatgt ccagagctaa caacattttg agaacattgc ggtatgggac ctcctattta    240
aaagctcggg aaatggaaag agatattgtg ccaaggccaa gggtgttttt gcatagtttg    300
gatgatgtga aactgtcttt tggctgtcag atctcaaagg gaagattctc tgttttatgg    360
aaaaagcagg atgttattgt aaattttggg agtggaatga gaaagatgca tttcttattt    420
tcccacaaca atgtgcaata caaacttgag ctttcatatg agaacatttg gaagattgag    480
ctgcatcggc cacggaatga gactacacgt tatctgttga ttcagttact tggtgctccc    540
cgggtttttg agaacgatgt acctacatca acaaatatct ttgatgatcc tttgttcaac    600
ttcttcaaag atgcccctga tgagcaatgg atccgagcaa ttgatttcac tccagaaagt    660
cgtattgggc agtcctccgc catatgtctg gagcttccta atggccgaca acttccaaat    720
ttcagggaaa actttgctta ttatgaggaa agtgagaggc aatacacttt acagacagga    780
gttccctttt ctcaaaattg gggtcttgtc cccattgttg ctcctcctct aggtgttaaa    840
atatcatatg acatcttgtt taaagtcaat tcattggttc aacatgcatg tcttgcagga    900
cctgcacttg atggtgactt ctatcgcttg gttgatccac gtagaatgcc ccgtgaattt    960
attgaatatg ctttagaaaa gatttactat tcaaaggaat tttgttatga acccacaaag   1020
tggctgactg atcagtacaa aacatacctt gagtcaaaaa atcatcctcg gtcacctgca   1080
atatccttgg atacagggtt ggtatacgtt cgcagggttc agatcacgcc ttgcaaagta   1140
tacttttgtg gtccagagat gaatgtctca aatcgtgttc tccgtcattt ccgtgaacat   1200
attgataact ttctacgtgt ttcatttgtt gatgaagaat tggataaact gttttcaact   1260
gatttatcat cacgttcaca gaacaagaaa actgagatat acaccagaat tctttccatc   1320
cttaagaatg gcatagttgt tggtgataag aagtttgaat ttctagcatt ctcatcaagt   1380
cagttgcggg aaaactctct ctggatgttt gctcctacag aaactggatg tactgctgct   1440
tacataagga aatggatggg aaattttagc cagattagga atgttgctaa atatgctgct   1500
aggctggggc aatcttttgg ttcatctact gaaactctaa gtgtccatag ggatgaagtt   1560
gaaattattc ctgatgtgaa gaagcttaca tatgatggaa acgaatatgt cttctctgat   1620
ggaattggga aaatatctct tgaatttgcc cagaaagtgg ctaaaaaatg tggttatgat   1680
tgcactccat ctgcctttca gattcgatat ggtgggtaca aaggagttgt ggctgttgac   1740
cctaaatcat gctacaagtt atcactgagg aagagcatgc ggaagtatga ttcagataac   1800
acaaagttag atgttttggc ccgtagtaag tttcagccat gttatctgaa tcggcagtta   1860
atttctctct tatccactct tggtatcaag gatgatgttt ttgagaaaaa acaaagagaa   1920
actgttaatc aactgaacac tatactaaca gattcattaa aggctcagga agttctggac   1980
ttaatgtctg ctggagagat cactaatgtt ctgaaggaga tgctcatttg tggatacaag   2040
cctaatgaag aaccattcct ttcaatgatg cttcaaacat ttagggcatc aaaacttttg   2100
gaattgcgac ttaaatctag gatctttatt ccaaaaggaa gagcaatgat gggatgtcta   2160
gatgaaacta gaaccctaga atatggtcaa gtatttgttc agttctctaa caataggctg   2220
cagaatctat ctgatgattt tttttcatat gatttgccaa agaattatat ggttaaaggt   2280
aaggtagttg tagcaaaaaa cccctgcttg cacccaggtg atgtgcgtgt tttacaagct   2340
gtggatgtgc cagatttgta ccacatggtg gactgtgttg ttttccctca aaaaggacca   2400
agacctcatc caaatgagtg ttcgggaagt gatctggatg gagatatcta ctttgtttgt   2460
```

tgggaccatg aattgattcc ttctcgccca attgatccaa tggactatac tgctcctgca 2520
actgtggaat tggatcatga tgtgatgatc gaggaggttg aggagtattt tgccaattac 2580
atagtcaatg acagtctggg aataattgcc aatgcacaca ctgtctttgc agataaagaa 2640
catttgaaag caatgtctga tcaatgtgtt aagcttgcaa ggttgttttc aacagcagtt 2700
gactttccta aaactggtgt tccagctgtt atacctcctg aacttcatgt caaagaatat 2760
cctgacttca tggagaagcc tgacaaaccc acatacaaat cgcataacgt gataggaaag 2820
ctctttaggg aagtgaaaga aatatcaaca agtgccggct caattacatc cttcacaaag 2880
ttggttgcga gagactctta cgaccatgaa atggaagttg atggcttcat ggattatgtt 2940
gatgatgctt tctatcacaa aaccaattat gactacaagt tgggaaatct gatggactac 3000
tatgggatca aaactgaagc tgaaatcctc ggtgggaata ttatgaaaat gtcaaaatct 3060
ttcaacaaaa ggagggatgc agaagcaatc aatatggctg tgaggtccct aaggaaagag 3120
gccagggcct ggttcaatga aaacagcagt ggtgatgtag attcagggag tagtgatgtg 3180
tatgcaaaag cttctgcttg gtaccatgtt acttatcatc caagttactg ggttgctat 3240 aatgaaggca tgaataggga tcattatcta agtttctcat ggtgtgttta ccctcttctt 3300
gtccaaatca agaaagagaa actcagcatt agaaggtcct ctttggaata cagtttcagt 3360
gggttgcgtt tgagttga 3378

<210> SEQ ID NO 109
<211> LENGTH: 222
<212> TYPE: DNA
<213> ORGANISM: Glycine max

<400> SEQUENCE: 109
atggacaagg cacgatttgg gtttttcttc atgttgctca ttctcctttc ttctcagatg 60
gtggtacaaa cagagggaag gcactgtgag tcaaagagcc atcggtttaa agggatgtgc 120
ctcagtaagc acaactgcgc ttcggtttgc catcttgaag gcttcacggg tggcaagtgt 180
cgtggatttc gtagacgctg tttctgcacc aggcactgtt ag 222

<210> SEQ ID NO 110
<211> LENGTH: 981
<212> TYPE: DNA
<213> ORGANISM: Glycine max

<400> SEQUENCE: 110
atggcttcgt cttgttctag ctttatgatc actttggccc ttttggtcct cgtgttgggg 60
actaatacta gtagtgccaa tgccaatcca acacttcaca caaacttcta ctacagttct 120
tgcccaaaac tctttgacac tgtgaaacgc acagtggaat cggccatatc aaaggagacc 180
cgcatgggtg cttctctcct acgtttgttc ttccacgatt gctttgttaa tgggtgtgat 240
gggtcgattc tacttgatga cacatcaagc ttcaccggag agaagaacgc gggacctaac 300
aggaattctg cccgtggatt tgaagtgatc gaccaaatca aatcagctgt ggagaaagtg 360
tgtccgggtg tggtttcttg cgctgacatt cttgccatcg ctgccagaga ctctgttgag 420
atccttagag gcccaacatg ggatgtgaaa cttggaagaa gagactctag gacggcaagc 480
caatctgctg ccaacaatgg catcccaaga cccacttcaa acctcaacca acttatatcc 540
agatttaaca ctctcggact ttccaccaag gacttggtcg cactatctgg gggtcataca 600
attggacaag caaggtgcac aacctttaga gcccgaatct acaacgagag caacatagat 660

-continued

```
agctcttttg cccgcatgag acaatctagg tgtccccgaa cctcaggatc aggggacaac    720

aaccttgcac ccattgactt tgccactccc actttctttg acaaccacta cttcaagaac    780

ctcattcaga agaagggtct catccattcc gaccaagaac tcttcaatgg tggttccact    840

gactccttag tgcgtaccta cagcaccaac ccggcctcct ttttcgccga tttctccgcc    900

gccatgatca ggatgggaga cattagtccc ctcactggct cccgcggaga aataagggag    960

aactgcagga gggtcaacta a                                              981
```

```
<210> SEQ ID NO 111
<211> LENGTH: 1749
<212> TYPE: DNA
<213> ORGANISM: Glycine max

<400> SEQUENCE: 111

atgttagaga aagtggggga gtttaacatg gataaagtta tacaagagtt tgaattattg     60

acacgggatg cagaaagggt tcagagggaa acactgaaga ggattttgga ggataacgca    120

tcagcagagt acttgcagag tttgggtctc aatggaagaa ctgaccctga gagtttcaag    180

gcctgtgttc cactggtcac ccacaaagaa ttggaacctt atatctacag aattattgat    240

ggtgatgctt ctcctattct cactggaaaa cccatcacaa ccatgtcatt aagttctggc    300

actacccagg ggaagccaaa atatgtacct tggaatgatg aattgtatga aaccacaatg    360

cagatatacc tgacctcttt tgtctttaga aacagggagt ttcctataaa aaatgggaag    420

gctttaagct ttatatacgg tagcaaacag ttgaaaacaa agggggggtct ggcggctaga    480

actgccacaa gcaacgtgtt ctgtagtgct ggttacaagt gtgcaatgag ggcactccaa    540

tcccaatgct gcagcccgga tgaagtgata tttggtcctg attttttcca atcactgtac    600

tgccatctgt tgtgtggtct gattttccgg gaggaagttc agtttgtgtc ttccacattt    660

gcacatagca ttgtccatgc ttttagaacc tttgaacaag tgtgggaaga gctgtgtaac    720

gatatcagag aaggggttct caccagaaat gtcaccattc cttccattcg aatggccatg    780

tctaaactgc tcaaaccaaa ccctgaatta gccaacacga tccaccaaaa atgcagggga    840

ttgagcaact ggtacgggtt aataccagag ctttttccta atgcaaagta tatttatggc    900

atcatgactg ggtcgatgga gccttatttg aaaaaaatga ggcattatgc tggggagctg    960

cctttgttga ctgctgacta cggatcttct gagggatgga tagcagctaa tgtgaaccca   1020

caacttcctc ctgagtatgc cacttatgct gtgcttcctc acattggtta ctttgaattc   1080

attcctctct cagagtttga gaacaccaag ggtgaacctg atttcctctg tgttgatcct   1140

aagcccatgg gcctgactga agtcaaggtt ggtgaagagt atgaaattgt tatgacgaat   1200

ccagcaggtt tataccggta tagattaggg gatgtggtga aggttatggg attccacaat   1260

tcaactccag aactcaagtt tattcgaagg agcagtcttc tgctcaacat taacatcgac   1320

aagaacactg agaaggattt acaattagcc gtggaagctg cagggaagtt gctagcagag   1380

gagaaactgg aagtagttga cttcagtagc caggttgatt tatccaaaga accagggcac   1440

tatgtcatct tctgggaaat cagcggagaa gcgagccaag aactactcct cgaatgctgt   1500

aactgtttgg acaagtcttt cgttgatgca ggctacacca gttcgcgcaa agtgaactgc   1560

attggtgccc tcgaactacg acttgttcgg agaggaacat tccagaagat tcttgatcat   1620

tacctaggac taggaaccgc tgttagtcaa tacaagacac caagatgtgt tggtcctaca   1680

aacaccagag ttttgcaaat cttgagtgaa aatgttgtga acaactatct cagtaccgct   1740

ttcaattga                                                           1749
```

<210> SEQ ID NO 112
<211> LENGTH: 975
<212> TYPE: DNA
<213> ORGANISM: Glycine max

<400> SEQUENCE: 112
atgacagtag atctggtagg tgctgccaag atggggatgg aggagaatat agcgatacaa 60
gaagctgctt ccgctgggtt gaagagtatg gagcatctga ttcgtgtgct ttcttctcaa 120
atcccttctt ctgcttcgtc ttcttctaac gcacaccacc accgtcttaa tctcaaccac 180
cttgactgca ccgaaatcac cgacttcact gtctccaagt tcaaacaagt catcaacttg 240
ttgaatcgca cgggacacgc tcgctttcgt agcgcacctt ctcatccttc tccttctact 300
tctcttcctt ctcaacctca acctcaacca caaccacaac catatgcact gactcttgat 360
ttcgcaaaac ctgttatgct taagtcaaat cccaacccta acccttcttc taccgatttg 420
tcggtttctc aatattctaa gaccaaggac accaccacct ctagtatatc tcctcccgtg 480
tccaccacca cctcctcatt catgtcctcc atcaccgccg acggaagtgt ctccgacgga 540
aagatcggcc ccgccatcat cgctgccggc aagcctcctc tctcctcatc ccaccggaaa 600
aggtgtcacg acgccaccct ctctgccgga aaagcctctt cctccgctca ctgccattgc 660
tccaagagaa gaaaatctcg tgtgaaacga atgatacgtg tgccggcgat aagttcgaag 720
attgccgata tcccagtgga cgagtactca tggcgaaagt atggtcaaaa accaatcaaa 780
ggttcacctt acccgcgagg gtattacaag tgcagtagcg tgagagggtg tccggcgagg 840
aagcacgttg agcgagccca ggatgacccc aacatgctca tcgttaccta cgagggagag 900
caccgtcatc cgcaaccgcg tctgccggaa actgctgccg gcgccggcgg gacttttgcc 960
gctcatcctg tttaa 975

<210> SEQ ID NO 113
<211> LENGTH: 636
<212> TYPE: DNA
<213> ORGANISM: Glycine max

<400> SEQUENCE: 113
atgaagaaac agaaaacaag acaagaacac cttacgcgag tctttctgaa gcaaacagaa 60
atgccagcaa cggtgaccaa agtggcggcg ctttctggtt ccctcaaaaa aacctcatcc 120
cacacaggcc tcataccaat tgagttgagc aaaggagcaa ttgaaggcat tgaaattgag 180
ttcattgaga tttcggaact tcccatgttg aacactgatc ttgagaacaa tgggacatac 240
ccaccaatag ttgaagcttt tcgctgcaag attcttcaag ctcatagtgt tctcttcgct 300
tctcccgagt ataattactc tctcaccgct ccactgaaga atgcaattga ctgggcatct 360
agacccccaa atgtttgggc tggcaaagct gctgctatta taagtgctgg atatgatgac 420
tttggtgggg gaagggcaca gtatcatctt cgccaaattg gagtgtatct tgatcttcat 480
ttcataaata aaccagaatt cttccttaat tcattccagc cccctagaaa gtttaacagg 540
ggtggtgatt tgattgatga agaggccaag aataagttaa agcaagttct tctatccttg 600
caggaattta cccttggact tataagcaaa ggctga 636

<210> SEQ ID NO 114
<211> LENGTH: 762
<212> TYPE: DNA
<213> ORGANISM: Glycine max

<400> SEQUENCE: 114
atggcatcat ccccaacctt tgctttgaga accatctcct ctttctctgt gaaacctgtt 60
accaccacaa gatcatcact caccacctca tccaccacaa ccctcttacc atttacttca 120
acaaactcat ctctccccag aactctcaaa ctcaacacct cttccccaca tcctcacctt 180
tcactacccc acaagtcttt cacttgtaga agccaggctg agccatcttc tgattcagcc 240
aaagtccaag aactgagtgt gtatgagatc aatgagagag atcgtggaag ccctgcttat 300
cttagattga gccagaaaac tgtcaattcc cttggtgatc tagtcccctt cagcaacaag 360
ttgtattctg gatgtttgca aaagagggtg gggataacag ctggaatctg tgtcttgatc 420
caaaacaaag ccgagaagaa gggagatagg tatgaggcaa tctacagctt ctactttggg 480
gactacggtc acatttcagt gcagggttca tacctgacct atgaggacac ttatcttgct 540
gtgactggtg gatctggcat ctttgaaggg gcttatggtc aggtcaagct gcatcaaatt 600
gtgttcccct ttaaactatt ctacacattt tatcttaagg gcatcaagga cttgcctcag 660
gagcttcttt cccagcctgt tgagcccagc ccagctattg agcccagccc atctgccaag 720
gcctgtgaac cacatgctgt tattgctggc tttactgact ga 762

<210> SEQ ID NO 115
<211> LENGTH: 1011
<212> TYPE: DNA
<213> ORGANISM: Glycine max

<400> SEQUENCE: 115
atggctccca agggtttaac ctttctggct gtgttaatat gcgtttcagc actgtcactg 60
agtccttctg ttgcggggga agggcaaaat aatggccttg ttatgaactt ctacaaggaa 120
tcatgccctc aggctgaaga catcatcaca gaacaagtca agcttctcta caagcgccac 180
aagaacactg ctttctcctg gctcaggaac atcttccatg actgtgctgt tcagagttgt 240
gatgcttcac tgttgctgga ctccacaaga aggagcttgt ctgagaagga aacagataga 300
agctttgggt tgagaaattt caggtacatt gagaccatca aagaagcttt ggaaagagaa 360
tgccctggag ttgtttcatg tgctgatatc ctcgttctct ctgccagaga tggcattgtt 420
tcgctaggag gtccccatat ccctcttaag actggaagaa gggatggtag aaggagcaga 480
gctgatgtgg ttgagcagtt cctcccagac cacaatgagt ccatttctgc agttcttgac 540
aagtttggtg ccatgggaat tgacacccct ggcgtcgttg cactgcttgg agcacacagt 600
gttggtcgaa cccattgtgt gaagttggtg caccgtttgt acccagagat tgatccagct 660
ctgaaccctg accacgtccc tcacattctg aagaagtgcc ctgatgccat tccagaccct 720
aaggcggtgc agtacgtgag aaacgaccgt ggcactccca tgattctaga caacaactac 780
tacagaaaca tattagacag caagggtctc ttgatagtgg atcaccaact agccaatgac 840
aagaggacca agccttatgt gaagaaaatg gccaagagcc aagactattt cttcaaggag 900
ttctctagag ccattacctt gctctcagag aacaaccctc tcactggcac aaagggtgag 960
gtcagaaagc agtgcaatgt tgccaacaag caccatgatc aggacccttg a 1011

<210> SEQ ID NO 116
<211> LENGTH: 675
<212> TYPE: DNA
<213> ORGANISM: Glycine max

<400> SEQUENCE: 116
atgggaagcg aagaagtgaa gctgttgagc ttttttgcga gtccatttgg caaaagggtt 60

-continued

```
gaatgggcat tgaaactgaa gggtgtggag tatgagtaca tagaacaaga tatcttcaac    120

aagactagtc tccttctcca gttgaacccg gttcacaaga aggttccggt tcttgttcat    180

gcccacaaac ccatcgctga gtcattcgtc atcgttgaat acgttgatga aacatggaag    240

cagtatccac tgttgcctcg agacccttat caaagagcac ttgctcgatt ttgggctaat    300

ttcgctgagc aaaagctttt agatgcagca tggattggta tgtatagcag cggggatgag    360

cagcaaaacg ctgtgaaagt agccagagaa gcaatagaga agatagaaga agagattaag    420

gggaagaaat attttggagg ggagaatata ggataccttg acattgcact tggatggatc    480

tcttactggc ttcctatttg ggaggaagtt ggatcgatac agataattga cccattgaaa    540

tttccagcca tcactgcatg gatcaccaat tttcttagcc atcctgtgat caaggacaac    600

ttgcccccaa gagacaagat gcttgtttac ttccacagtc gcagaactgc gctttcttca    660

acttttcagg gctga                                                      675
```

<210> SEQ ID NO 117
<211> LENGTH: 1677
<212> TYPE: DNA
<213> ORGANISM: Glycine max

<400> SEQUENCE: 117

```
atgcgaatcc tcgtcctgct ctctctcgcc acccttctcc tcttctcctc cttctctccc     60

accttctgcg accacctcgc cgacgacgag gacctcagct tcctcgacga gccctccgcc    120

gcgccggagc acgaccacca ctacggcgcc gatgactcca atttcggcga ctttgaggac    180

ttcgaggagg acgacgcgga ggcgtacaag cagcccgagg tggacgagaa ggacgtcgtc    240

gttttgaagg agaagaactt caccgacgcc gtcaagaaca accgcttcgt catggtcgag    300

ttctacgcgc cctggtgcgg ccactgccag gccctcgcgc cggagtacgc cgccgccgcg    360

acggaactca agggcgaaga cgtaattttg gcaaaggtgg atgccaccga ggagaatgaa    420

ttggcgcagc agtacgatgt tcagggtttc cccactgtcc acttcttcgt tgatggcatt    480

cacaagcctt ataatggcca aaggaccaaa gatgctatag tgacgtggat taggaagaag    540

atcggacctg gcatatacaa cttgactaca gtggaggagg ctcaacgcat tttgaccaac    600

gaaactaaag ttgttttggg cttcctcaac tctttagttg gtcctgagag tgaggagctt    660

gctgctgctt caaggcttga ggatgatgtc aatttttatc aaactgtgaa tcctgatgtg    720

gcaaagcttt tccatattga ccaagatgtt aagcgtccag cattgatcct cattaagaaa    780

gaggaggaaa aacttaacca ctttgatgga aaattcgaga agtcagcaat agcggacttt    840

gtcttctcca acaagcttcc tttggtaaca atttttacaa gagaaagtgc cccatcagtc    900

tttgaaaatc caatcaagaa acagttgttg ctgtttgcaa cttcaaatga ttcagagact    960

ttggtcccag catttaaaga agcagcaaag tctttcaagg gaaagttgat ctttgtatat   1020

gtggaaatgg ataacgaaga tgttggaaag cctgtttcag aatactttgg tatcagtggg   1080

aatgctccaa aagtacttgg atacactggg aatgatgatg gaaaaaaatt tgtgcttgat   1140

ggagaggtga ctactgacaa aattaaggca tttggggaag atttcgttga agacaagcta   1200

aaacctttt acaagtcaga tccagttcct gaaagtaatg atggtgatgt gaaaatagta   1260

gttggtaata attttgatga aattgtcttg gatgagtcaa aggatgttct cctcgagatt   1320

tatgctccct ggtgtggcca ttgccaatca ctggagccaa tatacaacaa gcttgcaaaa   1380

catcttcgca atattgattc tcttgtaata gccaagatgg atggaacaac aaatgagcat   1440
```

cccagggcta agcctgatgg attccccact cttctcttct tcccggcagg aaacaagagt 1500
tttgacccta ttactgttga tacagatcgt acagtggtag ccttctacaa gttcctcaag 1560
aaacatgcat caatcccatt caagctccag aaaccaacct caacttctga atccgattcc 1620
aaggggagct ctgatgccaa agagagccag agtagtgatg tgaaggacga attatga 1677

<210> SEQ ID NO 118
<211> LENGTH: 774
<212> TYPE: DNA
<213> ORGANISM: Glycine max

<400> SEQUENCE: 118
atggcatcat cctcatcaac cgttgctttg agaaccatct cctctttctc tctgaaacct 60
gccaccacaa caagatcatt actcaacact agtacttcat ccaccataac cctcttaccc 120
tttacatcag caaactcatt tctctccaaa accctcaaac tcaacacctc ttccccacac 180
tctcaccttt cactacccct caacaagtct ttcacttgta gaagccaggc tgaaccatct 240
tctgactcag ccaaagtcca agaactgagt gtgtatgaga tcaatgagag agatcgtgga 300
agccctgctt atcttagatt gagccagaaa actgtcaatt cccttggtga cctagtcccc 360
ttcagcaaca agttgtactc tggatgtttg caaaagaggg tagggataac agctggaatt 420
tgtgtgttga tccaaaacaa atcagagaag aagggagata tgtatgaggc aatctacagc 480
ttctactttg ggactatgg tcacatttca gtgcagggtt catacctgac ctatgaagac 540
acttatcttg ctgtgactgg tggatctggc atctttgaag gggcttatgg tcaagtcaag 600
ctgcatcaaa ttgtgttccc ctttaaatta ttctacacat tttatcttaa gggcatcaag 660
gacttgcctc aggagcttct ttccaagcct gttgagccca gcccatctgt tgagcctagc 720
ccatctgcca aggcctgtga gccacatgct gttattgctg gcttcactga ctaa 774

<210> SEQ ID NO 119
<211> LENGTH: 708
<212> TYPE: DNA
<213> ORGANISM: Glycine max

<400> SEQUENCE: 119
atgggaaggt ccccttgctg tgagaaagca cacacaaaca aaggtgcatg gaccaaagaa 60
gaagatcatc gcctcatttc ttacattaga gctcacggtg aaggctgctg gcgctctctc 120
cccaaagccg ccggccttct ccgttgcggc aagagctgtc gtctccgctg gatcaactat 180
ctccgccctg acctcaagcg cggcaatttc tccctcgaag aagaccaact catcatcaaa 240
ctccacagcc tccttggcaa caagtggtct ctaattgctg gtagattgcc cggtagaact 300
gacaatgaga tcaagaatta ctggaatact cacatacgca ggaagcttct gagcagaggt 360
attgaccctg ccactcacag gcctctcaac gattcttctc atcaagaacc tgctgctgtc 420
tctgcccctc ctaaacatca agagtccttt caccatgaac gctgccctga cttgaacctt 480
gagctaacca ttagtcctcc ccatcatcct caacctgatc atccgcactt gaagaccctt 540
gtgacaaact caaacctttg ctttccctgc agtctgggtt tgcataatag caaagattgt 600
agctgtgccc tccacactag tactgccaac gctactgcta ctggctatga tttcttggcc 660
ttgaaaacca ccgtcgtttt ggattacaga accttgcaca tgaaatga 708

<210> SEQ ID NO 120
<211> LENGTH: 975
<212> TYPE: DNA
<213> ORGANISM: Glycine max

<400> SEQUENCE: 120
atgacagtag atctggtagg tgctgccaag atggggatgg aggagaatat agcgatacaa 60
gaagctgctt ccgctgggtt gaagagtatg gagcatctga ttcgtgtgct ttcttctcaa 120
atcccttctt ctgcttcgtc ttcttctaac gcacaccacc accgtcttaa tctcaaccac 180
cttgactgca ccgaaatcac cgacttcact gtctccaagt tcaaacaagt catcaacttg 240
ttgaatcgca cgggacacgc tcgctttcgt agcgcacctt ctcatccttc tccttctact 300
tctcttcctt ctcaacctca acctcaacca caaccacaac catatgcact gactcttgat 360
ttcgcaaaac ctgttatgct taagtcaaat cccaacccta acccttcttc taccgatttg 420
tcggtttctc aatattctaa gaccaaggac accaccacct ctagtatatc tcctcccgtg 480
tccaccacca cctcctcatt catgtcctcc atcaccgccg acggaagtgt ctccgacgga 540
aagatcggcc ccgccatcat cgctgccggc aagcctcctc tctcctcatc ccaccggaaa 600
aggtgtcacg acgccaccct ctctgccgga aaagcctctt cctccgctca ctgccattgc 660
tccaagagaa gaaaatctcg tgtgaaacga atgatacgtg tgccggcgat aagttcgaag 720
attgccgata tcccagtgga cgagtactca tggcgaaagt atggtcaaaa accaatcaaa 780
ggttcacctt acccgcgagg gtattacaag tgcagtagcg tgagagggtg tccggcgagg 840
aagcacgttg agcgagccca ggatgacccc aacatgctca tcgttaccta cgagggagag 900
caccgtcatc cgcaaccgcg tctgccggaa actgctgccg gcgccggcgg gacttttgcc 960
gctcatcctg tttaa 975

<210> SEQ ID NO 121
<211> LENGTH: 963
<212> TYPE: DNA
<213> ORGANISM: Glycine max

<400> SEQUENCE: 121
atggcagtag atctggcaaa tattaggatg gaagagaata tggcgattca agaagcagct 60
tccgctgggt tgaagagtat ggagcatctg attcgcgtcc tttcttctca aatcccttct 120
gcttcgtctt cttcttctaa cgcacaccac caccgtctta atctcaacca ccttgactgc 180
gcggaaatca ccgacttcac tgtctccaag ttcaaacaag tcatcaactt gttgaatcgc 240
accggccacg ctcgctttcg tcgcgcacct tctcatcctt ctccttcaat ttctccctct 300
caacctcaac ctcagccaca accacaacca cagacgctga ctcttgattt tgcaaaacct 360
gttatggtaa agtcaaatcc caaccctaac ccttcttcta ccgatttgtc ggtttctcaa 420
tattctaaga ccaaggacac aaccaccttt agtatatccc ctcccatgtc caccaccact 480
tcttccttcc tgtcatccat caccgccgac ggcagcgtct ctgacggcaa gatcggcccc 540
gccatcctcg ccgccggcaa gcctcctctc tcctcatccc accggaaaag gtgtcacgac 600
gccactctct ccgccggaaa agcctcttcc tccgctcact gccattgctc caagagaagg 660
aaatctcgtg tgaaacgaat gatacgtgtg ccggcgataa gttcgaagat tgccgatatc 720
ccagcggacg agtactcgtg gagaaagtat ggtcaaaaac caatcaaggg atcaccttac 780
ccacgagggt attataagtg cagtagcgtg agagggtgtc cggcgaggaa gcacgtggag 840
cgagcccagg atgaccccaa catgctcatc gttacctacg agggagagca ccgtcatccg 900
caaccgcgtc tgccggaaac ttctgccggc gccgccgcgg attttgtctc tcagcctgtt 960
taa 963

<210> SEQ ID NO 122
<211> LENGTH: 996
<212> TYPE: DNA
<213> ORGANISM: Glycine max

<400> SEQUENCE: 122
atggctccca agggtttaat ctttttggct gtgttatgct tctcagcact gtcactgagt 60
cgttgtcttg cggaggataa tggacttgtt atgaacttct acaaggaatc atgccctcag 120
gctgaagaca tcatcaaaga acaagtcaag cttctctaca agcgccacaa gaacactgct 180
ttctcctggc tcagaaacat cttccatgac tgtgctgttc agagttgtga tgcttcactg 240
ttgctggact ccacaagaag gagcttgtct gagaaggaaa cagatagaag ctttgggttg 300
agaaatttca ggtacattga gaccatcaaa gaagctttgg aaagggaatg cccaggagtt 360
gtttcctgtg ctgatatcct cgttctctct gccagagatg gcattgtttc gctaggaggt 420
ccccatatcc ctcttaaaac aggaagaagg gatggtagaa ggagcagagc cgatgtggta 480
gagcagttcc tcccagacca caatgaatcc atttctgcag ttcttgacaa gtttggtgcc 540
atgggaattg acacccccgg cgtagttgca ttgcttggag cacacagtgt tggtcgaacc 600
cattgtgtga agttggtgca ccgtttgtac ccagagattg atccagctct gaaccctgac 660
cacgtccctc acattctgaa gaagtgccct gatgccattc cagaccctaa ggccgtgcag 720
tacgtgagaa acgaccgtgg cacccccatg attctagaca acaattacta cagaaatata 780
ttggacaaca agggcttgtt gatagtggat caccaactag ccaatgacaa gaggaccaag 840
ccttatgtga agaaaatggc caagagccag gactatttct tcaaggagtt ttctagagcc 900
attactttgc tctctgagaa caaccctctc actggcacaa agggtgagat cagaaagcag 960
tgcaatgctg ccaacaagca ccatgaggag ccttaa 996

<210> SEQ ID NO 123
<211> LENGTH: 975
<212> TYPE: DNA
<213> ORGANISM: Glycine max

<400> SEQUENCE: 123
atgacagtag atctggtagg tgctgccaag atggggatgg aggagaatat agcgatacaa 60
gaagctgctt ccgctgggtt gaagagtatg gagcatctga ttcgtgtgct ttcttctcaa 120
atcccttctt ctgcttcgtc ttcttctaac gcacaccacc accgtcttaa tctcaaccac 180
cttgactgca ccgaaatcac cgacttcact gtctccaagt tcaaacaagt catcaacttg 240
ttgaatcgca cgggacacgc tcgctttcgt agcgcacctt ctcatccttc tccttctact 300
tctcttcctt ctcaacctca acctcaacca caaccacaac catatgcact gactcttgat 360
ttcgcaaaac ctgttatgct taagtcaaat cccaacccta acccttcttc taccgatttg 420
tcggtttctc aatattctaa gaccaaggac accaccacct ctagtatatc tcctcccgtg 480
tccaccacca cctcctcatt catgtcctcc atcaccgccg acggaagtgt ctccgacgga 540
aagatcggcc ccgccatcat cgctgccggc aagcctcctc tctcctcatc ccaccggaaa 600
aggtgtcacg acgccaccct ctctgccgga aaagcctctt cctccgctca ctgccattgc 660
tccaagagaa gaaaatctcg tgtgaaacga atgatacgtg tgccggcgat aagttcgaag 720
attgccgata tcccagtgga cgagtactca tggcgaaagt atggtcaaaa accaatcaaa 780
ggttcacctt acccgcgagg gtattacaag tgcagtagcg tgagagggtg tccggcgagg 840
aagcacgttg agcgagccca ggatgacccc aacatgctca tcgttaccta cgagggagag 900
caccgtcatc cgcaaccgcg tctgccggaa actgctgccg gcgccggcgg gacttttgcc 960
gctcatcctg tttaa 975

<210> SEQ ID NO 124
<211> LENGTH: 1299
<212> TYPE: DNA
<213> ORGANISM: Glycine max

<400> SEQUENCE: 124
atgaagcttg ctccagagta tgagaaagca gcctctatct tgagtagcaa tgatcctcca 60
gttattttgg ctaaagttga tgcgaatgag gaaaagaaca gagaacttgc aagccaattt 120
caggttcagg gatttccaac tattaagatt ctgagaaatg ggggcaaggt tgttcaagat 180
tacaaaggtc cccgtgaagc agatggtatt gttgactatt tgaagaagca aagtggtcct 240
gcaacaactg aaattaaatc tgcagatgat gctagtgctt tgattgacaa aaataaagtt 300
gttattgttg ggtctttcc aaaattttct ggggaggagt atgagaattt caatgcattg 360
gcagataaat tgcgttctga atatgatttc agtcacacat tgaatgccaa acaccttcca 420
cgtggagaat catcggtgac tggcctgta gttagattat tcaagccatt tgatgaactt 480
tttgttgact tctatgattt taatatggaa gccttatcga aatttgttga agaatctagt 540
gtccctattg tgactgtctt taacaatgac ccaagcaatc accctttgt tgtcaaattc 600 tttgacaatc caaatgtaaa ggcaatgatg ttcttcaact tcactgttga caatgcggat 660
tctctcaaat caaaattccg tgaatctgcc gagcaatata gacaacaggg cataagcttt 720
ctagtgggag accttgaggc tagtcaaggt gcattccagt attttggcct taaggaaaac 780
caagtgcctc taattgtcat tcaacataat gatgggaaaa agtttttgaa aactaatgtg 840
gaacctgatc acattgcaac ttggttgaag gcgtacaagg atggaagtgt tgaaccattc 900
aagaagtctg aacctattcc cgaagttaac aatgaatctg ttaaagtagt agttgcagac 960
aatcttcagg acattgtttt caactcaggg aaaaatgttt tgctggagat ttatgctcct 1020
tggtgtagtc actgcaaaaa gttggctccg atattggagg aagttgctgt ttcatatcaa 1080
agtaatcctg atgttattat tgcaaaactg gatgcaactg ccaacgatat accacgtgat 1140
acttttgatg tacaaggtta tccaacagtg tacttcaggt cagcaagtgg acagatatca 1200
cagtatgatg gaagtaggaa aaaggaagac atcatagatt tcattgaaaa gaaccgggat 1260
aaagtggatc agcaagaatc agtaaaagat gagctttga 1299

<210> SEQ ID NO 125
<211> LENGTH: 1749
<212> TYPE: DNA
<213> ORGANISM: Glycine max

<400> SEQUENCE: 125
atgttagaga aagtggggga gtttaacatg gataaagtta tacaagagtt tgaattattg 60
acacgggatg cagaaagggt tcagagggaa acactgaaga ggattttgga ggataacgca 120
tcagcagagt acttgcagag tttgggtctc aatggaagaa ctgaccctga gagtttcaag 180
gcctgtgttc cactggtcac ccacaaagaa ttggaacctt atatctacag aattattgat 240
ggtgatgctt ctcctattct cactggaaaa cccatcacaa ccatgtcatt aagttctggc 300
actacccagg ggaagccaaa atatgtacct tggaatgatg aattgtatga aaccacaatg 360
cagatatacc tgacctcttt tgtctttaga aacagggagt ttcctataaa aaatgggaag 420

-continued

```
gctttaagct ttatatacgg tagcaaacag ttgaaaacaa agggggggtct ggcggctaga    480

actgccacaa gcaacgtgtt ctgtagtgct ggttacaagt gtgcaatgag ggcactccaa    540

tcccaatgct gcagcccgga tgaagtgata tttggtcctg attttttcca atcactgtac    600

tgccatctgt tgtgtggtct gattttccgg gaggaagttc agtttgtgtc ttccacattt    660

gcacatagca ttgtccatgc ttttagaacc tttgaacaag tgtgggaaga gctgtgtaac    720

gatatcagag aaggggttct caccagaaat gtcaccattc cttccattcg aatggccatg    780

tctaaactgc tcaaaccaaa ccctgaatta gccaacacga tccaccaaaa atgcagggga    840

ttgagcaact ggtacgggtt aataccagag ctttttccta atgcaaagta tatttatggc    900

atcatgactg ggtcgatgga gccttatttg aaaaaaatga ggcattatgc tggggagctg    960

cctttgttga ctgctgacta cggatcttct gagggatgga tagcagctaa tgtgaaccca   1020

caacttcctc ctgagtatgc cacttatgct gtgcttcctc acattggtta ctttgaattc   1080

attcctctct cagagtttga gaacaccaag ggtgaacctg atttcctctg tgttgatcct   1140

aagcccatgg gcctgactga agtcaaggtt ggtgaagagt atgaaattgt tatgacgaat   1200

ccagcaggtt tataccggta tagattaggg gatgtggtga aggttatggg attccacaat   1260

tcaactccag aactcaagtt tattcgaagg agcagtcttc tgctcaacat taacatcgac   1320

aagaacactg agaaggattt acaattagcc gtggaagctg cagggaagtt gctagcagag   1380

gagaaactgg aagtagttga cttcagtagc caggttgatt tatccaaaga accagggcac   1440

tatgtcatct tctgggaaat cagcggagaa gcgagccaag aactactcct cgaatgctgt   1500

aactgtttgg acaagtcttt cgttgatgca ggctacacca gttcgcgcaa agtgaactgc   1560

attggtgccc tcgaactacg acttgttcgg agaggaacat tccagaagat tcttgatcat   1620

tacctaggac taggaaccgc tgttagtcaa tacaagacac caagatgtgt tggtcctaca   1680

aacaccagag ttttgcaaat cttgagtgaa aatgttgtga acaactatct cagtaccgct   1740

ttcaattga                                                          1749
```

<210> SEQ ID NO 126
<211> LENGTH: 1392
<212> TYPE: DNA
<213> ORGANISM: Glycine max

<400> SEQUENCE: 126

```
atgggtgcag tttacttttc tcaatcatgt tacaaaccta ggcaaatttt caatttggag     60

agagaaagca ctttggtggg aagatgtcct gttgttcaga ttagatgccg gagggttgtg    120

agtgcgtgtc ttaacgtgga tgttgatgca cctaatacag ggaatacaac atcggagaag    180

aagaaaacta aggatgtgat cgagatggaa gggatgtatt tggttgggac atatgcaaga    240

acaccagtgg tacttgagag gggggaaggt tgtaagttgt atgatgttga agggaatgaa    300

tatttagatt tgagtgctgg gattgctgtc aatgcactag gccatgggga tgcagactgg    360

ttgaaagctg ttgttgagca agccggcacc cttactcata ccagcaatat attccacaca    420

attcctcagg tagaacttgc aaagcgtctt gtggcttctt cttttgctga tcgtgtattc    480

tttgcaaatt ctggaactga ggcaaatgaa gcagctatca aatttgcaag aaagtatcag    540

aggcacacaa cttctaacgg gaaagttcca gcaacagagt tcatagcttt tagtaactgc    600

ttccatggaa gaaccctggg tgcacttgct ttgactagta aagtgcaata cagaatgcct    660

tttgaacctg ttatgcctgg agtgaccttt ttagagtatg gaaatgctca ggctgcagtt    720

gaattaatta agcagggcaa gattgctgca gtttttgttg agcccatcca aggagaaggt    780
```

ggaatttaca gtgctacaaa agaatttcta cagtctctac gtaatgcttg tgatgaaact 840
ggggcacttc ttgtgtttga tgaggttcaa tgtggtttag gtagatcagg gtttctctgg 900
gcccatgagg catatggtgt cttcccggat atgatgaccc ttgcgaagcc tcttgctgga 960
ggcctaccta ttggagcact cttagtgact gagagagttg cttctgctat aaattatggt 1020
gatcatggaa gcacttttgc tggaagccct ctagtttgta gtgctgctct tgctgttttg 1080
gataaaatat caaaacctga tttcctgtca tctgtatcta agaaaggcct ctacttcaaa 1140
gaactactta gggaaaagtt aggagaaaac cggcatgtga aagaaattcg tggtgttggg 1200
ctaatcatag gaatagattt agatgtacct gcatcacccc tcgtagatgc atgccggagt 1260
tctggcctcc tagtgttaac tgctggaaaa ggaaatgttg tcaggctagt cccgccattg 1320
atcataacag agaaggagct agagcaagcg gctggcattt tgtgccaaac tttaccagtt 1380
cttgataact ag 1392

<210> SEQ ID NO 127
<211> LENGTH: 1677
<212> TYPE: DNA
<213> ORGANISM: Glycine max

<400> SEQUENCE: 127
atgcgaatcc tcgtcctgct ctctctcgcc acccttctcc tcttctcctc cttctctccc 60
accttctgcg accacctcgc cgacgacgag gacctcagct tcctcgacga gccctccgcc 120
gcgccggagc acgaccacca ctacggcgcc gatgactcca atttcggcga ctttgaggac 180
ttcgaggagg acgacgcgga ggcgtacaag cagcccgagg tggacgagaa ggacgtcgtc 240
gttttgaagg agaagaactt caccgacgcc gtcaagaaca accgcttcgt catggtcgag 300
ttctacgcgc cctggtgcgg ccactgccag gccctcgcgc cggagtacgc cgccgccgcg 360
acggaactca agggcgaaga cgtaattttg gcaaaggtgg atgccaccga ggagaatgaa 420
ttggcgcagc agtacgatgt tcagggtttc cccactgtcc acttcttcgt tgatggcatt 480
cacaagcctt ataatggcca aaggaccaaa gatgctatag tgacgtggat taggaagaag 540
atcggacctg gcatatacaa cttgactaca gtggaggagg ctcaacgcat tttgaccaac 600
gaaactaaag ttgttttggg cttcctcaac tctttagttg gtcctgagag tgaggagctt 660
gctgctgctt caaggcttga ggatgatgtc aatttttatc aaactgtgaa tcctgatgtg 720
gcaaagcttt tccatattga ccaagatgtt aagcgtccag cattgatcct cattaagaaa 780
gaggaggaaa aacttaacca ctttgatgga aaattcgaga agtcagcaat agcggacttt 840
gtcttctcca acaagcttcc tttggtaaca atttttacaa gagaaagtgc cccatcagtc 900
tttgaaaatc caatcaagaa acagttgttg ctgtttgcaa cttcaaatga ttcagagact 960
ttggtcccag catttaaaga agcagcaaag tctttcaagg gaaagttgat ctttgtatat 1020
gtggaaatgg ataacgaaga tgttggaaag cctgtttcag aatactttgg tatcagtggg 1080
aatgctccaa aagtacttgg atacactggg aatgatgatg gaaaaaaatt tgtgcttgat 1140
ggagaggtga ctactgacaa aattaaggca tttggggaag atttcgttga agacaagcta 1200
aaaccttttt acaagtcaga tccagttcct gaaagtaatg atggtgatgt gaaaatagta 1260
gttggtaata attttgatga aattgtcttg gatgagtcaa aggatgttct cctcgagatt 1320
tatgctccct ggtgtggcca ttgccaatca ctggagccaa tatacaacaa gcttgcaaaa 1380
catcttcgca atattgattc tcttgtaata gccaagatgg atggaacaac aaatgagcat 1440

-continued cccagggcta agcctgatgg attccccact cttctcttct tcccggcagg aaacaagagt 1500
tttgacccta ttactgttga tacagatcgt acagtggtag ccttctacaa gttcctcaag 1560
aaacatgcat caatcccatt caagctccag aaaccaacct caacttctga atccgattcc 1620
aaggggagct ctgatgccaa agagagccag agtagtgatg tgaaggacga attatga 1677

<210> SEQ ID NO 128
<211> LENGTH: 501
<212> TYPE: DNA
<213> ORGANISM: Glycine max

<400> SEQUENCE: 128
atggctgaac aatcttccaa ctccatttac gatttcactg tcaaggacat cagtggaaat 60
gatgtgagtc tgaatgatta cagcgggaag gttctactga ttgtgaatgt cgcctctcaa 120
tgtggtttga cacagacaaa ttacaaagaa ttgaatgtat tgtacgagaa gtacaagaat 180
caaggatttg aaatcttggc atttccgtgc aaccagtttg ctggacagga accaggaaac 240
aatgaagaaa ttcaggaagt agtttgcaca aggttcaagg ctgaatttcc tatctttgat 300
aaggttgaag tcaatgggaa gaatgcagtg ccactttaca agtttttaaa ggagaagaaa 360
gggggaatat ttggcgatgg tatcaagtgg aacttcacaa agttcttagt aaacaaagaa 420
gggaaggttg tggacagata tgcacctacc acctcacctc tgaaaatcga gaaagacatc 480
gagaagctct tgcaatcttg a 501

<210> SEQ ID NO 129
<211> LENGTH: 600
<212> TYPE: DNA
<213> ORGANISM: Glycine max

<400> SEQUENCE: 129
atgaagtggt tgactttctg gaactgcata tctatcctcg tgttgtcttt tgctttcttc 60
ttcttctatt gtcacacata cacatctact ccttccctca tggctgagca atcttccaag 120
tccatttacg atttcacagt caaggacatc agtggaaatg atgtgagtct gaataattac 180
agcgggaagg ttctactgat tgtgaatgtc gcctcacaat gtggtttgac acagacaaat 240
tacaaagaat tgaatgtatt gtacgagaag tacaagaatc aaggatttga aatcttggca 300
tttccatgca accagtttgc tggacaggaa ccaggaaaca atgaagaaat tcaggaagtt 360
gtttgcacaa ggttcaaggc tgaatttcct atctttgata aggttgaagt caatgggaag 420
aatgcagcgc cactttataa gtttttaaag gagcagaaag ggggaatatt tggtgatggt 480
atcaagtgga acttcacaaa gttcttagta aacaaagaag ggaaggttgt ggacagatat 540
gcacctacca cctcacctct gaaaatcgag aaagacatag agaagctttt gcaatcttga 600

<210> SEQ ID NO 130
<211> LENGTH: 3942
<212> TYPE: DNA
<213> ORGANISM: Glycine max

<400> SEQUENCE: 130
atggaagcag agactttgaa tgcaaatcac cctcccggtt ttcttcaccg gtcgctcccc 60
gctgttgtgc ctatcctttt gatttcaata ggatatgttg accctggaaa gtgggtggca 120
attgctgaag gaggtgcacg atttgggttc gatctgatgg ccttcatgct tatctttaat 180
tttgcagcca tcttctgtca gtacatatca gcaaaaattg gtgttatcac aggaaaggat 240
cttgctcaga tttgcagtga tgagtacgat aattggacat gcatgcttct tggagttcag 300

-continued

```
gcagaacttt cggtgattat gctagacctt aacatgatat tgggcatggc acatggatta    360
aatattcttt ttgggtggga cttgttcact tgtgtctttt taattgctac tggtgctgtt    420
ttccatctcc ttctttttgc cctcctggac attgagaagg tgaagatcct gggcctgttt    480
gtgtcaggtt ttgtatttct ttcgtttgta cttggaacac tcattaatca accagacatt    540
ccattatcca ttaatggaat actaacaaag ttgagtgggg agagtgcatt tgtgctgatg    600
agtctattag gagcaactct tgtgcctcac aacttctacc ttcattcctc tattgtacag    660
tggcatcagg gatcaactac catttctaag gatgctttat gtcataacca tttttttggcc    720
atcatgtgtg tcttcagtgg cctttatttg gtaaataatg tgctgatgaa tgctgcagca    780
aatgagttct acagtatggg tcttgttttg actacttttc aggatgcatt atcaccaatg    840
gaacaggtgt tgcgtagtcc aatagccatg cttgcttttt tactcattct gtttttttca    900
aatcaaacca cagcattaac ttggagtttt ggtggagaag tagttgtgca aagtttctta    960
aaattggata ttccgggttg gcttcattat gctacaatta gagtaattgc tgttctgcct   1020
gccctttatt gtgtttggag ttcaggagct gaagggatgt atcaactact tatattcact   1080
cagattgttg tagctctgca acttccatct tctgtgatcc cccttttttcg gatcgcctca   1140
tctagatcaa taatgggggt acacaagatc cctcaatttg tggaattttt ggcattgatc   1200
atattcattg ggatgcttgg cttgaatatt gtctttgttg tagaaatgat atttggcagt   1260
agtgattggg tgggcaattt gagatggaat gtggggactg gtgtgtctct ctcttatttg   1320
gttcttcttt gcactgcgtt tgcatcattc tgtctgatgc tttggttagc tgccacacct   1380
ttaaagtctg ctagtgttca attggatgat cagcaatgga actgggacat gccacaggcc   1440
gtaccaaaat cacggattga taacgaggaa acagatttaa aagaaacaag atatcaagga   1500
gatgcatcag ttcaggggaa ggaaccatca ccagctctag caaggaccct ggaatattca   1560
gatgtaccag ttgcaagttt tcatcttgat ctacctgaaa ctatcatgga gcctgatgtt   1620
cctgtgacta ctgtaaggga gactcatcca tttacatcat ttccttgctc cccaacatct   1680
gttaaggaat cagcttccac ttcagaatcg gaggcagtac cagctgtaag taatgagact   1740
tctgatatta tattgggaca ttccaaaact ttgaaaacag aaactactgc ccctgttgag   1800
aaaactgtag aaattgaggg agattcaaat gccgaaaggg atgatgatga tggagattca   1860
tgggaaactg aagaaataca aaaagtggtc tcactagccc catcttcagc atcagatggc   1920
ccagcatcat tcaggagcct tagtgggaaa agtgatgatg gagggaatag cattggtagt   1980
ctttcgagat tagcaggttt agggcgcggt gcaagacgtc aactagctgc tattcttgat   2040
gaattctggg gacaacttta tggtttccat ggtcaattta cccaggaagc taaggccaag   2100
aaacttgatg ttttactggg aatagattca agactcactg gttctttgca aagaatggat   2160
ccatgtggaa aggaatattc tgaatattta atatctgtag gaagtagagc tccagatact   2220
ttaatgaact ctgctccata tgaatctccc aggcagaata ggatccaaag taatttagat   2280
gcttcctatg ggcctcaaag gagttcttcc tcactgcggg caaatcctgt ccagtttatg   2340
gatgaatatg ttcagacctc cagccgcaat ctcctcgatg ctggtgaaag gcgctattcc   2400
agtgtgcgca atttacctac gtctgcagcc tgggattatc agccagctac tatacatggt   2460
tatcaggttt catcgtatat taatcaggtt ggtaaagaca caaattctga taacttaaat   2520
ggtctgaggg aatccccttc catgggtaat acgaaccact acaggaattc tatgggtaat   2580
acgaactaca ggaattctat tgcatttgct ttgggtaaaa agttgcaaaa tggttcaggt   2640
```

```
ttaagccaac ccccagggtt ccagaacatt gctgtctcta agaatagcca attgccatct   2700

gagaggtcct attatgattc tcgcccttcc ggacctgtgg atagtacagt cagttcagtc   2760

aatgctaaaa agtaccacag cttgccagat atttcaggat atgccattcc tcacagggat   2820

gtttacatgt ctgataagag tgctccatgg gatggttctg ttggtggata tagatcttct   2880

gcaagtagga ctcattatga accgtcatta tattcaaact ctggatcaag gacaggagct   2940

cctttagcct ttgatgtact ctctccatca aaagcctaca gtgatgaact ttcttctcag   3000

ttgagttctg gttttggcac tggatccctc tggtccagac agcctttga gcagtttggg   3060

gtggatgata aaattcataa tgctgcaaca gaagatgttg gaaataggcc tagtgcaact   3120

actcaagaaa ctacttcagt ggtggatata gatggcaaac ttcttcaatc ttttagacaa   3180

tgtattttga aactcttaaa attggaaggg tctgattggt tgtttaaaca gaatgatggg   3240

gctgatgaag atctgattga tcgtgttgct gcaagggaga aatttgttta tgaaattgaa   3300

accacagaga tgaaccgcaa tcatatggga gaaactcgat atctttcttc tgatgggaag   3360

tcttgttctt caatgaagaa taatgaggct aattggtcta gtttttccgt aacctcaatc   3420

cctaactgtg gagatggatg tgtatggaga gcagacataa taataagctt tggggtgtgg   3480

tgtatcaaac gtgttcttga cctctcatta atggagagcc ggccagagct gtgggggaag   3540

tacacttatg tactcaatcg cctccagggc atcattgatc tggctttctc caagcctcgt   3600

agtcccatga ccccatgctt ttgccttcaa gttcccatga cttaccagca gaagtcaggc   3660

tcacctcctt ccaatgggat gctgcccct gcatcaaaac caggccgtgg aaaatgcaca   3720

actgcgtcag tggtgtttga gatggtcaag gatgtggaga tagcaatctc tagccggaaa   3780

ggtcgcacag gaactgctgc tggtgatgta gctttcccaa agggaaagga gaatttggca   3840

tctgttctca aacggtataa gcgtagatta tccaataaac cagttggcac tactcaagaa   3900

gggattcgca agattcccac atcagcacca tacaacttgt ag                      3942
```

<210> SEQ ID NO 131
<211> LENGTH: 3846
<212> TYPE: DNA
<213> ORGANISM: Glycine max

<400> SEQUENCE: 131

```
atggaagcag ggacattgag tcctaaccac cctccttgct ttcttcgtca gtcacttcct     60

gctgttgcac ctatgcttct gatttcaaca ggatatgttg accctggaaa gtgggtagcc    120

actgttgaag gtggtgcacg gtttgggttt gatctgatgg ctgtcatgct tattttcaat    180

tttgctgcta tcttctgtca gtacatatct gcaaggattg gtgcgattac tggaaaaagt    240

ctagctcaga tttgcagtga tgagtatgat acatggacat gcatgctcct tggagttcaa    300

acagaacttt cagtgataat gctagacctt aacatgatct tgggcatggc acaaggatta    360

aatcttattt ttgggtggga cttgttcact tgtgtctttt taactgctac tggtgctgtt    420

tttcatatac ttctctcagt tctccttgac attgagaagg caaaaatcct aggaccgttt    480

gttgctggtt ttgtattgct tgcttttata cttggactgc ttatcaatca accggaaatt    540

ccattttcca tgaatggaat accaacaagg ttgagtgggg agagtgcatt tgtgctaatg    600

agtcttctag gagcaaatct tgtacctcac aacttttacc ttcattcctc tattgtacag    660

tggcatcagg gattgacaag catttctaag aatgctttgt gtcataacca ctttttggcc    720

atattatgtg tttccagtgg tctttatttg gtaaataata tgctgatgac cgcctcagca    780

aatgagttct acagtacaga tcctgttctg cttacttttc aggatgcatt gtcacccatg    840
```

-continued

```
gaacaggtct tacgtagccc aatagctctg cttgggtttt tgctcatttt gtttcttgca    900
aatcaaacca cagcattaac ttggagttta ggcggagaag tagtagtgcg taatttctta    960
aaattggata ttccaggttg gcttcattat gctacaatta gagtgattgc tgttttgcct   1020
gccctttatt gtgtctggag ttcaggagct gaggggatgt atcagctact attatccaca   1080
caagttttgg tagctctgca acttccatct tttgtgatcc ctctttttcg agttgccaca   1140
tctagatcaa taatgggtgt acacaagata tcccagtttc tggaactttt ggcatcgatc   1200
atattcattg gtatgcttgg cttgaatatt gtcttcgtgg tagaaatgat attcggcaat   1260
agtgactggg caagtgattt gagatggaat gttgggagtg gtgtgtctgt ctcatattta   1320
gttcttctta ccgctgctat tacatcgtta tgtttgatgc tttggttagc cgccacacct   1380
ttaagatctg ccagtgtcca attagatgct cagacatgga actgggatat gccagagact   1440
ctgccaactc ctccagttgt tggggaggaa ttgtatttaa ctgaaaaaaa gtgtcatgaa   1500
gatgtatcta agcatgtgga ggaacacaca ccagctgtag caaaaagctt ggactactca   1560
gatgtatcac ttccaagttt tcatcctgat ctacctgaat ctttaatgga acctgaaccc   1620
catgtgaatg ctgtaaggga taattattct cttatatcga cttccacatc agagttagag   1680
gcagtatatg ctgtagttaa tgagacttct gattcttgtt tggaagacac caaaaccata   1740
acaatggaaa caaacgctga aagggatgac gatgattcat gggaaactga agaaccttct   1800
ggagtggtat cagccagtgt tccatcttca acatcagatg gccctgcatc attcaggagt   1860
cttaatggca aaagtgatga aggagggaat agctgtggaa gtctttcaag aatagaaggc   1920
ttagggcgtg cagcaaggcg tcagctagct actgttctta atgaattctg ggacaacta   1980
tatgatttgc atggacaagt aacccaggag gcaaaggctg ggaaaattga ccttttgctg   2040
ggagtgggtg tagattcaag gcccaccagt tccttgcaaa aagtggatgc atgtggaaag   2100
gattattctg aatacttagt atctgtcaga ggtagagctt ctgacgcatt aatgaactct   2160
gcttcatatg attcttccaa gcagcctatg atgcaaagta attcagagtc ttatggcctt   2220
caaaggagtt cttcctcaat gtgggcaaat cccatccaat tattggatgc atatgtacag   2280
aactctagcc acaatctcct cgattctggt gagaggcgct attcaagtgt gcgtaatcta   2340
cattcatcag aagcttggga ttatcaacca gctaccatac atggttatca gactgcatcc   2400
tatcttagcc ggcttggtaa agacagaaat tctgctaact taaattgtca ggtggacttg   2460
tcatcactga aatccccttc catagttaat acaaagtaca gggattcact tgcatttgct   2520
ttggggaaaa ggttgcaaag tggctcaggt gtgggccaac cccagggtt cccaaatgta    2580
gctgtctcta gagattccca attacaatct gagaggtttt attatgactt atgctcttct   2640
ggatctgcag ataatacagt caattcagtt aatactaaaa agtaccacag tttgccagac   2700
atttcaggat actccatccc ccacagggct ggttatgtgt ctgataaaaa tgctccaagg   2760
gatggttctg ttggatatgg atcttttgct agtaggacgt gctatgacca atcattatat   2820
ttaaattctg gatcaagaac aggaggtcat ttggccttca atgaacttcc tttgtctgaa   2880
gtttacaaca aggcactctc ttcacagttg agttctggtt ttgatactgg atccctccgg   2940
tctagattgc cttatgagca gtttggggta gctgagaaaa ttcctaatgt tgcaatggaa   3000
gctgttggaa ataggcctaa tgcaattgct caagaaacta cttcatttgt ggatatagag   3060
gggaaacttc ttcagtctat tagactttgc attgtgaagc tcttgaaact ggatgggtct   3120
gattggttgt ttagacagaa tggtggagcc gatgaggatc tgatagattc tgttgctgca   3180
```

-continued

```
agggagaagt tgttttatga aattgaaacc agggagatga atcaggtcat tcatatggat   3240

gaagctcatt attttccttc tgataggaaa tttggttctt caatgaagag taatggggca   3300

tattcttcag gtttttcggt gtcttcggtt ccaaattgcg ggcagggatg tatatggaaa   3360

acagatttaa taataagctt tggagtatgg tgtatccaca gtattcttaa cctctcaatt   3420

gtagaaagcc ggccggagct ttgggggaaa tacacctatg ttctcaatcg cctccagggc   3480

atcattgatc cagctttcct taagcctcgg agtcccttgg ctccatgctt ctgccttcaa   3540

gttcagcaaa agttaagccc ccatctttca aatgggatac tacccccaac gactacaaaa   3600

ccaggccagg gcaaatgcac aactgcatca acgttgcttg aacttatcaa ggaagtggag   3660

cttgccatct ctggcaggaa aggacgtacc ggaactgccg caggcgatgt ggctttccct   3720

atggggaagg aaaatttggc gtctgttctc aaacggtaca agcggaggct atctaacaag   3780

cccgttggca ctaatggagg gacaggttca cgcaagatcc ccacattagc accatacaac   3840

caataa                                                              3846
```

<210> SEQ ID NO 132
<211> LENGTH: 501
<212> TYPE: DNA
<213> ORGANISM: Glycine max

<400> SEQUENCE: 132

```
atggctgaac aatcttccaa ctccatttac gatttcactg tcaaggacat cagtggaaat     60

gatgtgagtc tgaatgatta cagcgggaag gttctactga ttgtgaatgt cgcctctcaa    120

tgtggtttga cacagacaaa ttacaaagaa ttgaatgtat tgtacgagaa gtacaagaat    180

caaggatttg aaatcttggc atttccgtgc aaccagtttg ctggacagga accaggaaac    240

aatgaagaaa ttcaggaagt agtttgcaca aggttcaagg ctgaatttcc tatctttgat    300

aaggttgaag tcaatgggaa gaatgcagtg ccactttaca agtttttaaa ggagaagaaa    360

gggggaatat ttggcgatgg tatcaagtgg aacttcacaa agttcttagt aaacaaagaa    420

gggaaggttg tggacagata tgcacctacc acctcacctc tgaaaatcga gaaagacatc    480

gagaagctct tgcaatcttg a                                              501
```

<210> SEQ ID NO 133
<211> LENGTH: 1494
<212> TYPE: DNA
<213> ORGANISM: Glycine max

<400> SEQUENCE: 133

```
atgagtggcg gaggaggagg agaagaggaa gcaactctgg agttcactcc gacgtgggtt     60

gtggccgccg tttgcacagt catcgtcgcc atatctctcg ctgctgagcg cctccttcat    120

tatggcggaa agtttctcaa agccaaggac cagaagtcgc tctacgaagc tctccagaag    180

atcaaagaag agctgatgct tctgggcttc atttccctgc ttctcacggt tacacaaaac    240

ggcattacca aaatctgcgt tcgtcccagt ttgacgcgcc acatgctccc ttgtaatctc    300

gacgccggtg aacactccac gcctgagtcc gagtccgcca ctaaaattgg ttactgcgtc    360

cgcaagaaca aggtaccttt attatctttg gaagcacttc accatcttca catcttcatt    420

tttgtcctcg ctgtcgtaca cgtctccttt tccttactca ccgttgtctt cggaggcgcc    480

agaatacgtc agtggaaaca ctgggaagat tcaattgcta aacagaacta cgaaactggc    540

cgagttctca aaccaaaggt cactcaggta caccagcatg attttatcag ggtcgtttt     600

gccggttttg acaaagactc tgctattgtc ggttggttgc tatccttttt aaagcagttt    660
```

```
tatggatctg tgacaaaatc agattatgtg acattgcgac atgggttcat tatgacccac     720

tgcaggacaa atccaaagtt taattttcac aagtacatga ttcgtgccct cgaagatgat     780

ttcaagcaag ttgttggtat aagttggtat ctttggctct ttgtggttat cttcttgttg     840

cttaacatca atggttggca tacgtatttc tggattgctt ttattcccgt cgttctttta     900

cttgctgtgg gcactaagct ggggcacgta ataacccaac tagctcaaga agtagctgaa     960

aagcatgcag ccatagaagg tgatttagtt gtgcagccat cagatgaaca tttttggttt    1020

catcggcccc atgttgtcct ctttttgatt cactttatcc ttttccaaaa tgcctttgag    1080

atagcatttt ttttctggat atgggtcaca tatggatttg actcctgtat aatgggacaa    1140

gttcgataca ttgttccaag gcttgttatt ggggtattta ttcaggtact atgtagctac    1200

agcaccctgc cactgtatgc aattgttacg cagatgggaa ctcactataa gagggcaata    1260

tttaatgagc atttgcaaca aaacattgtt ggttgggcac agaaggcgaa gaagaggaaa    1320

ggactaaaag ctgatggcaa tcctggccaa ggaagttctc aggagagtgc taatacagga    1380

atccagcttg ggtcaatttt caagaaggca tctgctccag gaggcaaaat atcacttctg    1440

atacccccac aggttgcctc accacaagct aggcaaaaat tgagtccaaa ttaa          1494
```

```
<210> SEQ ID NO 134
<211> LENGTH: 597
<212> TYPE: DNA
<213> ORGANISM: Glycine max

<400> SEQUENCE: 134

atggcagcgg tggccggagc atcctcgtcc gtgattaagg tggctgcact ttccggatct      60

ttaaggaaag gctcttacaa cagagccctc attcgttctg ctattgagct aagccaaggt     120

agagttgaag gccttcaaat cgagtacgtt gatatttcgc ctttgcccct tctcaacacc     180

gatcttgagg tgaatgggac ctacccccca caagttgaag cctttcgcca gaagattctc     240

gcagctgata gtatcctctt tgcttcccct gagtacaatt actctgtcgc aagtccttta     300

aagaatgcac ttgactgggc atcaagggca ccaaatgttt gggctggtaa acctgctgcc     360

atagtgagtg ctggaggagg ctttggtggt ggaagatcac aatatcatct acgccaaatt     420

ggagtattct tggatcttca tttcatcaac aaacctgaat tcttcctcaa tgcattccag     480

ccacctgcaa agtttaacaa tgatggtgac ttgattgatg aagatgccaa gaataggttg     540

aaggatgtcc ttctgtcctt gaaggaattt acccttagac ttcaaggaaa aaattga        597
```

```
<210> SEQ ID NO 135
<211> LENGTH: 1170
<212> TYPE: DNA
<213> ORGANISM: Glycine max

<400> SEQUENCE: 135

atggtggaga ttcacgaaga aatcaacccc tttgatcaag aagaaaatga agacattgga      60

gaggaagaaa tcgactatga ccagcttaag aagcggatgt ggaaggatcg gatactgctg     120

cagaagatga aggagaaacg gcccaaagaa gagccagtcc aagaagcaaa acaagaagca     180

tctaggcgga agaagatgtc aagagcgcaa gactcggtcc tcaagtacat gatgaagatt     240

atggaagttt gcaatgctca aggttttgtg tatgggattg tccctgagaa gggaaagcca     300

gtgactggtt cttctgacag cttgcgtgag tggtggaaag aaaaggtaaa gtttgatcaa     360

aacgcaccaa gttccattgc agaatacttg ccactccttg aaacagatga gttggatcca     420
```

-continued

```
agttcctaca tacatctcct taacgacttg caagacacta ctttgagttc actactttct    480

gctctgatgc aacattgcat acctccccaa agaagattcc ctcttgagag aggcttggct    540

ccaccttggt ggcccacagg ggcagagaat tggtggggtg aacaaggcct tctggcccat    600

gaacatggcc cacctcctta taagaagccc catgacctca aaaaggcttg gaaagtgtct    660

ctcttggctg cagtcatcaa acacatgtct cctgatttgt ataaacttag aaggtcggtg    720

actcagtcca agactttgca agataagatg acaaccaggg acacggcaac ttggtccaag    780

gtcatgaacc aggaagaaac tctgctgcaa ctggccaaca agtgcctcaa aatatctcca    840

tcagaggaag atgataaaaa tgagtgtgaa agctctacta gtagcagtac tatcatccat    900

gaagggagtc atttagatgc tgttattgat aagctatatg cttgccaata ctatcagtgt    960

ccacaaagtg aaatgggtat gggatttctt gacaaaaaca caagaatgaa ccatgagtcc   1020

ctctgtgctt accggactaa tgaaggccaa cgccctacaa atattaagtt cctcgcccca   1080

tgcttggatc aattgtgcac tgctataaag tgttgtcaac aatttttat ttacctatct   1140

ttattaaaaa ctgaaaagcc atctagctag                                  1170
```

```
<210> SEQ ID NO 136
<211> LENGTH: 969
<212> TYPE: DNA
<213> ORGANISM: Glycine max

<400> SEQUENCE: 136

atgacatggt gcaatgactc tgatgaggat agggttattg aatcaacgac gccaacaata     60

actattactc ctaacactga tggcataaag ctcaccgaag aaattagaac cataacatgc    120

ccctcgtgcg gccataacat tgaattcaaa gatcagggtg gaatccatga cttgccgggg    180

ttaccagctg gagtgaagtt tgacccaaat gaccaagaaa tattagaaca tttggaggca    240

aaagtggcgt ctgatgcatg caagcttcat ccccttattg acgagttcat accaacgctt    300

gaaggcgaaa atgggatctg ttatacacac ccagaaaagc taccaggtgt tagcaaagat    360

ggacagatcc gccacttctt tcacaggccc tcaaaagcat acacaactgg aacgaggaaa    420

agaagaaaag ttcacactga tgatgaagga agtgaaacaa gatggcacaa aacgggaaaa    480

actagagcag tttttgcagc agccggtggt gcagtaaaag gttttaagaa aatactagta    540

ctctacacca actatggaag acaaaagaag cctgagaaaa ctaattgggt gatgcatcaa    600

taccatcttg gcagtactga agaagagaaa gatggagaat tagttgtttc aaaggtcttc    660

tatcagacac aacctagaca atgtggcaat cccattataa taaaggattc atacgaaaaa    720

atgttgaatg atggaagtgg ccaagacaac attaatatat cattaatacc taaaactact    780

gcaactcttt tggattgcta cactgctcct tacatagatt atgatcacgt ccatgtgagt    840

cataacaggg aaagttcctc acaactaatt attcccagct cggttgttca agttgatggc    900

tcttatattc gcttaacaat ggatgcaaag aaagcaagat ttgaaagtaa cactgggaag    960

agattctag                                                         969
```

```
<210> SEQ ID NO 137
<211> LENGTH: 969
<212> TYPE: DNA
<213> ORGANISM: Glycine max

<400> SEQUENCE: 137

atgacatggt gcaatgactc tgatgaggat agggttattg aatcaacgac gccaacaata     60

actattactc ctaacactga tggcataaag ctcaccgaag aaattagaac cataacatgc    120
```

ccctcgtgcg gccataacat tgaattcaaa gatcagggtg gaatccatga cttgccgggg 180
ttaccagctg gagtgaagtt tgacccaaat gaccaagaaa tattagaaca tttggaggca 240
aaagtggcgt ctgatgcatg caagcttcat ccccttattg acgagttcat accaacgctt 300
gaaggcgaaa atgggatctg ttatacacac ccagaaaagc taccaggtgt tagcaaagat 360
ggacagatcc gccacttctt tcacaggccc tcaaaagcat acacaactgg aacgaggaaa 420
agaagaaaag ttcacactga tgatgaagga agtgaaacaa gatggcacaa aacgggaaaa 480
actagagcag tttttgcagc agccggtggt gcagtaaaag gttttaagaa aatactagta 540
ctctacacca actatggaag acaaaagaag cctgagaaaa ctaattgggt gatgcatcaa 600
taccatcttg gcagtactga agaagagaaa gatggagaat tagttgtttc aaaggtcttc 660
tatcagacac aacctagaca atgtggcaat cccattataa taaaggattc atacgaaaaa 720
atgttgaatg atggaagtgg ccaagacaac attaatatat cattaatacc taaaactact 780
gcaactcttt tggattgcta cactgctcct tacatagatt atgatcacgt ccatgtgagt 840
cataacaggg aaagttcctc acaactaatt attcccagct cggttgttca agttgatggc 900
tcttatattc gcttaacaat ggatgcaaag aaagcaagat ttgaaagtaa cactgggaag 960
agattctag 969

<210> SEQ ID NO 138
<211> LENGTH: 519
<212> TYPE: DNA
<213> ORGANISM: Glycine max

<400> SEQUENCE: 138
atgaagagag gcagagaaga gagtaagtta gacatggcta attgcttgat gctattgacg 60
aaagttggag agagtgaaac caattaccca atatcaaagg gtagtgatat tggtgatttc 120
aagtgcaaga cttgcaatag aaggttctct tcttttcaag cccttggtgg ccatagagca 180
agccacaaaa aaccaaagct catggtcaca gatctttcgt gccatcaaga gttaccgaac 240
ccaaccatga aacaacaacc taggatgcac ccgtgtccga tttgtgggct tgagtttgct 300
attggacaag ctttgggagg gcacatgaga aagcatagaa ctgctattaa tgatggcttg 360
ttgtgtggta aaccttcttc ttcgttgtcc atcttgaagg aatcatcgaa agatggtgat 420
caaaagttga atttgcgctt ggacttgaac ttgacgccat tggaggagga tgatcttaag 480
ctcaacctaa ggacgcccgt gctcaattgt ttcatttga 519

<210> SEQ ID NO 139
<211> LENGTH: 477
<212> TYPE: DNA
<213> ORGANISM: Glycine max

<400> SEQUENCE: 139
atgaacaaca acatgttagg aatgaagaga cggagagatg ataatgaagg gtccttggat 60
ttggcaaaat gtcttatgct gttttcttgt ccaatagaaa gcaacaagac acaacagaaa 120
agttttggtt ctgtggaatt tgagtgcaag acgtgcaacc gcaagttctc ttcttttcaa 180
gcactgggag ggcacagggc aagccacaag aggcagaagc tggaggggga agaactgaaa 240
gaacaggcca aaagtcttag cttgtggaac aaacccaaaa tgcacgagtg ctccatttgt 300
ggccttgaat tctctctggg ccaggctctg ggtggccaca tgagaaaaca cagagcttcc 360
ctcaacgaag ggtttcctat tattccttct atcgaccaag ttattgcgaa aatcccggtt 420

-continued

```
ttgaaaaggt cgaatagcac cagggttatg tgcttggact tggagttaca cctgtag       477
```

<210> SEQ ID NO 140
<211> LENGTH: 2502
<212> TYPE: DNA
<213> ORGANISM: Glycine max

<400> SEQUENCE: 140

```
atggattgtg gcaagtatgt gaggtacaca cctgaacagg tggaggcttt ggagagggtt     60
tatattgaat gtccaaagcc tagttcttcc agaaggcaac aaatcattag ggagtgtcca    120
ctccttgcta acattgaaac aaagcagatc aaagtgtggt tccagaatcg cagatgtcgt    180
gaaaagcagc ggaaggaagc ctctcgtctg cagacagtga atagaaagct gtctgcaatg    240
aacaagttgt tgatggaaga gaacgaccga ctgcagaagc aggtctcaca gttggtttat    300
gataatggat tcatgaaaca acaaatacat actgcatctg ctactactac tactgacaat    360
agctgtgaat ctgtggtagt gagtggtcaa cgccaacatc aaaaccccaa aattcagcat    420
ccccagtggg atgccaacaa cccagctggt cttcttgcaa ttgctcagga gaccctggcg    480
gcgttccttt caaaagctac tggaactgct gtcaactggg tccaaatgat tgggatgaag    540
cctggtccgg attctattgg aatcgttgct gtttcccgca actgtagtgg tgtagcggca    600
agagcctgtg gccttgtgag ccttgagccc acaaaggttg ctgagattct caaagatcgt    660
ccatcatggt atcgtgactg tcgatgcctc aatgtactga gtgtaatccc cacagggaat    720
gggggcacga tagagctcat gtacatgcag acatatgcac caacaacatt ggcagctgca    780
agagacttct ggactctgag atacactact agtttggaag atggaagtct tgtgatttgt    840
gaaaggtcct tgacttcttc aactggtggc cccacagggc ctgctgcttc aaacttcgtg    900
agagctgaaa tgcttcctag tggctatcta attagatcct gtgagggtgg tggatctatt    960
gttcacattg ttgatcatgt tgatttagat gtttggagtg ttcctgaagt acttagaccc   1020
ctctatgaat caccaaaatt cttggctcag aaattgacta ctgctgcctt gcgaaatgta   1080
agacaaattg cacaagaatc aagtggagaa gttcagtatg gtgggggtcg tcagcctgct   1140
gtcttgagga catttagtca aaggctttgc aaagggttca atgatgctgt caacgggttt   1200
gtggatgatg gttggtcatt gatgggtaat gatggggttg aagatgtgac cataggcata   1260
aactcatctc ccaacaagtt tttcagttcc cattacaata catcaatgct tcccgcattt   1320
ggaggtgggg tcttgtgtgc gaaagcatca atgctgctac agaatgttcc tcctgctttg   1380
cttgttcgtt ttctgaggga gcatcgttca gagtgggcta attatggggt tgatgcatac   1440
tcttctgcat gtctcaaagc tagtccttat gcagttcctt gtgcaagacc tagtggtttc   1500
ccgagcagcc atgtcattat accacttgct catactattg agcatgagga gttcttggag   1560
gtagttcgta ttgagggtaa tgcatttccc cctgatgatg tagctttggc atgtgatatg   1620
tatttaatgc agctgtgcag tggaattgat gaaaatgcaa tcggagcatg tgcacagctt   1680
gtgtttgcac ctatcgatga atcatttgca gatgatgctc tcttactgcc ttctggtttc   1740
cgcatcatac cattggatcc taaaacagat ggtccggctt caactaggac attggactta   1800
gcgtcaacac tggaaactgg atctggtaat gctcgctcag ctggtgaaag tgacctgaat   1860
aactacaacc ttaggtcggt cctcacaatt gcattccaat ttacctttga gaaccatttg   1920
cgggacaatg tggctgttat ggctcgccag tatgtgcgta atgttgtgcg atctgttcag   1980
agggttgcta tggcaattgc tccctctagg atcagtacac agttggggcc aaagtcactt   2040
cctggtccac cagaggccct taccttagca agatggatct gcaaaagcta cagtctccac   2100
```

acctgcacag agctttttag cgttgagtcc acatctggtg atgcaatctt gaagcaactt 2160
tggcaccatc cagatgcaat attgtgctgt tctgtaaaaa caaatgcatc tccagtgttc 2220
acctttgcaa accaagctgg acttgacatg cttgaaacca ctcttgttgc tcttcaagac 2280
ataatgctgg ataaagttct tgatgaagct ggcaggaagt ttctctgcat tgagttctcc 2340
aagataatgc aacagggatt tgcatatctg ccagcaggaa tatgtgtatc aagtatgaat 2400
cgaccagtgt cttatgagca ggccattgct tggaaagttc tcgatgatga tgattccaac 2460
cactgccttg cctttgtgtt catgaactgg tcttttgtct ga 2502

<210> SEQ ID NO 141
<211> LENGTH: 630
<212> TYPE: DNA
<213> ORGANISM: Glycine max

<400> SEQUENCE: 141
atgacaacag cagaagaaac ttcaaacttg gatctcatac gccaacacct attaggggaa 60
aatatcatct cagactcctc ctttttctcc aatctccttc atcatcctat gaaacttgaa 120
gcaccctcat caccagaatt tgatttcacc tcatatatct cagacaacac aagctttttc 180
actttccttg aaggctatga tttgatggca gacatgaaat ttgttgattc agacaacacc 240
atcccttcaa aggaggttaa gaaatgcaat atttctcctg aaccattggt gtcatcaaaa 300
gagaagccaa agaagttaga atacgataag gcaaagcgtt ataggggagt tagaagaagg 360
ccttggggaa aatttgctgc tgaaatccgt gaccctacaa ggaaagggac aagggtttgg 420
cttggaacct ttgacagtga aattgatgca gctaaggcct atgattgtgc tgctttcaag 480
atgagggggc agaaggctat tctgaacttc cctcttgagg ctggactgtc tgatcctaag 540
cctaacagtt gtggcaggaa aaggagaaga gagagccatg atcatgaatt ggagctgcca 600
caagtccaag ttcatcatgg tgtttcctga 630

<210> SEQ ID NO 142
<211> LENGTH: 240
<212> TYPE: DNA
<213> ORGANISM: Glycine max

<400> SEQUENCE: 142
atgtccacca ccgcaactac aacctctgaa gttagcagca atgagtggaa agtcatacac 60
atgagcgagc aagaggagga tctcattcgc aggatgtaca agctagtcgg ggacaagtgg 120
aatttgatag ccggtcgcat tcccagtcgt aaagcagaag aaatagagag attctggatt 180
atgagacacg gtgatgcttt ctctgttaaa agacacagaa gtaaagccca agactcatga 240

<210> SEQ ID NO 143
<211> LENGTH: 1233
<212> TYPE: DNA
<213> ORGANISM: Glycine max

<400> SEQUENCE: 143
atgatggaag agccggttgt ggttaacaaa ggagatgatc atgatcatga tcacgagcct 60
ttggatttgc ctccaggttt caggttccac cccacagatg aagagatcat cacttgttac 120
ctcacagaga aagtcctcaa tagaaccttc agtgcaactg ctattggaga agctgatttc 180
aacaagtgtg agccttggga cttgcccaag aaagcaaaga tgggggagaa agattggtac 240
ttcttttgcc aaagggatag gaagtatcca acaggcatga gaaccaatag agcaacccaa 300

-continued

```
tctgggtatt ggaaggccac tggcaaagac aaagagattt tcaaagggaa gaacaacctt    360

gttgggatga agaagaccct tgttttctat agaggaagag ctcctaaggg tgagaagtca    420

aattgggtta tgcatgaatt cagattggat ggcaaattcg catgttacaa ccttcccaag    480

gcttcaaagg atgaatgggt tgtgtgcaag gttttccaca agggcaacac cactactaca    540

gatgttgtta acaaaagggc actcccaata attaaccctt gccttttgag aatgaactca    600

tcaattggag aagatctatt tgatttctct tctctcccac ctctcgtgga tcctctcttt    660

gaccaaacct caaacaagca cattgacaat gatttcaagg gtactaataa cacgccttca    720

tcttcatcag ctaaaccacc atcaagtggc tactatcttc ccaacttcat caacaacaac    780

aacaatcagc acatgctaat gatgatgaag ccagaagaac acaaaatgta tgagattccc    840

accaacaact atgcctccac cagccaagtg aatttcacta ctactaataa cccaataatg    900

ggaattagca caggcaataa caataccctt ctttctcagc ctcaaattcg aacccaaaat    960

tcaacctcag tacccttcaa catgttccaa gattattata attatatgaa ccaaggaaaa   1020

caatgcaaga tggagcaatt ctcaaacact aagaaccagc ctgtggtcag tgcctctcaa   1080

gacacgtgcc tcagcaatga cacttcctcg gtggtttcta agcaagacaa caacatagga   1140

aggaacaagg cattgtacga ggataatttt gaagctcctt catcagttgc tactaccctc   1200

tcagatttgg aatgcctgtg ggatgattac tga                                1233
```

<210> SEQ ID NO 144
<211> LENGTH: 540
<212> TYPE: DNA
<213> ORGANISM: Glycine max

<400> SEQUENCE: 144

```
atggtagcaa ttctcaagag acagggagaa aacgaatccg aagaaaccat cataggcttg     60

gcaaaaagtc tcatgcaact ctcgcgtgtc caacaacaaa gcaataagcc tcttctcaaa    120

accttttctc caacggagtt cgagtgcaaa acctgtaacc gcaagttttc atcttttcaa    180

gctcttggtg gccacagggc tagccacaag aagcccaagt tcgaagctga agaactcaaa    240

gaagaagcca agaagactaa acccaaaatg cacgagtgtt caatttgtgg catggaattc    300

tctctgggcc aggcactggg gggtcacatg agaaaacaca gaggtgccat tagtgagaac    360

gacaataata atgaagcgtt gtcttctata aagcaagcaa ttgcaaaagc tccggttttg    420

aaacgatcga atagcaagag ggtcatgtgc ttggagatgg acctgaattt gacgcctttg    480

gagaatgact tgaagttgtt gttcggaaac aaggctccta gagtcgatct ttctttgtag    540
```

<210> SEQ ID NO 145
<211> LENGTH: 879
<212> TYPE: DNA
<213> ORGANISM: Glycine max

<400> SEQUENCE: 145

```
atgaagattc agtgcaacgt gtgcgaggcc gcggaggcca aggttctgtg ctgcgcggac     60

gaggcagcac tgtgctggga atgcgacgag aaggttcacg cagcaaacaa gctcgccagc    120

aagcaccaga gggtccctct ctctctctcc gcctctcaca tgcccaagtg tgacatatgc    180

caggaaatgg ttggttattt cttctgttta gaggatcgag ctttgctatg taggaattgt    240

gatgtatcta tacatacagc aaatgcctgt gtctctgatc atcaaaggtt tttgcttact    300

ggtgtgagag taggccttga agctactgag cgcggtgctt cctcgtcttc tgtgaagtca    360

cagtctgggg agaaaatgtc tgatgctaaa tcttcatcca tctccagaaa tgtttcctca    420
```

```
ctgccccagc catcaaatgc caatgaagtg ttacccctcc aaatgcaagg agttgaggag    480

tttccaccaa gcaatttctc aggttatact tctggaaacg tctcacaatg gcccattgaa    540

gaatttctcg gattaaatga actcagtcag tattataatt acatggatgg atcatctaag    600

gctgacagtg gtaaacttgg ggattctgat tcttctgttt tgaggtctgg tgaagaggat    660

atggatgatg acggcttctt gggacgtgtt ccagattcat cctggacagt tcctcagatc    720

ccttcccctc ctacagcttc gggtttatat tggccgaaag tccctcaata tacatctgac    780

agtgccatgt ctgttcctga catatgcttt tctcatgtgc gacagcccca ccatgcccag    840

cataattcta atgtttccaa aaggcgtagg caactataa                           879
```

<210> SEQ ID NO 146
<211> LENGTH: 1224
<212> TYPE: DNA
<213> ORGANISM: Glycine max

<400> SEQUENCE: 146

```
atggaagagc ctattgtggt gaacaaaggt gaggagcctt tagatttgcc tccaggtttc     60

aggttccacc ctaccgatga agagataatc acttattatc tcactgagaa ggtgaagaat    120

agcattttca gtgcaattgc tattggagag gctgatttga acaagtgtga accttgggat    180

ttaccaaaga aagccaagat aggggagaaa gagtggtact tcttctgtca aaaggatagg    240

aagtacccaa ctgggatgag aaccaataga gcaacagaat ctgggtactg gaaggccaca    300

ggaaaagata aggagattta caaagggaaa gggaaccttg tggggatgaa gaagaccctc    360

gtgttctata aagggagagc tccaaagggt gagaagagca attgggtcat gcatgaattc    420

agattggaag gcaaatttgc tagttacaat cttcctaagg cagcaaagga tgaatgggtt    480

gtctcaaggg tttttcacaa gaacacagat gtcaaaaagt cctcaattcc tggccttttg    540

aggataaact ctattgggga tgatcttctt gattattctt cactcccatc tctcatggat    600

cctccttatg gcaacaacac caacaccacc aacaacaaca acaacaatgc taacccactt    660

tcatcaacta aattatcaca atcagagggc tattatcttc ccagtttctc catcaacaac    720

aaccaccacc agcttctcat caagccagaa gaccaccaca accacagaat ctatgaattt    780

cccacaatta acttcacctc caaccaaacc aatctcagca gcaacaacgt taacccaatg    840

gggaacaaca acacactctc atcacagccc ttaaacatgt tctcagctga ttactatgta    900

caccaaaaca ggatcaaaag ctccatcatg ccaagtgttg caggctcagg ttttgttagc    960

gacaacaata accatgatga agctatccta agagcatttg cagccaagaa caacgagcac   1020

atacagtgca agatggagca attttcttct aaccactcac aagacacggg cttgagcaac   1080

gacagaaaca caactgacac atcctcggtg gtttcgatgg gaagaaataa taataatagg   1140

gcactgtacg aggatcttga aggcccttct tcagttgcac ctctctcaga tttggaatgc   1200

ctgcagtggg atgatgacta ctga                                          1224
```

<210> SEQ ID NO 147
<211> LENGTH: 897
<212> TYPE: DNA
<213> ORGANISM: Glycine max

<400> SEQUENCE: 147

```
atggagcggt acaaatgcaa gctctgctcc agaacattct ccaatggcag agccctcggt     60

ggccacatga aggctcactt agccaccctc cctcttcccc cccaaaacca acaaccacca    120
```

-continued

```
ctttctccct ctgctgctgc ttccttctct tctaattcct cttcagaaca agaacaagcc    180

acacacgatg aaaagtccct gatttatggg ttaagagaga atcccaagaa atgcttcagg    240

ctcgcagatc ccgagtttga cacgggctct gtcgttcaag acagggagag cgagaccgag    300

tcaaagaacc caactcgccg acgatccaag cgaacccgaa ggcccgtgaa tttggaacaa    360

aaaaagccca aactgagttt catggagtcg cctgagcccg tgagttcggt ctccgacact    420

tcccccgagg aagatgtcgc catgtgtctc atgatgttgt cgagagaccg atggagtaag    480

aacaacaaca tcaacgttgt taatgttaat gatgaggatg ttgtcgaaga ggaagaagaa    540

gaagaagaag aggaggagga gggtgggaga tcagtactag agataaagtt gaggagagtt    600

cgcgggaagc accagtgtca gagctgcggg aagacgtttc gatcttcacg cgcattgggc    660

agtcacagaa gcatttgcga aggttcgggt aacgatagta aaatcttcca atgccccttt    720

tgttccaagg tgtttgggtc tggtcaagca cttggtggcc acaagagatc tcacctcatg    780

ccttcttctt ccacaaccgc taataatgat tctgttagat tgaaagagag cttcatagat    840

ctcaacttgc cagctccgcc cgaagatgac gaccttagtg ttgtttctga tgcctga       897
```

```
<210> SEQ ID NO 148
<211> LENGTH: 1797
<212> TYPE: DNA
<213> ORGANISM: Glycine max

<400> SEQUENCE: 148
```

```
atgggttcgg tggactgtta tccttctcgt acggacgatg ctgccgtggt gtctttggat     60

tcgctgcctt tagggttccg attccgaccc accgacgagg aactcgtcaa ttactacctg    120

cgacagaaga tcaatggtaa tggtcgccag gtttgggtta tccgagaaat tgatgtctgc    180

aaatgggagc cttgggatat gcccggtttg tcggtggtac agaccaagga tccggaatgg    240

ttctttttct gtccacagga ccggaagtat ccaaatgggc atcgattgaa cagagcgaca    300

aataatgggt attggaaggc aacggggaag gatcgtagaa tcaagtctgg gaaggattta    360

attggaatga agaagacttt ggtgttctac actggtcgtg cacccaaagg gaataggacc    420

aattgggtta tgcacgagta tcgtcccact ttgaaggagc ttgatggtac taatcctgga    480

cagaatccat atgtcctttg tcgtttgttt aagaaacatg atgagagcct tgaagtttca    540

cactgtgatg aagcagagca gactgcttcc actcctgtgg cttactccac agaggaaata    600

caatctgatc tggctgttgt tgcaggatcc ccctcacaag ttaccgaaga tgataagcac    660

caggcaatga tccctgcaca ctctgaggaa gcaatatcca atgttgtaac cccggttgtt    720

tgccgtagtg acagatatga tgcttgtcat gcaccaaatc aaattgtatt accaactgcg    780

gaggagtttc aaccattgaa ctattatgac ccaagaaacg agctattgga tgataaatta    840

ttctcccctg tacttgcaca tattcaacca gaatttcatt atcaagcaaa catcgaatca    900

gatgattggt atgggcttca atatggtaca aatgagacaa acatgtcaga ctttttgaat    960

tcagttgtga attgggatca agtatccttt gaggatctca attgtcaaca gcagagctac   1020

cccttgttta atgttaagga tagcgtatta agcagcgatc tagattctga acttgccatt   1080

atgacatgta tgcatgctgg ttctgcggag gggccaaata acggaaggaa acctttggtg   1140

ataacttcag aatttcgcag caccactggc atccctgttg actgtggtgg tgacgagcaa   1200

aaaagcaatg ttgggttatt tcaaaacaat tcccagagag cttttactga tgttaatata   1260

ggccaagtat ataatgtagt cgatgattat gagcaacgag gaatctacag tgcagttgct   1320

agtggcaata ctggaatcat taggaggcat cgtgaggtac aaaatgaaca gctaagctca   1380
```

aattcaaccc aaggtactgc acagagaaga attcgtttgt caatggctac acatggctca 1440
aataagatgg tgaaaagtgg aagttgtgca caagaagagc ttaatttaaa atccgtcatt 1500
gctatggagg agaaagcttc agaaagccat atttctgatg aaagttctac tcttactaat 1560
gacgggaatg aactgccgaa gacatccaaa tcatccggca aaagaaagat ttctcgacaa 1620
gctacaaaag caggctcaac cttggggttg aaagactttt tattgctcag aagggtgcct 1680
tacatttcga aggcttcctc aaatcgtgcc aagtgctctt ctgtttttgt agtttctgcc 1740
tttgtaatgg tcaccttagt ggtctttact gacatctggg gatatcttaa attttaa 1797

<210> SEQ ID NO 149
<211> LENGTH: 876
<212> TYPE: DNA
<213> ORGANISM: Glycine max

<400> SEQUENCE: 149
atgaagggag aattagagtt gccacctggg ttcagatttc accccactga tgaagaattg 60
gtgaatcact acttgtgtag gaagtgcgct ggtcaaccaa tcgcggttcc cgtcatcaaa 120
gaggtcgatt tgtacaagtt tgatccatgg cagcttccag aaattggttt ttacggcgag 180
aaagaatggt acttcttttc tcctcgggac cggaaatacc cgaacggttc acggccgaac 240
cgcgccgccg gaagcggcta ttggaaagcc accggcgctg ataaaccgat cggaaaaccg 300
aaagcgcttg ggatcaagaa agctctggtt ttttacgccg gaaaagcccc caaaggtgtg 360
aaaaccaatt ggattatgca cgaatatcgc ctcgccaatg ttgaccgatc tgcctccaag 420
aaaaaaaaca acaacttgag gcttgatgat tgggtgttgt gtcgaatcta caacaagaaa 480
gggaagattg agaaatacaa cacaggcgca gcgaagatga atgttgagat ggttcatagt 540
tttgagcacg agaacgagac gaagccagag attcataagc taggaaatga gcaattgtac 600
atggagactt cggattcggt gccaaggttg aacacggact cgagcagttc ggagcacgtg 660
gtttcgcccg atgtcacgtg cgagagggag gtgcagagcg accccaagtg gaacgatgat 720
ctggacctaa agctagaaaa cgcgtttgat tttcagttta attacttgga cgataataac 780
ctttccgtgg atgattacct ttttggcact gttcagtatc aaatgggcca gctctcgccc 840
ttgcaggaca tgttcatgta cctacagaag atgtga 876

<210> SEQ ID NO 150
<211> LENGTH: 1440
<212> TYPE: DNA
<213> ORGANISM: Glycine max

<400> SEQUENCE: 150
atgggtcgcg aaactatgtg cctttcaacc ccaccaccaa ccactgccac caccacagtg 60
aacccagtgc cgccaccgcc accagcacca cctacctctc ttgctccagg cttcaggttc 120
cacccaactg atgaggagct tgttatttat tacctcaagc gcaaggtttc tggcaaaagc 180
ttccgatttg atgccatatc tgaggttgac atatacagga gcgaaccctg ggacctagca 240
gacaagtcaa ggttgaagac tagggaccag gagtggtatt ttttcagtgc attggacaag 300
aaatatggga atggtgggag gatgaacagg gctaccagca aagggtactg gaaagccact 360
gggaatgatc gaccggtgag gcatgaccaa aggaccgtgg ggctgaagaa aacgttggtg 420
tttcatagtg gcagagctcc tgatgggaag aggactaact gggtcatgca tgagtacagg 480
cttgttgaag aggagcttga gagggctggg actggatcct gtcagcctca gaaggatgcg 540

-continued

```
tatgttttgt gtagagtgtt tcacaaaaat aacataggac ctccaaatgg gcaacggtat    600

gcgcccttca ttgaagaaga gtgggatgac gcatcaggaa tggttccagg ggcagaccat    660

gtggataacc gctcttttgc ccaccaacca cgtgttgaag gcaatggtga tgttgtcatc    720

gaagttctga tatgttgcca atcgcaagta gagctactgg tgcatgtaag ccacaagctg    780

ccatcttgtc ttttgttcat gatcgcgctg ccacaaaatc aacaacccat tgacactcaa    840

tctttcaaca aagctccatt tgatgtgaac aagcttccta tagaaactca aaatcttcta    900

gctgatgata ataattgtaa gcacatggat gactaccctt cacctcaaac agataatcca    960

aagcctttct ctcaaatata caaacgaagg cgtcataact tgaactccaa caactctaat   1020

gtttctggag attcagtccg aaccagccag gatccgtgct cctctacaat aactaccgct   1080

gcaactgcac tcccaaccgc aactgttgct ggcacagcca ccaacactgc accgaaaaaa   1140

cattttctgt ctgcactggt ggagttttcc ctgctagaat cccttgaatc aaaggacaac   1200

cttgcttcaa ttaaggcacc ggattttgac actgaaaatc tcgagtcatc catgcctcca   1260

agttgcgcaa agttcatcaa gcaaatgcag agtgagatgc agaagctttc agttgaaaag   1320

gagacgataa ggtttgagat gatgagcgca caagcgatga ttaacattct ccagtctcgc   1380

atcgacgttc tcagcaaaga aaatgaggat ttgaagagga tggtggccca aaatccatag   1440
```

<210> SEQ ID NO 151
<211> LENGTH: 3339
<212> TYPE: DNA
<213> ORGANISM: Glycine max

<400> SEQUENCE: 151

```
atgaaggctc ctcccagtgg ttacttgcct aattctggcg aaggggaaag gaagaccatc     60

aattcagagt tatggcatgc ttgtgctgga ccactggttt ctttacctcc tgttggaagt    120

cttgtggttt acttccctca aggacacagt gagcaagttg cagcatccat gcaaaaggag    180

gctgacttca tacccagtta tcctaacctt ccatccaagt tgatttgcat gcttcacaat    240

gttgccctgc acgctgatcc tgaaactgat gaagtctatg cacagatgac ccttcaacct    300

gtaaataaat atgacaagga agcaatattg gcatcagaca tgggtctcaa acaaaaccaa    360

caacctactg agttcttttg caaaactctt acagctagtg acacaagcac ccatggtgga    420

ttttctgtgc ctcgtagagc agctgagaaa atattccctc ctctggattt ttctatgcaa    480

cctccagctc aggagattgt agccaaagat ttgcatgaca atacatggac atttagacat    540

atttatcgcg gacaaccaaa gaggcatcta ctgacgactg gttggagtgt ctttgttagc    600

actaaaaggc tgtttgctgg agattcagtt ctttttatta gagatgaaaa acaacaactt    660

cttttaggta taaagagggc taatagacag cagccagcac tatcttcatc agtaatatcc    720

agtgacagta tgcatattgg cattcttgct gctgcagctc atgcagcttc aaataacagc    780

ccatttacta tattttataa tccaagggcc agcccttctg aatttgtaat cccatcggcc    840

aagtataata aggccttgta caatcacgct tcccttggaa tgagattcag aatgatgttt    900

gagactgagg agtcaggggt acgcagatat atgggtacaa tcactggtat cactgatgtg    960

gatcctgtcc gatggaagaa ttcacagtgg cgcaatcttc aggttggatg ggatgaatcg   1020

acagctggtg agcgcccgag cagggtttca atttgggata ttgaaccagt ggtgactcct   1080

ttctatattt gtcctcctcc atttttcagg cccaagttcc ccaaggagcc aggaatgcca   1140

gatgatgagt ctgatataga aaatgctttc aagagagcaa tgccttggct tggagatgac   1200

cttggcatga aggatgcctc tagttcagtc ttccctggtt ttagtttgat gcaatggatg   1260
```

agcatgcagc agaataatca gttctctgct gcccaatctg gatttatacc cccatccatg 1320
ctttcatcca atgcactgca tggtaacctt accactgatg atccatccaa attattgagc 1380
tttcaagctc ctgtcctctc ttcaccaaat cttcaattta acaaacctaa tttagcaaac 1440
caagtcaacc aattgcaaca atccccaacg tcatggcctc cgcagcagca gcagcaacag 1500
cagaagctgc agtcaatgtt gcaaacaccc ttaaacccac tccagcagca gcagcaacag 1560
aggcaacagc agctgcctca acagccccaa atgcctcaac agagagcaca acagccacaa 1620
caacagcaac agcagtcgtg tcaacagacc atcatgagta acgggacagt tgcttctaac 1680
cagattccaa atcagtgtgt acaacaacca gtaacatact cacaacttca gcaacaacaa 1740
ttactctcag gaagtatccc accccaacaa agttttcaat cacccaataa gaatgcattg 1800
ttgatgacat ccttaccaca agactcacag tttcagcaac aaatagacca gcaagctagt 1860
ctcttacaga ggcagcagca gcagcagaca cagttgcaat catctccgtt gcagttattg 1920
caacaaagct tgtcacagag ggcatcacag caaccacaaa tgactcaaat gtgtcagcaa 1980
aacagctcag agcaacaacc acagttgcag ttgctacaaa aattgcagca acagcagcag 2040
cagcagcaac aacaacaaca gcaacaactc ctttccactt ctagcccact tttgcagtct 2100
cagcttctac atcaacaaaa tactcatcaa caaaaccagc aattgccgca gctgcctcta 2160
tcacagggtc atcagcctca acagcttgga aacaatgctt tctcaatgga gaagcttctc 2220
aatggaaaca actactctac ttcatctctg atgcaaacac agcagctttc tgtgaaccaa 2280
ccccataata cacagaaatc actgactaat actagagctc cctctactct tacagatgga 2340
gatgccccat catgctcaac ttcaccatct actaataatt gccagatatc tccaaatctg 2400
atgaaaagaa atcaacatgt accggcaaca ttaggaggac cttcagtact tgaacccacc 2460
aatcatctga tgcagggact tcatagcaag tctgagatgc agatcaaaca tgaattacct 2520
agtgtaagag gaactgatca gctgaagttc aaagggacag ttgctgatca gatggaagct 2580
tcttctggaa catcttactg tattgatcct aataatatcc accagaactt cccacttccc 2640
aacttctgca tggatgggga tgtccaatca aacccaagaa acaatcttcc atttgcctct 2700
aatcttgatg gattaacacc tgatactttt ctctcaagag ggtatgattc tcaaaaggat 2760
cttcaaaact tgctgtctaa ttatggtggt gctccaagag acattgaaac tgagctgtcc 2820
actgctgctc ttagtccaca gccgtttggg gtgccaggca ttccttttaa gcctggatgc 2880
tcaagtgata ttgccatcaa tgatcctggg gttttgaata atggcttgtg ggctaatcag 2940
actcaacgaa tgcgaacata tactaaggtt caaaaatgtg gctctgttgg aagatgtatt 3000
gatgtcaccc gttacaaggg gtatgatgaa ctccggcatg atttggctcg gatgtttggg 3060
attgaagggc agctagaaga tcctcaaagg actgagtgga aactagtata tgtcgatcat 3120
gaaaatgaca ttcttcttgt tggtgatgac ccttgggaag aatttgtaag ctgtgtccag 3180
agcataaaga tattgtcatc tgctgaggta cagaaaatga gcttggatgg ggatttaggt 3240
catgttccag tccccaatca agcttgtagt ggaacagata acggcaatgc atggagggga 3300
cagtatgagg ataactcggc agcctcattt aatcgataa 3339

<210> SEQ ID NO 152
<211> LENGTH: 453
<212> TYPE: DNA
<213> ORGANISM: Glycine max

<400> SEQUENCE: 152
atgtcctccc aatctgacgc cgttggctgt aacttgaagg agacggagct caccttaggc 60
cttcccggca ccaaaactaa tggcacaaaa cgtggcttct ccgacaccct taacacttct 120
cataataaaa tgttgcgccc cacctccaag gaacaagtgg tggggtggcc gccggtgagg 180
gcaagcagga aaaatgctat gaagatgagt tgcaagttgg tgaaggtggc ggtggatgga 240
gctccttatc taagaaaagt ggatcttgaa atgtacgaga cttatgagca tttgatgagg 300
gaattagaga ccatgttttg tggcttagcc attcgtaatc atttgatgaa tgagaggaaa 360
ctgatggagt ctggaaatgg gattgaatac atgcccacct atgaggacaa agatggtgac 420
tggatgttgg tcggggatgt accctggaag taa 453

<210> SEQ ID NO 153
<211> LENGTH: 1371
<212> TYPE: DNA
<213> ORGANISM: Glycine max

<400> SEQUENCE: 153
atgagtgatg caaaagaaaa cgaggaagct ggccaggggg tgccctcggt cgtggaagaa 60
aaccagcagt tggttgatgc agaggttcaa gatcaacctg aagctgcctc tgctcctgtt 120
ccagtagagg aaacttcaaa tcatgttgaa attgggtcag atcatgttga aaatacgaag 180
gaagagccac ctgctgagga taaaaatgta gaattagagg ttgtttcaga gggaattcca 240
caagatgttc aaaatactct tctctctgtc ccagtagagg ctgatgctca aattttggat 300
aggactgagt ctgaagaagc tgaagcttct ggtgcgaagg tggaggctga tgaattacca 360
cagaataata aggaggctga gaataatgat gatattcatc aaaaaagtaa tggcgatgtt 420
gagatggctg tggaggttaa gcctgaagac tgtggaatgg ctgatagtaa agcatgtgat 480
aatggtgacc ctgtgcttgc aagtcataat gagcctgcta cgccacagcc tgctcctgca 540
gatacaaaca ctgaaattat gaatgtatta gaagttgaga ataaggttga tgaaaagcaa 600
gtggctgaac ctgcagataa cgggaattca aactcaaagc acatgctttt cttggatgcc 660
gaccattcct atgatggtaa tgagtcagga acagaggaag aacagtcagc atttatgaag 720
gagcttgaaa acttctttag ggagaggagc atggaattca aacctcccaa attctacgga 780
gaaggactaa attgccttaa gctgtggaga gctgtaacga gattgggcgg ctatgacaag 840
gtgacttcat gtaaattatg gcggcaagtg ggagagtctt tcaaacctcc gaagacatgc 900
accactgtct catggacttt tcggggattt tatgagaagg cacttcttga ttatgaaaga 960
cataaaatac aaggtggtga gctgaatgtg cctgttgctt ctcatccaga gcctataaat 1020
attgaaaatc aggcctcagc atcaggtaga gcccggagag atgctgcagc acgggctatg 1080
cagggttggc actcacaacg tctcctaggc aatggtgaag ttagtgaccc tattattaag 1140
gataggaatt ctgtgtctgt gcaaaagcgt gaaaagcagc ttaaaagcat caatatacac 1200
aaacgaaaga agccatcttc accttacatg gataatgcag tcaaagctgc acgcagtaaa 1260
ccatctaaac cacaattgga cacaactgtg attgatattg ggcctcctgc tgattgggta 1320
aaagtgaatg tacaaaaaac tgtaagttct ctatcttgtt caaataaatg a 1371

<210> SEQ ID NO 154
<211> LENGTH: 846
<212> TYPE: DNA
<213> ORGANISM: Glycine max

<400> SEQUENCE: 154
atggagggga tggctcccaa ttcatgtgca aggccagttc tagagaaaaa aacaaggcca 60

```
caagagcaac tgaattgtcc aaggtgcaat tcaaccaaca caaagttctg ttattacaac    120

aactacagcc tcacacagcc aagatacttc tgcaagactt gtagaaggta ttggacagaa    180

ggagggtctc tgagaaacgt tccagttgga ggtggttcaa gaaagaacaa gaaggtctct    240

gtgacagctt catcatcatc atcaccaaag gttccagacc taaacccacc aattaacctc    300

tcatcagtct cagctatctc ctcacaaaac cctaaaataa tgcatggtgg ccaagatctc    360

aacctggctt tcccagctat ggaaaagtac catcatggca tgccacctta tgttgagatg    420

caaaacagtg acaccaccac cactcatcat catcaccaaa cctcttcttc ttgttctgct    480

cctccagctt ctctttcagc tcttgagcta cttaggtcaa gcatggcatc taggggtttg    540

aacccttatg ctccttcttc ttccttgatg ccaaactcaa caaacagcaa tgccctttac    600

tcatcagggt ttcccatgca agaagttaaa cctagtctta acttttcttc agctgatggg    660

atgggaaata gatcatatga tcatcatcag attcaagaga ggggtggtgg cagacttttg    720

ttccctttttg gagatgtcaa gcagctttct gctgctgcag gtgctgatca agtggaacac    780

aataaagaac aacaagggaa ttcaactggt tattggactg gaatgattgg tgaaggaacg    840

tggtaa                                                               846
```

```
<210> SEQ ID NO 155
<211> LENGTH: 1011
<212> TYPE: DNA
<213> ORGANISM: Glycine max

<400> SEQUENCE: 155

atgggaaggc aaccttgctg tgacaaagtg ggggttgaaga aggggccatg gaccgcagag     60

gaggataaga aactcatcaa tttcatcctc actaatggcc aatgttgctg gagagctgtc    120

cctaaactag cagggctgtt aaggtgtggc aaaagttgca ggctcaggtg gacaaattat    180

ctgaggccag acttgaagag aggccttcta tcagaatatg aagagaaaat ggtcattgat    240

ctccatgctc aacttggcaa tagatggtct aagattgctt ctcatctccc aggaagaact    300

gataatgaga tcaagaatca ctggaacacc cacataaaga aaaagctcaa gaaaatggga    360

attgatcctg ttactcacaa gccactttcc aataaaactg agcaaactca agcccaacca    420

gatgaacaac aaacccacca accattgcaa gaacaacaag aagaacctat cccagttgag    480

aaagacacca aatttgaacc tgaaaaagag caaaacaagg agccagagaa gccagagagt    540

tcaattgaat cattaaccat cactgaagaa gccaaggagg aagaccaaat tatgacaccc    600

ttatttgact catgggaact aatgaatgag ttctgcactg atgaagttcc cataatagaa    660

tcaaatgaga ttctagttcc ttctgctcct tcttccactt caccaaccac tactactact    720

acatcatctt caacatcaac atcagcatct tcaaattcaa attcatccaa cttccttgaa    780

gaccttctgc tcccagattt tgagtggtct gatgattaca atgatactaa ttttgacaat    840

aataacaata gcagcatggc cttgtgggat gatgacttta ttagaagttg gaatttgctt    900

attaatgatg atgatggtga tggtgacaga aagcaagtgt ttgaggctcc tatcaatcag    960

tacccaagag tgatcatgga ttcagattct tgggcctatg gcttgttttg a            1011
```

```
<210> SEQ ID NO 156
<211> LENGTH: 1017
<212> TYPE: DNA
<213> ORGANISM: Glycine max

<400> SEQUENCE: 156
```

-continued

```
atggtttgca ctgccaatga tttacaagga tggaaagatt tcccaaaggg acttagagtt     60
cttctgcttg aaggagatag tagttctgct gctgagataa gagaacaact tgaggccatg    120
gactataagg tttccacttt ctacgacgag aatgaagcct tgtcagcact ctcaagtagt    180
cctaaaggct tccatgttgc catagtggag gtgagtacaa gctgtagcct tggaggtttc    240
aaatttcttg agaatgcaaa ggacttgcct accattatga cttcaaagga ccagtgtctg    300
aacaccatga tgaagtgcat tgcgcttggt gcagttgagt ttctcagtaa accactctct    360
gaggacaagc tcaagaatat ttggcagcat gttgttcaca aggtagactg gacacctgag    420
ctgcataaaa aatttgtaaa ggctgtcgaa caactaggta ttgatcaagc cattccttct    480
agaatattgg agataatgaa agtggaaggt ttgacaaggc acaatgtggc aagccatctt    540
cagaaatata gaatacacaa gagacaaagt gcacccaggg aagaagatcg gaaatggcat    600
aatcaagggg atgcaatgca aaggaactat tatatgcaaa gaccaatcat ggcatacccct    660
ccatatcatt cacatcacac cctttctcca gctcctatat atcctatgtg gggacaacct    720
ggcagtcaaa cagccggtgt acagatttgg ggccatcctg gttatcccat gtggcatcct    780
acagaaagtt ggcactggaa gccttatccg gggggtgcatg tggatgcttg gggatgcccg    840
ttggtgccac ctcctcaagc tccttgtttt ccctacaatc aaaatacacc tggattgcac    900
aatcctaaag cagttgacta tagattcagc atgccacgaa gttcctttga gcatcatccg    960
gtaaggcagt actttccttt cagttccttc taccatgtca tgaatttttt tctctag      1017
```

```
<210> SEQ ID NO 157
<211> LENGTH: 582
<212> TYPE: DNA
<213> ORGANISM: Glycine max

<400> SEQUENCE: 157
```

```
atgcaggcca gggagatcac aggactcaat tatttactcc ctccagaccc ttgtttcaac     60
tacagcatgg ttcagaacac catccccaca tttcaactcc acaaactctc aaaccaattc    120
tatggtttgc agaaacctcc tcctcaagtg cttgcagact tcagcccccc tcagtcctca    180
tgcatcagca gcaactcaac ctctgatgaa gcagatgagc agcagcaaag cctcatcaat    240
gagaggaagc acaggaggat gatatcgaac cgcgaatcgg cacgccggtc acgcatgagg    300
aagcagaagc accttgatga gctgtggtca caggtggttt ggctcaggaa tgaaaatcac    360
cagctcatgg acaagctgaa ccatgtgtct gagtcacatg ataaagttgc tcaagagaat    420
gttcagctga gagaagaagc ctcagaactt cgccaaatga tatgtgacat gcagctacac    480
agtccatacc accctcctcc cttgagtccc attgatgatg atgtttctcc ctatgtcaaa    540
tctgattcct caatcacaga ctctttggac ctgcttggtt ga                       582
```

```
<210> SEQ ID NO 158
<211> LENGTH: 585
<212> TYPE: DNA
<213> ORGANISM: Glycine max

<400> SEQUENCE: 158
```

```
atgtgtggcg gagcaatcat cgcagatttc atacctcggc agcgtccccg caccctcaca     60
gcctccgaac tctggcccaa gcgcagcgaa cctcaacctc aacctcctcc tcctccagtt    120
aagaggcaga ggaaaaacct ctacagaggg atcaggcagc ggccctgggg caaatgggcc    180
gcggagattc gcgatccacg taaaggagtt cgtgtctggc ttggcacctt caacaccgcc    240
gaagaagccg ccagagccta cgacaaagaa gcccgaaaaa tccgcggcaa gaaagccaaa    300
```

gtcaatttcc ccaacgagga cgaccctctg ccgcaatacg gatcttgcaa gagcctcaac 360
ttggagttcg gttacgatct caaccaaaca gggcttttcc cttcttctaa cgctgatgag 420
aattgcgggt cccacgtggc ttactccgtt acggaagcca acaacaaagt agagaagctt 480
tccgaggagc ttatggcgta cgagaattta atgaggtttt atcagattcc ggaaaacgtc 540
gttggggatt tgtgggcctt tcctgacacc tctccacctc tctga 585

<210> SEQ ID NO 159
<211> LENGTH: 696
<212> TYPE: DNA
<213> ORGANISM: Glycine max

<400> SEQUENCE: 159
atgaaggtgc atcagttcgc acgtggattc tgggagcacg aaccctccct cacactcggg 60
tgcaaacgct tacgcccccct tgcccccaag ctttccaaca ccgacaccat ttctccacct 120
catcatcctg ttacaacctt cgacctcaag agcttcatca aacctgaaag tgcctccaga 180
aaacttggaa ttggatcctc cgatgataat actaataaga gagacccatc ttcaccccag 240
ggccaggctg aaacgcatat tccaggaggg acacggtgga atccgactca agaacaaata 300
gggatattgg agatgctgta cagaggaggg atgcgaactc cgaatgctca acaaatagag 360
cagatcacag cacagcttag caagtacggc aagatcgaag ggaagaacgt gttctattgg 420
ttccaaaacc acaaagcacg cgagagacag aagcagaagc gtaacaacct aggccttgct 480
catagtcctc gtactactct caccacttca cccccccttta gttgttgtgt aattaccact 540
atggacacca caaaacgggg ggaagtagta gaaagagagg aggaagatag cccgttgaag 600
aagtgtagga gctgggcgtt tgagtacttg gaagaccaaa gagaggagga acatagaact 660
ctggagcttt tcccattgca cccggaaggc agatga 696

<210> SEQ ID NO 160
<211> LENGTH: 1980
<212> TYPE: DNA
<213> ORGANISM: Glycine max

<400> SEQUENCE: 160
atgattacat tcatggacac aaaagagaaa ttaaaggagg tggagaggtg tttggatcct 60
cagctatggc atgcgtgtgc aggtggtatg gtacaaatgc caacagtgaa cactaaggtc 120
tattacttcc ctcaaggtca tgctgagcat gcatgtggac cagttaactt caagacttgt 180
cctaaggttc cacctttttgt tccatgtaga gtggttgctg tcaaatacat ggctgatcct 240
gagacagatg aggtctatgc caaactcaag ctcgttcctc tgaatgccaa tgatgttgat 300
tatgaccatg atgttattgg ggctgaaact cgagacaagc cagcttcatt tgcaaaaacc 360
ttgacccaat ctgatgctaa caatggtggg ggattttctg ttcctaggta ttgtgctgag 420
acaattttcc ctcgtttgga ctactcagct gaccctcccg ttcaaaacat ccttgccaag 480
gatgttcatg gggaaacatg gaaattcaga cacatctata ggggcacgcc aaggcgacat 540
ttgttgacca ctgggtggag tacttttgtg aatcacaaga agcttgttgc tggggactca 600
attgtgtttt tgagggcaga aaatggggat ttgtgtgttg gtattcggcg agcaaagaag 660
gggattggcg gtggacttga gacttcctca gggtggaatc ctgcaggagg aaattttcct 720
atgccttata gtggattttc tcccttttttg agggaggatg ataatagaat cttgagaaat 780
ggcaatagca atggattgaa ccctagtgta agtatgatgg gaaagggaaa agtgaggcca 840

```
gaagcaatta ttgaagctgc aaatcttgca gccaataaga aaccctttga ggttgtttac    900

taccctcggg caagtactcc cgagttttgt gtgaaggcct cactagttga agcagcaatg    960

cagactaggt ggtattctgg aataaggttc aagatggcct ttgaaacgga agactcctcg   1020

cgaataagtt ggtttatggg aactatatct tcggttcagg ttgctgatcc cctaaactgg   1080

cctaactcac cttggaggct tctccaggtt acatgggatg aaccagattt acttcaaaat   1140

gtgagaaggg tgagcccgtg gctggttgaa ttggtgtcaa acatgcctgc cattcatttt   1200

tcccctttct caccaccacg gaagaaattg agattgcctc agcacccaga tttccccctt   1260

gatggccaga ttcctttgcc gacacttccc aacaaccttc taggtcccaa caacaccaac   1320

caatttggtt gtctactcga aagtactcct gctggcatgc agggagccag gcatgctcat   1380

tatggtctat ccttatcgga tctccacctc agtaaattgc aatcaggtct atcttcggct   1440

ggtttcccgc ctcttgatca cgctgctacg ccaatgaagg tctcaaataa cagacattgc   1500

aaaagcctag catcaatctg tccgagcagc tctgttgata cactctcccc agttcttacc   1560

agaaattgtt cgacagatgg aaatgtcaat aaagtgacta atttttttga tggttttgga   1620

tcagctcttc atcagcaagg tttacacgaa cactcctctt gtgagaggtt ccagtggtgt   1680

aaggataatc accaagaaat tgaggccaat atggagactg gccattgtaa agtttttatg   1740

gagtccgaag atgtaggccg aactatggac ctatcgttgc ttcgatctta cgatgaatta   1800

catagaaagt tggcagacat gtttggcata gaaaaatctg aaatgttaag tagggtgctt   1860

tactgcgatt cagttggggc tatcaaacac attggtgatg agccattcag tgacttcaca   1920

agaacagcca aaaggttgac tattctaatg gattctggca gcaacaatgt aggagtgtag   1980
```

```
<210> SEQ ID NO 161
<211> LENGTH: 2535
<212> TYPE: DNA
<213> ORGANISM: Glycine max

<400> SEQUENCE: 161

atgaagcttt caacatcagg gttggggcag cagggacatg aaggagggga gaagaagtgt     60

ctgaattctg agctatggca tgcatgtgcg gggcccctgg tgtccctacc aactgcaggg    120

actcgtgtgg tttacttccc tcagggtcat agtgagcagg ttgctgcaac aactaataga    180

gaaattgatg gacatattcc caattatcct agcttgccac cccagttgat ttgccaactt    240

cacaatatta caatgcatgc agatgttgaa acggatgaag tatatgctca aatgacattg    300

cagccattga ctccgcaaga gcagaaggat acatttcttc ctatggaatt gggcattcct    360

agtaagcagc catcaaatta tttttgcaag acgttaacag ccagcgacac cagcacacat    420

gggggattct ctgttcctcg tcgtgcagct gagaaagttt tccctccact ggatttctcg    480

cagcaaccgc cggcacagga actaattgct agggatctcc atgatgttga atggaaattt    540

cgacatattt ttcgaggaca gccaaaacga caccttctta ctacaggctg gagtatattt    600

gttagtgcca agagacttgt ggctggagat tctgtgcttt tcatatggaa tgagaagaat    660

caacttcttt tgggaatacg tcgtgccaat cgaccgcaaa ctgtaatgcc gtcatctgtt    720

ctatccagtg atagcatgca tattggactt cttgcagccg ctgcccatgc tgcagcaacc    780

aatagctgtt ttaccgtatt ttataatcca agggctagtc catctgagtt cgtcatacca    840

ctttcaaaat atatcaaagc tgtgtaccat acacgtattt ctgttggtat gcgtttcagg    900

atgctttttg agactgaaga gtcaagtgtc cgcaggtata tgggtacaat aactggcata    960

agtgatttgg attctgttag gtggccgaat tctcattggc gctctgtcaa ggttggttgg   1020
```

```
gatgaatcaa cagctggaga gagacaacca cgagtgtctc tgtgggaaat tgagccatta   1080

acaacattcc cgatgtatcc gtcattattt cccctcagac tgaagcgtcc atggcatcct   1140

ggcacctcat ctttgcatga tgggagagat gaagctacta acgggttaat gtggctgaga   1200

ggtggacctg tagaccaagg tctcaattcc ctaaattttc aaggagctgg cggtatgttg   1260

ccctggatgc agcagagact ggatccaact ttactaggaa atgatcagaa tcaacagtac   1320

caagccatgt tggcagctgg tttacagaac ttaggtagtg gatatctcat gaagcaacaa   1380

ttgatgaatt ttcagcagcc ttaccactat cttcaacaat ctggaaacag taattctcct   1440

ttgcaacttc agcagcagca accaattcaa caatccgtgt cttctaacat gctgcagcca   1500

caaacacatg tactgacaga gaacctatct cagcacctcc ttcagaaacc acataacaat   1560

caagaagtcc aggcacaaca gcagcaacat acttatcaag actcgctctc aattctgggt   1620

gatcagctcc atcagagaca acactctggc attccttcat catcatattc aaaaccggat   1680

ttcttggatt cgagcatgaa gttccctgct tcagtttccc ctgggcaaaa catgcttagt   1740

tcactttgtc ccgaaggaag tggcagtctc ttgaatttat ccaggagtgg tcagtccttg   1800

ctgaccgaac agttacccca acagcaatgg actcaaaaat atgcacctgt gcaggtcaat   1860

gcctatggaa gcactgtgtc acatccacaa tattccggaa aagattctgt aatggtgcta   1920

ccacattgta actcagatgc ccaaaattct actcttttg gtgtcaatat cgattcatct   1980

ggccttctcc tccccaccac cgtccctggt tacaccacct cgtccgctga cactaattca   2040

tcaacaatgc cattagcgga gtctggtttc cagggttctc tatatggttg catgcaagat   2100

tcatcggagt tgttgcaaag tgcagggcat actgacccag aaaaccagac tcaaaccttt   2160

gtcaaggttt acaaatcagg gtcagttgga cgctcacttg acatatcccg gttcagcagc   2220

tatcatgaac tgcgtgagga gttggctcag atgtttggaa ttgaggggaa gttagaagac   2280

cctcttagat caggctggca gcttgtgttc gtcgacaggg agaacgatgt tcttctcctt   2340

ggagatgatc cgtgggaatc atttgtcaat aatgtttggt atatcaaaat actttcacct   2400

gaagacattc agaaaatggg ggatcaagcg gtagaatccc ttgctctagg ttcaggacaa   2460

aggctaaacg gcactggtgc tgagtctcag gacattgttt ctggaccacc atcaatcggc   2520

tcacttgagt actga                                                    2535
```

<210> SEQ ID NO 162
<211> LENGTH: 3387
<212> TYPE: DNA
<213> ORGANISM: Glycine max

<400> SEQUENCE: 162

```
atgaagcttg atccatccaa accacccttt tcttatgacc aacattggcc ctatgccggc     60

aattttgggc accctacttc cccacatttc tgctgtggcc acaacaactt cccttgtcat    120

tatagctaca tgccttcata tcctcatgcc ccttctccaa tgtactattc tggaacttgt    180

ccttcatata gtgaaccata ttttgttcgt tattccccac aaccacatta taccatggag    240

ctgcctaggt atgaaaatga caaatgcatg ccccgagagc ttcattgttc tggttctgct    300

aatcatccat gcaaccaaaa ggaaggtaga agtgtgaaga ttgaagagca tgaactggat    360

ggtggaaaga aagagaatga tgctttggtc ccaattcagc tcaagaatta tccatatccc    420

ttagtttgga ttccacagga gtacacaagt aacaaacagc tgaaaaatcc tagtacaatg    480

gaagttcgtg aacaaaacaa gccttctagt cttgagaatt ctaatgttga tgcacagcca    540
```

-continued

```
acacaggagc ctatagtatg gaatggatgg cttcccttca atataaaggg tgcccggaac    600
atgattcacg atggatatgg aacaagaaac cagaaacagg agtctggcaa taatagaggg    660
gaatctgaaa atggaaaaat agaccagaaa catcaaagtg aacagaagag gtcagaattc    720
ccattcccta tcttctggtt gccttattac aataagcagg aggagagtgg agagactaag    780
aaccaggaga aaaacatttc ttcaccaaaa attgttgagg aggtacccca tacattcaaa    840
tttgttccag tgaagtctca tgttgatgaa ggtggtagga acggaaccgg atcaaatcaa    900
gctgatcaat ccacaaatac aaatgcttct tcggatgctg tagagaaagt gaataatgcc    960
agaagcatac ctgtgaagca gatagaatcc cacgaaggaa aaaatgtttc tctcgatcaa   1020
atggaagaga atgtgacaca aaaggactct tgcactgggg acaaaaagag acaatctaca   1080
tcttcaccta aaggatccaa gttacctccg gtttgtctga gagttgatcc actaccaagg   1140
aagaaaaatg gcctcgggag ttcgagttcg aggtccccaa gtccaccttc atcaaaaggg   1200
aattcccaag ctacaactgg tgaaacattc aagactcctg tgagtggcac acgtgacaag   1260
gctcagccaa atttgaatca tcagaatgct ccaaacacca gtgagaaagt taaaccaaag   1320
gagaacacca ttccggtgtc agaatgcatg actaatgaaa acaagggtgt tgactgtagg   1380
gatggatgtc agagccagat gaaagtaaac atacccagta aaggtctgaa aggggcaagg   1440
gaaacatgtc cagatgatga tgactataag actgaagata aaaaggcaga gaaaggagca   1500
gaaaatatga tggaggaaac tactgaatca agggaagaga aggattcaag cacacgaact   1560
gatgcaggtc gaaaagatgg aagagttttg tcagatgcag atgctgctgt tttgatacaa   1620
gctgcatatc gcagttatct agttagaaaa tgggaaccgt tgaagacgtt gaagcagata   1680
gatgaagtca ggaaggaggt gactcgtgtt caaggccgtg ttcaagcttt tgagagatct   1740
cccgaacttc aaaatgatga caaacaaaaa attgcaattg gagagaccat aatgagactc   1800
ctgctgaagt tggatactat actgggtttg catccaagtt tcagggagat cagaaaatcc   1860
ttggctaggg agctcataat cttgcaagaa aggcttgatt ctataatggc caagaaacct   1920
cagcagcaga tgccggatgt tcaggaacac gttgaaatca ctccaatgaa catgcagagt   1980
gaagaacatg tgcaaaagca gcaagaagaa aaggttgctg taccagagga ttcagctgaa   2040
ggcactaggg atgatgtaaa aggtccttgt gctaatgatg gtggaagtga atctcagtca   2100
ccagttgatc ctccatcaat tgagggagca gagtctgttg cacttccaaa tggctcagat   2160
aatgaggaca ccagccaagt ggttacatct gatgcattga attcttcaag tgatctgtct   2220
gagagtgaca aaatggctgt ggaatccgaa gctaaatcag aagcgaaaga caatccgatt   2280
gcggaagaca ttcccattga ggttgataaa ttggacaaga ctgtttggga agaattgcct   2340
gtgggagtta ttgatgaaga tatcaatgat gttagtattg agaaggaaga acatgatgat   2400
gttagatcgg gaagtctccc agccatggtg aatgattcgg cacaagaagg attaaattca   2460
gagagctatg caatgatgga actgccattg ggattacatg aggagcatga aagggacaat   2520
gaaatgaata tttctaatgg agaaacacgg tctgagaatg agatatttat tgaggagctt   2580
cctgtgggac tgcacgatga agatacaaca atatctaaag ataagaggga tggtcaagct   2640
aagcctaaaa catataaaga ggttcgacta gctcaagaag gggaatgcaa tgcagatgag   2700
gaaacaagtt cttccacaga tgacactgcc aacgaaactc aactagagca acagcagaag   2760
ctgaaagagc aagaagaggt gcattcttct agggaatcag atggctgggt aaaaattgag   2820
tacccggaag aaggtgaact caatggtgat gcaccaatgg atataagagt tgagtgcaag   2880
tcaggtgagg aagctggaac tgatactaag ttgcttcctt taacaacaca agtcagtgat   2940
```

```
aatgaaccag aaaatgaaga tgtattctca gaagcaaatt atgtaaataa caaattaacc   3000

gagccaatgg agtttgtacc ttccaatgac acacagaagg aggagacacc agagatggtt   3060

gctgaagagg caattatccc tgatgataaa gacacagaaa atttggccaa agagaaaact   3120

gaagtatctg cagaaccacc acctgcactg caagaccgag ggttaaacgg tgactcgaag   3180

ttattagaag agaatgagaa gttaagggag atgatgaaga agttgcttga agccgggaat   3240

gaacagttaa gcgtgatatc agatttgact gtcagagtga aggacttgga gaagaaatta   3300

gccaggagaa ggagtaagag agtgaagaca aaacagtata gacccgcagc ttccaaaatg   3360

tctacccatg aaatgaaatc ctcctaa                                       3387
```

```
<210> SEQ ID NO 163
<211> LENGTH: 1128
<212> TYPE: PRT
<213> ORGANISM: Glycine max

<400> SEQUENCE: 163

Met Lys Leu Asp Pro Ser Lys Pro Pro Phe Ser Tyr Asp Gln His Trp
1               5                   10                  15

Pro Tyr Ala Gly Asn Phe Gly His Pro Thr Ser Pro His Phe Cys Cys
            20                  25                  30

Gly His Asn Asn Phe Pro Cys His Tyr Ser Tyr Met Pro Ser Tyr Pro
        35                  40                  45

His Ala Pro Ser Pro Met Tyr Tyr Ser Gly Thr Cys Pro Ser Tyr Ser
    50                  55                  60

Glu Pro Tyr Phe Val Arg Tyr Ser Pro Gln Pro His Tyr Thr Met Glu
65                  70                  75                  80

Leu Pro Arg Tyr Glu Asn Asp Lys Cys Met Pro Arg Glu Leu His Cys
                85                  90                  95

Ser Gly Ser Ala Asn His Pro Cys Asn Gln Lys Glu Gly Arg Ser Val
            100                 105                 110

Lys Ile Glu Glu His Glu Leu Asp Gly Gly Lys Lys Glu Asn Asp Ala
        115                 120                 125

Leu Val Pro Ile Gln Leu Lys Asn Tyr Pro Tyr Pro Leu Val Trp Ile
    130                 135                 140

Pro Gln Glu Tyr Thr Ser Asn Lys Gln Leu Lys Asn Pro Ser Thr Met
145                 150                 155                 160

Glu Val Arg Glu Gln Asn Lys Pro Ser Ser Leu Glu Asn Ser Asn Val
                165                 170                 175

Asp Ala Gln Pro Thr Gln Glu Pro Ile Val Trp Asn Gly Trp Leu Pro
            180                 185                 190

Phe Asn Ile Lys Gly Ala Arg Asn Met Ile His Asp Gly Tyr Gly Thr
        195                 200                 205

Arg Asn Gln Lys Gln Glu Ser Gly Asn Asn Arg Gly Glu Ser Glu Asn
    210                 215                 220

Gly Lys Ile Asp Gln Lys His Gln Ser Glu Gln Lys Arg Ser Glu Phe
225                 230                 235                 240

Pro Phe Pro Ile Phe Trp Leu Pro Tyr Tyr Asn Lys Gln Glu Glu Ser
                245                 250                 255

Gly Glu Thr Lys Asn Gln Glu Lys Asn Ile Ser Ser Pro Lys Ile Val
            260                 265                 270

Glu Glu Val Pro His Thr Phe Lys Phe Val Pro Val Lys Ser His Val
        275                 280                 285
```

-continued

```
Asp Glu Gly Gly Arg Asn Gly Thr Gly Ser Asn Gln Ala Asp Gln Ser
    290                 295                 300

Thr Asn Thr Asn Ala Ser Ser Asp Ala Val Glu Lys Val Asn Asn Ala
305                 310                 315                 320

Arg Ser Ile Pro Val Lys Gln Ile Glu Ser His Glu Gly Lys Asn Val
                325                 330                 335

Ser Leu Asp Gln Met Glu Glu Asn Val Thr Gln Lys Asp Ser Cys Thr
            340                 345                 350

Gly Asp Lys Lys Arg Gln Ser Thr Ser Ser Pro Lys Gly Ser Lys Leu
        355                 360                 365

Pro Pro Val Cys Leu Arg Val Asp Pro Leu Pro Arg Lys Lys Asn Gly
    370                 375                 380

Leu Gly Ser Ser Ser Ser Arg Ser Pro Ser Pro Pro Ser Ser Lys Gly
385                 390                 395                 400

Asn Ser Gln Ala Thr Thr Gly Glu Thr Phe Lys Thr Pro Val Ser Gly
                405                 410                 415

Thr Arg Asp Lys Ala Gln Pro Asn Leu Asn His Gln Asn Ala Pro Asn
            420                 425                 430

Thr Ser Glu Lys Val Lys Pro Lys Glu Asn Thr Ile Pro Val Ser Glu
        435                 440                 445

Cys Met Thr Asn Glu Asn Lys Gly Val Asp Cys Arg Asp Gly Cys Gln
    450                 455                 460

Ser Gln Met Lys Val Asn Ile Pro Ser Lys Gly Leu Lys Gly Ala Arg
465                 470                 475                 480

Glu Thr Cys Pro Asp Asp Asp Asp Tyr Lys Thr Glu Asp Lys Lys Ala
                485                 490                 495

Glu Lys Gly Ala Glu Asn Met Met Glu Glu Thr Thr Glu Ser Arg Glu
            500                 505                 510

Glu Lys Asp Ser Ser Thr Arg Thr Asp Ala Gly Arg Lys Asp Gly Arg
        515                 520                 525

Val Leu Ser Asp Ala Asp Ala Ala Val Leu Ile Gln Ala Ala Tyr Arg
    530                 535                 540

Ser Tyr Leu Val Arg Lys Trp Glu Pro Leu Lys Thr Leu Lys Gln Ile
545                 550                 555                 560

Asp Glu Val Arg Lys Glu Val Thr Arg Val Gln Gly Arg Val Gln Ala
                565                 570                 575

Phe Glu Arg Ser Pro Glu Leu Gln Asn Asp Asp Lys Gln Lys Ile Ala
            580                 585                 590

Ile Gly Glu Thr Ile Met Arg Leu Leu Leu Lys Leu Asp Thr Ile Leu
        595                 600                 605

Gly Leu His Pro Ser Phe Arg Glu Ile Arg Lys Ser Leu Ala Arg Glu
    610                 615                 620

Leu Ile Ile Leu Gln Glu Arg Leu Asp Ser Ile Met Ala Lys Lys Pro
625                 630                 635                 640

Gln Gln Gln Met Pro Asp Val Gln Glu His Val Glu Ile Thr Pro Met
                645                 650                 655

Asn Met Gln Ser Glu Glu His Val Gln Lys Gln Gln Glu Glu Lys Val
            660                 665                 670

Ala Val Pro Glu Asp Ser Ala Glu Gly Thr Arg Asp Asp Val Lys Gly
        675                 680                 685

Pro Cys Ala Asn Asp Gly Gly Ser Glu Ser Gln Ser Pro Val Asp Pro
    690                 695                 700

Pro Ser Ile Glu Gly Ala Glu Ser Val Ala Leu Pro Asn Gly Ser Asp
```

-continued

```
705                 710                 715                 720

Asn Glu Asp Thr Ser Gln Val Val Thr Ser Asp Ala Leu Asn Ser Ser
                725                 730                 735

Ser Asp Leu Ser Glu Ser Asp Lys Met Ala Val Glu Ser Glu Ala Lys
            740                 745                 750

Ser Glu Ala Lys Asp Asn Pro Ile Ala Glu Asp Ile Pro Ile Glu Val
        755                 760                 765

Asp Lys Leu Asp Lys Thr Val Trp Glu Glu Leu Pro Val Gly Val Ile
    770                 775                 780

Asp Glu Asp Ile Asn Asp Val Ser Ile Glu Lys Glu Glu His Asp Asp
785                 790                 795                 800

Val Arg Ser Gly Ser Leu Pro Ala Met Val Asn Asp Ser Ala Gln Glu
                805                 810                 815

Gly Leu Asn Ser Glu Ser Tyr Ala Met Met Glu Leu Pro Leu Gly Leu
            820                 825                 830

His Glu Glu His Glu Arg Asp Asn Glu Met Asn Ile Ser Asn Gly Glu
        835                 840                 845

Thr Arg Ser Glu Asn Glu Ile Phe Ile Glu Glu Leu Pro Val Gly Leu
    850                 855                 860

His Asp Glu Asp Thr Thr Ile Ser Lys Asp Lys Arg Asp Gly Gln Ala
865                 870                 875                 880

Lys Pro Lys Thr Tyr Lys Glu Val Arg Leu Ala Gln Glu Gly Glu Cys
                885                 890                 895

Asn Ala Asp Glu Glu Thr Ser Ser Ser Thr Asp Asp Thr Ala Asn Glu
            900                 905                 910

Thr Gln Leu Glu Gln Gln Gln Lys Leu Lys Glu Gln Glu Glu Val His
        915                 920                 925

Ser Ser Arg Glu Ser Asp Gly Trp Val Lys Ile Glu Tyr Pro Glu Glu
    930                 935                 940

Gly Glu Leu Asn Gly Asp Ala Pro Met Asp Ile Arg Val Glu Cys Lys
945                 950                 955                 960

Ser Gly Glu Glu Ala Gly Thr Asp Thr Lys Leu Leu Pro Leu Thr Thr
                965                 970                 975

Gln Val Ser Asp Asn Glu Pro Glu Asn Glu Asp Val Phe Ser Glu Ala
            980                 985                 990

Asn Tyr Val Asn Asn Lys Leu Thr  Glu Pro Met Glu Phe  Val Pro Ser
        995                 1000                1005

Asn Asp  Thr Gln Lys Glu Glu  Thr Pro Glu Met Val  Ala Glu Glu
    1010                1015                1020

Ala Ile  Ile Pro Asp Asp Lys  Asp Thr Glu Asn Leu  Ala Lys Glu
    1025                1030                1035

Lys Thr  Glu Val Ser Ala Glu  Pro Pro Pro Ala Leu  Gln Asp Arg
    1040                1045                1050

Gly Leu  Asn Gly Asp Ser Lys  Leu Leu Glu Glu Asn  Glu Lys Leu
    1055                1060                1065

Arg Glu  Met Met Lys Lys Leu  Leu Glu Ala Gly Asn  Glu Gln Leu
    1070                1075                1080

Ser Val  Ile Ser Asp Leu Thr  Val Arg Val Lys Asp  Leu Glu Lys
    1085                1090                1095

Lys Leu  Ala Arg Arg Arg Ser  Lys Arg Val Lys Thr  Lys Gln Tyr
    1100                1105                1110

Arg Pro  Ala Ala Ser Lys Met  Ser Thr His Glu Met  Lys Ser Ser
    1115                1120                1125
```

<210> SEQ ID NO 164
<211> LENGTH: 3858
<212> TYPE: DNA
<213> ORGANISM: Glycine max

<400> SEQUENCE: 164
atgaagcttg atccatccaa accacccttt tcttatgacc aacattggcc ctatgccggc 60
aattttgggc accctacttc cccacatttc tgctgtggcc acaacaactt cccttgtcat 120
tatagctaca tgccttcata tcctcatgcc ccttctccaa tgtactattc tggaacttgt 180
ccttcatata gtgaaccata ttttgttcct tattccccac aaccacatta taccatggag 240
ctgcctaggt atgaaaatga caaatgcatg ccccgagagc ttcattgttc tggttctgct 300
aatcatccat gcaaccaaaa ggaaggtaga agtgtgaaga ttgaagagca tgaactggat 360
ggtggaaaga aagagaatga tgctttggtc ccaattcagc tcaagaatta tccatatccc 420
ttagtttgga ttccacagga gtacacaagt aacaaacagc tgaaaaatcc tagtacaatg 480
gaagttcgtg aacaaaacaa gccttctagt cttgagaatt ctaatgttga tgcgcagcca 540
acacaggagc ctatagtatg gaatggatgg cttcccttca atataaaggg tgcccggaac 600
atgattcacg atggatatgg aacaagaaac cagaaacagg agtctggcaa taatagaggg 660
gaatctgaaa atggaaaaat agaccagaaa catcaaagtg aacagaagag gtcagaattc 720
ccattcccta tcttctggtt gccttattac aataagcagg aggagagtgg agagactaag 780
aaccaggaga aaaacatttc ttcaccaaaa attgttgagg aggtacccca tacattcaaa 840
tttgttccag tgaagtctca tgttgatgaa ggtggtagga acagaaccgg atcaaatcaa 900
gctgatcaat ccacaaatac aaatgcttct tcggatgctg tagagaaagt gaataatgcc 960
agaagcatac ctgtgaagca gatagaatcc cacgaaggaa aaaatgtttc tctcgatcaa 1020
atggaagaga atgtgacaca aaaggactct tgcactgggg acaaaaagag acaatctaca 1080
tcttcaccta aaggatccaa gttacctccg gtttgtctga gagttgatcc actaccaagg 1140
aagaaaaatg gccacgggag ttcgagttcg aggtccccaa gtccaccttc atcaaaaggg 1200
aattcccaag ctacaactgg tgaaacattc aagactcctg tgagtggcac acatgacaag 1260
gctcagccaa atttgaatca tcagaatgct ccaaacacca gtgagaaagt taaaccaaag 1320
gagaacacca ttccggtgtc agaatgcatg actaatgaaa acaagggtgt tgactgtagg 1380
gatggatgtc agagccagat gaaagtaaac atacccagta aaggtctgaa aggggcaagg 1440
gaaacatgtc cagatgatga tgactataag actgaagata aaaggcaga gaaaggagca 1500 gaaaatatga tggaggaaac tactgaatca agggaagaga aggattcaag cacacgaact 1560
gatgcgggtc gaaaagatgg aagagttttg tcagatgcag atgctgctgt tttgatacaa 1620
gctgcatatc gcagttatct agttagaaaa tgggaaccgt tgaagaagtt gaagcagata 1680
gatgaagtca ggaaggaggt gactcgtgtt caaggccgtg ttcaagcttt tgagagatct 1740
cccgaacttc aaaatgatga caaacaaaaa attgcaattg aagagaccat aatgaaactc 1800
ctgctgaagt tggatactat actggtactt gtcagattac cctatttact tatgatgaaa 1860
tctgtagtcc actttttgat attctttgat tcattgacaa taaacattac acagaatatt 1920
aaagtgtttt gattttgtat tttacggtca aaattctcct acgtatttat tagctaatct 1980
taattaattg agattcatga catctgtgat agagttttga tattatctta tgatcttatc 2040
ttgggatatc atggcatcag tgacatagtt ttgatatttc ttcattttat ggatatggaa 2100

-continued

```
aatgaatttt tttaagctat taaaaagcac tctgcttaac cgcatttgaa ctaagatgag   2160
cattttgatc tacacagata agtgttgttt gtggtttgtc tgagctatta gtcattgatc   2220
atcttaatta tgatggttaa tatagttctc cttttttgtt caatgttatg cttacattcg   2280
ttcaatctat atcagggttt gcatccaagt ttcagggaga tcagaaaatc cttggctagg   2340
gagctcataa tcttgcaaga aaggcttgat tctataatgg ccaagaaacc tcagcagcag   2400
atgccggatg ttcaggaaca cgttgaaatc actccaatga acatgcagag tgaagaacat   2460
gtgcaaaagc agcaagaaga aaaggttgct gtaccagagg attcagctga aggcactagg   2520
gatgatgtaa aaggtccttg tgctaatgat ggtggaagtg aatctcagtc accagttgat   2580
cctccatcaa atgagggagc agagtctgtt gcacttccaa atggctcaga taatgaggac   2640
accagccaag tggttacatc tgatgcattg aattcttcaa gtgatctgtc tgagagtgac   2700
aaaatggctg tggaatccga agctaaatca gaagtgaaag acaatccgat tgcggaagac   2760
attcccattg aggttgataa attggacaag actgtttggg aagaattgcc tgtgggagtt   2820
attgatgaag atatcaatga tgttagtatt gagaaggaag aacatgatga tattagatcg   2880
ggaagtctcc cagccatggt gaatgattcg gcacaagaag gattaaattc agagagctat   2940
gcaatgatgg aactgccatt gggattacat gaggagcatg aaagggacaa tgaaatgaat   3000
atttctaatg gagaaacacg gtctgagaat gagatattta ttgaggagct tcctgtggga   3060
ctgcacgatg aagatacaac aatatctaaa gataagaggg atggtcaagc taagcctaaa   3120
acatataaag aggttcgact agctcaagaa ggggaatgca atgcagatga ggaaacaagt   3180
tcttccacag atgacactgc caacgaaact caactagagc aacagcagaa gctgaaagag   3240
caagaagagg tgcattattc tagggaatca gatggctggg taaaaattga gtacccggaa   3300
gaaggtgaac tcaatggtga tgcaccaatg gatataagag ttgagtgcaa gtcaggtgag   3360
gaagctggaa ctgatactaa gttgcttcct ttaacaacac aagtcagtga taatgaacca   3420
gaaaatgaag atgtattctc agaagcaaat tatgtaaata acaaattaac cgagccaatg   3480
gagtttgtac cttccaatga cacacagaag gaggagacac cagagatggt tgctgaagag   3540
gcaattatcc ctgatgataa agacacagaa aatttggcca aagagaaaac tgaagtatct   3600
gcagaaccac cacctgcatt gcaagaccga gggttaaacg gtgactcgaa gttattagaa   3660
gagaatgaga agttaaggga gatgatgaag aagttgcttg aagccgggaa tgaacagtta   3720
agcgtgatat cagatttgac tgtcagagtg aaggacttgg agaagaaatt agccaggaga   3780
aggagtaaga gagtgaagac aaaacagtat agacccgcag cttccaaaat gtctacccat   3840
gaaatgaaat cctcctaa                                                  3858
```

<210> SEQ ID NO 165
<211> LENGTH: 2991
<212> TYPE: DNA
<213> ORGANISM: Glycine max

<400> SEQUENCE: 165

```
atgaagcttg atccatccaa accacccttt tcttatgacc aacattggcc ctatgccggc     60
aattttgggc accctacttc cccacatttc tgctgtggcc acaacaactt cccttgtcat    120
tatagctaca tgccttcata tcctcatgcc ccttctccaa tgtatgaaaa tgacaaatgc    180
atgccccgag agcttcattg ttctggttct gctaatcatc catgcaacca aaaggaaggt    240
agaagtgtga agattgaaga gcatgaactg gatggtggaa agaaagagaa tgatgctttg    300
gtcccaattc agctcaagaa ttatccatat cccttagttt ggattccaca ggagtacaca    360
```

```
agtaacaaac agctgaaaaa tcctagtaca atggaagttc gtgaacaaaa caagccttct    420
agtcttgaga attctaatgt tgatgcgcag ccaacacagg agcctatagt atggaatgga    480
tggcttccct tcaatataaa gggtgcccgg aacatgattc acgatggata tggaacaaga    540
aaccagaaac aggagtctgg caataataga ggggaatctg aaaatggaaa aatagaccag    600
aaacatcaaa gtgaacagaa gaggtcagaa ttcccattcc ctatcttctg gttgccttat    660
tacaataagc aggaggagag tggagagact aagaaccagg agaaaaacat ttcttcacca    720
aaaattgttg aggaggtacc ccatacattc aaatttgttc cagtgaagtc tcatgttgat    780
gaaggtgaga aagtgaataa tgccagaagc atacctgtga agcagataga atcccacgaa    840
ggaaaaaatg tttctctcga tcaaatggaa gagaatgtga cacaaaagga ctcttgcact    900
ggggacaaaa agagacaatc tacatcttca cctaaaggat ccaagttacc tccggtttgt    960
ctgagagttg atccactacc aaggaagaaa aatggccacg ggagttcgag ttcgaggtcc   1020
ccaagtccac cttcatcaaa agggaattcc caagctacaa ctggtgaaac attcaagact   1080
cctagccaga tgaaagtaaa catacccagt aaaggtctga aggggcaag ggaaacatgt   1140
ccagatgatg atgactataa gactgaagat aaaaaggcag agaaaggagc agaaaatatg   1200
atggaggaaa ctactgaatc aagggaagag aaggattcaa gcacacgaac tgatgcgggt   1260
cgaaaagatg gaagagtttt gtcagatgca gatgctgctg ttttgataca agctgcatat   1320
cgcagttatc tagttagaaa atgggaaccg ttgaagaagt tgaagcagat agatgaagtc   1380
aggaaggagg tgactcgtgt tcaaggccgt gttcaagctt ttgagagatc tcccgaactt   1440
caaaatgatg acaaacaaaa aattgcaatt gaagagacca taatgaaact cctgctgaag   1500
ttggatacta tactgggttt gcatccaagt ttcagggaga tcagaaaatc cttggctagg   1560
gagctcataa tcttgcaaga aaggcttgat tctataatgg ccaagaaacc tcagcagcag   1620
atgccggata gtgaagaaca tgtgcaaaag cagcaagaag aaaaggttgc tgtaccagag   1680
gattcagctg aaggcactag ggatgatgta aaaggtcctt gtgctaatga tggtggaagt   1740
gaatctcagt caccagttga tcctccatca aatgagggag cagagtctgt tgcacttcca   1800
aatggctcag ataatgagga caccagccaa gtggttacat ctgatgcatt gaattcttca   1860
agtgatctgt ctgagagtga caaaatggct gtggaatccg aagctaaatc agaagtgaaa   1920
gacaatccga ttgcggaaga cattcccatt gaggttgata aattggacaa gactgtttgg   1980
gaagaattgc ctgtgggagt tattgatgaa gatatcaatg atgttaccat ggtgaatgat   2040
tcggcacaag aaggattaaa ttcagagagc tatgcaatga tggaactgcc attgggatta   2100
catgaggagc atgaaaggga caatgaaatg aatatttcta atggagaaac acggtctgag   2160
aatgagatat ttattgagga gcttcctgtg ggactgcacg atgaagatac aacaatatct   2220
aaagataaga gggatggtca agctaagcct aaaacatata aagaggttcg actagctcaa   2280
gaaggggaat gcaatgcaga tgaggaaaca agttcttcca cagatgacac tgccaacgaa   2340
actcaactag agcaacagca gaagctgaaa gagcaagaag aggtgcatta ttctagggaa   2400
tcagatggct gggtaaaaat tgagtacccg gaagaaggtg aactcaatgg tgatgcacca   2460
atggatataa gagttgagtg caagtcaggt gaggaagctg gaactgatac taagttgctt   2520
cctttaacaa cacaagtcag tgataatgaa ccagaaaatg aagatgtatt ctcagaagca   2580
aattatgtaa ataacaaatt aaccgagcca atggagtttg taccttccaa tgacacacag   2640
aaggaggaga caccagagat ggttgctgaa gaggcaatta tccctgatga taaagacaca   2700
```

gaaaatttgg ccaaagagaa aactgaagta tctgcagaac caccacctgc attgcaagac 2760
cgagggttaa acggtgactc gaagttatta gaagagaatg agaagttaag ggagatgatg 2820
aagaagttgc ttgaagccgg gaatgaacag ttaagcgtga tatcagattt gactgtcaga 2880
gtgaaggact tggagaagaa attagccagg agaaggagta agagagtgaa gacaaaacag 2940
tatagacccg cagcttccaa aatgtctacc catgaaatga aatcctccta a 2991

<210> SEQ ID NO 166
<211> LENGTH: 996
<212> TYPE: PRT
<213> ORGANISM: Glycine max

<400> SEQUENCE: 166

Met Lys Leu Asp Pro Ser Lys Pro Pro Phe Ser Tyr Asp Gln His Trp
1 5 10 15

Pro Tyr Ala Gly Asn Phe Gly His Pro Thr Ser Pro His Phe Cys Cys
20 25 30

Gly His Asn Asn Phe Pro Cys His Tyr Ser Tyr Met Pro Ser Tyr Pro
35 40 45

His Ala Pro Ser Pro Met Tyr Glu Asn Asp Lys Cys Met Pro Arg Glu
50 55 60

Leu His Cys Ser Gly Ser Ala Asn His Pro Cys Asn Gln Lys Glu Gly
65 70 75 80

Arg Ser Val Lys Ile Glu Glu His Glu Leu Asp Gly Gly Lys Lys Glu
85 90 95

Asn Asp Ala Leu Val Pro Ile Gln Leu Lys Asn Tyr Pro Tyr Pro Leu
100 105 110

Val Trp Ile Pro Gln Glu Tyr Thr Ser Asn Lys Gln Leu Lys Asn Pro
115 120 125

Ser Thr Met Glu Val Arg Glu Gln Asn Lys Pro Ser Ser Leu Glu Asn
130 135 140

Ser Asn Val Asp Ala Gln Pro Thr Gln Glu Pro Ile Val Trp Asn Gly
145 150 155 160

Trp Leu Pro Phe Asn Ile Lys Gly Ala Arg Asn Met Ile His Asp Gly
165 170 175

Tyr Gly Thr Arg Asn Gln Lys Gln Glu Ser Gly Asn Asn Arg Gly Glu
180 185 190

Ser Glu Asn Gly Lys Ile Asp Gln Lys His Gln Ser Glu Gln Lys Arg
195 200 205

Ser Glu Phe Pro Phe Pro Ile Phe Trp Leu Pro Tyr Tyr Asn Lys Gln
210 215 220

Glu Glu Ser Gly Glu Thr Lys Asn Gln Glu Lys Asn Ile Ser Ser Pro
225 230 235 240

Lys Ile Val Glu Glu Val Pro His Thr Phe Lys Phe Val Pro Val Lys
245 250 255

Ser His Val Asp Glu Gly Glu Lys Val Asn Asn Ala Arg Ser Ile Pro
260 265 270

Val Lys Gln Ile Glu Ser His Glu Gly Lys Asn Val Ser Leu Asp Gln
275 280 285

Met Glu Glu Asn Val Thr Gln Lys Asp Ser Cys Thr Gly Asp Lys Lys
290 295 300

Arg Gln Ser Thr Ser Ser Pro Lys Gly Ser Lys Leu Pro Pro Val Cys
305 310 315 320

Leu Arg Val Asp Pro Leu Pro Arg Lys Lys Asn Gly His Gly Ser Ser

-continued

```
                325                 330                 335

Ser Ser Arg Ser Pro Ser Pro Pro Ser Ser Lys Gly Asn Ser Gln Ala
            340                 345                 350

Thr Thr Gly Glu Thr Phe Lys Thr Pro Ser Gln Met Lys Val Asn Ile
        355                 360                 365

Pro Ser Lys Gly Leu Lys Gly Ala Arg Glu Thr Cys Pro Asp Asp Asp
    370                 375                 380

Asp Tyr Lys Thr Glu Asp Lys Lys Ala Glu Lys Gly Ala Glu Asn Met
385                 390                 395                 400

Met Glu Glu Thr Thr Glu Ser Arg Glu Glu Lys Asp Ser Ser Thr Arg
                405                 410                 415

Thr Asp Ala Gly Arg Lys Asp Gly Arg Val Leu Ser Asp Ala Asp Ala
            420                 425                 430

Ala Val Leu Ile Gln Ala Ala Tyr Arg Ser Tyr Leu Val Arg Lys Trp
        435                 440                 445

Glu Pro Leu Lys Lys Leu Lys Gln Ile Asp Glu Val Arg Lys Glu Val
    450                 455                 460

Thr Arg Val Gln Gly Arg Val Gln Ala Phe Glu Arg Ser Pro Glu Leu
465                 470                 475                 480

Gln Asn Asp Asp Lys Gln Lys Ile Ala Ile Glu Glu Thr Ile Met Lys
                485                 490                 495

Leu Leu Leu Lys Leu Asp Thr Ile Leu Gly Leu His Pro Ser Phe Arg
            500                 505                 510

Glu Ile Arg Lys Ser Leu Ala Arg Glu Leu Ile Ile Leu Gln Glu Arg
        515                 520                 525

Leu Asp Ser Ile Met Ala Lys Lys Pro Gln Gln Gln Met Pro Asp Ser
    530                 535                 540

Glu Glu His Val Gln Lys Gln Gln Glu Glu Lys Val Ala Val Pro Glu
545                 550                 555                 560

Asp Ser Ala Glu Gly Thr Arg Asp Asp Val Lys Gly Pro Cys Ala Asn
                565                 570                 575

Asp Gly Gly Ser Glu Ser Gln Ser Pro Val Asp Pro Pro Ser Asn Glu
            580                 585                 590

Gly Ala Glu Ser Val Ala Leu Pro Asn Gly Ser Asp Asn Glu Asp Thr
        595                 600                 605

Ser Gln Val Val Thr Ser Asp Ala Leu Asn Ser Ser Ser Asp Leu Ser
    610                 615                 620

Glu Ser Asp Lys Met Ala Val Glu Ser Glu Ala Lys Ser Glu Val Lys
625                 630                 635                 640

Asp Asn Pro Ile Ala Glu Asp Ile Pro Ile Glu Val Asp Lys Leu Asp
                645                 650                 655

Lys Thr Val Trp Glu Glu Leu Pro Val Gly Val Ile Asp Glu Asp Ile
            660                 665                 670

Asn Asp Val Thr Met Val Asn Asp Ser Ala Gln Glu Gly Leu Asn Ser
        675                 680                 685

Glu Ser Tyr Ala Met Met Glu Leu Pro Leu Gly Leu His Glu Glu His
    690                 695                 700

Glu Arg Asp Asn Glu Met Asn Ile Ser Asn Gly Glu Thr Arg Ser Glu
705                 710                 715                 720

Asn Glu Ile Phe Ile Glu Glu Leu Pro Val Gly Leu His Asp Glu Asp
                725                 730                 735

Thr Thr Ile Ser Lys Asp Lys Arg Asp Gly Gln Ala Lys Pro Lys Thr
            740                 745                 750
```

```
Tyr Lys Glu Val Arg Leu Ala Gln Glu Gly Glu Cys Asn Ala Asp Glu
        755                 760                 765

Glu Thr Ser Ser Ser Thr Asp Asp Thr Ala Asn Glu Thr Gln Leu Glu
    770                 775                 780

Gln Gln Gln Lys Leu Lys Glu Gln Glu Glu Val His Tyr Ser Arg Glu
785                 790                 795                 800

Ser Asp Gly Trp Val Lys Ile Glu Tyr Pro Glu Glu Gly Glu Leu Asn
                805                 810                 815

Gly Asp Ala Pro Met Asp Ile Arg Val Glu Cys Lys Ser Gly Glu Glu
            820                 825                 830

Ala Gly Thr Asp Thr Lys Leu Leu Pro Leu Thr Thr Gln Val Ser Asp
        835                 840                 845

Asn Glu Pro Glu Asn Glu Asp Val Phe Ser Glu Ala Asn Tyr Val Asn
    850                 855                 860

Asn Lys Leu Thr Glu Pro Met Glu Phe Val Pro Ser Asn Asp Thr Gln
865                 870                 875                 880

Lys Glu Glu Thr Pro Glu Met Val Ala Glu Glu Ala Ile Ile Pro Asp
                885                 890                 895

Asp Lys Asp Thr Glu Asn Leu Ala Lys Glu Lys Thr Glu Val Ser Ala
            900                 905                 910

Glu Pro Pro Pro Ala Leu Gln Asp Arg Gly Leu Asn Gly Asp Ser Lys
        915                 920                 925

Leu Leu Glu Glu Asn Glu Lys Leu Arg Glu Met Met Lys Lys Leu Leu
    930                 935                 940

Glu Ala Gly Asn Glu Gln Leu Ser Val Ile Ser Asp Leu Thr Val Arg
945                 950                 955                 960

Val Lys Asp Leu Glu Lys Lys Leu Ala Arg Arg Arg Ser Lys Arg Val
                965                 970                 975

Lys Thr Lys Gln Tyr Arg Pro Ala Ala Ser Lys Met Ser Thr His Glu
            980                 985                 990

Met Lys Ser Ser
        995
```

<210> SEQ ID NO 167
<211> LENGTH: 3850
<212> TYPE: DNA
<213> ORGANISM: Glycine max

<400> SEQUENCE: 167

```
atgaagcttg atccatccaa accacccttt tcttatgacc aacattggcc atatgctggc      60

aacttagggc accctattcc cccacatttc tgctgtggcc acaacaactt cccttgtcat     120

tatagctaca tgccttcaaa tcctcatgct ccttctccaa tgtactattc tggaacttgt     180

ccttcatata gtgaaccata ttttgttcct tattcactac aaccacatta tactatggat     240

ctgcccaggt atgaatatga caaatttatg ccccgagagc atcattgttg tggctgtcct     300

aatcatccat gcagccaaaa ggaaggtaga agtgtgaaga ttgaagaaca tgaacctgat     360

ggtggaaaga aagtgaatga tgctttggct ccaatccagc tcaagaatta cccatatccc     420

ttagtttgga ttccacagga gtacacaagt aacaaacagc tgaagaatcc taatacaatg     480

gaagttgggg aacaagacaa gtctcctcgt tttgagaatt ctaatgctga tgcacagcca     540

gcacaggatc ctagagtatg gaatggatgg cttcccttca atataaaggg tgccccgaac     600

gtgattcacg atggatatgg aacaagaaac cagaaacagg agtctggcaa taatagaggg     660
```

-continued

```
gaatctgaag atggaaaagt ggaccagaaa catcaaagtg aacagaatag gtcagaattt    720
ccattcccta tcttctggtt gccttattac aataagccgg aggagggtgg tgagactaaa    780
aaccaggaga agaatacttt ttcaccaaaa gttattgagg aggtacccca tacattaaaa    840
tctgttccag caaagtctca tgttgatgaa ggtggtagga ataggaacgg aaccggatca    900
aatcaagctg aatacacaaa tacaaatgct gcggatgttg tagagaaagt gactaatgcc    960
agaagcatac ctgtgaagca aatggaagag aatgtgacaa aaaaggactc ctgcactggt   1020
gacaaaaaga ggcaatctgc atcttcacca aaaggatcca agttacctcc ggtttgtctg   1080
agagttgatc cactaccaag gaagaaaaat ggcaacggga gtttgagttt gagttcaagg   1140
tcgaggtccc caagtccacc ttcatcaaaa gggcaatccc aagctacaac tggtgaaaca   1200
ttcaagactc ctgtgagtgg aacacatgat aaaggtcagc caaattcgga tcatcagaat   1260
gggccaacaa acaccagtga gagagttaaa ccaaaggaga agaccattcc ggtgtcagaa   1320
atatgcaaga ctaatgaaaa ccagggtgtt gagtgtaggg atggatgtca aagccagata   1380
aatgtaaaca tacctagtga agatccgaaa gggacaaggg gaacatgtcc agatggtgat   1440
gacttcaaga ctgaagataa aaaggcagat aaaggggcag ataaaatgag ggagaaaact   1500
gcagaactaa aagatgtgaa ggattcaagc gcacaaactg acgcaggtca aaaggaggta   1560
agagttctgt cagatgcaga tgcttctgtt ttgatacaag ctgcatatcg cggacatcaa   1620
gttagaaaat gggaagcatt gaagaagttg aagcagatag atgaagtcag gaaggaggtg   1680
actgatgttc gagaccgtgt tcaagccttt gagagatctt ctgatcttca aaatgatgac   1740
aagcaaaaaa ttgcaattgg agagaccatt atgagactcc tgctgaagtt ggatactata   1800
caggtacatg tcagataacc gttacttaaa atgaaatcag taatgcattt tttatatttt   1860
tgattcattg acaataaaca ttacatggaa tatgaaattg ttttgctttt gtacttcagt   1920
aaaaagattc catttttatt tattaggtaa tcttaattga gatatcatga catcagagta   1980
tagttttgat attagctaat cttagttaga tatcatgaca tctgtaatat agttttgata   2040
tttcttcatt catggatatg ggtagtgact tttacatgcc taattacctg ttacaactta   2100
caagcactcc gcatttgaac aaagattagc attttgatct gcacagatat gaatgttggt   2160
tgtggtttgt ctgagctatt aatcgttgtt catcttattt atgatttttt ttaatttagt   2220
tatacttcct tgttcaatgt tatgcttaca tatcgctcaa catttatatc agggtttgca   2280
tccaagtatc agggagatca gaaaatcctt ggctagagag ctgacaattt tgcaagaaag   2340
gcttgattat ataatggcca agaaacctca gcagcaggtg caggatttca atgttcagga   2400
acatgttgaa gtcactccaa tgaatatgca gaatgaagaa caagttgctg taccagcaga   2460
ctcagctgaa ggcattagtg atgatgcaaa aggtccttgt gctaatgttg gtggaagtga   2520
atcccagtca ccagttgatc ctacatcaga taagggagca gagtctgttg tgcttccgaa   2580
tggctcgcat aatgatgata ctagccaagt ggttacagat gacacattga attctacaag   2640
tgatctgtct gagacggaca aaatggctgt ggaacccgaa gctaaatcag aagcgaaaga   2700
cattcccact gcggaagaca ttctaaacga ggttgataaa ttgtataaga ctgttttgga   2760
agaatttcct gtgggagttg ttgatgaaga tatcgatgat gttattattg agaaggaaga   2820
acaagatgat gttagttctg gaagtctcca agccatggtg gatgattcgg cacgagatgg   2880
attagagaac catgcaatga tggaaatgcc agtgggatta tttgatgagg atgaaaggaa   2940
caatgaaatg aatatttcta aagagggaac acaaactgag aatgacatat ttattgagct   3000
tcctatggga ctacttgatg aggatacagc aatatctgaa gttaagaagc acgatcgagc   3060
```

```
taagcctaaa acatataaag aggttctact agctcaagaa ggggaatgca atgcagatga   3120

gaaaacaagt tcttcaacag ataacactgc gaacgaaact caactagggc aacagcagaa   3180

gctggaagag caaaaagagg tgcattcttc tggggaatgc tgggtgaaaa tcaagtacca   3240

ggaagaaggt gaactcaatg gtgatgcacc aatagatata agaactgagt gtaagtcagg   3300

tgaggaagtt gaaaatgata ctaagttacc tcctttgaca acacaagtca atgatcatgg   3360

accaggaaat gaagatgtat gctcaaaagc aaatgatgta aataacatat cgcccgaggc   3420

caagccaatg gagttagtac cttccaatga aacacagaag gaggaggaac cagaagagaa   3480

gattgcactt agggagacac aagagatggt tactgagcag gcaattggtg ctgatgataa   3540

agacccagaa gctttgttta aagagaaaac cgaactatct tcgcctccac ctgcattaca   3600

agaacctgag ctgcctgcgg ccatgcgcga tggagagttc aacggtgaca cgaagttact   3660

ggaagagaat gagaatttaa gggagatgat gaagaagttg cttgaagccg ggaatgaaca   3720

gttaagcgtg ataacaaatt tgactggcag agtgaaggac ttggagaaga aactagccag   3780

gagcaggagt aagagagtga agacaaaacg gtatagacca gcaacttcca aaatgtcttg   3840

catgaaatga                                                          3850
```

<210> SEQ ID NO 168
<211> LENGTH: 2715
<212> TYPE: DNA
<213> ORGANISM: Glycine max

<400> SEQUENCE: 168

```
atgaagcttg atccatccaa accacccttt tcttatgacc aacattggcc atatgctggc     60

aacttagggc accctattcc cccacatttc tgctgtggcc acaacaactt cccttgtcat    120

tatagctaca tgccttcaaa tcctcatgct ccttctccaa tgtatgaata tgacaaattt    180

atgccccgag agcatcattg ttgtggctgt cctaatcatc catgcagcca aaaggaaggt    240

agaagtgtga agattgaaga acatgaacct gatggtggaa agaaagtgaa tgatgctttg    300

gctccaatcc agctcaagaa ttacccatat cccttagttt ggattccaca ggagtacaca    360

agtaacaaac agctgaagaa tcctaataca atggaagttg gggaacaaga caagtctcct    420

cgttttgaga attctaatgc tgatgcacag ccagcacagg atcctagagt atggaatgga    480

tggcttccct tcaatataaa gggtgccccg aacgtgattc acgatggata tggaacaaga    540

aaccagaaac aggagtctgg caataataga ggggaatctg aagatggaaa agtggaccag    600

aaacatcaaa gtgaacagaa taggtcagaa tttccattcc ctatcttctg gttgccttat    660

tacaataagc cggaggaggg tggtgagact aaaaaccagg agaagaatac tttttcacca    720

aaagttattg aggaggtacc ccatacatta aaatctgttc cagcaaagtc tcatgttgat    780

gaaggtggta ggaataggaa cggaaccgga tcaaatcaag ctgaatacac aaatacaaat    840

gctgcggatg ttgtagagaa agtgactaat gccagaagca tacctgtgaa gcaaatggaa    900

gagaatgtga caaaaaagga ctcctgcact ggtgacaaaa agaggcaatc tgcatcttca    960

ccaaaaggat ccaagttacc tccggtttgt ctgagagttg atccactacc aaggaagaaa   1020

aatggcaacg ggagtttgag tttgagttca aggtcgaggt ccccaagtcc accttcatca   1080

aaagggcaat cccaagctac aactggtgaa acattcaaga ctcctgtgag tggaacacat   1140

gataaagatc cgaaagggac aaggggaaca tgtccagatg gtgatgactt caagactgaa   1200

gataaaaagg cagataaagg ggcagataaa atgagggaga aaactgcaga actaaaagat   1260
```

-continued

```
gtgaaggatt caagcgcaca aactgacgca ggtcaaaagg aggtaagagt tctgtcagat   1320

gcagatgctt ctgttttgat acaagctgca tatcgcggac atcaagttag aaaatgggaa   1380

gcattgaaga agttgaagca gatagatgaa gtcaggaagg aggtgactga tgttcgagac   1440

cgtgttcaag cctttgagag atcttctgat cttcaaaatg atgacaagca aaaaattgca   1500

attggagaga ccattatgag actcctgctg aagttggata ctatacaggg tttgcatcca   1560

agtatcaggg agatcagaaa atccttggct agagagctga caattttgca agaaaggctt   1620

gattatataa tggccaagaa acctcagcag caggtgcagg atttcaatgt tcaggaacat   1680

gttgaagtca ctccaatgaa tatgcagaat gaagaacaag ttgctgtacc agcagactca   1740

gctgaaggca ttagtgatga tgcaaaaggt ccttgtgcta atgttggtgg aagtgaatcc   1800

cagtcaccag ttgatcctac atcagataag ggagcagagt ctgttgtgct tccgaatggc   1860

tcgcataatg atgatactag ccaagtggtt acagatgaca cattgaattc tacaagtgat   1920

ctgtctgaga cggacaaaat ggctgtggaa cccgaagcta aatcagaagc gaaagacatt   1980

cccactgcgg aagacattct aaacgaggtt gataaattgt ataagactgt tttggaagaa   2040

tttcctgtgg gagttgttga tgaagatatc gatgatgtta ttattgagaa ggaagaacaa   2100

gatgatgtta gttctggaac aatatctgaa gttaagaagc acgatcgagc taagcctaaa   2160

acatataaag aggttctact agctcaagaa ggggaatgca atgcagatga gaaaacaagt   2220

tcttcaacag ataacactgc gaacgaaact caactagggc aacagcagaa gctggaagag   2280

caaaaagagg tgcattcttc tggggaatgc tgggtgaaaa tcaagtacca ggaagaaggt   2340

gaggaagttg aaaatgatac taagttacct cctttgacaa cacaagcaat tggtgctgat   2400

gataaagacc cagaagcttt gtttaaagag aaaaccgaac tatcttcgcc tccacctgca   2460

ttacaagaac ctgagctgcc tgcggccatg cgcgatggag agttcaacgg tgacacgaag   2520

ttactggaag agaatgagaa tttaagggag atgatgaaga agttgcttga agccgggaat   2580

gaacagttaa gcgtgataac aaatttgact ggcagagtga aggacttgga gaagaaacta   2640

gccaggagca ggagtaagag agtgaagaca aaacggtata gaccagcaac ttccaaaatg   2700

tcttgcatga aatga                                                    2715
```

<210> SEQ ID NO 169
<211> LENGTH: 904
<212> TYPE: PRT
<213> ORGANISM: Glycine max

<400> SEQUENCE: 169

```
Met Lys Leu Asp Pro Ser Lys Pro Pro Phe Ser Tyr Asp Gln His Trp
1               5                   10                  15

Pro Tyr Ala Gly Asn Leu Gly His Pro Ile Pro Pro His Phe Cys Cys
            20                  25                  30

Gly His Asn Asn Phe Pro Cys His Tyr Ser Tyr Met Pro Ser Asn Pro
        35                  40                  45

His Ala Pro Ser Pro Met Tyr Glu Tyr Asp Lys Phe Met Pro Arg Glu
    50                  55                  60

His His Cys Cys Gly Cys Pro Asn His Pro Cys Ser Gln Lys Glu Gly
65                  70                  75                  80

Arg Ser Val Lys Ile Glu Glu His Glu Pro Asp Gly Gly Lys Lys Val
                85                  90                  95

Asn Asp Ala Leu Ala Pro Ile Gln Leu Lys Asn Tyr Pro Tyr Pro Leu
            100                 105                 110
```

```
Val Trp Ile Pro Gln Glu Tyr Thr Ser Asn Lys Gln Leu Lys Asn Pro
        115                 120                 125

Asn Thr Met Glu Val Gly Glu Gln Asp Lys Ser Pro Arg Phe Glu Asn
    130                 135                 140

Ser Asn Ala Asp Ala Gln Pro Ala Gln Asp Pro Arg Val Trp Asn Gly
145                 150                 155                 160

Trp Leu Pro Phe Asn Ile Lys Gly Ala Pro Asn Val Ile His Asp Gly
                165                 170                 175

Tyr Gly Thr Arg Asn Gln Lys Gln Glu Ser Gly Asn Asn Arg Gly Glu
            180                 185                 190

Ser Glu Asp Gly Lys Val Asp Gln Lys His Gln Ser Glu Gln Asn Arg
        195                 200                 205

Ser Glu Phe Pro Phe Pro Ile Phe Trp Leu Pro Tyr Tyr Asn Lys Pro
    210                 215                 220

Glu Glu Gly Gly Glu Thr Lys Asn Gln Glu Lys Asn Thr Phe Ser Pro
225                 230                 235                 240

Lys Val Ile Glu Glu Val Pro His Thr Leu Lys Ser Val Pro Ala Lys
                245                 250                 255

Ser His Val Asp Glu Gly Gly Arg Asn Arg Asn Gly Thr Gly Ser Asn
            260                 265                 270

Gln Ala Glu Tyr Thr Asn Thr Asn Ala Ala Asp Val Val Glu Lys Val
        275                 280                 285

Thr Asn Ala Arg Ser Ile Pro Val Lys Gln Met Glu Glu Asn Val Thr
    290                 295                 300

Lys Lys Asp Ser Cys Thr Gly Asp Lys Lys Arg Gln Ser Ala Ser Ser
305                 310                 315                 320

Pro Lys Gly Ser Lys Leu Pro Pro Val Cys Leu Arg Val Asp Pro Leu
                325                 330                 335

Pro Arg Lys Lys Asn Gly Asn Gly Ser Leu Ser Leu Ser Ser Arg Ser
            340                 345                 350

Arg Ser Pro Ser Pro Pro Ser Ser Lys Gly Gln Ser Gln Ala Thr Thr
        355                 360                 365

Gly Glu Thr Phe Lys Thr Pro Val Ser Gly Thr His Asp Lys Asp Pro
    370                 375                 380

Lys Gly Thr Arg Gly Thr Cys Pro Asp Gly Asp Asp Phe Lys Thr Glu
385                 390                 395                 400

Asp Lys Lys Ala Asp Lys Gly Ala Asp Lys Met Arg Glu Lys Thr Ala
                405                 410                 415

Glu Leu Lys Asp Val Lys Asp Ser Ser Ala Gln Thr Asp Ala Gly Gln
            420                 425                 430

Lys Glu Val Arg Val Leu Ser Asp Ala Asp Ala Ser Val Leu Ile Gln
        435                 440                 445

Ala Ala Tyr Arg Gly His Gln Val Arg Lys Trp Glu Ala Leu Lys Lys
    450                 455                 460

Leu Lys Gln Ile Asp Glu Val Arg Lys Glu Val Thr Asp Val Arg Asp
465                 470                 475                 480

Arg Val Gln Ala Phe Glu Arg Ser Ser Asp Leu Gln Asn Asp Asp Lys
                485                 490                 495

Gln Lys Ile Ala Ile Gly Glu Thr Ile Met Arg Leu Leu Leu Lys Leu
            500                 505                 510

Asp Thr Ile Gln Gly Leu His Pro Ser Ile Arg Glu Ile Arg Lys Ser
        515                 520                 525

Leu Ala Arg Glu Leu Thr Ile Leu Gln Glu Arg Leu Asp Tyr Ile Met
```

-continued

```
    530                 535                 540

Ala Lys Lys Pro Gln Gln Gln Val Gln Asp Phe Asn Val Gln Glu His
545                 550                 555                 560

Val Glu Val Thr Pro Met Asn Met Gln Asn Glu Glu Gln Val Ala Val
                565                 570                 575

Pro Ala Asp Ser Ala Glu Gly Ile Ser Asp Asp Ala Lys Gly Pro Cys
            580                 585                 590

Ala Asn Val Gly Gly Ser Glu Ser Gln Ser Pro Val Asp Pro Thr Ser
        595                 600                 605

Asp Lys Gly Ala Glu Ser Val Val Leu Pro Asn Gly Ser His Asn Asp
    610                 615                 620

Asp Thr Ser Gln Val Val Thr Asp Asp Thr Leu Asn Ser Thr Ser Asp
625                 630                 635                 640

Leu Ser Glu Thr Asp Lys Met Ala Val Glu Pro Glu Ala Lys Ser Glu
                645                 650                 655

Ala Lys Asp Ile Pro Thr Ala Glu Asp Ile Leu Asn Glu Val Asp Lys
            660                 665                 670

Leu Tyr Lys Thr Val Leu Glu Glu Phe Pro Val Gly Val Val Asp Glu
        675                 680                 685

Asp Ile Asp Asp Val Ile Ile Glu Lys Glu Glu Gln Asp Asp Val Ser
    690                 695                 700

Ser Gly Thr Ile Ser Glu Val Lys Lys His Asp Arg Ala Lys Pro Lys
705                 710                 715                 720

Thr Tyr Lys Glu Val Leu Leu Ala Gln Glu Gly Glu Cys Asn Ala Asp
                725                 730                 735

Glu Lys Thr Ser Ser Ser Thr Asp Asn Thr Ala Asn Glu Thr Gln Leu
            740                 745                 750

Gly Gln Gln Gln Lys Leu Glu Glu Gln Lys Glu Val His Ser Ser Gly
        755                 760                 765

Glu Cys Trp Val Lys Ile Lys Tyr Gln Glu Glu Gly Glu Glu Val Glu
    770                 775                 780

Asn Asp Thr Lys Leu Pro Pro Leu Thr Thr Gln Ala Ile Gly Ala Asp
785                 790                 795                 800

Asp Lys Asp Pro Glu Ala Leu Phe Lys Glu Lys Thr Glu Leu Ser Ser
                805                 810                 815

Pro Pro Pro Ala Leu Gln Glu Pro Glu Leu Pro Ala Ala Met Arg Asp
            820                 825                 830

Gly Glu Phe Asn Gly Asp Thr Lys Leu Leu Glu Glu Asn Glu Asn Leu
        835                 840                 845

Arg Glu Met Met Lys Lys Leu Leu Glu Ala Gly Asn Glu Gln Leu Ser
    850                 855                 860

Val Ile Thr Asn Leu Thr Gly Arg Val Lys Asp Leu Glu Lys Lys Leu
865                 870                 875                 880

Ala Arg Ser Arg Ser Lys Arg Val Lys Thr Lys Arg Tyr Arg Pro Ala
                885                 890                 895

Thr Ser Lys Met Ser Cys Met Lys
            900
```

<210> SEQ ID NO 170
<211> LENGTH: 21
<212> TYPE: DNA
<213> ORGANISM: Glycine max

<400> SEQUENCE: 170
ggaggcaggg aagttcactg t 21

<210> SEQ ID NO 171
<211> LENGTH: 20
<212> TYPE: DNA
<213> ORGANISM: Glycine max

<400> SEQUENCE: 171
aaccactcag ggccttggat 20

<210> SEQ ID NO 172
<211> LENGTH: 27
<212> TYPE: DNA
<213> ORGANISM: Glycine max

<400> SEQUENCE: 172
taaatacggt cgaacttgtt agaggtt 27

<210> SEQ ID NO 173
<211> LENGTH: 26
<212> TYPE: DNA
<213> ORGANISM: Glycine max

<400> SEQUENCE: 173
agcacctaaa aaagcatatc acagaa 26

<210> SEQ ID NO 174
<211> LENGTH: 21
<212> TYPE: DNA
<213> ORGANISM: Glycine max

<400> SEQUENCE: 174
tcttgagagc aaagtcaccg c 21

<210> SEQ ID NO 175
<211> LENGTH: 20
<212> TYPE: DNA
<213> ORGANISM: Glycine max

<400> SEQUENCE: 175
ttgtcacacc acagggttgg 20

<210> SEQ ID NO 176
<211> LENGTH: 19
<212> TYPE: DNA
<213> ORGANISM: Glycine max

<400> SEQUENCE: 176
ttcctcgcca caagactgc 19

<210> SEQ ID NO 177
<211> LENGTH: 19
<212> TYPE: DNA
<213> ORGANISM: Glycine max

<400> SEQUENCE: 177
aaaatctgcg gcgaggatt 19

<210> SEQ ID NO 178
<211> LENGTH: 21
<212> TYPE: DNA
<213> ORGANISM: Glycine max

<400> SEQUENCE: 178
aatgcacctt ctagcaaggc c 21

<210> SEQ ID NO 179
<211> LENGTH: 20
<212> TYPE: DNA
<213> ORGANISM: Glycine max

<400> SEQUENCE: 179
aggcaggctg caaagagtgt 20

<210> SEQ ID NO 180
<211> LENGTH: 21
<212> TYPE: DNA
<213> ORGANISM: Glycine max

<400> SEQUENCE: 180
gcctcgggtg ctaaagctaa a 21

<210> SEQ ID NO 181
<211> LENGTH: 23
<212> TYPE: DNA
<213> ORGANISM: Glycine max

<400> SEQUENCE: 181
aaaggtgcat aacattttgg ctg 23

<210> SEQ ID NO 182
<211> LENGTH: 21
<212> TYPE: DNA
<213> ORGANISM: Glycine max

<400> SEQUENCE: 182
cactgctcaa catcaggacc a 21

<210> SEQ ID NO 183
<211> LENGTH: 19
<212> TYPE: DNA
<213> ORGANISM: Glycine max

<400> SEQUENCE: 183
ccgaatcgac ccgtttacg 19

<210> SEQ ID NO 184
<211> LENGTH: 27
<212> TYPE: DNA
<213> ORGANISM: Glycine max

<400> SEQUENCE: 184
gggacaacaa cctaagagac agattac 27

<210> SEQ ID NO 185
<211> LENGTH: 22
<212> TYPE: DNA
<213> ORGANISM: Glycine max

<400> SEQUENCE: 185
tcattttcaa ctggttcgag ca 22

<210> SEQ ID NO 186
<211> LENGTH: 20
<212> TYPE: DNA
<213> ORGANISM: Glycine max

<400> SEQUENCE: 186
gtgttgttgg cttgattgcg 20

<210> SEQ ID NO 187
<211> LENGTH: 21
<212> TYPE: DNA
<213> ORGANISM: Glycine max

<400> SEQUENCE: 187
tcaaacttgg gaaggcactc a 21

<210> SEQ ID NO 188
<211> LENGTH: 20
<212> TYPE: DNA
<213> ORGANISM: Glycine max

<400> SEQUENCE: 188
gaacatgctg gttgcatcgt 20

<210> SEQ ID NO 189
<211> LENGTH: 20
<212> TYPE: DNA
<213> ORGANISM: Glycine max

<400> SEQUENCE: 189
aggtgccctg atgcctacag 20

<210> SEQ ID NO 190
<211> LENGTH: 20
<212> TYPE: DNA
<213> ORGANISM: Glycine max

<400> SEQUENCE: 190
tacagccacc tggataggcc 20

<210> SEQ ID NO 191
<211> LENGTH: 21
<212> TYPE: DNA
<213> ORGANISM: Glycine max

<400> SEQUENCE: 191
tgtttgcttg tgtgttttgg g 21

<210> SEQ ID NO 192
<211> LENGTH: 21
<212> TYPE: DNA
<213> ORGANISM: Glycine max

<400> SEQUENCE: 192
agacgtggaa ggtggtgact g 21

<210> SEQ ID NO 193
<211> LENGTH: 21
<212> TYPE: DNA
<213> ORGANISM: Glycine max

<400> SEQUENCE: 193
agaatgccgc ttcacagaat g 21

<210> SEQ ID NO 194
<211> LENGTH: 19
<212> TYPE: DNA
<213> ORGANISM: Glycine max

<400> SEQUENCE: 194
attgagggac tttcggcca 19

<210> SEQ ID NO 195
<211> LENGTH: 20
<212> TYPE: DNA
<213> ORGANISM: Glycine max

<400> SEQUENCE: 195
tcccttcccc tcctacagct 20

<210> SEQ ID NO 196
<211> LENGTH: 21
<212> TYPE: DNA
<213> ORGANISM: Glycine max

<400> SEQUENCE: 196
acactgatac aagggcatgg c 21

<210> SEQ ID NO 197
<211> LENGTH: 19
<212> TYPE: DNA
<213> ORGANISM: Glycine max

<400> SEQUENCE: 197
ggtggcccca aatccatag 19

<210> SEQ ID NO 198
<211> LENGTH: 21
<212> TYPE: DNA
<213> ORGANISM: Glycine max

<400> SEQUENCE: 198
agcaagttcc acacgctctg t 21

<210> SEQ ID NO 199
<211> LENGTH: 20
<212> TYPE: DNA
<213> ORGANISM: Glycine max

<400> SEQUENCE: 199
ggtgccgttt agcatctcgt 20

<210> SEQ ID NO 200
<211> LENGTH: 20
<212> TYPE: DNA
<213> ORGANISM: Glycine max

<400> SEQUENCE: 200
accctcccag ggtttcactc 20

<210> SEQ ID NO 201
<211> LENGTH: 20
<212> TYPE: DNA
<213> ORGANISM: Glycine max

<400> SEQUENCE: 201
gcagaggagg ctccgatttt 20

<210> SEQ ID NO 202
<211> LENGTH: 20
<212> TYPE: DNA

<213> ORGANISM: Glycine max

<400> SEQUENCE: 202
cttggtccgt ccagcttctg 20

<210> SEQ ID NO 203
<211> LENGTH: 21
<212> TYPE: DNA
<213> ORGANISM: Glycine max

<400> SEQUENCE: 203
ttcgtacgtc caatctacgc c 21

<210> SEQ ID NO 204
<211> LENGTH: 26
<212> TYPE: DNA
<213> ORGANISM: Glycine max

<400> SEQUENCE: 204
aaccttaaac gagctatccc ttttta 26

<210> SEQ ID NO 205
<211> LENGTH: 22
<212> TYPE: DNA
<213> ORGANISM: Glycine max

<400> SEQUENCE: 205
tgcagcttct tgtttgttga ca 22

<210> SEQ ID NO 206
<211> LENGTH: 20
<212> TYPE: DNA
<213> ORGANISM: Glycine max

<400> SEQUENCE: 206
gggagcatgc aaatctcgat 20

<210> SEQ ID NO 207
<211> LENGTH: 19
<212> TYPE: DNA
<213> ORGANISM: Glycine max

<400> SEQUENCE: 207
gctcaacaaa gccctcgct 19

<210> SEQ ID NO 208
<211> LENGTH: 21
<212> TYPE: DNA
<213> ORGANISM: Glycine max

<400> SEQUENCE: 208
aatcagcctt ctcccaaatg c 21

<210> SEQ ID NO 209
<211> LENGTH: 20
<212> TYPE: DNA
<213> ORGANISM: Glycine max

<400> SEQUENCE: 209
cggctgagga agctcgtaag 20

<210> SEQ ID NO 210
<211> LENGTH: 21

<212> TYPE: DNA
<213> ORGANISM: Glycine max

<400> SEQUENCE: 210
ggaaagtatg gcaccgacag a 21

<210> SEQ ID NO 211
<211> LENGTH: 21
<212> TYPE: DNA
<213> ORGANISM: Glycine max

<400> SEQUENCE: 211
gttaattgca aacggcggtt a 21

<210> SEQ ID NO 212
<211> LENGTH: 21
<212> TYPE: DNA
<213> ORGANISM: Glycine max

<400> SEQUENCE: 212
actgcaggga aagcaaaggt t 21

<210> SEQ ID NO 213
<211> LENGTH: 20
<212> TYPE: DNA
<213> ORGANISM: Glycine max

<400> SEQUENCE: 213
ccgcacttga agacccttgt 20

<210> SEQ ID NO 214
<211> LENGTH: 20
<212> TYPE: DNA
<213> ORGANISM: Glycine max

<400> SEQUENCE: 214
ttgttgccgt gagtcagcat 20

<210> SEQ ID NO 215
<211> LENGTH: 21
<212> TYPE: DNA
<213> ORGANISM: Glycine max

<400> SEQUENCE: 215
cagggaaaag tgtggcaagt g 21

<210> SEQ ID NO 216
<211> LENGTH: 21
<212> TYPE: DNA
<213> ORGANISM: Glycine max

<400> SEQUENCE: 216
aaggtcacca tgtcccaaca c 21

<210> SEQ ID NO 217
<211> LENGTH: 20
<212> TYPE: DNA
<213> ORGANISM: Glycine max

<400> SEQUENCE: 217
gagggaagcg tgcaatagct 20

<210> SEQ ID NO 218

<211> LENGTH: 25
<212> TYPE: DNA
<213> ORGANISM: Glycine max

<400> SEQUENCE: 218
ttcctaaggc ctaagctttc agtgt 25

<210> SEQ ID NO 219
<211> LENGTH: 25
<212> TYPE: DNA
<213> ORGANISM: Glycine max

<400> SEQUENCE: 219
gcaaaaaaag ataaagacga tttgg 25

<210> SEQ ID NO 220
<211> LENGTH: 21
<212> TYPE: DNA
<213> ORGANISM: Glycine max

<400> SEQUENCE: 220
cacggagagc ttcatggaga a 21

<210> SEQ ID NO 221
<211> LENGTH: 21
<212> TYPE: DNA
<213> ORGANISM: Glycine max

<400> SEQUENCE: 221
catgcaactc attccctttg g 21

<210> SEQ ID NO 222
<211> LENGTH: 21
<212> TYPE: DNA
<213> ORGANISM: Glycine max

<400> SEQUENCE: 222
tcaggaaaag ctgtgggaag a 21

<210> SEQ ID NO 223
<211> LENGTH: 20
<212> TYPE: DNA
<213> ORGANISM: Glycine max

<400> SEQUENCE: 223
ccttttcgac gccaacgtaa 20

<210> SEQ ID NO 224
<211> LENGTH: 20
<212> TYPE: DNA
<213> ORGANISM: Glycine max

<400> SEQUENCE: 224
gcactgcccc aacacataga 20

<210> SEQ ID NO 225
<211> LENGTH: 19
<212> TYPE: DNA
<213> ORGANISM: Glycine max

<400> SEQUENCE: 225
gagaacggcg tgcagaaca 19

<210> SEQ ID NO 226
<211> LENGTH: 20
<212> TYPE: DNA
<213> ORGANISM: Glycine max

<400> SEQUENCE: 226
ggtgggatcg ggattaggtt 20

<210> SEQ ID NO 227
<211> LENGTH: 24
<212> TYPE: DNA
<213> ORGANISM: Glycine max

<400> SEQUENCE: 227
caagaatcca aaagcaatga acaa 24

<210> SEQ ID NO 228
<211> LENGTH: 21
<212> TYPE: DNA
<213> ORGANISM: Glycine max

<400> SEQUENCE: 228
tcaccgtcag aatccaattc c 21

<210> SEQ ID NO 229
<211> LENGTH: 20
<212> TYPE: DNA
<213> ORGANISM: Glycine max

<400> SEQUENCE: 229
tgcatgatgg ctggtgagtt 20

<210> SEQ ID NO 230
<211> LENGTH: 23
<212> TYPE: DNA
<213> ORGANISM: Glycine max

<400> SEQUENCE: 230
gccagtacct atccacaatt gct 23

<210> SEQ ID NO 231
<211> LENGTH: 23
<212> TYPE: DNA
<213> ORGANISM: Glycine max

<400> SEQUENCE: 231
cctcgaaggc agtttctttt aca 23

<210> SEQ ID NO 232
<211> LENGTH: 20
<212> TYPE: DNA
<213> ORGANISM: Glycine max

<400> SEQUENCE: 232
tggtgctgac ccttttggt 20

<210> SEQ ID NO 233
<211> LENGTH: 21
<212> TYPE: DNA
<213> ORGANISM: Glycine max

<400> SEQUENCE: 233
gggtgacgat cacttggtga t 21

<210> SEQ ID NO 234
<211> LENGTH: 19
<212> TYPE: DNA
<213> ORGANISM: Glycine max

<400> SEQUENCE: 234
agaaccccgt ggtgatcga 19

<210> SEQ ID NO 235
<211> LENGTH: 21
<212> TYPE: DNA
<213> ORGANISM: Glycine max

<400> SEQUENCE: 235
ggaaagaaga agcgcacgat a 21

<210> SEQ ID NO 236
<211> LENGTH: 22
<212> TYPE: DNA
<213> ORGANISM: Glycine max

<400> SEQUENCE: 236
ccccaaagat gacccaaata ag 22

<210> SEQ ID NO 237
<211> LENGTH: 24
<212> TYPE: DNA
<213> ORGANISM: Glycine max

<400> SEQUENCE: 237
ggtcttccaa tatggcttct tctg 24

<210> SEQ ID NO 238
<211> LENGTH: 26
<212> TYPE: DNA
<213> ORGANISM: Glycine max

<400> SEQUENCE: 238
cttctcaggt tcttcctgtg attaaa 26

<210> SEQ ID NO 239
<211> LENGTH: 25
<212> TYPE: DNA
<213> ORGANISM: Glycine max

<400> SEQUENCE: 239
accattttgg acatcattga atctg 25

<210> SEQ ID NO 240
<211> LENGTH: 21
<212> TYPE: DNA
<213> ORGANISM: Glycine max

<400> SEQUENCE: 240
gggttgacca ctccaacctt t 21

<210> SEQ ID NO 241
<211> LENGTH: 19
<212> TYPE: DNA
<213> ORGANISM: Glycine max

<400> SEQUENCE: 241
gcaccctctg gccaagaaa 19

<210> SEQ ID NO 242
<211> LENGTH: 20
<212> TYPE: DNA
<213> ORGANISM: Glycine max

<400> SEQUENCE: 242
ggatggtgcc ggagtatctg 20

<210> SEQ ID NO 243
<211> LENGTH: 20
<212> TYPE: DNA
<213> ORGANISM: Glycine max

<400> SEQUENCE: 243
tcatcactcc cgaagcaatg 20

<210> SEQ ID NO 244
<211> LENGTH: 22
<212> TYPE: DNA
<213> ORGANISM: Glycine max

<400> SEQUENCE: 244
caaactttga agcaccaagc at 22

<210> SEQ ID NO 245
<211> LENGTH: 24
<212> TYPE: DNA
<213> ORGANISM: Glycine max

<400> SEQUENCE: 245
tgttcaaggc ttgattgata agga 24

<210> SEQ ID NO 246
<211> LENGTH: 22
<212> TYPE: DNA
<213> ORGANISM: Glycine max

<400> SEQUENCE: 246
ttaaacgggt gaaggaaaaa cc 22

<210> SEQ ID NO 247
<211> LENGTH: 19
<212> TYPE: DNA
<213> ORGANISM: Glycine max

<400> SEQUENCE: 247
atatcccacg ggcaaaagg 19

<210> SEQ ID NO 248
<211> LENGTH: 20
<212> TYPE: DNA
<213> ORGANISM: Glycine max

<400> SEQUENCE: 248
tctgcaaaca tggccgataa 20

<210> SEQ ID NO 249
<211> LENGTH: 16
<212> TYPE: DNA
<213> ORGANISM: Glycine max

<400> SEQUENCE: 249
gctccgccgg aggaat 16

<210> SEQ ID NO 250
<211> LENGTH: 21
<212> TYPE: DNA
<213> ORGANISM: Glycine max

<400> SEQUENCE: 250
tgatcactca cggcaacaag a 21

<210> SEQ ID NO 251
<211> LENGTH: 21
<212> TYPE: DNA
<213> ORGANISM: Glycine max

<400> SEQUENCE: 251
ttggataggg ctgaccttca a 21

<210> SEQ ID NO 252
<211> LENGTH: 25
<212> TYPE: DNA
<213> ORGANISM: Glycine max

<400> SEQUENCE: 252
tggaacaact cttcatgagt gagaa 25

<210> SEQ ID NO 253
<211> LENGTH: 29
<212> TYPE: DNA
<213> ORGANISM: Glycine max

<400> SEQUENCE: 253
aagtctcatt aaccatagct ttcaagttt 29

<210> SEQ ID NO 254
<211> LENGTH: 29
<212> TYPE: DNA
<213> ORGANISM: Glycine max

<400> SEQUENCE: 254
gtggaaagct aatgttgaaa ataatacag 29

<210> SEQ ID NO 255
<211> LENGTH: 23
<212> TYPE: DNA
<213> ORGANISM: Glycine max

<400> SEQUENCE: 255
cggcatcagg taaaacaaga ttg 23

<210> SEQ ID NO 256
<211> LENGTH: 18
<212> TYPE: DNA
<213> ORGANISM: Glycine max

<400> SEQUENCE: 256
cccgcagctt ccaaaatg 18

<210> SEQ ID NO 257
<211> LENGTH: 20
<212> TYPE: DNA
<213> ORGANISM: Glycine max

<400> SEQUENCE: 257
gagagccttt gatgttgcaa 20

<210> SEQ ID NO 258
<211> LENGTH: 27
<212> TYPE: DNA
<213> ORGANISM: Glycine max

<400> SEQUENCE: 258
gctatatatt tcatgtgtgc tctgcat 27

<210> SEQ ID NO 259
<211> LENGTH: 27
<212> TYPE: DNA
<213> ORGANISM: Glycine max

<400> SEQUENCE: 259
ccatatttgg gaaagttcat ttttttt 27

<210> SEQ ID NO 260
<211> LENGTH: 20
<212> TYPE: DNA
<213> ORGANISM: Glycine max

<400> SEQUENCE: 260
gccgtaccct tgctgactac 20

<210> SEQ ID NO 261
<211> LENGTH: 20
<212> TYPE: DNA
<213> ORGANISM: Glycine max

<400> SEQUENCE: 261
atggtgtcgg agctttcaac 20

<210> SEQ ID NO 262
<211> LENGTH: 40
<212> TYPE: DNA
<213> ORGANISM: Glycine max

<400> SEQUENCE: 262
aaaaaagcag gctatagagt gactattatt ctctttttac 40

<210> SEQ ID NO 263
<211> LENGTH: 36
<212> TYPE: DNA
<213> ORGANISM: Glycine max

<400> SEQUENCE: 263
agaaagctgg gtatgttgag agagagagag agttag 36

<210> SEQ ID NO 264
<211> LENGTH: 38
<212> TYPE: DNA
<213> ORGANISM: Glycine max

<400> SEQUENCE: 264
aaaaaagcag gctatagaga agttacaaga gtagtttc 38

<210> SEQ ID NO 265
<211> LENGTH: 34
<212> TYPE: DNA
<213> ORGANISM: Glycine max

<400> SEQUENCE: 265
aagaaagctg ggtaggctac tacgtaggtc ggtt 34

<210> SEQ ID NO 266
<211> LENGTH: 39
<212> TYPE: DNA
<213> ORGANISM: Glycine max

<400> SEQUENCE: 266
aaaaaagcag gctatgtatt tcattgactc tcatttttc 39

<210> SEQ ID NO 267
<211> LENGTH: 34
<212> TYPE: DNA
<213> ORGANISM: Glycine max

<400> SEQUENCE: 267
aagaaagctg ggtatccaga agttggtgtt ggtg 34

<210> SEQ ID NO 268
<211> LENGTH: 38
<212> TYPE: DNA
<213> ORGANISM: Glycine max

<400> SEQUENCE: 268
aaaaaagcag gctatttcct tcgtaaactg atatcatg 38

<210> SEQ ID NO 269
<211> LENGTH: 35
<212> TYPE: DNA
<213> ORGANISM: Glycine max

<400> SEQUENCE: 269
aagaaagctg ggtagtgctt ttgctattga agaag 35

<210> SEQ ID NO 270
<211> LENGTH: 39
<212> TYPE: DNA
<213> ORGANISM: Glycine max

<400> SEQUENCE: 270
aaaaaagcag gctatttcgc gtctcatact ataaattaa 39

<210> SEQ ID NO 271
<211> LENGTH: 39
<212> TYPE: DNA
<213> ORGANISM: Glycine max

<400> SEQUENCE: 271
aagaaagctg ggtatataat tctaaggttc aatgtttca 39

<210> SEQ ID NO 272
<211> LENGTH: 39
<212> TYPE: DNA
<213> ORGANISM: Glycine max

<400> SEQUENCE: 272
aaaaaagcag gctatcttaa gagaagtagt tcttgtatt 39

<210> SEQ ID NO 273
<211> LENGTH: 36
<212> TYPE: DNA
<213> ORGANISM: Glycine max

<400> SEQUENCE: 273
aagaaagctg ggtagaggga aagaaagtta aggatt 36

<210> SEQ ID NO 274
<211> LENGTH: 38
<212> TYPE: DNA
<213> ORGANISM: Glycine max

<400> SEQUENCE: 274
aaaaaagcag gctatctagt tcttttgtgc ataaaaca 38

<210> SEQ ID NO 275
<211> LENGTH: 35
<212> TYPE: DNA
<213> ORGANISM: Glycine max

<400> SEQUENCE: 275
aagaaagctg ggtatgttca aagatcaaag ccgag 35

<210> SEQ ID NO 276
<211> LENGTH: 36
<212> TYPE: DNA
<213> ORGANISM: Glycine max

<400> SEQUENCE: 276
aaaaaagcag gctatttttc ttccactcat ccctgt 36

<210> SEQ ID NO 277
<211> LENGTH: 36
<212> TYPE: DNA
<213> ORGANISM: Glycine max

<400> SEQUENCE: 277
aagaaagctg ggtatctact aatcctacta gtacta 36

<210> SEQ ID NO 278
<211> LENGTH: 38
<212> TYPE: DNA
<213> ORGANISM: Glycine max

<400> SEQUENCE: 278
aaaaaagcag gctataattg tctcatctct acatttac 38

<210> SEQ ID NO 279
<211> LENGTH: 35
<212> TYPE: DNA
<213> ORGANISM: Glycine max

<400> SEQUENCE: 279
aagaaagctg ggtagtccac aaatctgata cacag 35

<210> SEQ ID NO 280
<211> LENGTH: 34
<212> TYPE: DNA
<213> ORGANISM: Arabidopsis thaliana

<400> SEQUENCE: 280
aaaaaagcag gctatccttg tcaactcctc taga 34

<210> SEQ ID NO 281
<211> LENGTH: 34
<212> TYPE: DNA

-continued

```
<213> ORGANISM: Arabidopsis thaliana

<400> SEQUENCE: 281

agaaagctgg gtatgttgtt cttcttcttc tctc                              34


<210> SEQ ID NO 282
<211> LENGTH: 37
<212> TYPE: DNA
<213> ORGANISM: Glycine max

<400> SEQUENCE: 282

aaaaaagcag gctattagga tgagcacatt ttacgtt                           37


<210> SEQ ID NO 283
<211> LENGTH: 34
<212> TYPE: DNA
<213> ORGANISM: Glycine max

<400> SEQUENCE: 283

aagaaagctg ggtacctctc tcccaataca atct                              34


<210> SEQ ID NO 284
<211> LENGTH: 29
<212> TYPE: DNA
<213> ORGANISM: Artificial Sequence
<220> FEATURE:
<223> OTHER INFORMATION: PCR primer

<400> SEQUENCE: 284

ggggacaagt ttgtacaaaa aagcaggct                                    29


<210> SEQ ID NO 285
<211> LENGTH: 29
<212> TYPE: DNA
<213> ORGANISM: Artificial Sequence
<220> FEATURE:
<223> OTHER INFORMATION: PCR primer

<400> SEQUENCE: 285

ggggaccact ttgtacaaga aagctgggt                                    29
```

GENES IMPLICATED IN RESISTANCE TO SOYBEAN CYST NEMATODE INFECTION AND METHODS OF THEIR USE

RELATED APPLICATIONS

This application claims benefit of priority to U.S. Provisional Patent Application Ser. No. 61/430,120 filed Jan. 5, 2011, the contents of which are incorporated by reference into this application.

SEQUENCE LISTING

This application is accompanied by a sequence listing in a computer readable form that accurately reproduces the sequences described herein.

BACKGROUND

1. Field of the Invention

The present disclosure relates to proteins and genes responsible for plant defense against soybean cyst nematode (SCN) and the regulation of their expression in plant defense against SCN infection.

2. Description of the Related Art

Soybean cyst nematode (SCN; *Heterodera glycines*) is an obligate sedentary endoparasite, and is the most important pathogen for soybean. The average amount of soybean lost to SCN in the United States from 2006 to 2009 was 128.6 million bushels annually, which was valued at $1.286 billion annually (Koenning and Wrather, 2010). The successful invasion of soybean by SCN depends upon SCN's ability to establish a permanent feeding cell (also known as "syncytium") within the roots of soybean. Infective juveniles penetrate into the root and migrate toward the vasculature. Near the vasculature, each juvenile selects a single cell, which is modified to allow for the incorporation of adjacent cells through progressive cell wall dissolution to form a multinucleate syncytium. The nematode derives nutrients from the syncytium for its growth and reproduction.

The primary management practice for this pathogen is by developing resistant soybean cultivars. Resistant cultivars have been developed by identifying SCN-resistant soybean germplasm from collections of plant introductions (PI) and incorporating the trait through conventional breeding programs. Although several sources of resistance have been identified, only a few PIs have been used in breeding programs due to undesirable traits associated with other resistance sources. The most predominant sources of resistance found in commercially available cultivars are derived from PI 88788, PI 54840 (Peking), and PI 437654. In all resistant cultivars, the infective juveniles are capable of penetrating into roots and can induce the formation of syncytia, but the syncytia become necrotic soon after establishment and the nematodes starve to death. Although necrosis is a common theme, the timing of necrosis and degeneration of syncytia vary among resistant cultivars, depending on the source of resistance (Acedo et al., 1984). For example in Peking, syncytial collapse is observed as early as 48 hours post infection (Mahalingam and Skorupska, 1996); whereas, the onset of the resistance response is much slower in PI 209332, with degeneration of the syncytia not occurring until 8-10 days post infection ("dpi") (Acedo et al., 1984).

Despite the extensive histological studies documenting the cellular changes associated with degenerating syncytia in soybean (Endo, 1965; Riggs et al., 1973; Acedo et al., 1984), very little is known about the molecular mechanisms underlying this hypersensitive-like resistance response. Research conducted in the past decade has identified a number of quantitative trait loci (QTLs) associated with SCN resistance (reviewed in Concibido et al., 2004) in different PIs that serve as sources of resistance in breeding programs. Among these, two major QTLs are Rhg1 on soybean chromosome 18 (formerly linkage group G) and Rhg4 on chromosome 8 (formerly linkage group A2). Rhg1 exhibits incomplete dominance and contributes to a significant portion of SCN resistance in most PIs tested, including PI 88788, PI 90763, PI 209332, and Peking (Concibido et al., 2004). In addition, Rhg1 is effective against a broad spectrum of SCN populations. Rhg4 is dominant and is required for full resistance to certain SCN populations in some (e.g., Peking, PI 437654), but not all (e.g., PI 209332, PI 88788), resistant sources (Brucker et al., 2005).

Microarray analyses have been carried out to study this plant-nematode interaction. Initial studies used whole soybean roots infected with SCN to assess transcriptional changes during a compatible interaction (Khan et al., 2004; Alkharouf et al., 2006; Ithal et al., 2007a; Klink et al., 2007a). However, due to the specialized nature of the interaction and the location of syncytia well within the root, it is very difficult to draw meaningful conclusions using whole roots to understand this pathosystem.

Laser capture microdissection (LCM) of syncytial cells coupled with microarray analysis has been particularly useful in extending our understanding of the SCN-soybean interaction, as indicated by recently published studies (Klink et al., 2005; Ithal et al., 2007b). These studies have provided new insights into the underlying molecular events occurring during syncytium development. More recently, the same technology has been applied to study incompatible SCN-soybean interactions (Klink et al., 2007b; Klink et al., 2009; Klink et al., 2010). Two studies reported on a comparative microarray analysis of soybean genes induced in response to either a virulent or an avirulent SCN population on Peking (Klink et al., 2007b; Klink et al., 2009), demonstrating that soybean can differentiate between nematode populations prior to feeding cell establishment (Klink et al., 2007b). The same group also published a microarray study that examined the transcriptional changes occurring in syncytia induced by an avirulent SCN population on PI 88788 at three time points after infection (Klink et al., 2010).

There have been no reports of a direct comparative analysis of syncytia gene expression profiles using near-isogenic lines (NILs) to identify transcripts regulated by specific soybean resistance genes. NILs have several advantages over PIs for comparative analyses of plant gene expression between resistant and susceptible soybean in response to SCN. Theoretically, NILs can share up to 98% of their genome, differing only in a region encompassing a trait of interest (Li et al., 2004); thus, NILs are powerful tools to study the effects of specific gene loci with reduced genetic background effects. Consequently, the use of NILs for molecular studies is becoming more popular. For instance, NILs have been used in a microarray analysis of iron efficient and inefficient cultivars of soybean (O'Rourke et al., 2009) and a wheat leaf rust resistance gene Lr10 (Manickavelu et al., 2010). NILs have also been used recently to help identify the effects of the *Arabidopsis* gene FLC on seed germination (Chiang et al., 2009). Despite intensive cytological and molecular genetic studies, the genes responsible for SCN resistance have not been identified (Melito et al., 2010), and the mechanism for resistance on a molecular level has yet to be fully elucidated.

SUMMARY

The instrumentalities described herein overcome the problems outlined above and advance the art by providing genes and DNA regulatory elements in plant roots that may play an important role in plant defense against SCN infection. More specifically, gene expression levels in root tissues are compared between soybean lines that are resistant to SCN infection ("resistant lines) and lines that are susceptible to SCN infection ("susceptible lines"). The expression levels of a number of genes have been found to be significantly higher in the SCN resistant lines as compared to the expression levels of the same genes in the susceptible lines. Conversely, a number of genes have been found to be expressed at a significantly lower level in the SCN resistant lines as compared to the expression levels of the same genes in the susceptible lines. For purpose of this disclosure, all these genes whose levels are up- or down-regulated in the SCN resistant lines as compared to the expression levels of the same genes in the susceptible lines are termed "SCN responsive gene(s)," or "SCNRG." For purpose of this disclosure, a gene having a sequence that is substantially identical to an SCNRG is considered a member of the SCNRG family. A gene encoding a protein having an amino acid sequence that is substantially identical to the amino acid sequence of a protein encoded by an SCNRG is also considered a member of the SCNRG family. In another embodiment, a gene from a different plant species or from the same species, which shares similar domain structure with a SCNRG disclosed herein and which performs similar cellular function as that of the SCNRG disclosed herein is also considered a member of the SCNRG family, and may be referred to as a homolog of the SCNRG for purpose of this disclosure.

Planting of resistant soybean cultivars has been the primary strategy for managing SCN population levels in the field. Despite widespread use of SCN-resistant soybean, SCN still causes an estimated $1.286 billion annually in yield losses. Lack of understanding of the molecular basis of resistance to this pathogen continues to hinder progress to enhance the effectiveness and durability of natural plant resistance. This lack of knowledge also hinders efforts to design novel strategies for resistance through biotechnological approaches. Rhg1, a major resistance locus in almost all SCN-resistant germplasm, is required for resistance against multiple SCN Hg types (Concibido et al., 2004); however, the molecular nature of the resistance gene underlying Rhg1 (Melito et al., 2010) is not known. Moreover, the downstream signaling and response genes mediated by Rhg1 have yet to be identified. The Rhg1 gene has been mapped to chromosome 18 and is within 0.4 cm of SSR marker satt_309 (Cregan et al., 1999), enabling the generation of NILs differing only at this locus (Mudge, 1999). Due to the multigenic nature of SCN resistance, these NILs are very useful for dissecting the SCN-soybean incompatible interaction.

In order to better understand the molecular events associated with Rhg1-mediated resistance against SCN, NILs have been used for a comparative analysis of syncytial gene expression using LCM and microarrays. These NILs have been used previously to study the effects of Rhg1 on root penetration and development of SCN (Li et al., 2004). Although root penetration by SCN juveniles is similar between NIL-R and NIL-S, the growth, development, and fecundity of nematode females is suppressed on NIL-R (Li et al., 2004), suggesting that Rhg1 may have a negative impact on syncytium development and maintenance. The histological characteristics of syncytia in resistant soybean cultivars to SCN infection are well documented (Ross, 1958; Endo, 1965; Riggs et al., 1973; Acedo et al., 1984). Second-stage SCN juveniles (J2s) induce the formation of syncytia in all resistant cultivars, but syncytial collapse several days later leads to nematode starvation and death. In one type of resistance (PI 437654; Peking type), syncytial collapse is very rapid and begins to occur within 48 hours of induction of the syncytium (Mahalingam and Skorupska, 1996).

To gain new insight into the cause of the aberrant syncytia development that occurs in resistant soybean in response to SCN infection, gene expression is analyzed in syncytia induced in soybean NILs differing at the Rhg1 locus (Mudge, 1999). Laser capture microdissection (LCM) coupled with comparative microarray profiling of syncytia isolated from the resistant NIL (NIL-R) and susceptible NIL (NIL-S) results in the identification of 1,447 differentially expressed genes with the false discovery rate set at 10%. Many of the genes induced in the NIL-R are soybean homologs of genes known to play important roles in disease resistance responses of other plant species to various pathogens, including canonical resistance genes (e.g., CC-NB-LRR class of receptors), genes associated with the hypersensitive-like response (HR), apoptotic cell death, the salicylic acid (SA)-mediated resistance pathway, and several transcription factors with defense-related roles. These results have also been validated by syncytia-specific quantitative PCR (qPCR), time course qPCR on infected whole root pieces, and promoter-GUS reporter experiments. These results suggest that Rhg1 may mediate a complex defense response within syncytia formed in resistant soybean plants, ultimately limiting the growth and development of the nematode.

Because the NILs used in the present disclosure show a delayed type of resistance (Acedo et al., 1984; Li et al., 2004) with notable histological changes to syncytia occurring by 8-10 dpi (FIG. 1), 5 and 8 dpi time points are chosen for laser-capture of syncytia to reflect gene expression prior to the onset of syncytium collapse. The comparison of syncytia gene expression between NIL-R and NIL-S by microarray analysis identified 1,447 differentially expressed probe sets (Tables 1-11). A relatively high representation of stress- and defense-related genes have been identified (241 probe sets representing 16.8% of the total; FIG. 2; Table 8), including genes involved in oxidative, heat, cold, salt, and drought stress.

In one embodiment, a gene coding for a BAG (BCL2-associated athanogene) domain protein with highest homology to the *Arabidopsis* BAG6 protein (AtBAG6) is the most highly up-regulated gene in syncytia of the resistant line. BAG proteins are anti-apoptotic in animals; however, AtBAG6 causes programmed cell death in yeast and *Arabidopsis* in overexpression studies (Kang et al., 2006). AtBAG6 is up-regulated by heat stress, and the HSF A-2 (Probe set GmaAffx.71308.2.A1_at, 4.0 fold) is involved in its regulation (Nishizawa et al., 2006). Increased expression of BAG6 gene in the resistant line suggests that the syncytia may be undergoing an apoptotic-like cell death response.

Several genes related to ER stress were also found to be up-regulated (e.g., BZIP60 homolog, BIP2 homolog, Calnexin, Bax inhibitor genes, and several protein disulphide isomerases). ER stress is a cellular condition in which unfolded proteins accumulate in the ER. Mis-folding of proteins may be the result of mutations, disturbances in calcium homeostasis, and the heightened need for protein folding. In order to maintain ER homeostasis under such conditions, signaling pathways are activated that are collectively known as the UPR. When ER stress is not relieved, apoptotic cell death may occur (Urade, 2009). It has recently been reported that water deficit or drought leads to programmed cell death mediated by the ER stress response pathway in *Arabidopsis* roots (Duan et al., 2010). Several drought and ABA-induced genes were found to be up-regulated in syncytia of the resistant NIL. Taken together, these data suggest that multiple stresses are induced by an upstream signaling event that ultimately leads to the activation of an HR-like programmed cell death (PCD) causing the pathogen to starve and die. It is also possible that pathogen death occurs before the syncytial HR-PCD. The HR may represent the final stages of the resistance response where a certain threshold of defense-related responses has been reached (Morel and Dangl, 1997). For example, the *Arabidopsis* dnd1 mutant expresses resistance to pathogens that otherwise induce HR on wild-type plants (Clough et al., 2000).

In general, the SA pathway has been shown to be activated in resistance against biotrophs and the JA pathway has been shown to be activated in resistance to necrotrophs and insects (Glazebrook, 2005; Bari and Jones, 2009). The SA pathway has also been implicated in resistance to the root-knot nematode in tomato (Branch et al., 2004). Here, several homologs of genes belonging to the SA-mediated defense signaling pathway have been identified to be up-regulated in SCN-induced syncytia of the NIL-R lines. These included soybean homologs of *Arabidopsis* NDR1 and NDR1/HIN1-like (NHLs) genes, which are key signal transducers in SA-mediated signaling. NDR1 is a plasma membrane localized protein required for disease resistance to *P. syringae* pv. tomato DC3000 carrying avirulence genes avrRpm1, avrRpt2, avrPph3, and avrB. It is also required for resistance against avirulent isolates of the fungal pathogen *Peronospora parasitica* (Century et al., 1995; Century et al., 1997). The requirement for resistance against a diverse group of pathogens suggests that this is a common downstream element in R-gene-mediated resistance in plants. *Arabidopsis* ndr1 mutants have reduced ROS production and SA accumulation in response to avirulent bacteria (Shapiro and Zhang, 2001). Conversely, overexpression of NDR1 in *Arabidopsis* leads to enhanced resistance to virulent *P. syringae* pv. tomato (Coppinger et al., 2004). NHL proteins have sequence homology to NDR1 of *Arabidopsis* and HIN1 of tobacco and are pathogen-induced in *Arabidopsis* (Varet et al., 2002). NHL3 overexpression in *Arabidopsis* is associated with enhanced resistance to virulent strains of *P. syringae* (Varet et al., 2003). A homolog of *Arabidopsis* PBS3 (WIN3) has also been identified, which interacts with the *P. syringae* effector protein HopW1-1 and is important for responses induced by several effectors in *Arabidopsis*. PBS3 is an important component of NDR1-dependent RPS2-mediated resistance against *P. syringae* pv. tomato carrying avrRpt2 and also plays a role in basal resistance (Lee et al., 2007). PBS3 is an acyl adenylase, and the *Arabidopsis* pbs3 mutant exhibits enhanced susceptibility to *P. syringae* pv. tomato carrying avrPphB (Nobuta et al., 2007). In the pbs3 mutant, induced free and conjugated SA levels are reduced. A homolog of another *Arabidopsis* gene related to SA accumulation, WIN1, is down-regulated in syncytia of NIL-R. Overexpression of WIN1 delays SA accumulation in response to several effectors, including HopW1-1 (Lee et al., 2008), which indicates WIN1 is a negative regulator. Thus, down-regulation of this gene would be predicted to have a positive impact on SA levels.

It has been previously reported that the majority of JA pathway components are suppressed during a compatible soybean-SCN interaction (Ithal et al., 2007b). Here, a homolog of *Arabidopsis* lipoxygenase 1 (AtLOX1) has been found to be up-regulated in syncytia of the NIL-R, suggesting the involvement of lipid peroxides in the resistance response. The up-regulation of soybean LOX genes is also reported in syncytia induced on Peking and PI 88788 by an avirulent population of SCN (Klink et al., 2009; Klink et al., 2010). Lipoxygenases have a role in basal resistance to the root-knot nematode in maize (Gao et al., 2008). Recently, mutations in AtLOX1 and silencing of a homologous gene of *Capsicum annuum* (CaLOX1) have been shown to increase susceptibility to diverse microbial pathogens (Hwang and Hwang, 2010). CaLOX1-silenced plants show lowered SA and ROS levels. However, we also identified down-regulation of two soybean genes corresponding to homologs of allene oxide cyclases (AOCs) involved in JA biosynthesis and a homolog of JAR1, a protein required to convert JA to the biologically active JA-isoleucine. These discrepancies emphasize the need for further studies directed at silencing the genes involved in SA and JA biosynthesis and quantifying hormone levels in nematode-infected roots to clarify the role of these small molecules in SCN-induced resistance in soybean.

In another aspect, evidence is presented for the potential involvement of a complex stress and defense-related response, including increased expression of genes involved in the production of ROS, the unfolded protein response, SA-mediated signaling, and plant PCD in Rhg1-mediated resistance to SCN. Involvement of almost all hormones shows an intricate network of cross-talk associated with this defense response. The instant disclosure also highlights the importance of conducting a direct comparison between syncytia transcriptomes in the resistant versus susceptible NILs using the same nematode population to identify genes potentially involved in resistance. Inadvertently, a large number of genes would be overlooked in a direct comparison of syncytia transcriptomes induced in the resistant line by an avirulent versus a virulent SCN population. It is shown here that the plant still mounts a defense response against the virulent nematode population, albeit somewhat attenuated compared to its response against the avirulent nematode population. In contrast, the response of the susceptible line to the avirulent population is minimal.

Additionally, several nematode-inducible soybean promoters have been identified. Some of these promoters have restricted expression in roots but are highly up-regulated in syncytia. These promoters may be used for targeted RNAi silencing of certain genes. The instant disclosure, together with the newly developed functional analysis tools in soybean such as VIGS (Zhang et al., 2009; Zhang et al., 2010) and the recently completed soybean genome sequencing (Schmutz et al., 2010), may hasten research to understand this relatively unknown, but fascinating, below-ground incompatible plant-pathogen interaction and may ultimately lead to the development of novel strategies to enhance nematode resistance in crop plants.

In one embodiment, one or more of the SCNRGs or fragments thereof may be introduced into a host plant where they are expressed at a level that is higher than the normal expression levels of the same gene(s) in the host plant. The transgenic plant thus generated may be more resistant to soybean cyst nematode (SCN) infection when compared to the host plant. The SCNRG or fragment thereof may encode a protein that is capable of rendering the plant more resistant to SCN infection via a number of different mechanisms. The one or more SCNRGs may be endogenous to the host plant, or they many be exogenous to the host plant.

In another embodiment, the promoters regulating the up-regulation or down-regulation of these SCNRG may be used to control the expression of certain genes. For instance, chimeric construct may be built and introduced into a host plant where the promoter modulates the expression of certain proteins that help render the host plant resistant to SCN. Such construct may contain genes known to play a role in plant defense against SCN infection, or it may contain genes that play a role in an unknown pathway that contribute to SCN resistance. Some of these promoters may be constitutive, others may only be turned on upon detection of SCN invasion by the plant. In another aspect, the promoters may be tissue specific. For example, some promoters may only modulate gene expression in the root tissues. Other promoters may drive a more universal expression of genes in a number of different tissues. These promoters may be used to direct expression of a heterologous gene in a host plant where the heterologous gene encodes a protein that help fight or prevent SCN infection.

In another embodiment, a plant may be modified such that the expression levels of certain SCN responsive genes are altered in a way that render the plant more resistant to SCN infection. For instance, a breeding program may be implemented to select for lines that have elevated levels of one or more of such responsive genes. In one aspect, a method may be used for generating a transgenic plant that is more resistant to SCN infection from a host plant. This method may include a step of altering the expression levels of a protein encoded by an SCNRG or a fragment thereof, wherein the SCNRG is endogenous to the host plant.

In another embodiment, the expression level of the protein encoded by the SCNRG may be altered so that the level is higher in the transgenic plant than the expression level of the protein in the host plant. In one aspect, the level of the protein encoded by the SCNRG is at least two fold, three fold, or even five fold higher in the transgenic plant than the expression level of the protein in the host plant.

In another embodiment, the expression of the SCNRG may be placed under control of a nematode inducible promoter, such that expression of the SCNRG is induced when the plant is in contact with nematode.

It is to be recognized that not all SCN responsive contribute positively to SCN resistance. As disclosed here, in a SCN resistant line, certain genes may be down-regulated in response to SCN infection. Down-regulation of these genes may contribute to defense against SCN by the resistant lines. In one embodiment, the expression level of certain proteins encoded by certain SCNRGs may be lower in the transgenic plant than the expression level of the protein in the host plant.

In another embodiment, the host plant is a soybean plant that is susceptible to soybean cyst nematode (SCN) infection.

In another embodiment, the expression levels of two more proteins encoded by two or more SCNRGs may be altered in the transgenic plant in order to obtain a transgenic plant that is less susceptible to nematode infection that the host plant. In one aspect, the SCNRG may be any of the disclosed genes that are either up- or down-regulated in the SCN resistant line as compared to the SCN sensitive line. In another aspect, the SCNRG may be GmBAG6, GmAP2, GmBAG6 homolog, GmAP2 homolog, or combination thereof.

BRIEF DESCRIPTION OF THE DRAWINGS

FIG. 11 shows a table summarizing the distribution of phenotypes in *Arabidopsis* overexpressing BAG6 gene.

FIG. 15 shows the sequences of the soybean BAG6 genes, GmBAG6A and GmBAG6B, including sequences of cDNA, genomic DNA and the encoded proteins.

DETAILED DESCRIPTION

Figure 1:
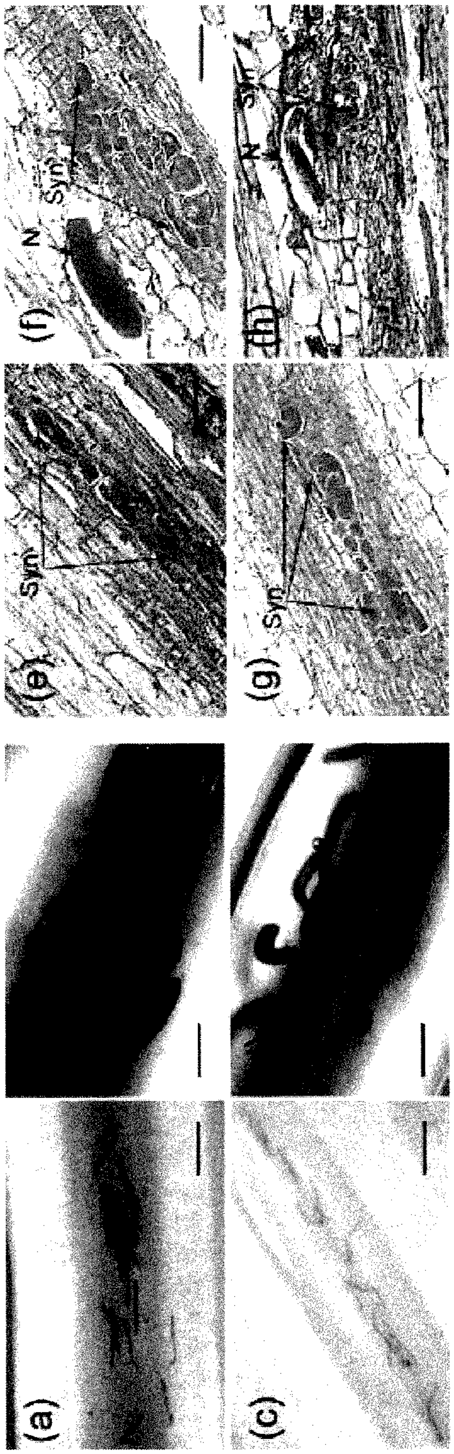
FIG. 1 shows nematode development and syncytia formation on near-isogenic lines (NIL) of soybean.

Unless otherwise defined in this disclosure, all technical and scientific terms used herein have the same meaning as commonly understood by one of ordinary skill in the related art. The following terminology and grammatical variants are used in accordance with the definitions set out below.

The term "genetically altered plant" or "genetically modified plant" refers to a plant whose genetic make-up has been altered or modified such that the modified plant expresses one or more protein that is not normally expressed by the unmodified plant or is expressed at different time or different tissue of the unmodified plant.

The term "transgenic plant" refers to a host plant into which a gene construct has been introduced. A gene construct, also referred to as a construct, an expression construct, or a DNA construct, generally contains as its components at least a coding sequence and a regulatory sequence. A gene construct typically contains at least one component that is foreign to the host plant. For purpose of this disclosure, all components of a gene construct may be from the host plant, but these components are not arranged in the host in the same manner as they are in the gene construct. A regulatory sequence is a non-coding sequence that typically contribute to the regulation of gene expression, at the transcription or translation levels. It is to be understood that certain segments in the coding sequence may be translated but may be later removed from the functional protein. An example of these segments is the so-called signal peptide, which may facilitate the maturation or localization of the translated protein, but is typically removed once the protein reaches its destination. Examples of a regulatory sequence include but are not limited to a promoter, an enhancer, and certain post-transcriptional regulatory elements.

After its introduction into a host plant, a gene construct may exist separately from the host chromosomes. Preferably, the entire gene construct, or at least part of it, is integrated onto a host chromosome. The integration may be mediated by a recombination event, which may be homologous, or non-homologous recombination. The term "express" or "expression" refers to production of RNAs using DNAs as template through transcription or translation of proteins from RNAs or the combination of both transcription and translation.

A "host cell," as used herein, refers to a prokaryotic or eukaryotic cell that contains heterologous DNA which has been introduced into the cell by any means, e.g., electroporation, calcium phosphate precipitation, microinjection, transformation, viral infection, and/or the like. A "host plant" is a plant into which a transgene is to be introduced. A "parental plant" is the original plant into which genetic changes are to be introduced in order to create a genetically altered plant.

A "vector" is a composition for facilitating introduction, replication and/or expression of a selected nucleic acid in a cell. Vectors include, for example, plasmids, cosmids, viruses, yeast artificial chromosomes (YACs), etc. A "vector nucleic acid" is a nucleic acid vector into which heterologous nucleic acid is optionally inserted and which can then be introduced into an appropriate host cell. Vectors preferably have one or more origins of replication, and one or more sites into which the recombinant DNA can be inserted. Vectors often have convenient markers by which cells with vectors can be selected from those without. By way of example, a vector may encode a drug resistance gene to facilitate selection of cells that are transformed with the vector. Common vectors include plasmids, phages and other viruses, and "artificial chromosomes." "Expression vectors" are vectors that comprise elements that provide for or facilitate transcription of nucleic acids which are cloned into the vectors. Such elements may include, for example, promoters and/or enhancers operably coupled to a nucleic acid of interest.

"Plasmids" generally are designated herein by a lower case "p" preceded and/or followed by capital letters and/or numbers, in accordance with standard nomenclatures that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors are well known and readily available to those of skill in the art. Moreover, those of skill readily may construct any number of other plasmids suitable for use as described below. The properties, construction and use of such plasmids, as well as other vectors, is readily apparent to those of ordinary skill upon reading the present disclosure.

When a molecule is identified in or can be isolated from a organism, it can be said that such a molecule is derived from said organism. When two organisms have significant difference in the genetic materials in their respective genomes, these two organisms can be said to be genetically different. For purpose of this disclosure, the term "plant" means a whole plant, a seed, or any organ or tissue of a plant that may potentially develop into a whole plant.

The term "isolated" means that the material is removed from its original environment, such as the native or natural environment if the material is naturally occurring. For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment.

A "recombinant nucleic acid" is one that is made by recombining nucleic acids, e.g., during cloning, DNA evolution or other procedures. A "recombinant polypeptide" is a polypeptide which is produced by expression of a recombinant nucleic acid. An "amino acid sequence" is a polymer of amino acid residues (a protein, polypeptide, etc.) or a character string representing an amino acid polymer, depending on context. Either the given nucleic acid or the complementary nucleic acid can be determined from any specified polynucleotide sequence.

The terms "nucleic acid," or "polynucleotide" refer to a deoxyribonucleotide, in the case of DNA, or ribonucleotide in the case of RNA polymer in either single- or double-stranded form, and unless otherwise specified, encompasses known analogues of natural nucleotides that can be incorporated into nucleic acids in a manner similar to naturally occurring nucleotides. A "polynucleotide sequence" is a nucleic acid which is a polymer of nucleotides (A, C, T, U, G, etc. or naturally occurring or artificial nucleotide analogues) or a character string representing a nucleic acid, depending on context. Either the given nucleic acid or the complementary nucleic acid can be determined from any specified polynucleotide sequence.

A "subsequence" or "fragment" is any portion of an entire sequence of a DNA, RNA or polypeptide molecule, up to and including the complete sequence. Typically a subsequence or fragment comprises less than the full-length sequence, and is sometimes referred to as the "truncated version."

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. Similarly, nucleic acids and/or nucleic acid sequences are homologous when they are derived, naturally or artificially, from a common ancestral nucleic acid or nucleic acid sequence. The homologous molecules can be termed homologs. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The terms "identical" or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) *Adv. Appl. Math.* 2:482; by the alignment algorithm of Needleman and Wunsch (1970) *J. Mol. Biol.* 48:443; by the search for similarity method of Pearson and Lipman (1988) *Proc. Nat. Acad. Sci. U.S.A.* 85:2444; by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp (1988) *Gene* 73:237-244 and Higgins and Sharp (1989) CABIOS 5:151-153; Corpet et al. (1988) *Nucleic Acids Res.* 16:10881-10890; Huang et al (1992) *Computer Applications in the Biosciences* 8:155-165; and Pearson et al. (1994) *Methods in Molecular Biology* 24:307-331. Alignment is also often performed by inspection and manual alignment.

In one class of embodiments, the polypeptides herein are at least 70%, generally at least 75%, optionally at least 80%, 85%, 90%, 98% or 99% or more identical to a reference polypeptide, e.g., those that are encoded by DNA sequences as set forth by any one of the SCNRGs disclosed herein or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or more identical to a reference nucleic acid, e.g., those that are set forth by any one of the SCNRGs disclosed herein or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" as applied to nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The term "polypeptide" is used interchangeably with the terms "polypeptides" and "protein(s)", and refers to a polymer of amino acid residues. A 'mature protein' is a protein which is full-length and which, optionally, includes glycosylation or other modifications typical for the protein in a given cellular environment.

The term "variant" or "mutant" with respect to a polypeptide refers to an amino acid sequence that is altered by one or more amino acids with respect to a reference sequence. The variant may have "conservative" changes, wherein a substituted amino acid has similar structural or chemical properties, e.g., replacement of leucine with isoleucine. Alternatively, a variant may have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software.

A variety of additional terms are defined or otherwise characterized herein. In practicing the instrumentalities described herein, many conventional techniques in molecular biology, microbiology, and recombinant DNA are optionally used. These techniques are well known to those of ordinary skill in the art. For example, one skilled in the art would be familiar with techniques for in vitro amplification methods, including the polymerase chain reaction (PCR), for the production of the homologous nucleic acids described herein.

In addition, commercially available kits may facilitate the purification of plasmids or other relevant nucleic acids from cells. See, for example, EasyPrep™ and FlexiPrep™ kits, both from Pharmacia Biotech; StrataClean™ from Stratagene; and, QIAprep™ from Qiagen. Any isolated and/or purified nucleic acid can be further manipulated to produce other nucleic acids, used to transfect cells, incorporated into related vectors to infect organisms, or the like. Typical cloning vectors contain transcription terminators, transcription initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Various types of mutagenesis are optionally used to modify a gene and their encoded polypeptides, as described herein, to produce conservative or non-conservative variants. Any available mutagenesis procedure can be used. Such mutagenesis procedures optionally include selection of mutant nucleic acids and polypeptides for one or more activity of interest. Procedures that can be used include, but are not limited to: site-directed point mutagenesis, random point mutagenesis, in vitro or in vivo homologous recombination (DNA shuffling), mutagenesis using uracil-containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, mutagenesis by chimeric constructs, and many others known to persons of skill in the art.

In one embodiment, mutagenesis can be guided by known information about the naturally occurring molecule or altered or mutated naturally occurring molecule. By way of example, this known information may include sequence, sequence comparisons, physical properties, crystal structure and the like. In another class of mutagenesis, modification is essentially random, e.g., as in classical DNA shuffling.

Polypeptides may include variants, in which the amino acid sequence has at least 70% identity, preferably at least 80% identity, typically 90% identity, preferably at least 95% identity, more preferably at least 98% identity and most preferably at least 99% identity, to the amino acid sequences as encoded by the DNA sequences set forth in any one of the SCN responsive genes disclosed herein.

The aforementioned polypeptides may be obtained by any of a variety of methods. Smaller peptides (less than 50 amino acids long) are conveniently synthesized by standard chemical techniques and can be chemically or enzymatically ligated to form larger polypeptides. Polypeptides can be purified from biological sources by methods well known in the art, for example, as described in *Protein Purification, Principles and Practice, Second Edition* Scopes, Springer Verlag, N.Y. (1987) Polypeptides are optionally but preferably produced in their naturally occurring, truncated, or fusion protein forms by recombinant DNA technology using techniques well known in the art. These methods include, for example, in vitro recombinant DNA techniques, synthetic techniques and in vivo genetic recombination. See, for example, the techniques described in Sambrook et al. (2001) *Molecular Cloning, A Laboratory Manual*, Third Edition, Cold Spring Harbor Press, N.Y.; and Ausubel et al., eds. (1997) *Current Protocols in Molecular Biology*, Green Publishing Associates, Inc., and John Wiley & Sons, Inc., N.Y (supplemented through 2002). RNA encoding the proteins may also be chemically synthesized. See, for example, the techniques described in *Oligonucleotide Synthesis*, (1984) Gait ed., IRL Press, Oxford, which is incorporated by reference herein in its entirety.

The nucleic acid molecules described herein may be expressed in a suitable host cell or an organism to produce proteins. Expression may be achieved by placing a nucleotide sequence encoding these proteins into an appropriate expression vector and introducing the expression vector into a suitable host cell, culturing the transformed host cell under conditions suitable for expression of the proteins described or variants thereof, or a polypeptide that comprises one or more domains of such proteins. The recombinant proteins from the host cell may be purified to obtain purified and, preferably, active protein. Alternatively, the expressed protein may be allowed to function in the intact host cell or host organism.

Appropriate expression vectors are known in the art, and may be purchased or applied for use according to the manufacturer's instructions to incorporate suitable genetic modifications. For example, pET-14b, pcDNA1Amp, and pVL1392 are available from Novagen and Invitrogen, and are suitable vectors for expression in *E. coli*, mammalian cells and insect cells, respectively. These vectors are illustrative of those that are known in the art, and many other vectors can be used for the same purposes. Suitable host cells can be any cell capable of growth in a suitable media and allowing purification of the expressed protein. Examples of suitable host cells include bacterial cells, such as *E. coli, Streptococci, Staphylococci, Streptomyces* and *Bacillus subtilis* cells; fungal cells such as *Saccharomyces* and *Aspergillus* cells; insect cells such as *Drosophila* S2 and *Spodoptera* Sf9 cells, mammalian cells such as CHO, COS, HeLa, 293 cells; and plant cells.

Culturing and growth of the transformed host cells can occur under conditions that are known in the art. The conditions will generally depend upon the host cell and the type of vector used. Suitable culturing conditions may be used such as temperature and chemicals and will depend on the type of promoter utilized.

Purification of the proteins or domains of such proteins, if desired, may be accomplished using known techniques without performing undue experimentation. Generally, the transformed cells expressing one of these proteins are broken, crude purification occurs to remove debris and some contaminating proteins, followed by chromatography to further purify the protein to the desired level of purity. Host cells may be broken by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well known techniques for refolding proteins can be used to obtain the active conformation of the protein when the protein is denatured during intracellular synthesis, isolation or purification.

Sequence information of the SCN responsive genes may also be used to design oligonucleotides for detecting their mRNA levels in the cells or in plant tissues. For example, the oligonucleotides can be used in a Northern blot analysis to quantify the levels of the mRNA. Moreover, full-length or fragment of the SCN responsive genes may be used in preparing microarrays (or gene chips). Full-length or fragment of the SCN responsive genes may also be used in microarray experiments to study expression profile of the SCN responsive genes. High-throughput screening can be conducted to measure expression levels of the SCN responsive genes in different cells or tissues. Various compounds or other external factors may be screened for their effects expression of the SCN responsive gene expression.

Sequences of the SCN responsive genes and proteins identified herein may also provide a tool for identification of other proteins that may be involved in plant defense against SCN. For example, chimeric SCN resistant proteins can be used as a "bait" to identify other proteins that interact with SCN resistant proteins in a yeast two-hybrid screening. Recombinant SCN resistant proteins can also be used in pull-down experiment to identify their interacting proteins. These other proteins may be cofactors that enhance the function of the SCN resistant proteins, or they may be SCN resistant proteins themselves which have not been identified in the experiments disclosed herein.

The SCN resistant polypeptides may possess structural features which can be recognized, for example, by using immunological assays. The generation of antisera which specifically bind the SCN resistant polypeptides, as well as the polypeptides which are bound by such antisera, are a feature of the disclosed embodiments.

In order to produce antisera for use in an immunoassay, one or more of the immunogenic SCN resistant polypeptides or fragments thereof are produced and purified as described herein. For example, recombinant protein may be produced in a host cell such as a bacterial or an insect cell. The resultant proteins can be used to immunize a host organism in combination with a standard adjuvant, such as Freund's adjuvant. Commonly used host organisms include rabbits, mice, rats, donkeys, chickens, goats, horses, etc. An inbred strain of mice may also be used to obtain more reproducible results due to the virtual genetic identity of the mice. The mice are immunized with the immunogenic SCNRG polypeptides in combination with a standard adjuvant, such as Freund's adjuvant, and a standard mouse immunization protocol. See, for example, Harlow and Lane, *Antibodies, A Laboratory Manual*, Cold Spring Harbor Publications, New York (1988), which provides comprehensive descriptions of antibody generation, immunoassay formats and conditions that can be used to determine specific immunoreactivity. Alternatively, one or more synthetic or recombinant SCN resistant polypeptides or fragments thereof derived from the sequences disclosed herein is conjugated to a carrier protein and used as an immunogen.

Antisera that specifically bind the SCN resistant proteins may be used in a range of applications, including but not limited to immunofluorescence staining of cells for the expression level and localization of the SCN resistant proteins, cytological staining for the expression of SCN resistant proteins in tissues, as well as in Western blot analysis.

Another aspect of the disclosure includes screening for potential or candidate modulators of SCN resistant protein activity. For example, potential modulators may include small molecules, organic molecules, inorganic molecules, proteins, hormones, transcription factors, or the like, which can be contacted to a cell or certain tissues that express the SCN resistant proteins to assess the effects, if any, of the candidate modulator upon SCN resistant protein activity.

Alternatively, candidate modulators may be screened to modulate expression of SCN resistant proteins. For example, potential modulators may include small molecules, organic molecules, inorganic molecules, proteins, hormones, transcription factors, or the like, which can be contacted to a cell or certain tissues that express the SCN resistant proteins, to assess the effects, if any, of the candidate modulator upon SCN resistant protein expression. Expression of a SCN responsive gene described herein may be detected, for example, via Northern blot analysis or quantitative (optionally real time) RT-PCR, before and after application of potential expression modulators. Alternatively, promoter regions of the various SCN responsive genes may be coupled to reporter constructs including, without limitation, CAT, beta-galactosidase, luciferase or any other available reporter, and may similarly be tested for expression activity modulation by the candidate modulator. Promoter regions of the various genes are generally sequences in the proximity upstream of the start site of transcription, typically within 1 Kb or less of the start site, such as within 500 bp, 250 bp or 100 bp of the start site. In certain cases, a promoter region may be located between 1 and 5 Kb from the start site.

In either case, whether the assay is to detect modulated activity or expression, a plurality of assays may be performed in a high-throughput fashion, for example, using automated fluid handling and/or detection systems in serial or parallel fashion. Similarly, candidate modulators can be tested by contacting a potential modulator to an appropriate cell using any of the activity detection methods herein, regardless of whether the activity that is detected is the result of activity modulation, expression modulation or both.

A method of modifying a plant may include introducing into a host plant one or more SCN responsive genes described above. The SCN responsive genes may be placed in an expression construct, which may be designed such that the SCN resistant protein(s) are expressed constitutively, or inducibly. The construct may also be designed such that the SCN resistant protein(s) are expressed in certain tissue(s), but not in other tissue(s). The SCN resistant protein(s) may enhance the ability of the host plant to defend SCN infection. The host plant may include any plants whose growth and/or yield may be enhanced by a modified SCN response. Methods for generating such transgenic plants is well known in the field. See e.g., Leandro Peña (Editor), Transgenic Plants: Methods and Protocols (Methods in Molecular Biology), Humana Press, 2004.

The use of gene inhibition technologies such as antisense RNA, antificial microRNA, or co-suppression or double stranded RNA interference is also within the scope of the present disclosure. In these approaches, the isolated gene sequence is operably linked to a suitable regulatory element. In one embodiment of the disclosure, the construct contains a DNA expression cassette that contains, in addition to the DNA sequences required for transformation and selection in said cells, a DNA sequence that encodes a SCN resistant proteins or a SCN resistant modulator protein, with at least a portion of said DNA sequence in an antisense orientation relative to the normal presentation to the transcriptional regulatory region, operably linked to a suitable transcriptional regulatory region such that said recombinant DNA construct expresses an antisense RNA or portion thereof of an antisense RNA in the resultant transgenic plant.

It is apparent to one of skill in the art that the polynucleotide encoding the SCN resistant proteins or a SCN resistant modulator proteins can be in the antisense (for inhibition by antisense RNA) or sense (for inhibition by co-suppression) orientation, relative to the transcriptional regulatory region. Alternatively a combination of sense and antisense RNA expression can be utilized to induce double stranded RNA interference. See, e.g., Chuang and Meyerowitz, PNAS 97: 4985-4990, 2000; see also Smith et al., Nature 407: 319-320, 2000.

These methods for generation of transgenic plants generally entail the use of transformation techniques to introduce the gene or construct encoding the SCN resistant proteins or a SCN resistant modulator proteins, or a part or a homolog thereof, into plant cells. Transformation of a plant cell can be accomplished by a variety of different methodology. Methods that have general utility include, for example, *Agrobacterium* based systems, using either binary and/or cointegrate plasmids of both *A. tumifaciens* and *A. rhyzogenies*, (See e.g., U.S. Pat. No. 4,940,838, U.S. Pat. No. 5,464,763), the biolistic approach (See e.g, U.S. Pat. No. 4,945,050, U.S. Pat. No. 5,015,580, U.S. Pat. No. 5,149,655), microinjection, (See e.g., U.S. Pat. No. 4,743,548), direct DNA uptake by protoplasts, (See e.g., U.S. Pat. No. 5,231,019, U.S. Pat. No. 5,453,367) or needle-like whiskers (See e.g., U.S. Pat. No. 5,302,523). Any method for the introduction of foreign DNA into a plant cell and for expression therein may be used within the context of the present disclosure.

Plants that are capable of being transformed encompass a wide range of species, including but not limited to soybean, corn, potato, rice, wheat and many other crops, fruit plants, vegetables and tobacco. See generally, Vain, P., Thirty years of plant transformation technology development, Plant Biotechnol J. 2007 March; 5(2):221-9. Any plants that are capable of taking in foreign DNA and transcribing the DNA into RNA and/or further translating the RNA into a protein may be a suitable host.

The modulators described above that may alter the expression levels or the activity of the SCN resistant proteins (collectively called SCN resistant modulators) may also be introduced into a host plant in the same or similar manner as described above. In one embodiment, the SCN resistant modulators are primarily transcription factors that regulate the transcription of the SCN responsive genes.

The SCN resistant proteins or the SCN resistant modulators may be used to modify a target plant by causing them to be assimilated by the plant. Alternatively, the SCN resistant proteins or the SCN resistant modulators may be applied to a target plant by causing them to be in contact with the plant, or with a specific organ or tissue of the plant. In one embodiment, organic or inorganic molecules that can function as SCN resistant modulators may be caused to be in contact with a plant such that these chemicals may enhance defense against SCN by the target plant.

In addition to the SCN resistant modulators, SCN resistant polypeptides or SCN resistant nucleic acids, a composition containing other ingredients may also be introduced, administered or delivered to the plant to be modified. In one aspect, a composition containing an agriculturally acceptable ingredient may be used in conjunction with the SCN resistant modulators to be administered or delivered to the plant.

Bioinformatic systems are widely used in the art, and can be utilized to identify homology or similarity between different character strings, or can be used to perform other desirable functions such as to control output files, provide the basis for making presentations of information including the sequences and the like. Examples include BLAST, discussed supra. For example, commercially available databases, computers, computer readable media and systems may contain character strings corresponding to the sequence information herein for the SCN resistant polypeptides and nucleic acids described herein. These sequences may include specifically the SCN resistant sequences listed herein and the various silent substitutions and conservative substitutions thereof.

The bioinformatic systems contain a wide variety of information that includes, for example, a complete sequence listings for the entire genome of an individual organism representing a species. Thus, for example, using the SCN resistant sequences as a basis for comparison, the bioinformatic systems may be used to compare different types of homology and similarity of various stringency and length on the basis of reported data. These comparisons are useful to identify homologs or orthologs where, for example, the basic SCNRG gene ortholog is shown to be conserved across different organisms. Thus, the bioinformatic systems may be used to detect or recognize the homologs or orthologs, and to predict the function of recognized homologs or orthologs. By way of example, many homology determination methods have been designed for comparative analysis of sequences of biopolymers including nucleic acids, proteins, etc. With an understanding of hydrogen bonding between the principal bases in natural polynucleotides, models that simulate annealing of complementary homologous polynucleotide strings can also be used as a foundation of sequence alignment or other operations typically performed on the character strings corresponding to the sequences herein. One example of a software package for calculating sequence similarity is BLAST, which can be adapted to the present invention by inputting character strings corresponding to the sequences herein.

The software can also include output elements for controlling nucleic acid synthesis (e.g., based upon a sequence or an alignment of a sequences herein) or other operations which occur downstream from an alignment or other operation performed using a character string corresponding to a sequence herein.

EXAMPLES

The following nonlimiting examples report general procedures, reagents and characterization methods that teach by way of example, and should not be construed in a narrowing manner that limits the disclosure to what is specifically disclosed. Those skilled in the art will understand that numerous modifications may be made and still the result will fall within the spirit and scope of the present invention.

Plant and Nematode Material

Seeds of soybean (*Glycine max* (L.) Merr) near-isogenic lines (NIL) differing at the Rhg1 locus (NIL-R and NIL-S) were derived from a cross between the resistance source PI 209332 and the susceptible cultivar Evans (Mudge, 1999). The SCN (*Heterodera glycines,* Ichinohe) inbred populations PA3 and TN19 were obtained from a publicly available collection at the University of Illinois at Urbana-Champaign and mass-selected according to standard procedures (Niblack et al., 1993) on soybean cv. Williams 82 and PI 437654, respectively. HG-type tests (Niblack et al., 2002) confirmed that the PA3 population was HG-type 0 and the TN19 population was HG-type 1-7.

Laser Capture Microdissection

PA3 and TN19-infected root pieces (~1 cm) of the NIL-R and NIL-S were excised at 5 dpi or 8 dpi and immediately processed for laser capture microdissection according to Ithal et al. (2007b).

Microarray Hybridization, Statistical Analysis, and qPCR Validation

RNA extraction, amplification, and labeling were performed according to Ithal et al. (2007b). The samples were sent to the Iowa State University GeneChip microarray core facility for fragmentation, hybridization, staining, and scanning of the GeneChip Soybean Genome Array (Affymetrix). The logarithms of the Affymetrix MAS 5.0 signals were normalized by computing the median of the log signals on each chip and then aligning these medians to a common value. These normalized expression data were analyzed on a gene-by-gene basis using SAS. Each analysis was based on a randomized complete block design with three replications as blocks and the four combinations of genotype (resistant versus susceptible) and days post infection (5 dpi and 8 dpi) as treatments. Tests for genotype main effects, dpi main effects, and genotype by dpi interaction were conducted for each gene. The resulting p-values were converted to q-values as described by Storey and Tibshirani (2003). These q-values were used to control the estimated False Discovery Rate (FDR) at desired levels. For example, by declaring differential expression between resistant and susceptible genotypes for all genes with q-values less than or equal to 0.10, the proportion of false positives among all genes declared differentially expressed is expected to be approximately 10%. Annotations and classifications were based on SoyBase Affymetrix™ GeneChip® Soybean Genome Array Annotation, Version 2 (http://soybase.org/AffyChip/). *Arabidopsis* unique gene identifiers (At-numbers) were downloaded from The *Arabidopsis* Information Resource (TAIR, www.arabidopsis.org) for the top hits. The microarray data are deposited in the ArrayExpress database at the European Bioinformatics Institute under accession number X (submitted). qPCR validation studies were conducted according to Ithal et al (2007b).

All sequence in Tables 1-17 contain soybean genome database sequences that are publicly available (Schmutz J, et al., "Genome sequence of the palaeopolyploid soybean," *Nature* 463, 178-183, January 2010) and are identified by a unique sequence identifier in those databases, which are hereby incorporated by reference into this disclosure.

Lengthy table referenced here

US09371541-20160621-T00001

Please refer to the end of the specification for access instructions.

Lengthy table referenced here

US09371541-20160621-T00002

Please refer to the end of the specification for access instructions.

Lengthy table referenced here

US09371541-20160621-T00003

Please refer to the end of the specification for access instructions.

Lengthy table referenced here

US09371541-20160621-T00004

Please refer to the end of the specification for access instructions.

Lengthy table referenced here

US09371541-20160621-T00005

Please refer to the end of the specification for access instructions.

Lengthy table referenced here

US09371541-20160621-T00006

Please refer to the end of the specification for access instructions.

Lengthy table referenced here

US09371541-20160621-T00007

Please refer to the end of the specification for access instructions.

Lengthy table referenced here

US09371541-20160621-T00008

Please refer to the end of the specification for access instructions.

Lengthy table referenced here

US09371541-20160621-T00009

Please refer to the end of the specification for access instructions.

Lengthy table referenced here

US09371541-20160621-T00010

Please refer to the end of the specification for access instructions.

Lengthy table referenced here

US09371541-20160621-T00011

Please refer to the end of the specification for access instructions.

TABLE 12 qPCR Primers Used for Microarray Validation and Time Course-qPCR

| Affychip ID | qPCR Primer Name | Primer Sequence (5'-3') | SEQ ID |
|---|---|---|---|
| GmaAffx.11502.1.S1_at | FX11502.1F | GGAGGCAGGGAAGTTCACTGT | 170 |
| | FX11502.1R | AACCACTCAGGGCCTTGGAT | 171 |
| GmaAffx.3568.1.S1_at | FX3568.1F | TAAATACGGTCGAACTTGTTAGAGGTT | 172 |
| | FX3568.1R | AGCACCTAAAAAAGCATATCACAGAA | 173 |
| GmaAffx.78421.1.S1_at | FX78421.1F | TCTTGAGAGCAAAGTCACCGC | 174 |
| | FX78421.1R | TTGTCACACCACAGGGTTGG | 175 |
| GmaAffx.84808.1.S1_at | FX84808.1F | TTCCTCGCCACAAGACTGC | 176 |
| | FX84808.1R | AAAATCTGCGGCGAGGATT | 177 |
| GmaAffx.89435.1.A1_s_at | FX89435.1F | AATGCACCTTCTAGCAAGGCC | 178 |
| | FX89435.1R | AGGCAGGCTGCAAAGAGTGT | 179 |
| Gma.10240.1.A1_at | MA10240.1F | GCCTCGGGTGCTAAAGCTAAA | 180 |
| | MA10240.1R | AAAGGTGCATAACATTTTGGCTG | 181 |

TABLE 12-continued qPCR Primers Used for Microarray Validation and Time Course-qPCR

| Affychip ID | qPCR Primer Name | Primer Sequence (5'-3') | SEQ ID |
|---|---|---|---|
| Gma.10796.1.S1_a_at | MA10796.1F | CACTGCTCAACATCAGGACCA | 182 |
| | MA10796.1R | CCGAATCGACCCGTTTACG | 183 |
| Gma.9553.1.A1_at | MA9553.1F | GGGACAACAACCTAAGAGACAGATTAC | 184 |
| | MA9553.1R | TCATTTTCAACTGGTTCGAGCA | 185 |
| Gma.7526.1.A1_at | MA7526.1F | GTGTTGTTGGCTTGATTGCG | 186 |
| | MA7526.1R | TCAAACTTGGGAAGGCACTCA | 187 |
| Gma.2821.1.S1_at | MA2821.1F | GAACATGCTGGTTGCATCGT | 188 |
| | MA2821.1R | AGGTGCCCTGATGCCTACAG | 189 |
| Gma.4589.1.S1_s_at | MA4589.1F | TACAGCCACCTGGATAGGCC | 190 |
| | MA4589.1R | TGTTTGCTTGTGTGTTTTGGG | 191 |
| Gma.8586.1.S1_at | MA8586.1F | AGACGTGGAAGGTGGTGACTG | 192 |
| | MA8586.1R | AGAATGCCGCTTCACAGAATG | 193 |
| Gma.16807.1.S1_at | MA16807.1F | ATTGAGGGACTTTCGGCCA | 194 |
| | MA16807.1R | TCCCTTCCCCTCCTACAGCT | 195 |
| Gma.7381.1.S1_at | MA7381.1F | ACACTGATACAAGGGCATGGC | 196 |
| | MA7381.1R | GGTGGCCCCAAATCCATAG | 197 |
| Gma.17843.1.S1_at | MA17843.1F | AGCAAGTTCCACACGCTCTGT | 198 |
| | MA17843.1R | GGTGCCGTTTAGCATCTCGT | 199 |
| Gma.1423.1.S1_a_at | MA1423.1F | ACCCTCCCAGGGTTTCACTC | 200 |
| | MA1423.1R | GCAGAGGAGGCTCCGATTTT | 201 |
| Gma.8859.1.A1_at | MA8859.1F | CTTGGTCCGTCCAGCTTCTG | 202 |
| | MA8859.1R | TTCGTACGTCCAATCTACGCC | 203 |
| Gma.1445.1.S1_at | MA1445.1F | AACCTTAAACGAGCTATCCCTTTTTA | 204 |
| | MA1445.1R | TGCAGCTTCTTGTTTGTTGACA | 205 |
| Gma.11334.1.S1_a_at | MA11334.1F | GGGAGCATGCAAATCTCGAT | 206 |
| | MA11334.1R | GCTCAACAAAGCCCTCGCT | 207 |
| Gma.2139.2.S1_s_at | MA2139.2F | AATCAGCCTTCTCCCAAATGC | 208 |
| | MA2139.2R | CGGCTGAGGAAGCTCGTAAG | 209 |
| Gma.3504.2.S1_at | MA3504.2F | GGAAAGTATGGCACCGACAGA | 210 |
| | MA3504.2R | GTTAATTGCAAACGGCGGTTA | 211 |
| Gma.4207.1.S1_at | MA4207.1F | ACTGCAGGGAAAGCAAAGGTT | 212 |
| | MA4207.1R | CCGCACTTGAAGACCCTTGT | 213 |
| Gma.4565.1.S1_s_at | MA4565.1F | TTGTTGCCGTGAGTCAGCAT | 214 |
| | MA4565.1R | CAGGGAAAAGTGTGGCAAGTG | 215 |
| Gma.5283.1.S1_at | RS-MA5283.1F | AAGGTCACCATGTCCCAACAC | 216 |
| | RS-MA5283.1R | GAGGGAAGCGTGCAATAGCT | 217 |
| Gma.6062.1.S1_at | RS-MA6062.1F | TTCCTAAGGCCTAAGCTTTCAGTGT | 218 |
| | RS-MA6062.1R | GCAAAAAAAGATAAAGACGATTTGG | 219 |
| Gma.596.1.S1_at | RS-MA596.1F | CACGGAGAGCTTCATGGAGAA | 220 |
| | RS-MA596.1R | CATGCAACTCATTCCCTTTGG | 221 |
| Gma.3990.1.S1_s_at | RS-MA3990.1F | TCAGGAAAAGCTGTGGGAAGA | 222 |
| | RS-MA3990.1R | CCTTTTCGACGCCAACGTAA | 223 |
| GmaAffx.21079.1.A1_at | RS-MA21079.1F | GCACTGCCCCAACACATAGA | 224 |
| | RS-MA21079.1R | GAGAACGGCGTGCAGAACA | 225 |
| Gma.16613.1.S1_s_at | RS-MA16613.1F | GGTGGGATCGGGATTAGGTT | 226 |
| | RS-MA16613.1R | CAAGAATCCAAAAGCAATGAACAA | 227 |
| Gma.15972.1.A1_at | RS-MA15972.1F | TCACCGTCAGAATCCAATTCC | 228 |
| | RS-MA15972.1R | TGCATGATGGCTGGTGAGTT | 229 |
| Gma.10701.2.S1_at | RS-MA10701.2F | GCCAGTACCTATCCACAATTGCT | 230 |
| | RS-MA10701.2R | CCTCGAAGGCAGTTTCTTTTACA | 231 |

TABLE 12-continued qPCR Primers Used for Microarray Validation and Time Course-qPCR

| Affychip ID | qPCR Primer Name | Primer Sequence (5'-3') | SEQ ID |
|---|---|---|---|
| Gma.14272.1.S1_at | RS-MA14272.1F | TGGTGCTGACCCTTTTTGGT | 232 |
| | RS-MA14272.1R | GGGTGACGATCACTTGGTGAT | 233 |
| GmaAffx.74588.1.S1_at | RS-FX74588.1F | AGAACCCCGTGGTGATCGA | 234 |
| | RS-FX74588.1R | GGAAAGAAGAAGCGCACGATA | 235 |
| GmaAffx.70008.1.S1_at | RS-FX70008.1F | CCCCAAAGATGACCCAAATAAG | 236 |
| | RS-FX70008.1R | GGTCTTCCAATATGGCTTCTTCTG | 237 |
| GmaAffx.494.1.S1_at | RS-FX494.1F | CTTCTCAGGTTCTTCCTGTGATTAAA | 238 |
| | RS-FX494.1R | ACCATTTTGGACATCATTGAATCTG | 239 |
| GmaAffx.46603.1.S1_at | RS-FX46603.1F | GGGTTGACCACTCCAACCTTT | 240 |
| | RS-FX46603.1R | GCACCCTCTGGCCAAGAAA | 241 |
| GmaAffx.29929.1.S1_at | RS-FX29929.1F | GGATGGTGCCGGAGTATCTG | 242 |
| | RS-FX29929.1R | TCATCACTCCCGAAGCAATG | 243 |
| GmaAffx.2744.1.S1_at | RS-FX2744.1F | CAAACTTTGAAGCACCAAGCAT | 244 |
| | RS-FX2744.1R | TGTTCAAGGCTTGATTGATAAGGA | 245 |
| Gma.11004.1.S1_at | RS-MA11004.1F | TTAAACGGGTGAAGGAAAAACC | 246 |
| | RS-MA11004.1R | ATATCCCACGGGCAAAAGG | 247 |
| GmaAffx.88182.1.S1_at | RS_FX88182.1F | TCTGCAAACATGGCCGATAA | 248 |
| | RS_FX88182.1R | GCTCCGCCGGAGGAAT | 249 |
| Gma.4071.1.S1_at | RS-MA4071.1F | TGATCACTCACGGCAACAAGA | 250 |
| | RS-MA4071.1R | TTGGATAGGGCTGACCTTCAA | 251 |
| Gma.7737.1.S1_at | RS-MA7737.1F | TGGAACAACTCTTCATGAGTGAGAA | 252 |
| | RS-MA7737.1R | AAGTCTCATTAACCATAGCTTTCAAGTTT | 253 |
| Primers for Timecourse-qPCR | | | |
| GmaAffx.68498.1.S1_at | p5-F | GTGGAAAGCTAATGTTGAAAATAATACAG | 254 |
| | p5-R | CGGCATCAGGTAAAACAAGATTG | 255 |
| Gma.7623.1.A1_at | RBAG-F | CCC GCAGCTTCCA AAATG | 256 |
| | RBAG-R | GAG AGCCTTTGAT GTTGCAA | 257 |
| GmaAffx.46603.1.S1_at | Rgram-F | GCTATA TATTTCATGT GTGCTCTGCA T | 258 |
| | Rgram-R | CCATA TTTGGGAAAG TTCATTTTTT TT | 259 |
| | GmUBQ F | GCCGTACCCTTGCTGACTAC | 260 |
| | GmUBQ R | ATGGTGTCGGAGCTTTCAAC | 261 |

TABLE 13

Gateway Cloning Primers for Promoter-GUS Constructs.

| AffyChip ID | Primer Name | Primer Sequence (5'-3') | SEQ ID |
|---|---|---|---|
| Gma.15997.1.S1_at | 2-15997P-F | AAAAAAGCAGGCTat AGA GTG ACT ATT ATT CTC TTT TTA C | 262 |
| | 2-15997P-R | AGAAAGCTGG GTA TGT TGA GAG AGA GAG AGA GTT AG | 263 |
| Gma.986.1.S1_at | ZF986p-F | AAAAAAGCAGGCTAT AGA GAA GTT ACA AGA GTA GTT TC | 264 |
| | ZF986p-R | AAGAAAGCTGG GTA GGC TAC TAC GTA GGT CGG TT | 265 |
| GmaAffx.2469.1.S1_at | AP2469P-F | AAAAAAGCAGGCTAT GTA TTT CAT TGA CTC TCA TTT TTC | 266 |
| | AP2469P-R | AAGAAAGCTGG GTA TCC AGA AGT TGG TGT TGG TG | 267 |
| Gma.487.1.S1_at | AP487P-F | AAAAAAGCAGGCTAT TTC CTT CGT AAA CTG ATA TCA TG | 268 |
| | AP487P-R | AAGAAAGCTGG GTA GTG CTT TTG CTA TTG AAG AAG | 269 |

TABLE 13-continued

Gateway Cloning Primers for Promoter-GUS Constructs.

| AffyChip ID | Primer Name | Primer Sequence (5'-3') | SEQ ID |
|---|---|---|---|
| GmaAffx.45036.1.S1_at | SoyPro-45036-F | AAAAAAGCAGGCTAT TTC GCG TCT CAT ACT ATA AAT TAA | 270 |
| | SoyPro-45036-R | AAGAAAGCTGG GTA TAT AAT TCT AAG GTT CAA TGT TTC A | 271 |
| GmaAffx.80271.1.S1_at | SoyPro-80271-F | AAAAAAGCAGGCTAT CTT AAG AGA AGT AGT TCT TGT ATT | 272 |
| | SoyPro-80271-R | AAGAAAGCTGG GTA GAG GGA AAG AAA GTT AAG GAT T | 273 |
| Gma.7147.1.A1_at | SoyPro-7147-F | AAAAAAGCAGGCTAT CTA GTT CTT TTG TGC ATA AAA CA | 274 |
| | SoyPro-7147-R | AAGAAAGCTGG GTA TGT TCA AAG ATC AAA GCC GAG | 275 |
| GmaAffx.7387.1.S1_at | SoyPro-7387-F | AAAAAAGCAGGCTATTTT TCT TCC ACT CAT CCC TGT | 276 |
| | SoyPro-7387-R | AAGAAAGCTGG GTA TCT ACT AAT CCT ACT AGT ACT A | 277 |
| Gma.9553.1.A1_at | SoyPro-9553-F | AAAAAAGCAGGCTAT AAT TGT CTC ATC TCT ACA TTT AC | 278 |
| | SoyPro-9553-R | AAGAAAGCTGG GTA GTC CAC AAA TCT GAT ACA CAG | 279 |
| AtWRKY23 | AtWRKY23P-F | AAAAAAGCAGGCTAT CC TTG TCA ACT CCT CTA GA | 280 |
| | AtWRKY23P-R | AGAAAGCTGG GTA TGT TGT TCT TCT TCT TCT CTC | 281 |
| Gma.10412.1.A1_at | 10412-F | AAAAAAGCAGGCTAT TAG GAT GAG CAC ATT TTA CGT T | 282 |
| | 10412-R | AAGAAAGCTGG GTA CCT CTC TCC CAA TAC AAT CT | 283 |
| attB1-F | attB1-F | GGGGACAAGTTTGTACAAAAAAGCAGGCT | 284 |
| attB2-R | attB2-R | GGGG ACCACTTTGTACAAGAAAGCTGG GT | 285 |

Promoter-Reporter Constructs

Figure 4B:
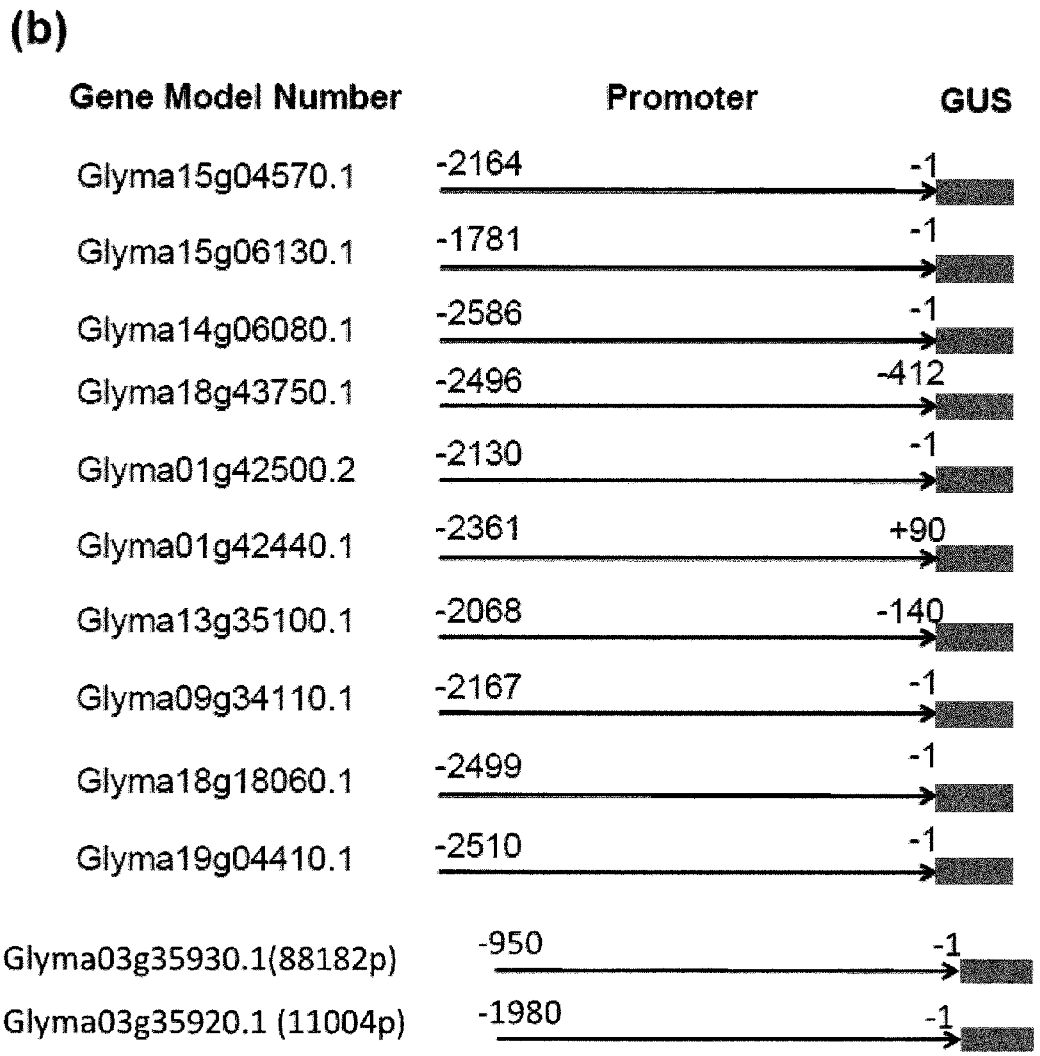
FIG. 4 shows description of promoter-GUS reporter constructs used for microarray validation. (a) Description of probe sets with soybean gene models used for promoter isolation and their putative function; (b) Schematic showing the lengths of promoter elements cloned and their coordinates with respect to the soybean gene model.

The promoter sequences for the genes used in the GUS reporter assays were identified and downloaded from the soybean genome database (Phytozome, Schmutz J, et al., "Genome sequence of the palaeopolyploid soybean," *Nature* 463, 178-183, January 2010). Primers (Table 12) were designed to amplify approximately a 2-kb sequence immediately 5' of the ATG start site (FIG. 4*b*). The promoter DNA fragments were PCR-amplified using soybean cv. Williams 82 genomic DNA as a template and cloned into the gateway cloning vector pDONR-Zeo (Invitrogen, Carlsbad, Calif., USA). The cloned promoters were sequenced using vector-specific primers and internal sequencing primers. The correct promoter fragments were then gateway cloned into a pYXT1 vector (Xiao et al., 2005) upstream of a β-glucuronidase (GUS) gene as a transcriptional fusion. The final plasmids were verified by PCR analysis and used for transformation of *Agrobacterium rhizogenes* (strain K599).

Hairy Root Transformation

Hairy roots transgenic for each promoter-GUS construct were generated using the method described by Wang et al. (2007) with the following modifications. The cotyledons were excised from 9-day-old aseptically grown soybean seedlings (NIL-R or cv. Williams 82) and vacuum infiltrated for 20 min with *A. rhizogenes* culture resuspended in ¼ Gamborg's salt solution (Phytotechnology Lab, Shawnee Mission, Kans., USA) carrying various reporter constructs. Cotyledons were co-cultivated with *A. rhizogenes* for 3 days. The cotyledons were later placed on MXB medium [1×MS basal nutrient salts (Gibco BRL), 1× Gamborg's vitamins, 3% w/v sucrose, and 0.8% w/v Daishin agar, pH 5.7] supplemented with kanamycin (200 μg per ml) and timentin (238 μg per ml) and incubated in a growth chamber at 26° C. set to a long-day photoperiod (16 h light/8 h dark). Hairy roots that emerged after 14 days were root-tip propagated twice on MXB medium with kanamycin (200 μg per ml) and timentin (238 μg per ml), after which the roots were transferred to MXB medium with timentin (237 μg per ml). Hairy roots at this stage were either used immediately for nematode inoculation experiments or maintained by subculturing for later use.

Nematode Infection of Transgenic Hairy Roots and GUS Staining

Infective second-stage juveniles (J2) were hatched from eggs as described in Wang et al. (2007). Nematodes were surface-sterilized with sterilizing solution (0.004% w/v mercuric chloride, 0.004% w/v sodium azide and 0.002% v/v Triton X-100) for 8 min followed by 5 washes with sterile water and resuspended in 0.1% w/v agarose. Hairy roots (3-4 cm) grown on MXB medium were inoculated ~1 cm above the root tip with 200±25 J2s per root in a 25-μl volume. The roots were cut and stained for GUS expression at 5 dpi. GUS staining was done according to Jefferson et al. (1987). Briefly, hairy roots were cut 1-2 cm above the infection zone and placed in GUS staining solution (100 mM Tris pH 7.0, 50 mM NaCl, 1 mM X-Gluc, 1.5 mM potassium ferricyanide pH 7.0, 0.06% v/v Triton X-100). The root tissues were vacuum-infiltrated twice for 10 min each and incubated at 37° C. overnight. The GUS staining reaction was stopped by replacing staining solution with 70% v/v ethanol. GUS stained roots were photographed under a Leica MZFLIII stereoscope (Leica Microsystems, Bannockburn, Ill.) fitted with an Optronics MagnaFire, version 2.0, camera (Optronics, Goleta, Calif.).

Sample Preparation for Time-Course qPCR Analysis

Infected root tissues for time course qPCR analysis were prepared as described in Ithal et al. (2007a), except that samples were collected at 2, 4, 6, and 8 dpi. Excised root pieces from 12-15 different plants were pooled for each genotype/inoculum combination. Samples were quick frozen in liquid nitrogen and stored at −80° C. until RNA isolation. Nematode penetration was verified by staining the nematodes in at least five sample roots for each treatment at 24 hours post-inoculation as described by Ithal et al. (2007a). Infected root tissues from three independent biological replicates were prepared.

RNA Isolation and qPCR

Total RNA was isolated from root tissues using the RNeasy plant miniprep kit (Qiagen, Valencia, Calif., USA), according to the manufacturer's instructions. First strand cDNA synthesis was carried out using a Superscript III first strand synthesis kit (Invitrogen, USA), according to the manufacturer's instructions. Real-time qPCR was carried out using an Applied Biosystems 7500 real-time PCR system. Gene-specific primers (Table 13) were designed using the primer express software (Applied Biosystems, CA, USA). All qRT-PCR reactions were carried out in triplicate. PCR was performed using the following cycling parameters: 50° C. for 2 min, 95° C. for 10 min, and 40 cycles of 95° C. 15 s and 60° C. for 1 min. The soybean ubiquitin gene (Acc. No D28123) was used as an endogenous control. Expression was quantified using the ΔΔCT method in comparison to the endogenous control. Fold-changes were determined relative to the NIL-R mock-inoculated sample for each time point. There were no significant expression differences between mock-treated NIL-S and NIL-R roots.

Response of NILs to SCN

Soybean NILs, derived from a cross between the susceptible cultivar Evans and the resistant PI 209332, were chosen for these studies. These NILs are predicted to share 98% of their genome, differing at the major SCN resistance locus, Rhg1 (Mudge, 1999). NIL-S is susceptible and NIL-R is resistant to SCN inbred line PA3 (HG type 0). The Rhg1 allele in PI 209332 is likely similar to the Rhg1 allele in PI 88788, the source of SCN resistance found in greater than 90% of commercially available SCN-resistant soybean cultivars. Field populations of SCN that can break PI 88788 resistance typically can break PI 209332 resistance, suggesting that these PIs share a similar type of resistance (Colgrove and Niblack, 2008). The delayed resistance response in PI 209332 and PI 88788 is thought to be due to the absence of the Rhg4 resistance allele which is present in Peking, a cultivar that exhibits a rapid resistance response to SCN. The experimental system disclosed herein takes advantage of this slow resistance response to characterize Rhg1-mediated differences in gene expression during syncytium formation.

In laboratory inoculation assays, the penetration and development of SCN and the formation of syncytia on the two NILs were examined to identify appropriate time points for LCM analysis. Freshly hatched second-stage juveniles (J2s) were used for synchronized infection of soybean roots. Roots of two-day-old seedlings were infected with an equal number of SCN (PA3) juveniles, and the roots were acid fuschin-stained at different days post-inoculation (dpi). Infected roots were harvested at different time points and stained with acid fuchsin to monitor the infection process. The results are shown in FIG. 1. FIGS. 1(*a*)-(*d*) show penetration and development of soybean cyst nematode (SCN) PA3 on resistant (NIL-R) and susceptible (NIL-S) lines (a) NIL-S, 2 dpi; (b) NIL-S, 10 dpi; (c) NIL-R, 2 dpi; (d) NIL-R, 10 dpi. FIGS. 1(*e*)-(*h*) show developmental differences between PA3-induced syncytia on NIL-S and NIL-R roots (e) NIL-S syncytium at 5 dpi; (f) NIL-S syncytium at 8 dpi; (g) NIL-R syncytium at 5 dpi; and (h) NIL-R syncytium at 8 dpi. N—nematode, Syn—syncytia. Scale bar: (a)-(d) 250 μm; (e)-(h) 50 μM.

Similar numbers of nematodes were observed in both NIL-R and NIL-S at 2 days post inoculation (dpi) (FIGS. 1*a* and 1*c*) indicating that resistance controlled by Rhg1 does not affect penetration and migration of nematodes in soybean roots. At 10 dpi significant differences in the development of nematodes were observed between NIL-S and NIL-R. Late fourth-stage juveniles (J4) and early adult females were observed in the NIL-S (FIG. 1*b*) by 10 dpi whereas the majority of the nematodes had only advanced to third-stage (J3) and early J4 stages in the NIL-R (FIG. 1*d*). These results are consistent with results reported by Li et al., (2004) in greenhouse bioassays using these NILs.

To assess the differences in syncytium development at a more refined level, infected root samples at 5, 8, and 10 dpi were sectioned for microscopic examination. At 5 dpi, syncytia appeared normal in both the NIL-S (FIG. 1*e*) and NIL-R (FIG. 1*g*). Normal syncytium development was observed at 8 dpi in NIL-S (FIG. 1*f*) whereas degenerating cells both in and around developing syncytia were observed in NIL-R at 8 dpi (FIG. 1*h*). The majority of the syncytia were degenerated by 10 dpi in NIL-R. Based on these observations, gene expression changes were assayed within syncytia at 5 and 8 dpi in the NILs.

Transcript Profiling of Syncytia in NILs

Figure 2:
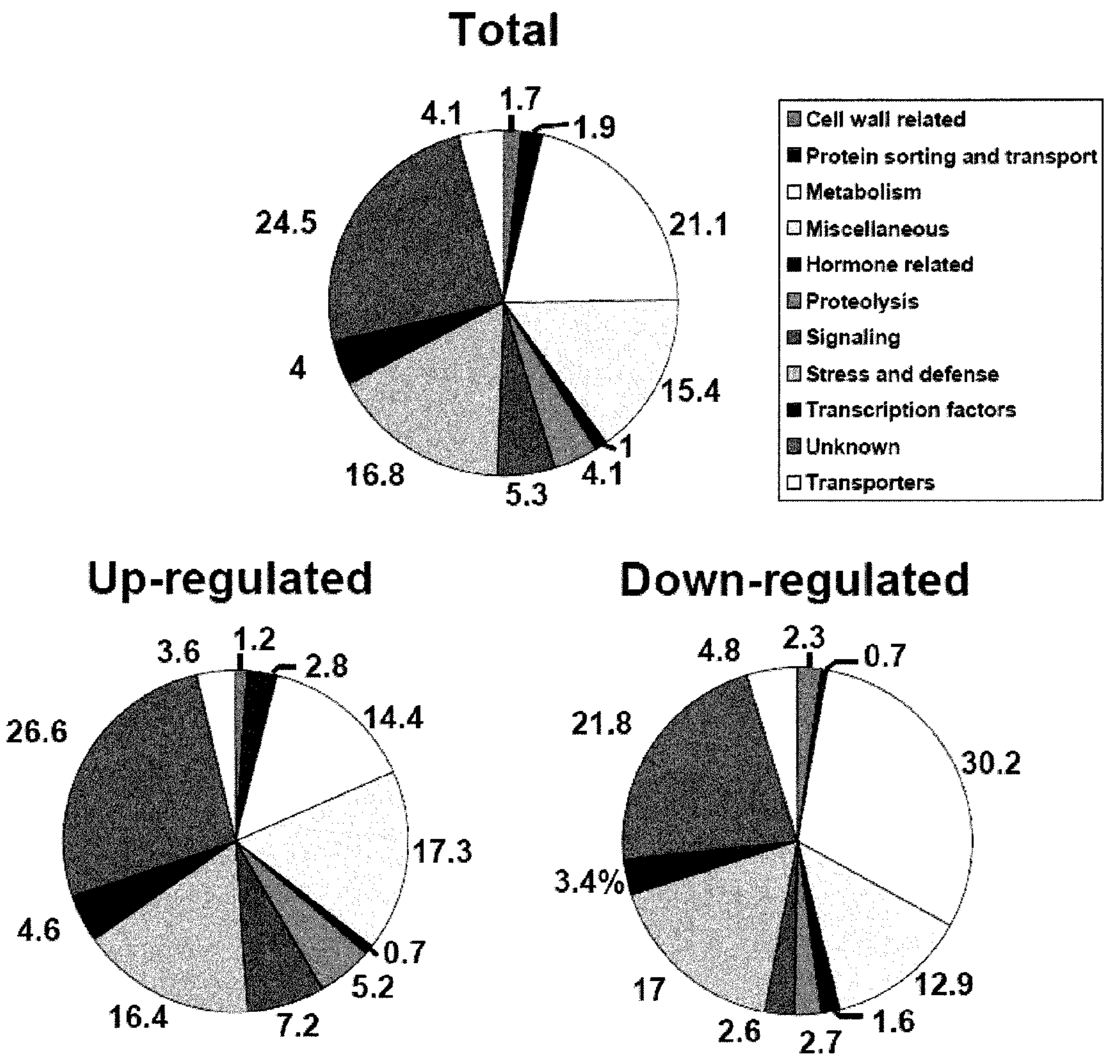
FIG. 2 shows the functional classification of differentially expressed genes identified by microarray analysis.

The GeneChip Soybean Genome Array (Affymetrix), which carries 37,593 probe sets representing 35,611 soybean transcripts, was used to compare the transcriptional profiles of SCN-induced syncytia in NIL-R and NIL-S. The microarray analysis was carried out using cRNA generated from LCM syncytia at 5 and 8 dpi with SCN from either the NIL-S or NIL-R. No significant evidence of interaction was found between NIL and dpi. Thus, the instant studies were focused on the main effects of NIL and the differences between NIL-S and NIL-R that are averaged over 5 and 8 dpi. This comparison of expression profiles between genotypes resulted in the identification of 1,447 differentially expressed probe sets using a false discovery rate (FDR) set at 10%. Of the 1,447 probe sets, 828 were up-regulated, and 619 were down-regulated in the NIL-R compared to the NIL-S (Tables 1-11). The recently released SoyBase annotation (v.2) for the Affymetrix Soybean Genome Array was used to classify these genes into categories (FIG. 2). Of the 1,447 probe sets, 355 (24.5%) correspond to genes coding for unknown proteins and/or those with no known homologs in *Arabidopsis*, with a high confidence value cut-off (E value$<10^{-6}$). Two other major categories include cellular metabolism genes (306 probe sets; 21.1%) and stress- and defense-related genes (241 probe sets; 16.8%). Additional classifications include (in descending order) cellular signaling, transporters, proteolysis, transcription factors, protein sorting and transport, cell wall-related, and hormone-related genes. Probe sets that do not fit into any of these categories or fall into multiple categories are grouped as "miscellaneous" (223; 15.4%). A number of probe sets corresponding to different *Glycine max* gene models had the same *Arabidopsis* homologs; this is not surprising given the duplicated nature of the soybean genome (Schlueter et al., 2004; Schlueter et al., 2007). These probe sets may represent homeologous genes with the same function, especially when their expression patterns fall within±one-fold difference of each other.

qPCR Validation of Microarray Data

The microarray data were validated by qPCR analysis of selected genes using RNA isolated from syncytial cells laser microdissected from the roots of NIL-R and NIL-S at 5 dpi. The genes were selected to represent those that were either up- or down-regulated with fold changes ranging from 27.65 fold up-regulation to 17.63 fold down-regulation in the microarray analysis (Table 14). Of the 42 genes tested, 38 genes (90.5%) showed differential expression in the same direction as that observed in the microarray experiment (Table 14). Only four probe sets, which showed a down-regulation in the microarray (Gma.2139.2.S1_S_at, GmaAffx.78421.1.S1_at, GmaAffx 84808.1.S1_at, and Gma.3504.2.S1_at, Table 14), were slightly up-regulated in the qPCR analysis. Thus, overall the qPCR results agreed with the microarray results.

TABLE 14 qPCR Validation of microarray results

| SEQ ID | FCaAffyChip Probeset ID | Gene Model/EST Sequence | Putative Function | qPCR FC[a] [b]NIL-R/PA3 5 dpi | Microarray FC[a] [b]NIL-R/PA3 5 dpi | qPCR FC[a] [c]NIL-R/TN19 5 dpi |
|---|---|---|---|---|---|---|
| 1 | Gma.10240.1.A1_at | BE057471 | No predicted gene model | −23.44 | −2.05 | −128.82 |
| 2 | Gma.10701.2.S1_at | Glyma05g27030.1 | P450 pseudogene-like, mandelate racemase N-terminal domain | −1.86 | −4.85 | −2.63 |
| 3 | Gma.10796.1.S1_a_at | Glyma15g43040.1 | Cellulose synthase, CEV1-like | 2.95 | 1.34 | 1.15 |
| 4 | Gma.11004.1.S1_at | Glyma03g35920.1 | Harpin-induced family protein (YLS9)/HIN1 family protein1 | 5.49 | 8.09 | 2.45 |
| 5 | Gma.11334.1.S1_a_at | BI967327 | Caffeoyl-CoA 3-O-methyltransferase, putative | 1.82 | −2.76 | −2.63 |
| 6 | Gma.1423.1.S1_a_at | Glyma01g38450.1 | Brassinosteroid signaling positive regulator-related | 2.57 | 1.65 | 1.91 |
| 7 | Gma.14272.1.S1_at | Glyma10g28300.1 | Hydrophobic protein (RCI2B)/low temp and salt responsive protein (LTI6B) | 33.88 | 11.69 | 2.09 |
| 8 | Gma.1445.1.S1_at | Glyma13g44700.1 | Cinnamoyl-CoA reductase, putative | −1.58 | −3.21 | −1.20 |
| 9 | Gma.15972.1.A1_at | Glyma04g17710.1 | Calcium-binding EF hand family protein | 16.60 | 27.65 | not tested |
| 10 | Gma.16613.1.S1_s_at | Glyma10g40400.1 | Zinc finger (C2H2 type) family protein | 9.55 | 4.67 | 2.00 |
| 11 | Gma.16807.1.S1_at | Glyma09g14880.1 | Zinc finger (B-box type) family protein | 4.37 | 2.68 | 2.40 |
| 12 | Gma.17843.1.S1_at | Glyma04g02660.1 | Gibberellin-regulated protein 1 (GASA1)/gibberellin-responsive protein | 116.98 | 2.62 | 2.75 |
| 13 | Gma.2139.2.S1_s_at | Glyma13g41960.1 | PfkB-type carbohydrate kinase family protein | 1.15 | −1.62 | <u>1.78</u> |
| 14 | Gma.2821.1.S1_at | Glyma01g42660.1 | Osmotin-like protein (OSM34) | 19.95 | 6.41 | −2.09 |
| 15 | Gma.3504.2.S1_at | Glyma13g00380.1 | WRKY family transcription factor | 1.48 | −2.59 | <u>1.95</u> |
| 16 | Gma.3990.1.S1_s_at | Glyma08g14370.1 | Ethylene-responsive calmodulin-binding protein | 2.09 | 1.9 | <u>7.76</u> |
| 17 | Gma.4071.1.S1_at | Glyma17g10050.2 | Gibberellin-regulated protein 2 (GASA2) | −2.75 | −5.26 | −6.17 |
| 18 | Gma.4207.1.S1_at | Glyma06g00630.1 | Myb family transcription factor (MYB32) | −1.23 | −2.15 | <u>1.78</u> |
| 19 | Gma.4565.1.S1_s_at | Glyma19g01590.2 | Gibberellin-regulated protein 3 (GASA3) | −1.38 | −4.76 | −20.89 |
| 20 | Gma.4589.1.S1_s_at | Glyma11g35800.1 | Senescence associated protein, SAG | 204.07 | 2.46 | 1.45 |
| 21 | Gma.5283.1.S1_at | Glyma06g07300.1 | Plant natriuretic peptide | −2.19 | −17.63 | −724.44 |
| 22 | Gma.596.1.S1_at | Glyma13g34580.4 | 14-3-3 protein (GRF9) | −1.12 | −2.96 | −3.80 |
| 23 | Gma.6062.1.S1_at | Glyma03g32130.1 | Dehydration-responsive protein-related | −1.26 | −2.69 | <u>1.45</u> |
| 24 | Gma.7381.1.S1_at | Glyma20g33430.1 | NAC domain containing protein | 2.45 | 1.67 | 2.34 |
| 25 | Gma.7526.1.A1_at | Glyma11g11430.1 | Senescence/dehydration-associated protein-related (ERD7) | 16.22 | 7.62 | 3.98 |
| 26 | Gma.7737.1.S1_at | BG650195MATE | efflux family protein | 467.74 | 14.73 | 10.96 |
| 27 | Gma.8586.1.S1_at | Glyma17g17330.2 | Proline-rich family protein | 6.92 | 3.39 | 6.61 |
| 28 | Gma.8859.1.A1_at | Glyma15g03110.1 | Hydroxyproline-rich glycoprotein family protein | 21.38 | 5.17 | 3.55 |
| 29 | Gma.9553.1.A1_at | Glyma14g06080.1 | DREB subfamily A-2 of ERF/AP2 transcription factor family | 22.91 | 8.08 | 8.13 |
| 30 | GmaAffx.11502.1.S1_at | Glyma16g01640.1 | Pectinesterase family protein | 5.89 | 2.13 | 2.29 |
| 31 | GmaAffx.21079.1.A1_at | Glyma03g32400.1 | Plasmodesmal protein | 2.95 | 2.15 | 2.04 |
| 32 | GmaAffx.2744.1.S1_at | Glyma04g40930.1 | Auxin-responsive family protein | 6.31 | 3.53 | 2.88 |
| 33 | GmaAffx.29929.1.S1_at | Glyma20g29410.1 | DREB subfamily A-1 of ERF/AP2 transcription factor family (CBF3) | 15.49 | 11.25 | 3.63 |
| 34 | GmaAffx.3568.1.S1_at | Glyma02g19870.1 | bZIP transcription factor family protein (bZIP60) | 5.89 | 3.21 | 2.57 |
| 35 | GmaAffx.46603.1.S1_at | Glyma19g27260.1 | GRAM domain-containing protein/ABA-responsive protein-related | 15.14 | 5.55 | 2.29 |
| 36 | GmaAffx.494.1.S1_at | Glyma16g28970.2 | Chitinase A (CHIA) | 6.92 | 4.99 | <u>10.00</u> |
| 37 | GmaAffx.70008.1.S1_at | BU762337 | Myb family transcription factor (MYB20) | −131.83 | −3.89 | −630.96 |
| 38 | GmaAffx.74588.1.S1_at | Glyma12g34210.1 | Non-race specific disease resistance protein, NDR1-like | 10.23 | 3.81 | 3.24 |
| 39 | GmaAffx.78421.1.S1_at | Glyma08g15650.1 | Pectinesterase family protein | 1.45 | −1.58 | −1.66 |
| 40 | GmaAffx.84808.1.S1_at | Glyma13g20810.2 | Ethylene-insensitive 2 (EIN2) | 1.91 | −1.59 | 1.82 |
| 41 | GmaAffx.88182.1.S1_at | Glyma03g35930.1 | Harpin-induced family protein/HIN1 family protein | 25.70 | 8.42 | 7.08 |
| 42 | GmaAffx.89435.1.A1_s_at | Glyma03g38190.2 | S-adenosylmethionine synthetase 2 (SAM2) | 2.24 | 1.77 | 1.32 |

[a]Fold-change compared to NIL-S/PA3/5 dpi
[b]"+" indicates genes upregulated; "−" indicates genes downregulated; Note that the fold-changes in expression for certain genes are opposite in qPCR and microarray;
[c]All of the genes are suppressed by the virulent TN19 SCN population except for those whose fold changes are not tested or underlined;
Underlining indicates that those genes are not suppressed by the virulent TN19 SCN population.

A comparative qPCR analysis for these genes was also carried out using RNA isolated from syncytial cells laser microdissected from soybean roots of the NIL-R infected with a virulent SCN population (TN19; HG type 1-7) at 5 dpi. Interestingly, a comparison between qPCR results of syncytia induced in the NIL-R by the virulent and avirulent (PA3; HG type 0) SCN populations showed that the extent of up-regulation or down-regulation of 35 (85.4%) of the 41 genes tested within syncytia induced by the virulent SCN was less than that attained by the avirulent population (Last column, Table 14). These data indicate that the expression of many of these genes is partially suppressed by the virulent SCN population for successful nematode reproduction and development on the NIL-R.

qPCR Analysis of Infected Whole Root Pieces

Figure 3:
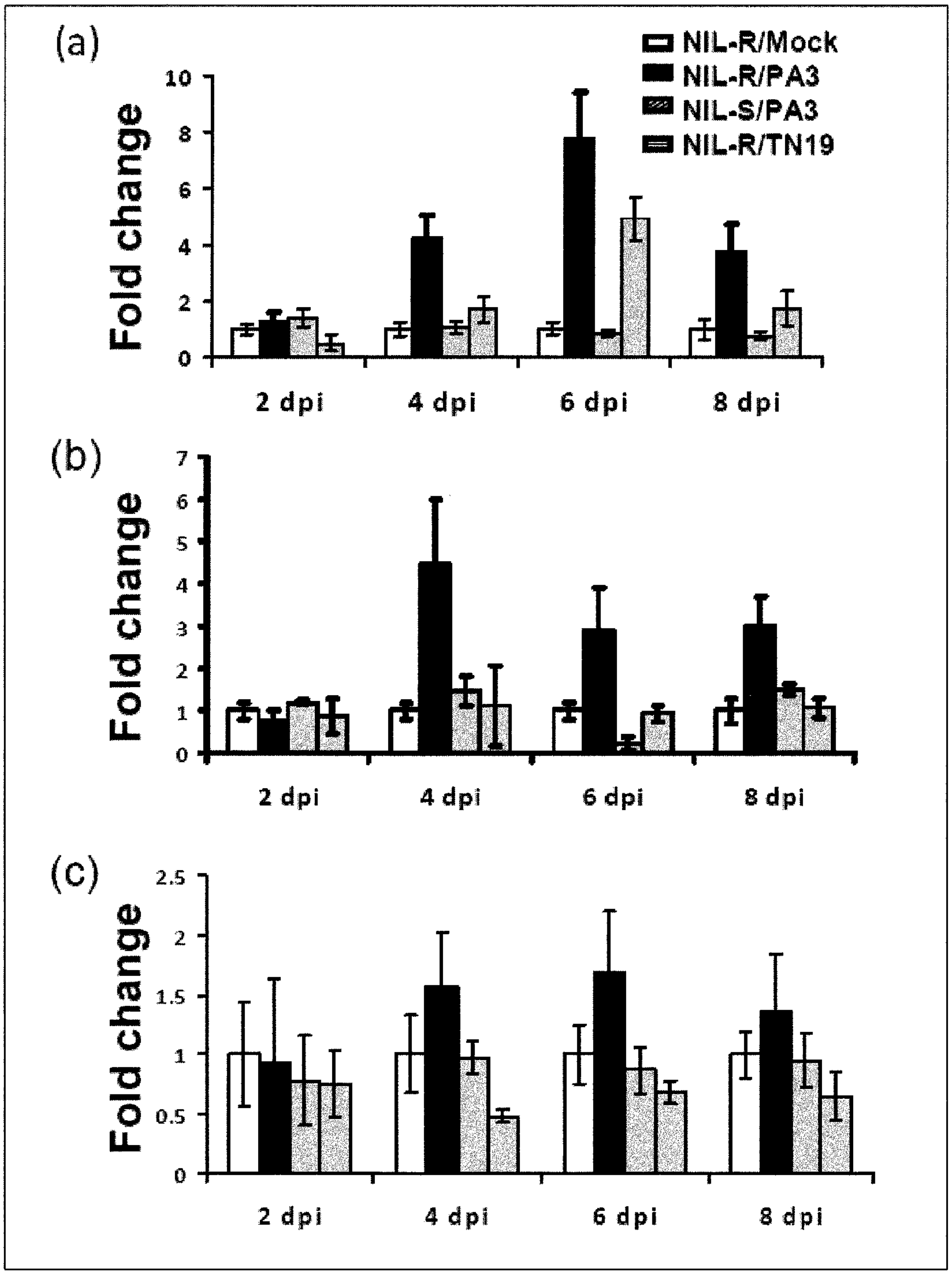
FIG. 3 shows qPCR analysis of up-regulated genes in excised infected whole root pieces of resistant (NIL-R) and susceptible (NIL-S) near-isogenic lines (NIL) at different days post inoculation (dpi) with avirulent (PA3) or virulent (TN19) soybean cyst nematodes (SCN).

For purposes of microarray validation and to obtain a detailed temporal expression pattern of select differentially expressed genes, a qPCR analysis was conducted for three genes using RNA isolated from excised SCN-infected whole root pieces at different time points post inoculation. FIG. 3 shows the results of the qPCR analysis of up-regulated genes in excised infected whole root pieces of resistant (NIL-R) and susceptible (NIL-S) near-isogenic lines (NIL) at different days post inoculation (dpi) with avirulent (PA3) or virulent (TN19) soybean cyst nematodes (SCN). Comparison of gene expression levels were made to the NIL-R mock-infected roots (taken as one) at the respective time points post-inoculation. (a) Gma.7623.1.A1_at (b) GmaAffx.68498.1.S1_at (c) GmaAffx.46603.1.S1_at. The qPCR results are normalized to a soybean ubiquitin (Accession No D28123) endogenous control. The graph is representative of 3 independent experiments, and the bars represent confidence intervals in technical replicates as described in Wang et al. (2007).

The NIL-R and NIL-S were mock-inoculated or infected with either the avirulent (PA3) or virulent (TN19) SCN population, and root pieces were excised from infection sites at 2, 4, 6, and 8 dpi. Total RNA was isolated from the bulked root pieces (n=10) for qPCR analysis. Time courses of expression were conducted for three different genes (represented by probe sets Gma.7623.1.A1_at, 87.9 fold; GmaAffx.68498.1.S1_at, 13.1 fold; and GmaAffx.46603.1.S1_at, 5.6 fold; Tables 1-11). The expression of mock-inoculated NIL-R at each time point was set as 1. At 2 dpi, the expression of all three genes was more or less equal between treatments (FIG. 3). However, by 4 dpi differential expression was observed for all three genes between the NIL-S and NIL-R. Up-regulation is very clear in the case of genes highly up-regulated in the microarray (FIG. 3*a, b*) and barely detectable in the case of GmaAffx.46603.1.S1_at (FIG. 3*c*), which had the lowest fold up-regulation based on microarray analysis. This study illustrates the dilution effect attributed to using infected whole root pieces for gene expression analyses in this pathosystem. For Gma.7623.1.A1_at, up-regulation in the NIL-R peaks at 6 dpi (FIG. 3*a*). The pattern is similar for GmaAffx.46603.1.S1_at (FIG. 3*c*). The expression pattern is slightly different for the gene represented by probe set GmaAffx.68498.1.S1_at in that the maximum up-regulation is observed at 4 dpi. These peaks in expression levels are consistent with the timing of the resistance response observed in syncytia of the NIL-R (FIG. 1). The observed trend in expression for each gene over the time course of infection was reproducible in three independent infection experiments; however, the level of up-regulation varied among experiments. This difference may be attributed to the biological variation inherent to nematode infection experiments, where it is impossible to achieve identical rates of infection. Similar to what was observed in qPCR analyses of RNA isolated from syncytia, infection by the virulent and avirulent SCN populations results in differential up-regulation of these genes. For all three genes tested, the level of up-regulation is lower in response to infection by the virulent nematode population (FIG. 3*a-c*). Additionally, in contrast to infection of the NIL-R, infection of the NIL-S with the avirulent population shows only a slight up-regulation for all three genes tested.

Promoter-GUS Expression Analysis

Promoter-GUS fusions were generated to provide further validation of the spatial expression pattern of the differentially expressed genes identified by microarray analysis and to isolate nematode-responsive soybean promoter sequences with high levels of expression within syncytia. For these experiments, primers corresponding to the 5' upstream sequences of 10 genes (FIG. 4*a*) chosen from the differentially expressed microarray data set (Tables 1-11) were designed by using the recently released Williams 82 soybean genome sequence (Schmutz et al., 2010). Promoter fragments were amplified by PCR using Williams 82 genomic DNA as a template and cloned upstream of a β-glucuronidase (GUS) reporter gene in the gateway binary vector pYXT1 (Xiao et al., 2005; FIG. 4*b*).

Figure 5:
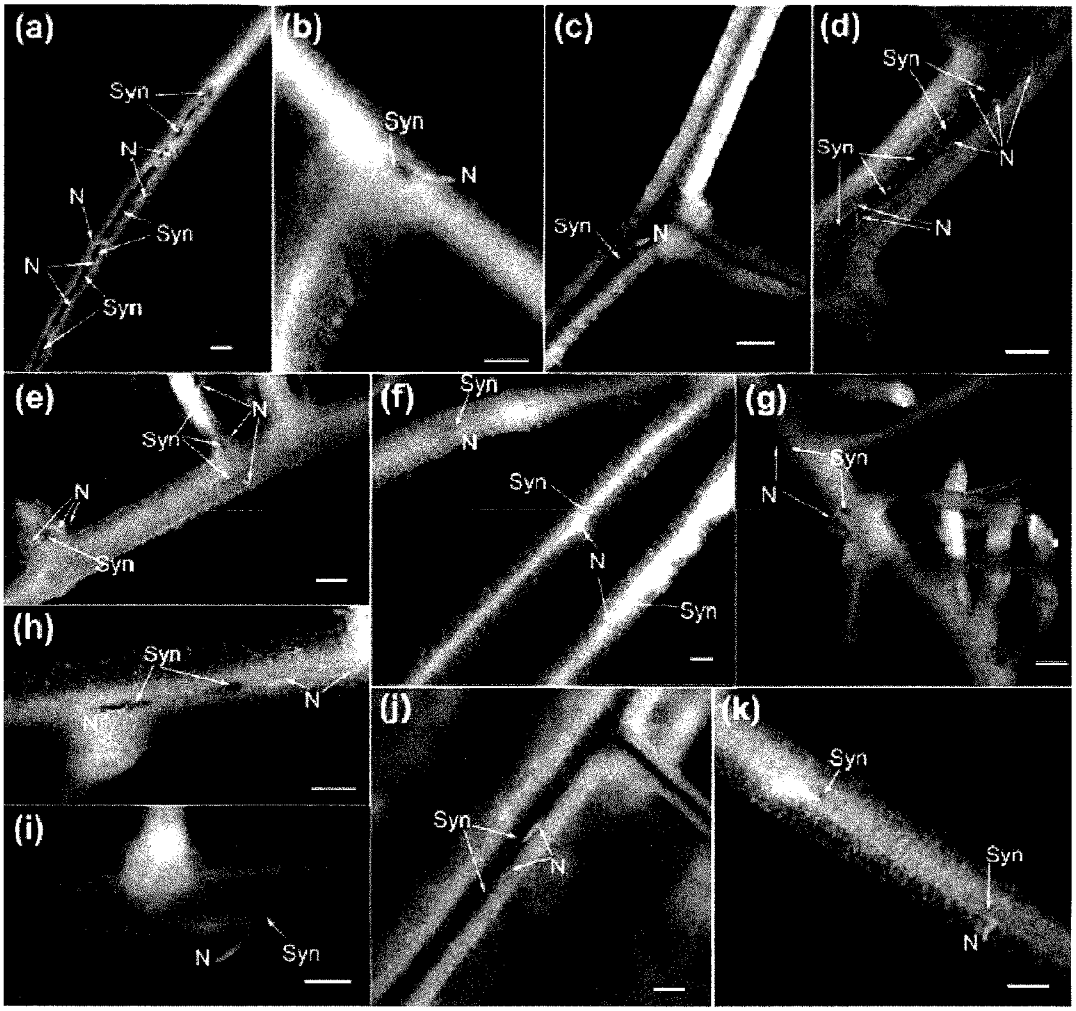
FIG. 5 shows the result of promoter-GUS expression in transgenic soybean hairy root lines of resistant near-isogenic lines (NIL-R) infected with PA3 soybean cyst nematodes (SCN).

Transgenic soybean hairy roots were generated in the NIL-R soybean background for each reporter construct. As a positive control, the *Arabidopsis* WRKY23 promoter (At2g47260) was tested in soybean; At2g47260 is induced within syncytia in *Arabidopsis* upon infection with the beet cyst nematode, *Heterodera schachtii* (Grunewald et al., 2008). The transgenic hairy roots were infected with the avirulent (PA3) SCN population. The positive control and all 10 promoter-GUS lines show induced GUS gene expression at the nematode feeding sites at 5 dpi (FIG. 5). FIG. 5 shows the result of promoter-GUS expression in transgenic soybean hairy root lines of resistant near-isogenic lines (NIL-R) infected with PA3 soybean cyst nematodes (SCN). Promoter-GUS constructs representing ten genes up-regulated in NIL-R identified from the microarray analysis and the nematode-inducible AtWRKY23 were infected with SCN and stained for GUS expression at 5 days post-inoculation (dpi). (a) AtWRKY23 (At2g47260); (b) Glyma15g04570.1; (c) Glyma15g06130.1; (d) Glyma14g06080.1; (e) Glyma09g34110.1; (f) Glyma01g42500.2; (g) Glyma01g42440.1; (h) Glyma18g43750.1; (i) Glyma18g18060.1; (j) Glyma19g04410.1; (k) Glyma13g35100.1. Pictures are representative of at least five independent hairy root lines for each promoter-GUS fusion construct. Syn—syncytia, N—nematode. Scale bar=500 μm.

Figure 6:
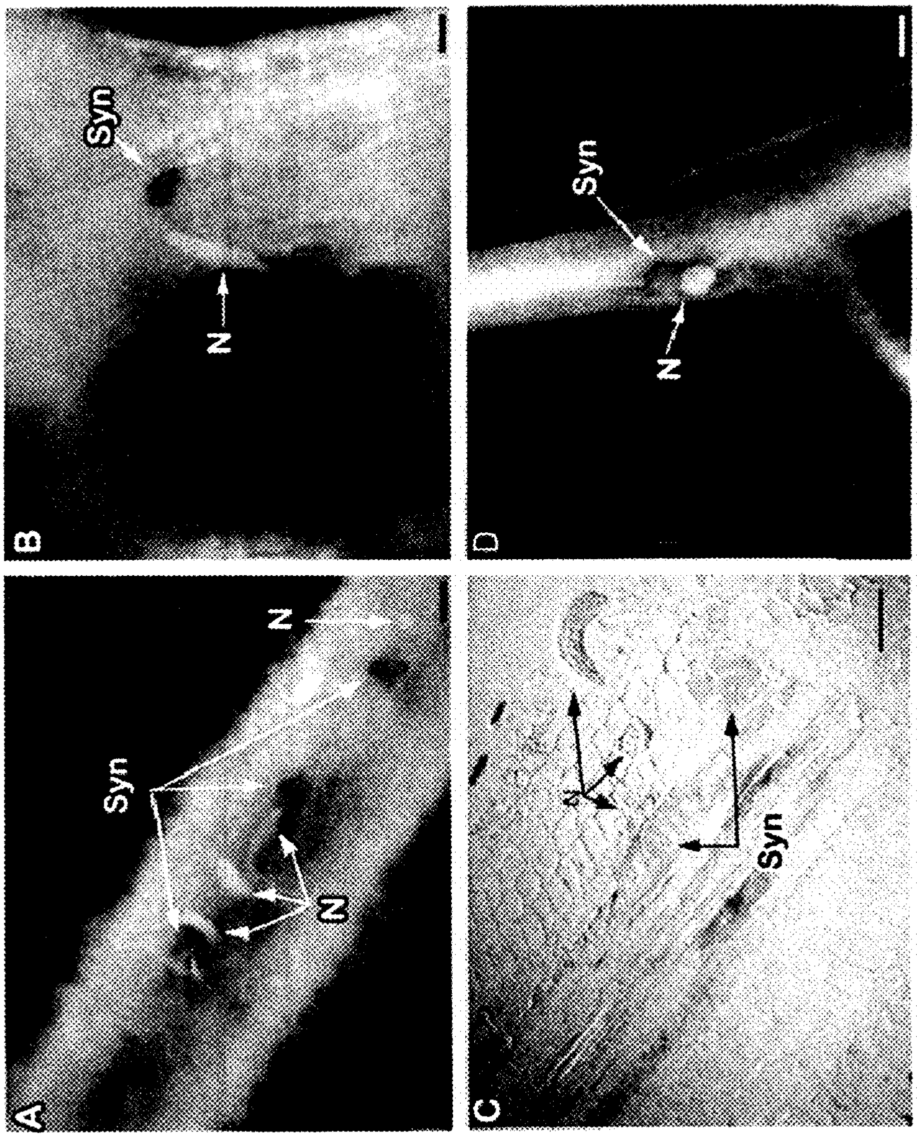
FIG. 6 shows the result of promoter-GUS expression in transgenic soybean hairy root lines of resistant near-isogenic lines (NIL-R) infected with PA3 soybean cyst nematodes (SCN) using Glyma03g35930.1 (88182p) as the promoter.
Figure 7:
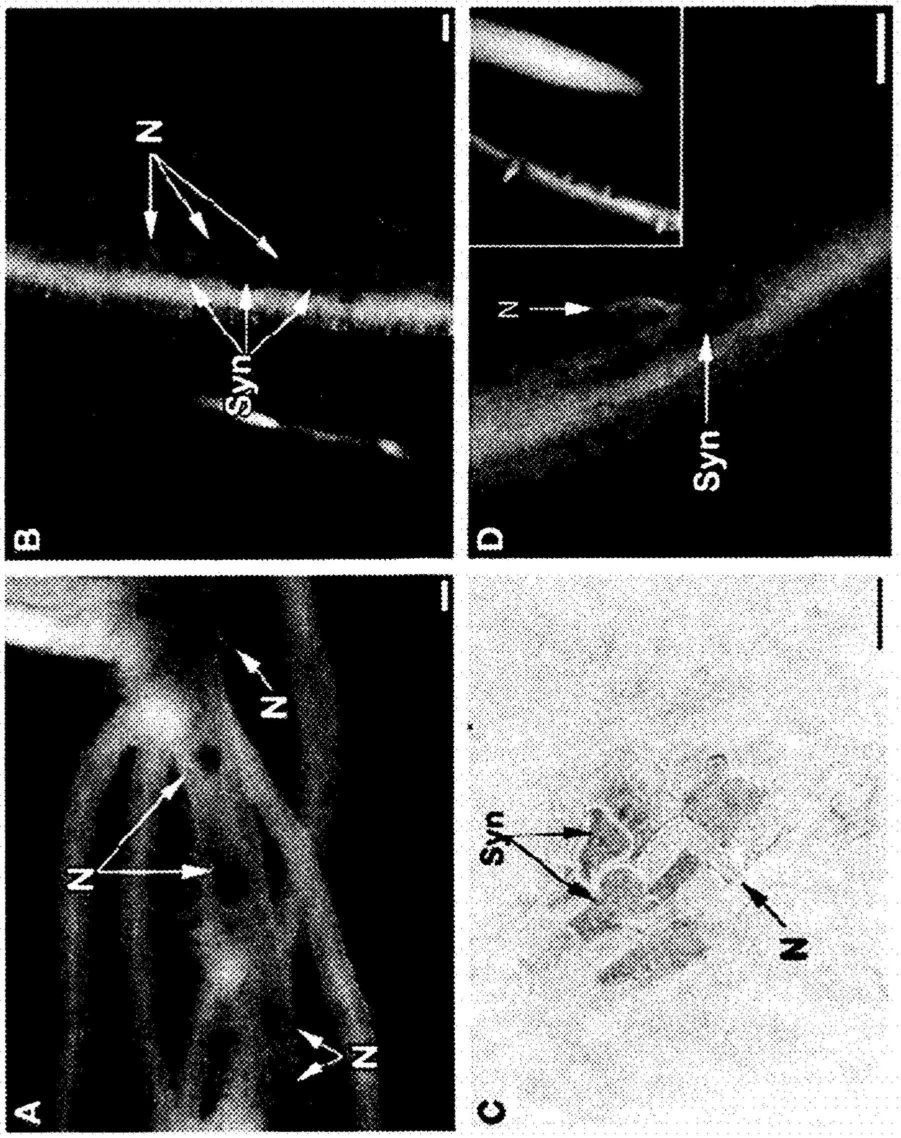
FIG. 7 shows the result of promoter-GUS expression in transgenic soybean hairy root lines of resistant near-isogenic lines (NIL-R) infected with PA3 soybean cyst nematodes (SCN) using Glyma03g35920.1 (11004p) as the promoter.

For several promoter-GUS lines, GUS expression is observed throughout the root (FIG. 4*c, d, i*, and *j*) but further induced at nematode feeding sites. Several promoters have an expression pattern that is very low or more restricted to specific cell types within roots and an up-regulation of GUS expression is clearly distinguishable at the nematode feeding sites (FIG. 4*a, b, e, f, g, h*, and *k*). FIGS. 6-7 show similar results using two other promoters, namely, Glyma03g35930.1 (88182p) and Glyma03g35920.1 (11004p).

Figure 8:
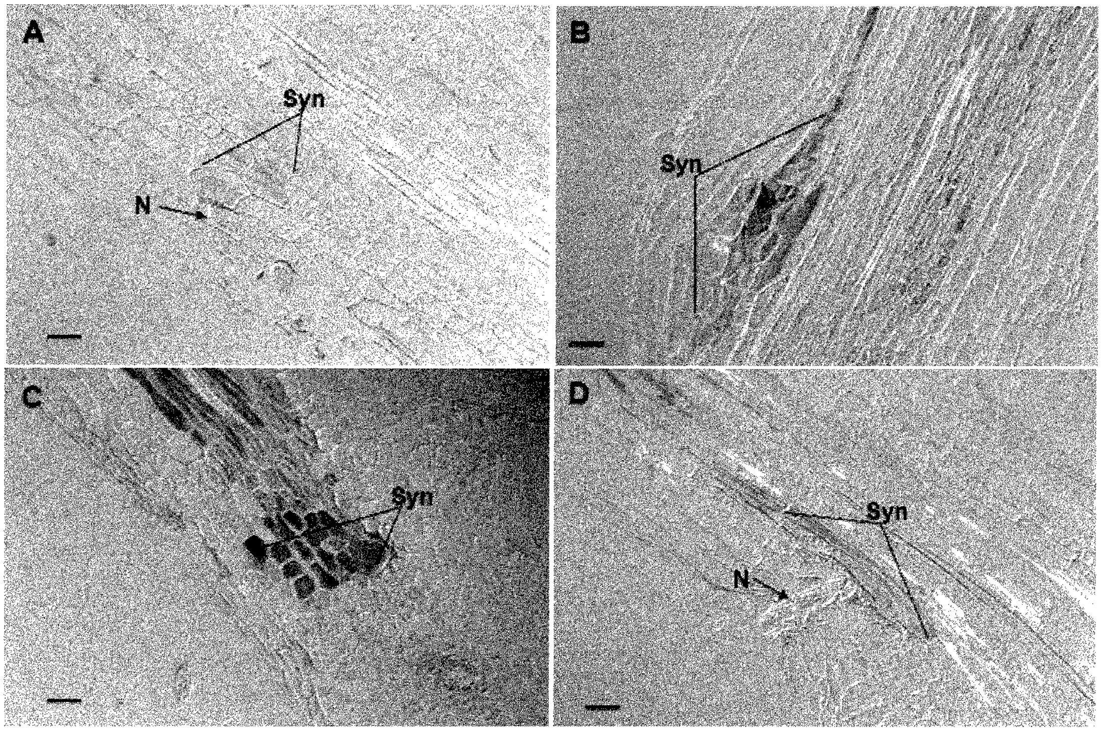
FIG. 8 shows longitudinal cross sections of promoter-GUS stained transgenic soybean hairy root lines in the resistant (NIL-R) background infected with PA3 soybean cyst nematodes (SCN).

FIG. 8 shows longitudinal cross sections of promoter-GUS stained transgenic soybean hairy root lines in the resistant (NIL-R) background infected with PA3 soybean cyst nematodes (SCN). Promoter-GUS stained root pieces of 4 different promoters shown in FIG. 5 were fixed in 4% paraformaldehydein phosphate-buffered saline overnight and then paraffin embedded. Serial sections of 10 μm thickness were taken. (A) Glyma15g04570.1; (B) Glyma15g06130.1; (C) Glyma14g06080.1; (D) Glyma18g43750.1. Pictures are representative of several syncytia for each promoter-GUS fusion construct. Syn—syncytia, N—nematode. Scale bar=50 μm.

TABLE 15

Differential expression of stress- and defense-related genes

| | AffyChip Probeset ID | Q-value | Fold-Change | Gene Model | AT # | Description |
|---|---|---|---|---|---|---|
| 43 | Gma.7623.1.A1_at | 0.0313 | 87.891 | Glyma07g06750.1 | AT2G46240.1 | Similar to AtBAG6 |
| 44 | GmaAffx.75438.1.S1_at | 0.0641 | 62.307 | Glyma17g13820.1 | AT1G76650.1 | Similar to *Arabidopsis* CML38 |
| 45 | GmaAffx.25859.1.S1_at | 0.0764 | 30.214 | Glyma14g06910.1 | AT3G46230.1 | Class I small heat-shock protein (sHSP) family |
| 46 | GmaAffx.39393.1.S1_at | 0.0347 | 16.162 | Glyma10g32000.1 | AT4G10250.1 | Endomembrane-localized small heat shock protein |
| 47 | GmaAffx.91194.1.S1_at | 0.0376 | 14.499 | Glyma01g41920.1 | AT4G17260.1 | Putative L-lactate/malate dehydrogenase |
| 48 | Gma.17947.1.S1_at | 0.0565 | 13.481 | Glyma08g07340.1 | AT2G29500.1 | Small heat shock protein (HSP17.6B-Class I) |
| 49 | Gma.14272.1.S1_at | 0.0396 | 11.694 | Glyma10g28300.1 | AT3G05890.1 | Rare-cold-inducible 2B (RCI2B) |
| 50 | Gma.10763.1.S1_at | 0.0664 | 11.364 | Glyma04g05720.1 | AT5G12020.1 | Class II heat shock protein (HSP17.6-Class II) |
| 51 | GmaAffx.29929.1.S1_at | 0.0268 | 11.25 | Glyma20g29410.1 | AT4G25480.1 | DREB subfamily A-1 of ERF/AP2 transcription factor family (CBF3) |
| 52 | Gma.2044.1.S1_at | 0.0722 | 10.771 | Glyma09g31740.1 | AT5G66400.2 | ABA and drought-induced glycine-rich dehydrin protein |
| 53 | GmaAffx.68621.1.A1_at | 0.0988 | 9.439 | Glyma20g29770.1 | AT5G52300.2 | Induced in response to water deprivation |
| 54 | GmaAffx.88182.1.S1_at | 0.0448 | 8.423 | Glyma03g35930.1 | AT2G35980.1 | NDR1 and Harpin-like (NHL) gene |
| 55 | Gma.11004.1.S1_at | 0.036 | 8.094 | Glyma03g35920.1 | AT2G35980.1 | NDR1 and Harpin-like (NHL) gene |
| 56 | Gma.9553.1.A1_at | 0.0317 | 8.079 | Glyma14g06080.1 | AT2G40340.1 | DREB subfamily A-2 of ERF/AP2 transcription factor family |
| 57 | Gma.5637.1.S1_at | 0.0595 | 7.885 | Glyma10g28610.1 | AT2G47180.1 | *Arabidopsis* galactinol synthase 1 (AtGolS1) |
| 58 | Gma.7526.1.A1_at | 0.0312 | 7.621 | Glyma11g11430.1 | AT2G17840.1 | Drought-inducible gene |
| 59 | GmaAffx.63418.1.S1_at | 0.0568 | 7.081 | Glyma09g16810.1 | AT5G06720.1 | Endomembrane located putative peroxidase |
| 60 | Gma.2821.1.S1_at | 0.0362 | 6.407 | Glyma01g42660.1 | AT4G11650.1 | Osmotin-like protein, soybean PR5 |
| 61 | GmaAffx.30428.1.S1_at | 0.0996 | 6.375 | Glyma17g08020.1 | AT1G16030.1 | Heat shock protein 70B (HSP70b) |
| 62 | Gma.8386.1.S1_at | 0.0268 | 6.08 | Glyma04g37040.1 | AT1G76650.1 | Similar to *Arabidopsis* CML38 |
| 63 | GmaAffx.6438.1.S1_at | 0.0678 | 5.926 | Glyma11g29720.1 | AT2G38470.1 | Similar to WRKY33 |
| 64 | GmaAffx.92590.1.S1_at | 0.0766 | 5.848 | Glyma02g33070.1 | AT2G41680.1 | NADPH thioredoxin sulphide reductase |
| 65 | Gma.13195.1.S1_s_at | 0.0274 | 5.445 | Glyma01g20860.1 | AT1G13340.1 | Unknown protein; oxidative stress |
| 66 | GmaAffx.6519.1.S1_at | 0.0624 | 5.408 | Glyma08g29470.1 | AT1G13340.1 | Unknown protein; oxidative stress |
| 67 | Gma.1622.1.A1_s_at | 0.0273 | 5.246 | Glyma05g17470.1 | AT5G66900.1 | Putative disease resistance protein (CC-NBS-LRR class) |
| 68 | Gma.5820.1.S1_s_at | 0.0268 | 4.856 | Glyma06g19810.1 | AT1G19020.1 | Unknown protein; oxidative stress |
| 69 | Gma.1439.1.S1_at | 0.0317 | 4.217 | Glyma04g14800.3 | AT3G22370.1 | Alternative oxidase AOX1a |
| 70 | GmaAffx.71308.2.A1_at | 0.0337 | 4.003 | Glyma04g05500.2 | AT2G26150.1 | Similar to AtHSF-A2 |
| 71 | Gma.620.1.S1_at | 0.0661 | 3.931 | Glyma15g40190.1 | AT1G78380.1 | Glutathione transferase of Tau GST gene family |
| 72 | GmaAffx.74588.1.S1_at | 0.0398 | 3.806 | Glyma12g34210.1 | AT3G20600.1 | NDR1-like |
| 73 | Gma.4089.1.S1_at | 0.0276 | 3.722 | No Soybean Match | AT4G25200.1 | AtHSP23.6-mito mRNA |
| 74 | GmaAffx.36259.1.S1_s_at | 0.0581 | 3.493 | Glyma05g33200.1 | AT2G02120.1 | Plant defensin (PDF) family PR protein |
| 75 | Gma.8204.1.A1_at | 0.0771 | 3.462 | Glyma04g14800.3 | AT3G22370.1 | Alternative oxidase AOX1a |
| 76 | Gma.8458.1.S1_at | 0.0922 | 3.265 | Glyma08g20190.1 | AT1G55020.1 | Lipoxygenase, similar to AtLOX1 |
| 77 | GmaAffx.3568.1.S1_at | 0.0196 | 3.208 | Glyma02g19870.1 | AT1G42990.1 | Similar to AtbZIP60 |
| 78 | GmaAffx.92499.1.S1_s_at | 0.0613 | 3.123 | Glyma19g43460.1 | AT3G04720.1 | Similar to antifungal chitin-binding protein hevein, PR-4 |
| 79 | GmaAffx.80951.1.S1_at | 0.0682 | 3.042 | Glyma16g29750.1 | AT5G52640.1 | AtHSP90.1 homolog |
| 80 | GmaAffx.84566.1.S1_x_at | 0.0539 | 3.011 | Glyma18g49360.1 | AT3G28910.1 | Transcription factor AtMYB30 homolog |
| 81 | Gma.7922.1.A1_a_at | 0.0431 | 2.88 | Glyma05g02210.1 | AT5G62520.1 | Similarity to RCD1 but without the WWE domain |
| 82 | GmaAffx.92919.1.S1_at | 0.0878 | 2.674 | Glyma05g05290.1 | AT5G47120.1 | Encodes BI-1, a homolog of mammalian Bax inhibitor 1 |
| 83 | GmaAffx.93596.1.S1_at | 0.040 | 2.672 | Glyma17g03950.2 | AT5G49520.1 | Similar to WRKY48 |
| 84 | GmaAffx.34450.1.S1_at | 0.0734 | 2.669 | Glyma05g05290.1 | AT5G47120.1 | Encodes BI-1, a homolog of mammalian Bax inhibitor 1 |
| 85 | GmaAffx.19934.1.S1_at | 0.0416 | 2.593 | Glyma13g21490.2 | AT5G03720.1 | Heat stress transcription factor HSFA3 |
| 86 | GmaAffx.1338.1.S1_at | 0.0962 | 2.555 | Glyma02g35210.1 | AT3G11820.1 | Similar to SYP121(PENETRATION1/PEN1) |
| 87 | Gma.8336.1.S1_at | 0.047 | 2.398 | Glyma19g40560.1 | AT2G47260.1 | Similar to WRKY23 |
| 88 | Gma.4639.1.A1_at | 0.0963 | 2.281 | Glyma13g36340.1 | AT3G20600.1 | NDR1-like |
| 89 | GmaAffx.22821.1.S1_at | 0.0687 | 2.178 | Glyma19g44390.2 | AT3G03300.2 | Encodes a dicer-like 2 |
| 90 | Gma.11115.2.S1_at | 0.0268 | 2.146 | Glyma11g14950.1 | AT3G12580.1 | Heat shock protein 70 (HSP70) |
| 91 | GmaAffx.11781.1.S1_s_at | 0.0273 | 2.137 | Glyma02g35660.1 | AT5G06320.1 | NDR1 and Harpin-like (NHL) gene |
| 92 | GmaAffx.89654.1.A1_s_at | 0.0338 | 2.063 | No Soybean Match | AT1G21750.1 | Protein disulfide isomerase-like (PDIL) protein |
| 93 | GmaAffx.20155.1.S1_at | 0.0517 | 2.036 | Glyma02g35230.1 | AT3G11820.1 | Similar to SYP121(PENETRATION1/PEN1) |
| 94 | Gma.10639.1.S1_x_at | 0.065 | 1.793 | Glyma03g27560.1 | AT2G41010.1 | Similar to a calmodulin binding protein |
| 95 | Gma.6474.1.A1_s_at | 0.0655 | 1.727 | Glyma15g13470.1 | AT2G34690.1 | Similar to ACD11 gene |
| 96 | GmaAffx.1991.1.S1_at | 0.0637 | 1.665 | Glyma11g04040.2 | AT5G47120.1 | Encodes BI-1, a homolog of mammalian Bax inhibitor 1 |
| 97 | GmaAffx.80733.1.S1_at | 0.0396 | 1.578 | Glyma17g11240.1 | AT5G20320.1 | Encodes a dicer-like 4 |
| 98 | Gma_3755.1.S1_at | 0.0869 | 1.481 | Glyma03g30590.1 | AT5G13320.1 | Similar to PBS3/GH3.12 |
| 99 | GmaAffx.19777.1.A1_at | 0.0986 | 1.43 | No Soybean Match | AT4G31800.2 | Similar to WRKY18 pathogen-induced transcription factor |
| 100 | GmaAffx.48022.2.A1_at | 0.0658 | 1.429 | Glyma13g02470.3 | AT4G08500.1 | Encodes MEKK1, phosphorylates MEK1 |

Special attention was paid to the stress- and defense-related genes to gain a better understanding of the HR that occurs within developing syncytia of the NIL-R in response to SCN. The differential expression of this class of genes varies from 87-fold up-regulated to 17-fold down-regulated (Tables 15-16). In one embodiment, the expression of any of the genes listed in Tables 14-16 may be altered in order to obtain a nematode resistant plant. In another embodiment, the expression levels of up-regulated genes such as those listed in Table 15 may be increased in order to boost plant defense against nematode infection. In another embodiment, the expression levels of down-regulated genes such as those listed in Table 16 may be decreased in a host plant in order to boost plant defense against nematode infection.

Soybean orthologs of many known plant defense genes have not yet been identified; therefore, we relied on their similarity to *Arabidopsis* homologs. A total of 241 probe sets representing 16.8% of the total number of differentially expressed genes identified are classified in this group. These included genes involved in apoptosis and disease resistance. A large number of genes involved in oxidative, heat, drought, cold, osmotic, and salt stress responses are also differentially regulated. A natriuretic peptide with an expansin-like domain and many abscisic acid (ABA) induced genes are also among those differentially expressed (Tables 15-16).

The gene up-regulated with the highest fold change (87-fold, Table 15) is a probe set that corresponds to a soybean gene with similarity to *Arabidopsis* Bag6 (AtBag6). Bag6 encodes a stress-induced calmodulin-binding BAG (BCL2-associated athanogene) domain protein that is homologous to mammalian BAG proteins, which are regulators of BCL2 involved in apoptosis (Kang et al., 2006). Overexpression of Bag6 in yeast and *Arabidopsis* causes cell death (Kang et al., 2006). Another highly up-regulated gene (62-fold) is a soybean calmodulin with similarity to calmodulin-like 38 (CML38) of *Arabidopsis*, which has been shown to respond to wounding (Vanderbeld and Snedden, 2007). Several heat shock proteins (HSPs) of the small HSP superfamily are up-regulated as well (Table 15). HSPs are stress responsive proteins that have a protective function in promoting cellular stress tolerance (Wang et al., 2004). Small HSPs bind and stabilize denatured proteins to which other high molecular weight HSPs act as chaperones under stress conditions. Several other HSPs, including an HSP70 homolog (Gma.11115.2.S1_at), HSP70B homolog (GmaAffx.30428.1.S1_at), HSP90.1 homolog (GmaAffx.80951.1.S1_at), and two heat shock transcription factors (HSFs), Hsf-A2 homolog (GmaAffx.71308.2.A1_at, 4.0 fold) and Hsf-A3 homolog (GmaAffx.19934.1.S1_at, 2.6 fold), are up-regulated in syncytia of the NIL-R. HSP90 is a highly conserved molecular chaperone rapidly induced during pathogen challenge and a variety of environmental stresses. It interacts with the R protein, RPM1 (Hubert et al., 2003), and is required for RPS2-mediated resistance against *Pseudomonas syringae* pv. tomato DC 3000 (avrRpt2) (Takahashi et al., 2003). HSFs are involved in a variety of environmental stresses; HSF-A2, for example, is a key inducer of defense responses and is up-regulated during environmental stress and $H_2O_2$ treatment (Nishizawa et al., 2006). Several PR genes are also up-regulated. A soybean osmotin (Gma.2821.1. S1_at, Table 15), which is described as a salt stress-induced acidic isoform of PR-5 (Onishi et al., 2006) and has similarity to *Arabidopsis* osmotin 34, is up-regulated 6.4 fold. Osmotins are components of incompatible reactions against bacterial pathogens (Jia and Martin, 1999). Another up-regulated PR-protein is a hevein-like protein belonging to the PR-4 family, which is up-regulated during salt stress, in response to viral infection, and in systemic acquired resistance (SAR) (Potter et al., 1993). We found a 3.5-fold up-regulation of a defensin homologous to *Arabidopsis* defensin PDF2.1 (GmaAffx.36259.1.S1_s_at) but a down-3.5-fold down-regulation of another member of the same defensin family, PDF2.5 (Gma.4126.1.S1_at, Table 16).

TABLE 16

Down-regulated Stress and Defense-related genes

| | AffyChip Probeset ID | Q-value | Fold-Change | Gene Model | AT # | Description |
|---|---|---|---|---|---|---|
| 101 | Gma.5283.1.S1_at | 0.037 | −17.624 | Glyma06g07300.1 | AT2G18660.1 | Plant natriuretic peptide A (PNP-A) |
| 102 | Gma.5629.2.S1_a_at | 0.081 | −5.461 | Glyma15g05820.1 | AT2G41480.1 | Peroxidase, response to oxidative stress |
| 103 | GmaAffx.84317.1.S1_at | 0.054 | −5.457 | Glyma06g42310.1 | AT5G54250.2 | Similar to AtCNGC4, HR |
| 104 | Gma.5629.1.S1_at | 0.032 | −5.021 | No Soybean Match | AT2G41480.1 | Peroxidase, response to oxidative stress |
| 105 | Gma.5971.1.S1_at | 0.047 | −4.813 | Glyma11g07670.1 | AT5G66390.1 | Similar to *Arabidopsis* PER72, oxidative stress |
| 106 | GmaAffx.74124.1.S1_at | 0.083 | −3.937 | No Soybean Match | AT5G67400.1 | Similar to PER73(RHS19), oxidative stress |
| 107 | Gma.1539.1.S1_at | 0.064 | −3.677 | Glyma11g05300.2 | AT4G37520.1 | Peroxidase similar to PER50, oxidative stress |
| 108 | GmaAffx.73002.1.S1_at | 0.060 | −3.570 | Glyma02g09470.1 | AT1G14790.1 | Similar to RDRP |
| 109 | Gma.4126.1.S1_at | 0.058 | −3.461 | Glyma06g16810.1 | AT5G63660.1 | Similar to defensin PDF2.5 defense response |
| 110 | Gma.4919.1.S1_at | 0.027 | −3.198 | Glyma14g05840.1 | AT5G05340.1 | Peroxidase, response to oxidative stress |
| 111 | GmaAffx.92030.1.S1_at | 0.095 | −2.594 | Glyma19g44310.1 | AT2G46370.2 | Similar to JAR1 |
| 112 | Gma.3504.2.S1_at | 0.050 | −2.591 | Glyma13g00380.1 | AT4G31550.1 | Similar to WRKY11 |
| 113 | GmaAffx.65280.1.A1_at | 0.078 | −2.574 | Glyma13g26640.2 | AT3G27890.1 | NADPH quinone oxidoreductase |
| 114 | Gma.8020.3.S1_at | 0.074 | −2.521 | Glyma13g07490.1 | AT3G25780.1 | Similar to AOC3 |
| 115 | Gma.338.1.S1_at | 0.027 | −2.438 | Glyma07g39020.1 | AT4G21960.1 | Peroxidase, response to oxidative stress |
| 116 | Gma.1502.1.S1_at | 0.087 | −2.285 | Glyma05g29400.1 | AT2G29420.1 | Similar to *Arabidopsis* glutathione 5-transferase tau 7 |
| 117 | Gma.2350.1.S1_at | 0.054 | −2.227 | No Soybean Match | AT5G60640.1 | PDIL-4 homolog, oxidative stress |
| 118 | Gma.8020.2.S1_a_at | 0.084 | −2.112 | No Soybean Match | AT1G13280.1 | Similar to AOC4, jasmonic acid biosynthesis |
| 119 | Gma.4207.1.S1_at | 0.027 | −2.147 | Glyma06g00630.1 | AT4G34990.1 | AtMYB32 homolog |
| 120 | GmaAffx.6478.1.S1_s_at | 0.068 | −2.051 | Glyma13g00380.1 | AT4G31550.1 | Similar to WRKY11 |
| 121 | Gma.3504.1.S1_at | 0.095 | −1.965 | Glyma17g06450.1 | AT4G31550.1 | Similar to WRKY11 |
| 122 | Gma.4189.1.S1_at | 0.054 | −1.942 | Glyma17g01720.1 | AT4G21960.1 | PRXR1, oxidative stress |
| 123 | Gma.3504.2.S1_a_at | 0.079 | −1.923 | Glyma13g00380.1 | AT4G31550.1 | Similar to WRKY11 |
| 124 | GmaAffx.54278.1.S1_at | 0.078 | −1.782 | Glyma13g03600.1 | AT1G21750.1 | Similar to PDIL1-1, regulation of PCD |
| 125 | Gma.2677.1.S1_s_at | 0.064 | −1.731 | Glyma19g44310.1 | AT2G46370.2 | Similar to At AR1, production of JA-Ile |
| 126 | Gma.2749.1.S1_at | 0.048 | −1.699 | Glyma10g40140.1 | AT1G80600.1 | Similar to WIN1, defense response |
| 127 | Gma.2350.1.S1_s_at | 0.097 | −1.645 | Glyma13g40130.1 | AT5G60640.1 | PDI1-4, oxidative stress |
| 128 | Gma.4312.1.S1_at | 0.098 | −1.633 | Glyma08g05200.1 | AT2G31570.1 | Glutathione peroxidase 2 (GPX2) |
| 129 | GmaAffx.89649.1.S1_s_at | 0.052 | −1.631 | Glyma05g34490.4 | AT2G43350.1 | ATGPX3 |
| 130 | GmaAffx.84808.1.S1_at | 0.039 | −1.590 | Glyma13g20810.2 | AT5G03280.1 | Ethylene insensitive 2 (EIN2) |
| 131 | GmaAffx.85352.1.S1_at | 0.091 | −1.542 | Glyma03g33850.1 | AT5G03280.1 | Ethylene insensitive 2 (EIN2) |
| 132 | Gma.4312.1.S1_x_at | 0.097 | −1.461 | Glyma08g05200.1 | AT2G31570.1 | Glutathione peroxidase 2 (GPX2) |
| 133 | Gma.3301.1.S1_at | 0.093 | −1.426 | Glyma06g00440.1 | AT4G02600.2 | Homology to MLO1 protein, cell death defense response |
| 134 | GmaAffx.90444.1.S1_s_at | 0.058 | −1.323 | Glyma11g21260.1 | AT3G27890.1 | NADPH quinone oxidoreductase |

Several genes related to oxidative stress also were identified as differentially expressed, indicating that developing syncytia at 5 dpi are undergoing severe oxidative stress (Table 15). The production of reactive oxygen species (ROS) is a key aspect of the HR during R-mediated resistance to other pathogens (Lamb and Dixon, 1997). An NADPH thioredoxin reductase, similar to *Arabidopsis* NTRC, is up-regulated (5.8 fold, GmaAffx.92590.1.S1_at). Alternative oxidase (Gma.1439.1.S1_at, 4.2 fold; Gma.8204.1.A1_at, 3.46 fold), glutathione S-transferase (Gma.620.1.S1_at, 3.9 fold), and a gene similar to RCD1-5 involved in ROS regulation (Gma.7922.1.A1_a_at, 2.9 fold) are up-regulated. Several genes related to oxidative stress and regulation of ROS are also down-regulated (Table 16) as are many peroxidases (Gma.5629.2.S1_a_at, Gma.5629.1.S1_at, Gma.5971.1.S1_at, GmaAffx.74124.1.S1_at, Gma.1539.1.S1_at, Gma.4919.1.S1_at, Gma.338.1.S1_at, Gma.4189.1.S1_at, fold changes ranging from −5.4 to −1.9). Peroxidases are involved in $H_2O_2$ catabolism, and their down-regulation may suggest a positive impact on ROS generation; although, they can also generate ROS species (Passardi et al., 2004). Other down-regulated oxidative stress genes include two NADPH quinone oxidoreductases (GmaAffx.65280.1.A1_at, −2.57 fold; GmaAffx.90444.1.S1_s_at, −1.3 fold), glutathione peroxidase 2 and 3 homologs, and a protein disulphide isomerase-like 4 (PDI like-4) that belongs to the thioredoxin family.

Several soybean genes showing high similarity to defense genes of *Arabidopsis* that play a role in incompatible responses to other plant pathogens were found to be differentially expressed in syncytia of the NIL-R in response to SCN (Tables 15-16). Two soybean genes with homology to *Arabidopsis* NDR1 are up-regulated (GmaAffx.74588.1.S1_at, 3.8 fold; Gma.4639.1.A1 at, 2.3 fold). NDR1 is involved in SA-mediated disease resistance to biotrophic pathogens (Century et al., 1995). In addition, several NDR1 and harpin-like (NHL) genes are up-regulated (GmaAffx.88182.1.S1_at, 8.4 fold; Gma.11004.1.S1_at, 8.1 fold; GmaAffx.11781.1.S1_s_at, 2.1 fold; Table 15). NHL3 and NHL10 are induced in response to avirulent viral infection, in senescing leaves, and by spermine in *Arabidopsis* (Zheng et al., 2004). WRKY transcription factors are known to take part in defense responses to viral, bacterial, and fungal pathogens (Eulgem and Somssich, 2007). Several WRKY transcription factor homologs are up-regulated in syncytia of the NIL-R (Table 15). Also up-regulated are a homolog of AtWRKY33, a known regulator of defense pathways mediating resistance to *P. syringae* and fungal necrotrophic pathogens (Zheng et al., 2006) (GmaAffx.6438.1.S1_at, 5.9 fold); an AtWRKY48 homolog (GmaAffx.93596.1.S1_at, 2.67 fold); and a homolog of AtWRKY18, which is involved in SA-mediated defenses against viruses, bacteria, and fungi (GmaAffx.19777.1.A1_at, 1.4 fold). Interestingly, a soybean homolog of AtWRKY23 (Gma.8336.1.S1_at, 2.4 fold), which is involved in nematode feeding site establishment (Grunewald et al., 2008), is also up-regulated. Down-regulated WRKYs (Table 16) include a homolog of AtWRKY11 (GmaAffx.6478.1.S1_s_at, −2.05 fold; Gma.3504.1.S1_at, −2 fold; Gma.3504.2.S1a_at, −1.9 fold), a negative regulator of basal defense responses against bacterial pathogens (Journot-Catalino et al., 2006). Down-regulation of a negative regulator would lead to an enhanced defense response.

Several genes known to take part in SA-mediated defense responses were found to be either up-regulated or down-regulated. Probe set GmaAffx.84566.1.S1_x_at (Table 15) is up-regulated 3-fold; this probe set corresponds to a soybean MYB protein homologous to AtMYB30, an SA-dependent R2-R3MYB that acts as a positive regulator of HR cell death and is a modulator of SA levels (Vailleau et al., 2002; Raffaele et al., 2006). Soybean homologs of *Arabidopsis* ACD11 (Gma.6474.1.A1s_at, 1.7 fold) and PBS3 (Gma.3755.1.S1_at, 1.5 fold), which are involved in SA-mediated defense, are also up-regulated. A soybean homolog of *Arabidopsis* WIN1 (Gma.2749.1.S1_at, −1.7 fold), a negative regulator of SA accumulation, is down-regulated (Table 16).

Jasmonate-mediated response components are also differentially expressed. A soybean LOX gene homologous to *Arabidopsis* LOX1 is up-regulated (Gma.8458.1.S1_at, 3.3 fold; Table 15). However, a JAR1 homolog (GmaAffx.92030.1.S1_at, −2.6 fold; Gma.2677.1.S1_s_at, −1.7 fold) and AOC homologs (Gma.8020.3.S1_at_AOC3, −2.5 fold; Gma.8020.2.S1_a_at, −2.1 fold; Table 16) are down-regulated.

Also up-regulated are a CC-NB-LRR protein (Gma.1622.1.A1_s_at, 5.2 fold); genes associated with endoplasmic reticulum (ER) stress and the unfolded protein response (UPR), including an AtbZIP60 homolog (GmaAffx.3568.1.S1_at, 3.2 fold) and an AtBIP2 homolog (Gma.17631.1.S1_at, 2 fold) (Table 15); and a Bax inhibitor protein (BAX-I) homolog, an attenuator of apoptosis, (GmaAffx.1991.1.S1_at; GmaAffx.34450.1.S1_at; GmaAffx.92919.1.S1_at, 2.7-1.7 fold). The up-regulation of a MAP3K homolog (GmaAffx.48022.2.A1_at) implicates MAPK signaling in the regulation of resistance to SCN. A soybean gene encoding a protein with homology to *Arabidopsis* Syntaxin 121 (SYP121), a secretory pathway protein with known roles in defense responses, is also induced (GmaAffx.1338.1.S1_at, 2.6-fold GmaAffx.20155.1.S1_at 2-fold) as are several genes involved in cold, drought, dehydration, and ABA responses (Gma.14272.1.S1_at, 11.7 fold; Gma.2044.1.S1_at, 10.8 fold; GmaAffx.68621.1.A1_at, 9.4 fold; Gma.7526.1.A1_at, 7.6 fold) and two transcription factors of the AP2/ERF family involved in drought responses (GmaAffx.29929.1.S1_at, 11.2 fold; Gma.9553.1.A1_at, 8.1 fold). The high up-regulation of these genes may suggest new roles in HR against a biotrophic pathogen, or they are secondary physiological responses that potentiate HR.

The most highly down-regulated probe set (Gma.5283.1.S1_at, −17.6 fold) corresponds to a gene encoding a predicted natriuretic peptide with an expansin-like domain sharing homology to AtPNP-A (Table 16), which is involved in plant growth and homeostasis (Morse et al., 2004). AtPNP-A is induced by SA and is expressed at higher levels in *Arabidopsis* mutants with increased SA levels (Meier et al., 2008). Another highly down-regulated gene is a cyclic nucleotide-gated channel (CNGC) (GmaAffx.84317.1.S1_at, −5.5 fold, Table 16), which shares homology with *Arabidopsis* CNGC4/HLM1. *Arabidopsis* mutants of CNGC4/HLM1 produce a lesion mimic phenotype and altered HR (Balague et al., 2003).

Besides the defense-related transcription factors such as WRKYs and AP2/ERF, several other classes of transcription factors were found to be differentially expressed (Table 17). Major classes represented were the NAC domain transcription factors, $C_2H_2$-type zinc finger transcription factors, transcription factors involved in cell fate determination, and auxin response factors (ARFs). EIN3 (GmaAffx.65341.1.A1 at, 10 fold) which acts downstream of the histidine kinase ethylene receptor, ETR1 to regulate the ethylene signaling pathway (Chao et al., 1997) was upregulated. Several NAC domain factors were up-regulated. Two probe sets corresponding to soybean genes homologous to ANAC073 (Gma.8113.1.A1_at, 15 fold; GmaAffx.50811.2.S1_at, 11 fold) were upregulated. ANAC073 is involved in the regulation of secondary wall thickening (Zhong et al., 2008). Other NACs included an ANAC087 homolog (GmaAffx.64710.1.S1_at, 4.6 fold; GmaAffx.5448.1.S1_at, 2.5 fold), an ANAC014 homolog (GmaAffx.9475.1.A1_s_at, 1.84 fold), ATAF1 (GmaAffx.90028.1.S1_s_at, 1.9 fold), and an ANAC050 homolog (Gma.7381.1.S1_at, 1.7 fold). ATAF1 has been shown to be induced by wounding and is a negative regulator of defense to bacterial and fungal pathogens (Wang et al., 2009). Four $C_2H_2$-type zinc finger transcription factors were up-regulated (Gma.986.1.S1_at, 11 fold; Gma.17736.1.S1_at, 7.6 fold; Gma.4526.1.S1_at, 4.1 fold; GmaAffx.65885.1.A1_s_at, 1.9 fold). The role of these genes in defense or pathogenesis is currently unknown. A homolog of ZAT11 (Gma.4526.1.S1_at) is known to be up-regulated by $H_2O_2$(Gechev et al., 2005). A MYB domain 20 homolog (GmaAffx.70008.1.S1_at, −3.9 fold) involved in secondary wall thickening was down-regulated. ARF family genes play a central role in controlling sensitivity to the plant hormone auxin. A soybean homolog of ARF19 implicated in root cap development was up-regulated (Gma.9082.1.S1_at, 1.5 fold). Soybean homologs of ARF16 and ARF8 were down-regulated. In *Arabidopsis*, ARF16 is indispensible for root cap development and is regulated by miR160 (Wang et al., 2005). ARF8, along with ARF6 has been shown to affect jasmonate production in flowers (Nagpal et al., 2005).

TABLE 17

Differentially Expressed Transcription Factors.

| SEQ ID | AffyChip Probeset ID | Q-value | Fold-Change | Gene Model | AT # | Description |
|---|---|---|---|---|---|---|
| 135 | GmaAffx.65341.1.A1_at | 0.079 | 10.012 | Glyma08g14630.1 | AT5G10120.1 | EIN3 family protein |
| 136 | Gma.8113.1.A1_at | 0.027 | 15.780 | Glyma15g08480.2 | AT4G28500.1 | NAC domain similar to ANAC073 |
| 137 | GmaAffx.50811.2.S1_at | 0.058 | 11.475 | Glyma15g08480.2 | AT4G28500.1 | NAC domain similar to ANAC073 |
| 138 | Gma.986.1.S1_at | 0.034 | 11.089 | Glyma15g04570.1 | AT2G28710.1 | Zinc finger (C2H2) family protein |
| 139 | Gma.17736.1.S1_at | 0.054 | 7.533 | Glyma03g33070.1 | AT2G37430.1 | Zinc finger (C2H2) family protein (ZAT11) |
| 140 | GmaAffx.41136.1.S1_at | 0.063 | 5.735 | No Soybean Match Identified, E<10E−30, Perecent ID>95% | AT2G34710.1 | Similar to PHABULOSA, leaf pattern formation |
| 141 | Gma.16700.1.S1_at | 0.067 | 5.225 | Glyma20g16920.1 | AT5G61590.1 | ERF/AP2 transcription factor |
| 142 | GmaAffx.15955.1.S1_at | 0.054 | 5.082 | Glyma11g02060.1 | AT2G46410.1 | Similar to CAPRICE, trichoblast fate specification |
| 143 | GmaAffx.64710.1.S1_at | 0.073 | 4.641 | Glyma02g07760.1 | AT5G18270.1 | NAC domain similar to ANAC087 |
| 144 | Gma.4526.1.S1_at | 0.093 | 4.137 | Glyma10g05210.1 | AT2G37430.1 | Zinc finger (C2H2) family protein (ZAT11) |
| 145 | Gma.16807.1.S1_at | 0.040 | 2.685 | Glyma09g14880.1 | AT1G78600.1 | Similar to LZF1, zinc finger (C2H2 type) |
| 146 | GmaAffx.5448.1.S1_at | 0.086 | 2.520 | Glyma16g04720.1 | AT5G18270.1 | NAC domain similar to ANAC087 |
| 147 | GmaAffx.65885.1.A1_s_at | 0.089 | 1.959 | Glyma01g41780.1 | AT2G45120.1 | Zinc finger (C2H2 type) family protein |
| 148 | GmaAffx.9475.1.A1_s_at | 0.039 | 1.845 | Glyma06g14290.1 | AT1G33060.1 | NAC domain similar to ANAC014 |
| 149 | GmaAffx.90028.1.S1_s_at | 0.089 | 1.880 | Glyma04g38560.1 | AT1G01720.1 | NAC domain ATAF1, wound and ABA-induced |
| 150 | Gma.7381.1.S1_at | 0.035 | 1.669 | Glyma20g33430.1 | AT3G10480.1 | NAC domain similar to ANAC050 |
| 151 | Gma.9082.1.S1_at | 0.071 | 1.484 | Glyma15g19980.1 | AT1G19220.1 | Similar to ARF19 |
| 152 | Gma.7454.1.S1_a_at | 0.066 | 2.608 | Glyma13g43800.1 | AT1G04250.1 | Similar to AUX resistant 3 |
| 153 | GmaAffx.39527.1.S1_at | 0.032 | −8.937 | Glyma11g09370.2 | AT2G17410.1 | ARID/BRIGHT DNA-binding domain-containing protein |
| 154 | GmaAffx.4921.1.S1_at | 0.076 | −4.364 | Glyma07g05950.1 | AT3G61850.4 | Similar to DAG1, zinc finger family protein |
| 155 | GmaAffx.70008.1.S1_at | 0.032 | −3.889 | Ambiguous Hit | AT1G66230.1 | Similar to MYB20 |
| 156 | GmaAffx.29616.1.A1_at | 0.069 | −3.371 | Glyma11g04440.2 | AT4G18020.4 | Similar to APRR2 |
| 157 | Gma.8383.1.S1_at | 0.042 | −3.328 | Glyma08g28220.1 | AT3G30530.1 | Similar to ATbZIP42 |
| 158 | Gma.3066.1.S1_at | 0.059 | −3.042 | Glyma19g40070.1 | AT2G47520.1 | Similar to ERF2 subfamily B-2 |
| 159 | GmaAffx.83173.1.S1_at | 0.063 | −2.606 | Glyma14g09310.2 | AT1G46480.1 | Similar to WOX4 |
| 160 | GmaAffx.9569.2.S1_at | 0.074 | −2.207 | Glyma13g20370.2 | AT4G30080.1 | Similar to ARF16, root cap development |
| 161 | GmaAffx.2721.1.S1_s_at | 0.042 | −1.481 | No Soybean Match Identified, E<10E−30, Perecent ID>95% | AT5G37020.1 | Similar to ARF8 |

Other down-regulated genes included an arid-bright domain protein (GmaAffx.39527.1.S1_at, −8.9 fold). These proteins have been implicated in diverse roles during cell growth and differentiation (Wilsker et al., 2002). A soybean homolog of WUSCHEL-RELATED HOMEOBOX 4 (WOX4) implicated in procambium development was also down-regulated (Ji et al., 2010).

Example 1

Effects of Altered Expression of the GmBAG6 Gene or GmAP2 in Yeast and in Plants To determine the function of the GmBAG6 and GmAP2 transcription factor identified from the studies described above, Virus Induced Gene Silencing (VIGS) was used to down-regulate the expression of these genes in plants, respectively. VIGS was performed according to Meenu Padmanabhan and Savithramma P. Dinesh-Kumar, "Virus-Induced Gene Silencing as a Tool for Delivery of dsRNA into Plants." Cold Spring Harb. Protoc. (2009), with modifications.

Figure 9:
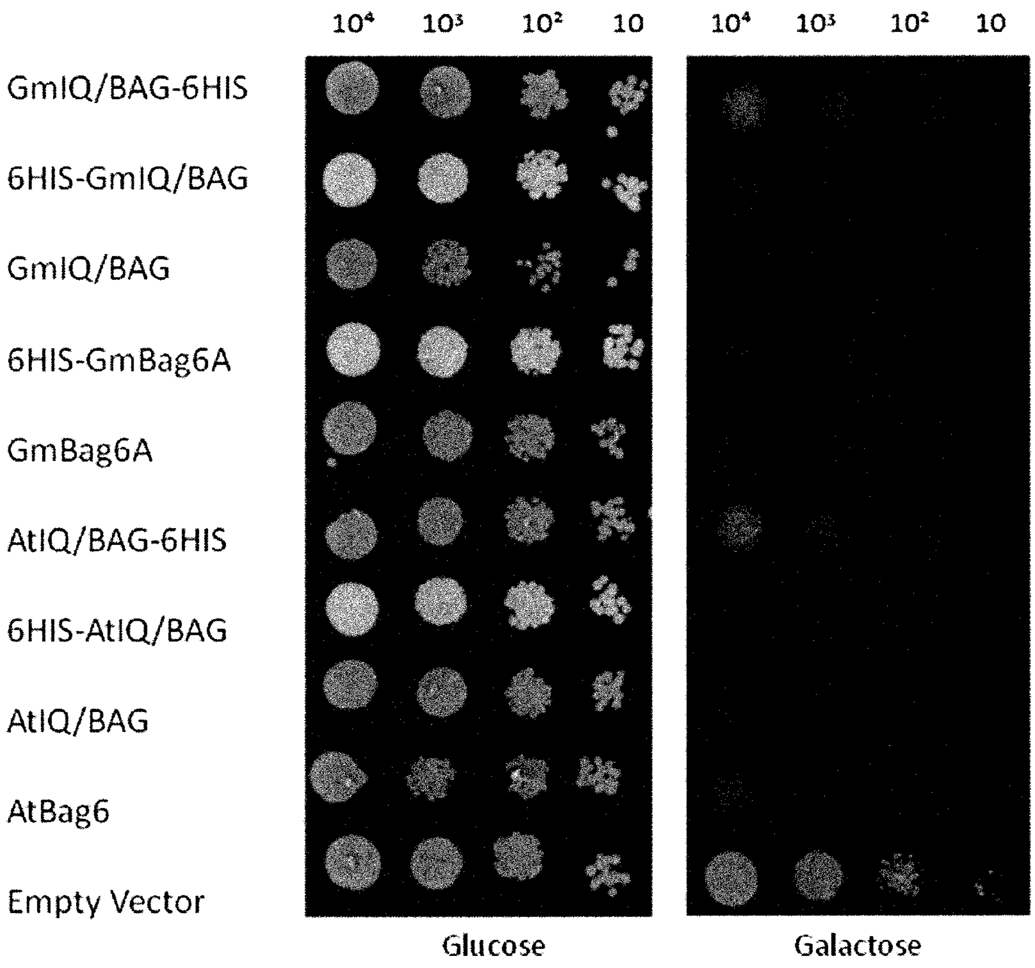
FIG. 9 shows cell death assay of soybean and *Arabidopsis* BAG proteins and IQ-BAG domains in yeast W303-1A cells.

Soybean and *Arabidopsis* BAG proteins and IQ-BAG domains were expressed in yeast W303-JA cells under control of galactose-inducible promoter. The transformed yeast cells were assessed for growth. All yeast cells were cultured in SD-Uracil glucose-based medium to an $OD_{600}$ of about 0.17. Equal numbers of cells were spotted on minimal SD-Uracil medium plates in the presence of glucose (non-inducing) or galactose (inducing). Photographs were taken after culturing at 30° C. for 2 days. FIG. 9 shows the results of the these cell death assay, demonstrating that GmBAG6 full length and just its IQ-BAG domains induce cell death when overexpressed in yeast.

Figure 10:
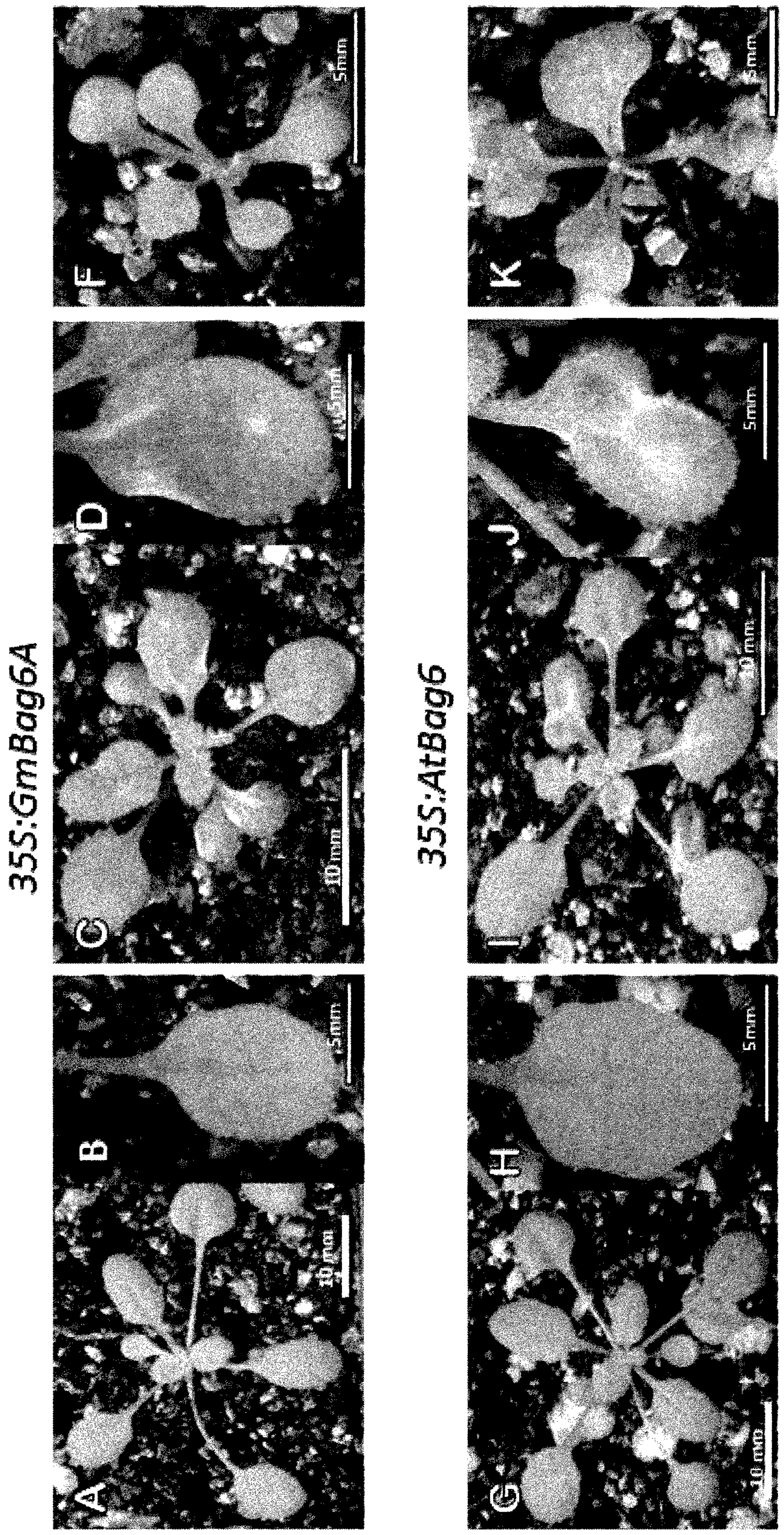
FIG. 10 shows the range of phenotypes associated with $T_1$ generation of different independent, two week-old 35S lines overexpressing GmBag6A (A-D and F) and AtBag6 (G-K) in transgenic *Arabidopsis*, Col-0.

FIG. 10 shows range of phenotypes associated with $T_1$ generation of different independent, two week-old 35S lines overexpressing GmBag6A (A-F) and AtBag6 (G-K) in transgenic *Arabidopsis*, Col-0. (A) Represents wild-type (WT) looking transgenic 35S:GmBag6A *Arabidopsis*. (B) Close up image of WT looking transgenic 35S:GmBag6A *Arabidopsis*. (C-D) Represents intermediate phenotype associated with 35S:GmBag6A, sporadic lesions, smaller rosette and leaf malformations. (F) Represents a severe phenotype associated with transgenic 35S:GmBag6A, stunted plant growth and accumulation of anthocyanin. (G) Represents wild-type (WT) looking transgenic 35S:AtBag6 *Arabidopsis*. (H) Close up image of WT looking leaf in transgenic 35S:AtBag6 (1-J) Represents intermediate phenotype associated with 35S:AtBag6, sporadic lesions, smaller rosette and leaf malformations. (K) Represents a severe phenotype associated with transgenic 35S:AtBag6, stunted plant growth and accumulation of anthocyanin.

FIG. 11 shows a table summarizing the results of the transgenic *Arabidopsis* overexpressing the AtBag6 or GmBag6 genes. The percentages of transgenic plants from two separate studies displaying different phenotypes are shown in the table.

Figure 12:
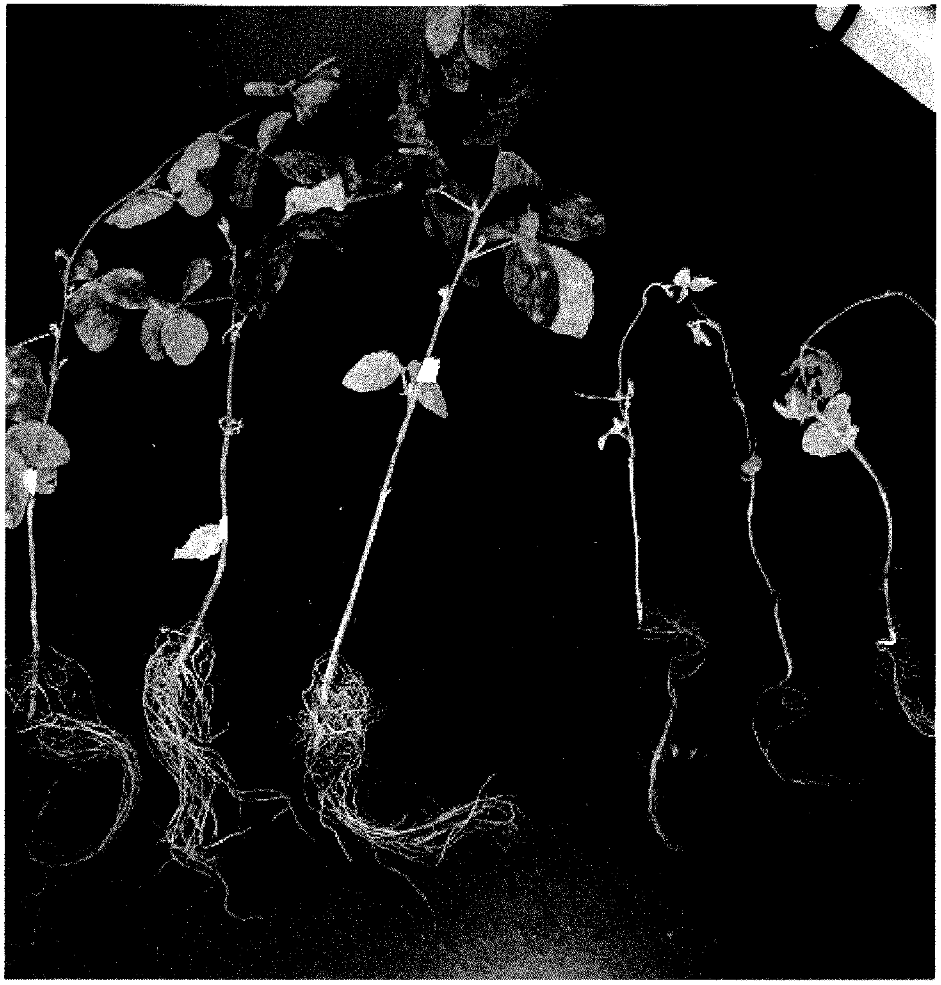
FIG. 12 shows that BPMV overexpression of IQ-BAG domain of GmBAG6A (7923R and Glyma07g06750) leads to stunting and cell death phenotype in soybean plants.

BPMV (bean pod mottle virus) was used to overexpress IQ-BAG domain of GmBAG6A (7923R and Glyma07g06750) in soybean plants. For general description of the methodology, see Zhang et al., Plant Physiol. 2010 May; 153(1): 52-65. The plants were inoculated with either BPMV vector control or IQ-BAG BPMV overexpression construct. As shown in FIG. 12, and by contrast to the vector control, transgenic soybean plants overexpressing the IQ-BAG domain of GmBAG6A display stunting and cell death phenotype. The plants shown are 66-day old.

Figure 13:
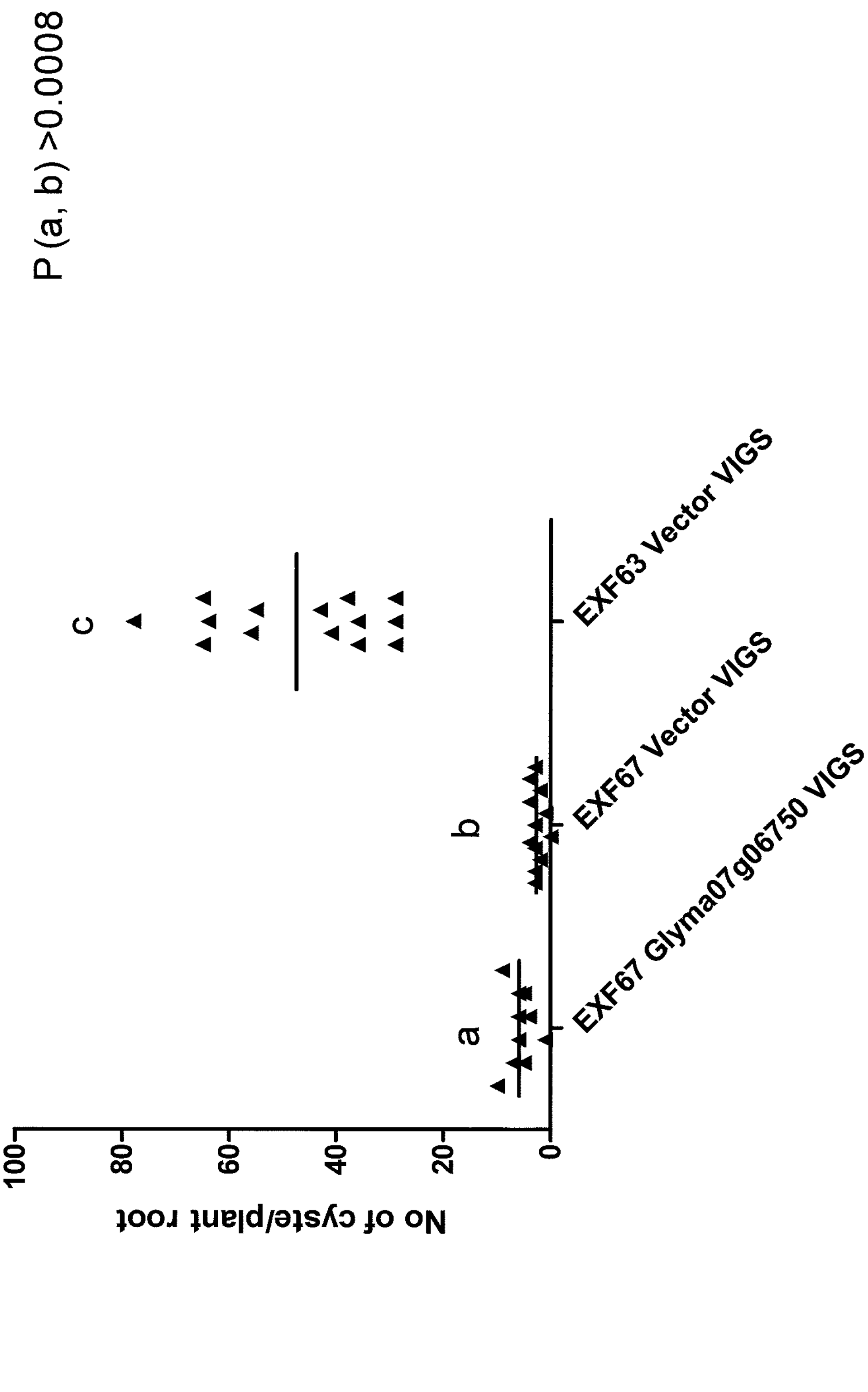
FIG. 13 shows that VIGS silencing of GmBAG6 (Glyma07g06750) leads to increased susceptibility of SCN resistant soybean plants to SCN.

FIG. 13 shows that VIGS silencing of GmBAG6 (Glyma07g06750) (SEQ ID No. 43) (indicated as (a)) led to increased susceptibility of SCN resistant soybean plants to SCN. This result suggests that GmBAG6 may play a role in SCN resistance. Control plants (EXF67, resistant; EXF63, susceptible) were infected with BPMV with empty vector and are indicated as (b) and (c).

Figure 14:
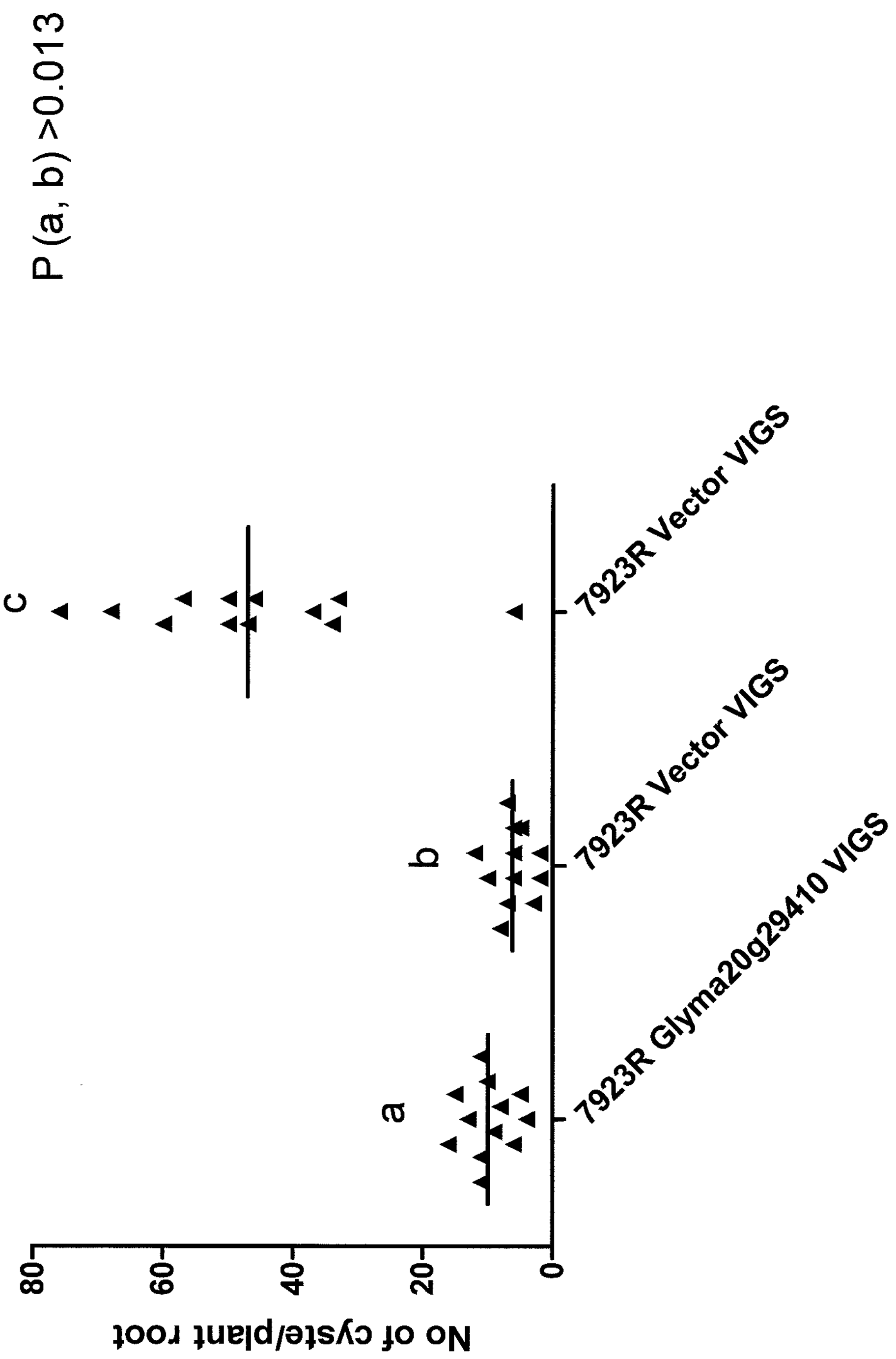
FIG. 14 shows that VIGS silencing of GmAP2 transcription factor (Glyma20g029410) leads to increased susceptibility of SCN resistant soybean plants to SCN.

FIG. 14 shows that VIGS silencing of GmAP2 transcription factor (Glyma20g029410) (SEQ ID No. 33) (indicated as (a)) led to increased susceptibility of SCN resistant soybean plants to SCN. This result suggests that GmAP2 may play a role in SCN resistance. Control plants (EXF67, resistant; EXF63, susceptible) were infected with BPMV with empty vector and are indicated as (b) and (c).

In another example, one or more of the SCNRGs, such as GmBAG6 or GmAP2, or their homologs, are placed under a nematode inducible promoter and are introduced into a plant, such as soybean. Expression of the transgene(s) is triggered by the nematode which would confer upon the transgenic plants nematode resistance.

FIG. 15 shows the sequences of GmBAG6A and GmBAG6B as well as their encoded protein sequences. It is to be understood that the materials and methods are taught by way of example, and not by limitation. The disclosed instrumentalities may be broader than the particular methods and materials described herein, which may vary within the skill of the art. It is also to be understood that the terminology used herein is for the purpose of describing particular embodiments only, and is not intended to be limiting.

While the foregoing instrumentalities have been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

REFERENCES

In addition to those references that are cited in full in the text, additional information for those abbreviated citations is listed below. The content of all patents, patent applications or other publications cited in this disclosure are incorporated by reference into this disclosure.

Acedo J R, Dropkin V H, Luedders V D (1984) Nematode population attrition and histopathology of *Heterodera glycines*-soybean associations. J Nematol 16: 48-56.

Alkharouf N R, Klink V P, Chouikha I B, Beard H S, MacDonald M H, Meyer S, Knap H T, Khan R, Matthews B F (2006) Time course microarray analyses reveal global changes in gene expression of susceptible *Glycine max* (soybean) roots during infection by *Heterodera glycines* (soybean cyst nematode). Planta 224: 838-852.

Balague C, Lin B, Alcon C, Flottes G, Malmstrom S, Kohler C, Neuhaus G, Pelletier G, Gaymard F, Roby D (2003) HLM1, an essential signaling component in the hypersensitive response, is a member of the cyclic nucleotide-gated channel ion channel family. Plant Cell 15: 365-379.

Bari R, Jones J D (2009) Role of plant hormones in plant defence responses. Plant Mol Biol 69: 473-488.

Branch C, Hwang C F, Navarre D A, Williamson V M (2004) Salicylic acid is part of the Mi-1-mediated defense response to root-knot nematode in tomato. Mol Plant Microbe Interact 17: 351-356.

Brucker E, Carlson S, Wright E, Niblack T, Diers B (2005) Rhg1 alleles from soybean PI 437654 and PI 88788 respond differentially to isolates of *Heterodera glycines* in the greenhouse. Theor Appl Genet. 111: 44-49.

Century K S, Holub E B, Staskawicz B J (1995) NDR1, a locus of *Arabidopsis thaliana* that is required for disease resistance to both a bacterial and a fungal pathogen. Proc Natl Acad Sci USA 92: 6597-6601.

Century K S, Shapiro A D, Repetti P P, Dahlbeck D, Holub E, Staskawicz B J (1997) NDR1, a pathogen-induced component required for *Arabidopsis* disease resistance. Science 278: 1963-1965.

Chiang G C, Barua D, Kramer E M, Amasino R M, Donohue K (2009) Major flowering time gene, flowering locus C, regulates seed germination in *Arabidopsis thaliana*. Proc Natl Acad Sci USA 106: 11661-11666.

Clough S J, Fengler K A, Yu I C, Lippok B, Smith R K Jr, Bent A F (2000) The *Arabidopsis* dnd1 "defense, no death" gene encodes a mutated cyclic nucleotide-gated ion channel. Proc Natl Acad Sci USA 97: 9323-9328.

Colgrove A L, Niblack T L (2008) Correlation of female indices from virulence assays on inbred lines and field populations of *Heterodera glycines*. J Nematol 40: 39-45.

Concibido V C, Diers B W, Arelli P R (2004) A decade of QTL mapping for cyst nematode resistance in soybean. Crop Sci 44: 1121-1131.

Coppinger P, Repetti P P, Day B, Dahlbeck D, Mehlert A, Staskawicz B J (2004) Overexpression of the plasma membrane-localized NDR1 protein results in enhanced bacterial disease resistance in *Arabidopsis thaliana*. Plant J 40: 225-237.

Cregan P B, Mudge J, Fickus E W, Danesh D, Denny R, Young N D (1999) Two simple sequence repeat markers to select for soybean cyst nematode resistance conditioned by the rhg1 locus. Theorl Appl Genet. 99: 811-818.

Duan Y, Zhang W, Li B, Wang Y, Li K, Sodmergen Han C, Zhang Y, Li X (2010) An endoplasmic reticulum response pathway mediates programmed cell death of root tip induced by water stress in *Arabidopsis*. New Phytol 186: 681-695.

Endo B Y (1965) Histological responses of resistant and susceptible soybean varieties, and backcross progeny to entry development of *Heterodera glycines*. Phytopathology 55: 375-381.

Eulgem T, Somssich I E (2007) Networks of WRKY transcription factors in defense signaling. Curr Opin Plant Biol 10: 366-371.

Gao X, Starr J, Gobel C, Engelberth J, Feussner I, Tumlinson J, Kolomiets M (2008) Maize 9-lipoxygenase ZmLOX3 controls development, root-specific expression of defense genes, and resistance to root-knot nematodes. Mol Plant Microbe Interact 21: 98-109.

Glazebrook J (2005) Contrasting mechanisms of defense against biotrophic and necrotrophic pathogens. Annu Rev Phytopathol 43: 205-227.

Grunewald W, Karimi M, Wieczorek K, Van de Cappelle E, Wischnitzki E, Grundler F, Inze D, Beeckman T, Gheysen G (2008) A role for AtWRKY23 in feeding site establishment of plant-parasitic nematodes. Plant Physiol 148: 358-368.

Hubert D A, Tornero P, Belkhadir Y, Krishna P, Takahashi A, Shirasu K, Dangl J L (2003) Cytosolic HSP90 associates with and modulates the *Arabidopsis* RPM1 disease resistance protein. EMBO J. 22: 5679-5689.

Hwang I S, Hwang B K (2010) The pepper 9-lipoxygenase gene CaLOX1 functions in defense and cell death responses to microbial pathogens. Plant Physiol 152: 948-967.

Ithal N, Recknor J, Nettleton D, Hearne L, Maier T, Baum T J, Mitchum M G (2007a) Parallel genome-wide expression profiling of host and pathogen during soybean cyst nematode infection of soybean. Mol Plant Microbe Interact 20: 293-305.

Ithal N, Recknor J, Nettleton D, Maier T, Baum T J, Mitchum M G (2007b) Developmental transcript profiling of cyst nematode feeding cells in soybean roots. Mol Plant Microbe Interact 20: 510-525.

Jia Y, Martin G B (1999) Rapid transcript accumulation of pathogenesis-related genes during an incompatible interaction in bacterial speck disease-resistant tomato plants. Plant Mol Biol 40: 455-465.

Jefferson R A (1987) Assaying chimeric genes in plants: the GUS gene fusion system. Plant Mol Biol Rep 5: 387-405.

Journot-Catalino N, Somssich I E, Roby D, Kroj T (2006) The transcription factors WRKY11 and WRKY17 act as negative regulators of basal resistance in *Arabidopsis thaliana*. Plant Cell 18: 3289-3302.

Kang C H, Jung W Y, Kang Y H, Kim J Y, Kim D G, Jeong J C, Baek D W, Jin J B, Lee J Y, Kim M O, Chung W S, Mengiste T, Koiwa H, Kwak S S, Bahk J D, Lee S Y, Nam J S, Yun D J, Cho M J (2006) AtBAG6, a novel calmodulin-binding protein, induces programmed cell death in yeast and plants. Cell Death Differ 13: 84-95.

Khan R, Alkharouf N, Beard H, Macdonald M, Chouikha I, Meyer S, Grefenstette J, Knap H, Matthews B (2004) Microarray analysis of gene expression in soybean roots susceptible to the soybean cyst nematode two days post invasion. J Nematol 36: 241-248.

Klink V P, Alkharouf N, MacDonald M, Matthews B (2005) Laser capture microdissection (LCM) and expression analyses of *Glycine max* (soybean) syncytium containing root regions formed by the plant pathogen *Heterodera glycines* (soybean cyst nematode). Plant Mol Biol 59: 965-979.

Klink V P, Overall C C, Alkharouf N R, MacDonald M H, Matthews B F (2007a) A time-course comparative microarray analysis of an incompatible and compatible response by *Glycine max* (soybean) to *Heterodera glycines* (soybean cyst nematode) infection. Planta 226: 1423-1447.

Klink V P, Overall C C, Alkharouf N R, MacDonald M H, Matthews B F (2007b) Laser capture microdissection (LCM) and comparative microarray expression analysis of syncytial cells isolated from incompatible and compatible soybean (*Glycine max*) roots infected by the soybean cyst nematode (*Heterodera glycines*). Planta 226: 1389-1409.

Klink V P, Hosseini P, Matsye P, Alkharouf N R, Matthews B F (2009) A gene expression analysis of syncytia laser microdissected from the roots of the *Glycine max* (soybean) genotype PI 548402 (Peking) undergoing a resistant reaction after infection by *Heterodera glycines* (soybean cyst nematode). Plant Mol Biol 71: 525-567.

Klink V P, Hosseini P, Matsye P D, Alkharouf N R, Matthews B F (2010) Syncytium gene expression in *Glycine max* ([PI 88788]) roots undergoing a resistant reaction to the parasitic nematode *Heterodera glycines*. Plant Physiol Biochem 48: 176-193.

Koenning S R, Wrather J A (2010). Suppression of soybean yield potential in the continental United States from plant diseases estimated from 2006 to 2009. Plant Health Progress, in press.

Lamb C, Dixon R A (1997) The oxidative burst in plant disease resistance. Annu Rev Plant Physiol Plant Mol Biol 48: 251-275.

Lee M W, Lu H, Jung H W, Greenberg J T (2007) A key role for the *Arabidopsis* WIN3 protein in disease resistance triggered by *Pseudomonas syringae* that secrete AvrRpt2. Mol Plant Microbe Interact 20: 1192-1200.

Lee M W, Jelenska J, Greenberg J T (2008) *Arabidopsis* proteins important for modulating defense responses to *Pseudomonas syringae* that secrete HopW1-1. Plant J 54: 452-465.

Li Y, Chen S, Young N D (2004) Effect of rhg1 gene on penetration, development, and reproduction of *Heterodera glycines* race 3. Nematology 6: 727-734.

Mahalingam R, Skorupska H T (1996) Cytological expression of early response to infection by *Heterodera glycines* Ichinohe in resistant PI 437654 soybean. Genome 39: 986-998.

Manickavelu A, Kawaura K, Oishi K, Shin I T, Kohara Y, Yahiaoui N, Keller B, Suzuki A, Yano K, Ogihara Y (2010) Comparative gene expression analysis of susceptible and resistant near-isogenic lines in common wheat infected by *Puccinia triticina*. DNA Res 17: 211-222.

Meier S, Bastian R, Donaldson L, Murray S, Bajic V, Gehring C (2008) Co-expression and promoter content analyses assign a role in biotic and abiotic stress responses to plant natriuretic peptides. BMC Plant Biol 8: 24.

Melito S, Heuberger A L, Cook D, Diers B W, MacGuidwin A E, Bent A F (2010) A nematode demographics assay in transgenic roots reveals no significant impacts of the Rhg1 locus LRR-Kinase on soybean cyst nematode resistance. BMC Plant Biol 10: 104.

Morel J B, Dangl J L (1997) The hypersensitive response and the induction of cell death in plants. Cell Death Differ 4: 671-683.

Morse M, Pironcheva G, Gehring C (2004) AtPNP-A is a systemically mobile natriuretic peptide immunoanalogue with a role in *Arabidopsis thaliana* cell volume regulation. FEBS Lett 556: 99-103.

Mudge J (1999) Marker assisted selection for soybean cyst nematode resistance and accompanying agronomic traits Ph.D. thesis University of Minnesota St. Paul, Minn.

Niblack T L, Arelli P R, Noel G R, Opperman C H, Orf J H, Schmitt D P, Shannon J G, Tylka G L (2002) A revised classification scheme for genetically diverse populations of *Heterodera glycines*. J. Nematol 34: 279-288.

Niblack T L, Heinz R D, Smith G S, Donald P A (1993) Distribution, density, and diversity of *Heterodera glycines* in Missouri. J. Nematol 25(4S): 880-886.

Nishizawa A, Yabuta Y, Yoshida E, Maruta T, Yoshimura K, Shigeoka S (2006) *Arabidopsis* heat shock transcription factor A2 as a key regulator in response to several types of environmental stress. Plant J 48: 535-547.

Nobuta K, Okrent R A, Stoutemyer M, Rodibaugh N, Kempema L, Wildermuth M C, Innes R W (2007) The GH3 acyl adenylase family member PBS3 regulates salicylic acid-dependent defense responses in *Arabidopsis*. Plant Physiol 144: 1144-1156.

O'Rourke J A, Nelson R T, Grant D, Schmutz J, Grimwood J, Cannon S, Vance C P, Graham M A, Shoemaker R C (2009) Integrating microarray analysis and the soybean genome to understand the soybeans iron deficiency response. BMC Genomics 10: 376.

Onishi M, Tachi H, Kojima T, Shiraiwa M, Takahara H (2006) Molecular cloning and characterization of a novel salt-inducible gene encoding an acidic isoform of PR-5 protein in soybean (*Glycine max* [L.] Merr.). Plant Physiol Biochem 44: 574-580.

Passardi F, Penel C, Dunand C (2004) Performing the paradoxical: how plant peroxidases modify the cell wall. Trends Plant Sci 9: 534-540.

Potter S, Uknes S, Lawton K, Winter A-M, Chandler D, DiMaio J, Novitzky R, Ward E, Ryals J (1993) Regulation of a hevein-like gene in *Arabidopsis*. Mol Plant-Microbe Interact 6: 680-685.

Raffaele S, Rivas S, Roby D (2006) An essential role for salicylic acid in AtMYB30-mediated control of the hypersensitive cell death program in *Arabidopsis*. FEBS Lett 580: 3498-3504.

Riggs R D, Kim K S, Gipson I (1973) Ultrastructural changes in Peking soybeans infected with *Heterodera glycines*. Phytopathology 63: 76-84.

Ross J P (1958) Host-parasite relationship of the soybean cyst nematode in resistant soybean roots. Phytopathology 48: 578-579.

Schlueter J A, Dixon P, Granger C, Grant D, Clark L, Doyle J J, Shoemaker R C (2004) Mining EST databases to resolve evolutionary events in major crop species. Genome 47: 868-876.

Schlueter J A, Lin J Y, Schlueter S D, Vasylenko-Sanders I F, Deshpande S, Yi J, O'Bleness M, Roe B A, Nelson R T, Scheffler B E, Jackson S A, Shoemaker R C (2007) Gene duplication and paleopolyploidy in soybean and the implications for whole genome sequencing. BMC Genomics 8: 330.

Schmutz J, Cannon S B, Schlueter J, Ma J, Mitros T, Nelson W, Hyten D L, Song Q, Thelen J J, Cheng J, Xu D, Helisten U, May G D, Yu Y, Sakurai T, Umezawa T, Bhattacharyya M K, Sandhu D, Valliyodan B, Lindquist E, Peto M, Grant D, Shu S, Goodstein D, Barry K, Futrell-Griggs M, Abernathy B, Du J, Tian Z, Zhu L, Gill N, Joshi T, Libault M, Sethuraman A, Zhang X C, Shinozaki K, Nguyen H T, Wing R A, Cregan P, Specht J, Grimwood J, Rokhsar D, Stacey G, Shoemaker R C, Jackson S A (2010) Genome sequence of the palaeopolyploid soybean. Nature 463: 178-183.

Shapiro A D, Zhang C (2001) The role of NDR1 in avirulence gene-directed signaling and control of programmed cell death in *Arabidopsis*. Plant Physiol 127:1089-1101.

Storey J D, Tibshirani R (2003) Statistical significance for genomewide studies. Proc Natl Acad Sci USA 100: 9440-9445.

Takahashi A, Casais C, Ichimura K, Shirasu K (2003) HSP90 interacts with RAR1 and SGT1 and is essential for RPS2-mediated disease resistance in *Arabidopsis*. Proc Natl Acad Sci USA 100: 11777-11782.

Urade R (2009) The endoplasmic reticulum stress signaling pathways in plants. Biofactors 35: 326-331.

Vailleau F, Daniel X, Tronchet M, Montillet J L, Triantaphylides C, Roby D (2002) A R2R3-MYB gene, AtMYB30, acts as a positive regulator of the hypersensitive cell death program in plants in response to pathogen attack. Proc Natl Acad Sci USA 99: 10179-10184.

Vanderbeld B, Snedden W A (2007) Developmental and stimulus-induced expression patterns of *Arabidopsis* calmodulin-like genes CML37, CML38 and CML39. Plant Mol Biol 64: 683-697.

Varet A, Parker J, Tornero P, Nass N, Nurnberger T, Dangl J L, Scheel D, Lee J (2002) NHL25 and NHL3, two NDR1/

HIN1-like genes in *Arabidopsis thaliana* with potential role(s) in plant defense. Mol Plant Microbe Interact 15: 608-616.

Varet A, Hause B, Hause G, Scheel D, Lee J (2003) The *Arabidopsis* NHL3 gene encodes a plasma membrane protein and its overexpression correlates with increased resistance to *Pseudomonas syringae* pv. tomato DC3000. Plant Physiol 132: 2023-2033.

Wang W, Vinocur B, Shoseyov O, Altman A (2004) Role of plant heat-shock proteins and molecular chaperones in the abiotic stress response. Trends Plant Sci 9: 244-252.

Wang X, Replogle A, Davis E L, Mitchum M G (2007) The tobacco Ce17 gene promoter is auxin-responsive and locally induced in nematode feeding sites of heterologous plants. Mol Plant Pathol 8: 423-436.

Xiao Y L, Smith S R, Ishmael N, Redman J C, Kumar N, Monaghan E L, Ayele M, Haas B J, Wu H C, Town C D (2005) Analysis of the cDNAs of hypothetical genes on *Arabidopsis* chromosome 2 reveals numerous transcript variants. Plant Physiol 139: 1323-1337.

Zhang C, Yang C, Whitham S A, Hill J H (2009) Development and use of an efficient DNA-based viral gene silencing vector for soybean. Mol Plant Microbe Interact 22: 123-131.

Zhang C, Bradshaw J D, Whitham S A, Hill J H (2010) The development of an efficient multipurpose bean pod mottle virus viral vector set for foreign gene expression and RNA silencing. Plant Physiol 153: 52-65.

Zheng M S, Takahashi H, Miyazaki A, Hamamoto H, Shah J, Yamaguchi I, Kusano T (2004) Up-regulation of *Arabidopsis thaliana* NHL10 in the hypersensitive response to Cucumber mosaic virus infection and in senescing leaves is controlled by signalling pathways that differ in salicylate involvement. Planta 218: 740-750.

Zheng Z, Qamar S A, Chen Z, Mengiste T (2006) *Arabidopsis* WRKY33 transcription factor is required for resistance to necrotrophic fungal pathogens. Plant J 48: 592-605.

Chao, Q., Rothenberg, M., Solano, R., Roman, G., Terzaghi, W., Ecker, J. R. (1997) Activation of the ethylene gas response pathway in *arabidopsis* by the nuclear protein ETHYLENE-INSENSITIVE3 and related proteins Cell, 89 (7), pp. 1133-1144

Gechev, T. S., Minkov, I. N., Hille, J. (2005) Hydrogen peroxide-induced cell death in *arabidopsis:* Transcriptional and mutant analysis reveals a role of an oxoglutarate-dependent dioxygenase gene in the cell death process IUBMB Life 57 (3), pp. 181-188

Ji, J., Strable, J., Shimizu, R., Koenig, D., Sinha, N., Scanlon, M. J. (2010) Wox4 promotes procambial development Plant Physiology 152 (3), pp. 1346-1356

Nagpal, P., Ellis, C. M., Weber, H., Ploense, S. E., Barkawi, Guilfoyle, T. J., Hagen, G., ( . . . ), Reed, J. W. (2005) Auxin response factors ARF6 and ARF8 promote jasmonic acid production and flower maturation Development 132 (18), pp. 4107-4118

Wang, X., Basnayake, B. M. V. S., Zhang, H., Li, G., Li, W., Virk, N., Mengiste, T., Song, F. (2009) The *Arabidopsis* ATAF1, a NAC transcription factor, is a negative regulator of defense responses against neurotrophic fungal and bacterial pathogens Molecular Plant-Microbe Interactions 22 (10), pp. 1227-1238

Wilsker, D., Patsialou, A., Dallas, P. B., Moran, E. (2002) ARID proteins: A diverse family of DNA binding proteins implicated in the control of cell growth, differentiation, and development Cell Growth and Differentiation 13 (3), pp. 95-106

Zhong, R., Lee, C., Zhou, J., McCarthy, R. L., Ye, Z.-H. (2008) A battery of transcription factors involved in the regulation of secondary cell wall biosynthesis in *Arabidopsis* Plant Cell 20 (10), pp. 2763-2782.

LENGTHY TABLES

The patent contains a lengthy table section. A copy of the table is available in electronic form from the USPTO web site (http://seqdata.uspto.gov/?pageRequest=docDetail&DocID=US09371541B2). An electronic copy of the table will also be available from the USPTO upon request and payment of the fee set forth in 37 CFR 1.19(b)(3).

We claim:

1. A transgenic soybean plant generated from a host soybean plant, said transgenic soybean plant comprising a construct comprising a nucleic acid encoding SEQ ID NO:166 operably linked to a heterologous promoter, wherein said transgenic soybean plant has an increased expression level of said protein compared to the host soybean plant and is more resistant to nematode infection when compared to the host soybean plant.

2. The transgenic soybean plant of claim 1, wherein the expression level of said protein is at least two fold higher in said transgenic soybean plant than in the host soybean plant.

3. The transgenic soybean plant of claim 1, wherein the promoter is a nematode inducible promoter.

4. The transgenic soybean plant of claim 1, wherein the SCNRG comprises the nucleic acid sequence as set forth in SEQ ID NO:43.

5. A method for generating a transgenic soybean plant using a host soybean plant, said transgenic soybean plant being more resistant to soybean cyst nematode (SCN) infection when compared to the host soybean plant, said method comprising:

introducing a construct comprising a nucleic acid encoding SEQ ID NO:166 operably linked to a heterologous promoter into said host soybean plant thereby obtaining a transgenic soybean plant.

6. The method of claim 5, wherein the promoter is a nematode inducible promoter.

7. The method of claim 5, wherein the SCNRG comprises the nucleic acid sequence as set forth in SEQ ID NO:43.

* * * * *